(12) United States Patent
Jin et al.

(10) Patent No.: US 12,264,367 B2
(45) Date of Patent: Apr. 1, 2025

(54) METHODS OF IN VIVO EVALUATION OF GENE FUNCTION

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Xin Jin, Cambridge, MA (US); Paola Arlotta, Cambridge, MA (US); Aviv Regev, Cambridge, MA (US); Feng Zhang, Cambridge, MA (US); Sean Simmons, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 1092 days.

(21) Appl. No.: 17/163,015

(22) Filed: Jan. 29, 2021

(65) Prior Publication Data
US 2021/0172017 A1    Jun. 10, 2021

Related U.S. Application Data

(63) Continuation of application No. 17/025,784, filed on Sep. 18, 2020, now abandoned.

(60) Provisional application No. 62/902,932, filed on Sep. 19, 2019.

(51) Int. Cl.
| | | |
|---|---|---|
| *C07H 21/02* | (2006.01) | |
| *C12N 15/90* | (2006.01) | |
| *C12Q 1/6883* | (2018.01) | |
| *C12Q 1/6897* | (2018.01) | |

(52) U.S. Cl.
CPC .......... *C12Q 1/6883* (2013.01); *C12N 15/907* (2013.01); *C12Q 1/6897* (2013.01); *C12N 2310/20* (2017.05); *C12N 2800/80* (2013.01); *C12Q 2600/136* (2013.01)

(58) Field of Classification Search
CPC .......................... C12N 15/113; C12N 2310/20
See application file for complete search history.

(56) References Cited

U.S. PATENT DOCUMENTS

| | | | |
|---|---|---|---|
| 11,732,299 B2* | 8/2023 | Ramachandran .... | C12Q 1/6874 506/4 |
| 2011/0265198 A1 | 10/2011 | Gregory et al. | |
| 2012/0017290 A1 | 1/2012 | Cui et al. | |
| 2013/0236946 A1 | 9/2013 | Gouble | |
| 2015/0291966 A1 | 10/2015 | Zhang et al. | |
| 2016/0060691 A1 | 3/2016 | Giresi et al. | |
| 2016/0208323 A1 | 7/2016 | Bernstein et al. | |
| 2017/0166903 A1 | 6/2017 | Zhang et al. | |
| 2018/0346543 A1* | 12/2018 | Qi ...................... | A61K 39/4636 |
| 2019/0203212 A1 | 7/2019 | Zhang et al. | |

FOREIGN PATENT DOCUMENTS

| | | |
|---|---|---|
| WO | 2014/018423 A2 | 1/2014 |
| WO | 2014/047556 A1 | 3/2014 |
| WO | 2014/093622 A2 | 6/2014 |
| WO | 2014/143158 A1 | 9/2014 |
| WO | 2014/204723 A1 | 12/2014 |
| WO | 2014/204726 A1 | 12/2014 |
| WO | 2014/210353 A2 | 12/2014 |
| WO | 2015/089486 A2 | 6/2015 |
| WO | 2016/040476 A1 | 3/2016 |
| WO | 2016/049251 A1 | 3/2016 |
| WO | 2016/106236 A1 | 6/2016 |
| WO | 2016/168584 A1 | 10/2016 |
| WO | 2017/075294 A1 | 5/2017 |
| WO | 2017/156336 A1 | 9/2017 |
| WO | 2017/164936 A1 | 9/2017 |
| WO | 2019/094984 A1 | 5/2019 |
| WO | 2020/033601 A1 | 2/2020 |
| WO | 2020/077236 A1 | 4/2020 |

OTHER PUBLICATIONS

Wroblewska et al. (2018, Cell, 175, 1141-1155).*
Burgess (Nature Reviews Genetics, 18, 67, 2017).*
Gruber, et al., "The Vienna RNA Websuite", Nucleic Acids Research, vol. 36, Apr. 19, 2008, W70-W74.
Adamson, et al., "A Multiplexed Single-Cell Crispr Screening Platform Enables Systematic Dissection of the Unfolded Protein Response", Cell, vol. 167, No. 7, Dec. 15, 2016, 49 pages.
Altschul, et al., "Basic Local Alignment Search Tool", Journal of Molecular Biology, vol. 215, No. 3, Oct. 5, 1990, 403-410.
Arlotta, et al., "Neuronal Subtype-specific Genes that Control Corticospinal Motor Neuron Development in Vivo", Neuron, vol. 45, No. 2, Jan. 20, 2005, 207-221.
Bercury, et al., "Dynamics and Mechanisms of CNS Myelination", Developmental Cell, vol. 42, No. 4, Feb. 23, 2015, 24 pages.
Bian, et al., "Single-cell Multiomics Sequencing and Analyses of Human Colorectal Cancer", Science, vol. 362, Issue 6418, Nov. 30, 2018, 4 pages.
Biswas, et al., "CRISPRTarget: Bioinformatic Prediction and Analysis of crRNA Targets", RNA Biology, vol. 10, No. 5, May 2013, 817-827.
Blondel, et al., "Fast Unfolding of Communities in Large Networks", Journal of Statistical Mechanics: Theory and Experiment, vol. 2008, Oct. 9, 2008, 12 pages.

(Continued)

*Primary Examiner* — Amy Rose Hudson
(74) *Attorney, Agent, or Firm* — F. Brent Nix, Esq.; Johnson, Marcou, Isaacs & Nix, LLC; Christopher D. Southgate, Esq.

(57) ABSTRACT

Described herein are methods and uses thereof for in vivo evaluating functions of multiple genes in parallel by combining in utero genetic perturbation of progenitor cells and single-cell transcriptomic profiling of progeny cells in animals. These methods can be used, among other things, to reveal in vivo gene functions in a cell type-specific manner.

24 Claims, 58 Drawing Sheets

Specification includes a Sequence Listing.

(56) References Cited

OTHER PUBLICATIONS

Buenrostro, et al., "Single-Cell Chromatin Accessibility Reveals Principles of Regulatory Variation", Nature, vol. 523, No. 7561, Jul. 23, 2015, 20 pages.

Buenrostro, et al., "Transposition of Native Chromatin for Fast and Sensitive Epigenomic Profiling of Open Chromatin, DNA-Binding Proteins and Nucleosome Position", Nature Methods, vol. 10, No. 12, Dec. 2013, pp. 1213-1218.

Butler, et al., "Integrating Single-cell Transcriptomic Data Across different Conditions, Technologies, and Species", Nature Biotechnology, vol. 36, No. 5, May 2018, 17 pages.

Cao, et al., "Comprehensive Single Cell Transcriptional Profiling of a Multicellular Organism by Combinatorial Indexing", Available at: BioRxiv https://doi.org/10.1101/104844, Feb. 2, 2017, 35 pages.

Cao, et al., "Comprehensive Single-cell Transcriptional Profiling of a Multicellular Organism", Science, vol. 357, No. 6352, Aug. 18, 2017, 7 pages.

Carr, et al., "Genome Engineering", Nature Biotechnology, vol. 27, No. 12, Dec. 9, 2009, 1151-1162.

Chen, et al., "Genome-Wide Crispr Screen in a Mouse Model of Tumor Growth and Metastasis", Cell, vol. 160, No. 6, Mar. 12, 2015, 28 pages.

Chen, et al., "The Emerging Picture of Autism Spectrum Disorder: Genetics and Pathology", Annual Review of Pathology, vol. 10, 2015, 111-144.

Cusanovich, et al., "Multiplex Single Cell Profiling of Chromatin Accessibility by Combinatorial Cellular Indexing", Science, vol. 348, No. 6237, May 22, 2015, 11 pages.

Datlinger, et al., "Pooled Crispr Screening with Single-cell Transcriptome Readout", Nature Methods, vol. 14, No. 3, Mar. 2017, 20 pages.

Dixit, et al., "Perturb-Seq: Dissecting Molecular Circuits with Scalable Single-Cell RNA Profiling of Pooled Genetic Screens", Cell, vol. 167, No. 7, Dec. 15, 2016, 32 pages.

Dobin, et al., "STAR: Ultrafast Universal RNA-seq Aligner", Bioinformatics, vol. 29, Issue 1, Oct. 25, 2012, 15-21.

Doench, et al., "Optimized sgRNA Design to Maximize Activity and Minimize Off-Target Effects of CRISPR-Cas9", Nature Biotechnology, vol. 34, No. 2, Feb. 2016, 35 pages.

Doench, et al., "Rational Design of Highly Active SgRNAs for Crispr-Cas9-Mediated Gene Inactivation", Nature Biotechnology, vol. 32, No. 12, Dec. 2014, 17 pages.

Drokhlyansky, et al., "The Enteric Nervous System of the Human and Mouse Colon at a Single-cell Resolution", Retrieved as on Oct. 6, 2020 "doi: https://doi.org/10.1101/746743", Sep. 4, 2019, 90 pages.

Duan, et al., "Model-based Understanding of Single-cell Crispr Screening", Nature Communications, vol. 10, No. 2233, May 20, 2019, 11 pages.

Durak, et al., "Chd8 Mediates Cortical Neurogenesis Via Transcriptional Regulation of Cell Cycle and WNT Signaling", Nature Neuroscience, vol. 19, No. 11, Nov. 2016, 32 pages.

Esvelt, et al., "Orthogonal Cas9 Proteins for RNA-guided Gene Regulation and Editing", Nature Methods, vol. 10, No. 11, 2013, 1116-11121.

Feldman, et al., "Lentiviral Co-Packaging Mitigates the Effects of Intermolecular Recombination and Multiple Integrations in Pooled Genetic Screens", BioRxiv, Feb. 8, 2018, 6 pages.

Finak, et al., "MAST: A Flexible Statistical Framework for Assessing Transcriptional Changes and Characterizing Heterogeneity in Single-cell RNA Sequencing Data", Genome Biology, vol. 16, No. 278, 2015, 13 pages.

Gandal, et al., "Shared Molecular Neuropathology across Major Psychiatric Disorders Parallels Polygenic Overlap", Science, vol. 359, Issue 6376, Feb. 9, 2018, 6 pages.

Gao, et al., "Engineered Cpf1 Enzymes with Altered PAM Specificities", Nature Biotechnology, vol. 35, No. 8, Dec. 4, 2016, 17 pages.

Gierahn, et al., "Seq-Well: Portable, Low-Cost RNA Sequencing of Single Cells at High Throughput", Nature Methods, vol. 14, No. 4, Apr. 2017., 8 pages.

Gleditzsch, et al., "PAM Identification by Crispr-Cas Effector Complexes: Diversified Mechanisms and Structures", RNA Biology, vol. 16. No. 4, 2019, 504-517.

Grissa, et al., "CrisprFinder: A Web Tool to Identify Clustered Regularly Interspaced Short Palindromic Repeats", Nucleic Acids Research, vol. 35, 2007, W52-W57.

Haber, et al., "A Single-cell Survey of the Small Intestinal Epithelium", Nature, vol. 551, No. 7680, Nov. 16, 2017, 40 pages.

Habib, et al., "Div-Seq: Single-Nucleus RNA-Seq Reveals Dynamics of Rare Adult Newborn Neurons", Science, vol. 353, No. 6302, Aug. 26, 2016, 925-928.

Habib, et al., "Massively Parallel Single-Nucleus RNA-seq with DroNc-seq", Nature Methods, vol. 14, No. 10, Oct. 2017, 18 pages.

Hashimshony, et al., "CEL-Seq: Single-Cell RNA-Seq by Multiplexed Linear Amplification", Cell Reports, vol. 2, No. 3, Sep. 27, 2012, 666-673.

Hill, et al., "On the design of Crispr-based Single-Cell Molecular Screens", Nature Methods, vol. 15, No. 4, Apr. 2018, 22 pages.

Hodge, et al., "Conserved Cell Types with Divergent Features in Human Versus Mouse Cortex", Nature, vol. 573, No. 7772, Sep. 5, 2019, 38 pages.

Hughes, et al., "Highly Efficient, Massively-Parallel Single-Cell RNA-Seq Reveals Cellular States and Molecular Features of Human Skin Pathology", Retrieved as on Jun. 10, 2020:—https://doi.org/10.1101/689273, Jul. 2, 2019, 51 pages.

Islam, et al., "Characterization of the Single-Cell Transcriptional Landscape by Highly Multiplex RNA-Seq", Genome Research, vol. 21, No. 7, Jul. 2011, 1160-1167.

Jaitin, et al., "Dissecting Immune Circuits by Linking Crispr-Pooled Screens with Single-Cell RNA-Seq", Cell, vol. 167, No. 7, Dec. 15, 2016, 29 pages.

Jiang, et al., "RNA-Guided Editing of Bacterial Genomes Using CRISPR-Cas Systems", Nature Biotechnology, vol. 31, No. 3, Mar. 2013, 233-239.

Jostins, et al., "Host-Microbe Interactions have Shaped the Genetic Architecture of Inflammatory Bowel Disease", Nature, vol. 491, No. 7422, Nov. 1, 2012, 18 pages.

Joung, et al., "Genome-Scale Crispr-Cas9 Knockout and Transcriptional Activation Screening", Nature Protocols, vol. 12, No. 4, Apr. 2017, 71 pages.

Kalisky, et al., "Genomic Analysis at the Single-Cell Level", Annual Review of Genetics, vol. 45, 2011, 22 pages.

Kalisky, et al., "Single-Cell Genomics", Nature Methods, vol. 8, No. 4, Apr. 2011, 311-314.

Katayama, et al., "CHD8 Haploinsufficiency Results in Autistic-like Phenotypes in Mice", Nature, vol. 537, No. 7622, Sep. 29, 2016, 19 pages.

Klein, et al., "Droplet Barcoding for Single-Cell Transcriptomics Applied to Embryonic Stem Cells", Cell, vol. 161, No. 5, May 21, 2015, 24 pages.

Kleinstiver, et al., "Engineered Crispr-Cas9 Nucleases with Altered Pam Specificities", Nature, vol. 523, No. 7561, Jul. 23, 2015, 17 pages.

Kline, et al., "Ankyrin-B Regulates Cav2.1 and Cav2.2 Channel Expression and Targeting*", Journal of Biological Chemistry, vol. 289, No. 8, Feb. 21, 2014, 5285-5295.

Konermann, et al., "Genome-Scale Transcriptional Activation by an Engineered Crispr-Cas9 Complex", Nature, vol. 517, No. 7536, Jan. 29, 2015, 583-588.

Koonin, et al., "Origins and Evolution of Crispr-Cas Systems", Philosophical Transactions of the Royal Society of London, vol. 374, Issue 1772, Oct. 24, 2018, 16 pages.

Langfelder, et al., "WGNCA: An R Package for Weighted Correlation Network Analysis", BMC Bioinformatics, vol. 9, No. 559, Dec. 29, 2008, 13 pages.

Leenay, et al., "Identifying and Visualizing Functional PAN Diversity across Crispr-Cas Systems", Molecular Cell, vol. 62, No. 1, Apr. 7, 2016, 137-147.

(56) References Cited

OTHER PUBLICATIONS

Lino, et al., "Delivering Crispr: A Review of the Challenges and Approaches", Drug Delivery, vol. 25, No. 1, May 7, 2018, 1234-1257.
Love, et al., "Moderated Estimation of Fold Change and Dispersion for RNA-seq Data with DESeq2", Genome Biology, vol. 15, No. 12, 2014, 21 pages.
Lun, et al., "Overcoming Confounding Plate Effects in Differential Expression Analyses of Single-cell RNA-seq Data", Biostatistics, vol. 18, No. 3, Jul. 1, 2017, 451-464.
Macosko, et al., "Highly Parallel Genome-Wide Expression Profiling of Individual Cells Using Nanoliter Droplets", Cell, vol. 161, No. 5, May 21, 2015, 25 pages.
Makarova, et al., "Classification and Nomenclature of Crispr-Cas Systems: Where from Here?", The Crispr Journal, vol. 1, No. 5, 2018, 325-336.
Makarova, et al., "Evolutionary Classification of Crispr-Cas Systems: A Burst of Class 2 and Derived Variants", Nature Reviews Microbiology, vol. 18, Dec. 19, 2019, 67-83.
Mancinelli, et al., "Decoding Neuronal Diversity in the Developing Cerebral Cortex: from Single Cells to Functional Networks", Current Opinion in Neurobiology, vol. 53, Dec. 2018, 146-155.
Marie, et al., "Oligodendrocyte Precursor Survival and Differentiation Requires Chromatin Remodeling by Chd7 and Chd8", Proceedings of the National Academy of Sciences of the United States of America, vol. 115, No. 35, Aug. 28, 2018, E8246-E8255.
Marraffini, et al., "Self Vs. Non-Self Discrimination During Crispr RNA-Directed Immunity", Nature, vol. 463, No. 7280, Jan. 28, 2010, 13 pages.
Martinez-Cerdeno, et al., "Neural Progenitor Cell Terminology", Frontiers in Neuroanatomy, vol. 12, No. 104, Dec. 2018, 8 pages.
Miller, et al., "Transcriptional Landscape of the Prenatal Human Brain", Nature, vol. 508, Apr. 10, 2014, 19 pages.
Mojica, et al., "Short Motif Sequences Determine the Targets of the Prokaryotic Crispr Defence System", Microbiology, vol. 155( pt 3), Mar. 2009, 733-740.
Mullins, et al., "Unifying Views of Autism Spectrum Disorders: A Consideration of Autoregulatory Feedback Loops", Neuron, vol. 89, No. 6, Mar. 16, 2016, 43 pages.
Nishiyama, et al., "Early Embryonic Death in Mice Lacking the Beta-Catenin-Binding Protein Duplin", Molecular and Cellular Biology, vol. 24, No. 19, Oct. 2004, 8386-8394.
Nowakowski, et al., "Spatiotemporal Gene Expression Trajectories Reveal Developmental Hierarchies of the Human Cortex", Science, vol. 358, Issue 6368, Dec. 8, 2017, 6 pages.
Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 16 pages.
Peters, et al., "Recruitment of Crispr-Cas Systems by Tn7-Like Transposons", Proceedings of the National Academy of Sciences, vol. 114, No. 35, 2017, E7358-E7366.
Picelli, et al., "Full-Length RNA-Seq from Single Cells using Smart-seq2", Nature Protocols, vol. 9, No. 1, Jan. 2, 2014, 171-181.
Platt, et al., "Chd8 Mutation Leads to Autistic-like Behaviors and Impaired Striatal Circuits", Cell Reports, vol. 17, Apr. 11, 2017, 17 pages.
Platt, et al., "Crispr-Cas9 Knockin Mice for Genome Editing and Cancer Modeling", Cell, vol. 159, No. 2, Oct. 9, 2014, 31 pages.
Qui, et al., "Mutation Detection Using Surveyor Nuclease", Biotechniques, vol. 36, No. 4, 2004, 702-707.
Ramskold, et al., "Full-Length mRNA-Seq from Single Cell Levels of RNA and Individual Circulating Tumor Cells", Nature Biotechnology, vol. 30 , No. 8, Aug. 2012, 20 pages.
Replogle, et al., "Combinatorial Single-cell Crispr Screens by Direct Guide RNA Capture and Targeted Sequencing", Nature Biotechnology, vol. 38, No. 8, Aug. 2020, 23 pages.
Ritchie, et al., "Limma Powers Differential Expression Analyses for RNA-sequencing and Microarray Studies", Nucleic Acids Research, vol. 43, No. 7, Jan. 20, 2015, 13 pages.
Roberts, et al., "stm: R Package for Structural Topic Models", Journal of Statistical Software, vol. 91, No. 2, Oct. 2019, 41 pages.
Rodriques, et al., "Slide-Seq: A Scalable Technology for Measuring Genome-wide Expression at High Spatial Resolution", Science, vol. 363, Issue 6434, Mar. 29, 2019, 6 pages.
Rosenberg, et al., "Scaling Single Cell Transcriptomics Through Split Pool Barcoding", Available at:Bio Rxiv http://dx.doi.org/10.1101/105163, Feb. 2, 2017, 13 pages.
Rosenberg, et al., "Single-Cell Profiling of the Developing Mouse Brain and Spinal Cord with Split-Pool Barcoding", Science, vol. 360, No. 6385, Apr. 13, 2018, 8 pages.
Rubin, et al., "Coupled Single-cell Crispr Screening and Epigenomic Profiling Reveals Causal Gene Regulatory Networks", Cell, vol. 176, No. 1-2, Jan. 10, 2019, 34 pages.
Sakamoto, et al., "A Novel Beta-catenin-binding Protein Inhibits Beta-catenin-dependent Tcf Activation and Axis Formation", Journal of Biological Chemistry, vol. 275, No. 42, Oct. 20, 2000, 32871-32878.
Sanders, et al., "De Novo Mutations Revealed by Whole-Exome Sequencing are Strongly Associated with Autism", Nature, vol. 485, No. 7397, Apr. 4, 2012, 14 pages.
Satterstrom, et al., "Large-Scale Exome Sequencing Study Implicates Both Developmental and Functional Changes in the Neurobiology of Autism", Cell, vol. 180, No. 3, Apr. 24, 2019, 43 pages.
Satterstrom, et al., "Novel Genes for Autism Implicate Both Excitatory and Inhibitory Cell Lineages in Risk", Retrieved as on Oct. 5, 2020 "https://doi.org/10.1101/484113", Dec. 1, 2018, 52 pages.
Saunders, et al., "Molecular Diversity and Specializations among the Cells of the Adult Mouse Brain", Cell, vol. 174, No. 4, Aug. 9, 2018, 1015-1030.
Schizophrenia Working Group of T, "Biological insights from 108 schizophrenia-associated genetic loci", Nature, vol. 511, 2014, 17 pages.
Scotland, et al., "Nervous System Defects of AnkyrinB (-/-) Mice Suggest Functional Overlap between the Cell Adhesion Molecule L1 and 440-kD AnkyrinB in Premyelinated Axons", Journal of Cell Biology, vol. 143, No. 5, Nov. 30, 1998, 1305-1315.
Shmakov, et al., "Discovery and Functional Characterization of Diverse Class 2 Crispr-Cas Systems", Molecular Cell, vol. 60, No. 3, Nov. 5, 2015, 385-397.
Swiech, et al., "In Vivo Interrogation of Gene Function in the Mammalian Brain Using Crispr-Cas9", Nature Biotechnology, vol. 33, No. 1, Jan. 2015, 102-106.
Tang, et al., "mRNA-Seq Whole-Transcriptome Analysis of a Single Cell", Nature Methods, vol. 6, No. 5, May 2009, 8 pages.
Tang, et al., "RNA-Seq Analysis to Capture the Transcriptome Landscape of a Single Cell", Nature Protocols, vol. 5, No. 3, Mar. 2010, 34 pages.
The Gene Ontology Consortium, "The Gene Ontology Resource: 20 Years and Still Going Strong", Nucleic Acids Research, vol. 47, Nov. 5, 2018, 9 pages.
Torre-Ubieta, et al., "Advancing the Understanding of Autism Disease Mechanisms Through Genetics", Nature Medicine, vol. 22, No. 4, Apr. 2016, 40 pages.
Tseng, et al., "Giant Ankyrin-G Stabilizes Somatodendritic Gabaergic Synapses through Opposing Endocytosis of GABAA Receptors", Proceedings of the National Academy of Sciences of the United States of America, vol. 112, No. 4, Jan. 27, 2015, 1214-1219.
Tuvia, et al., "Ankyrin-B Is Required for Intracellular Sorting of Structurally Diverse Ca2+ Homeostasis Proteins", Journal of Cell Biology, vol. 147, No. 5, Nov. 29, 1999, 13 pages.
Velasco, et al., "Individual Brain Organoids Reproducibly Form Cell Diversity of the Human Cerebral Cortex", Nature, vol. 570, Jun. 27, 2019, 18 pages.
Velmeshev, et al., "Single-cell Genomics Identifies Cell Type-Specific Molecular Changes in Autism", Science, vol. 364, No. 6441, May 17, 2019, 5 pages.
Vitak, et al., "Sequencing Thousands of Single-Cell Genomes with Combinatorial Indexing", Nature Methods, vol. 14, No. 3, Mar. 2017, 19 pages.
Wang, et al., "Three-dimensional Intact-tissue Sequencing of Single-cell Transcriptional States", Science, vol. 361, Issue 6400, Jul. 27, 2018, 11 pages.

(56) References Cited

OTHER PUBLICATIONS

Yang, et al., "ANK2 Autism Mutation Targeting Giant Ankyrin-b Promotes Axon Branching and Ectopic Connectivity", Proceedings of the National Academy of Sciences of the United States of America, vol. 116, No. 30, Jul. 23, 2019, 15262-15271.

Zeisel, et al., "Molecular Architecture of the Mouse Nervous System", Cell, vol. 174, No. 4, Aug. 9, 2018, 38 pages.

Zetsche, et al., "Cpf1 is a Single RNA-Guided Endonuclease of a Class 2 Crispr-Cas System", Cell, vol. 163, No. 3, Oct. 22, 2015, 759-771.

Zhao, et al., "Dual Requirement of CHD8 for Chromatin Landscape Establishment and Histone Methyltransferase Recruitment to Promote CNS Myelination and Repair", Developmental Cell, vol. 45, No. 6, Jun. 18, 2018, 24 pages.

Zheng, et al., "Haplotyping Germline and Cancer Genomes with High-Throughput Linked-Read Sequencing", Nature Biotechnology, vol. 34, No. 3, Mar. 2016, 303-311.

Zheng, et al., "Massively Parallel Digital Transcriptional Profiling of Single Cells", Nature Communications, vol. 8, No. 14049, Jan. 16, 2017, 12 pages.

Zilionis, et al., "Single-cell Barcoding and Sequencing Using Droplet Microfluidics", Nature Protocols, vol. 12, No. 1, Jan. 2017, 44-73.

\* cited by examiner

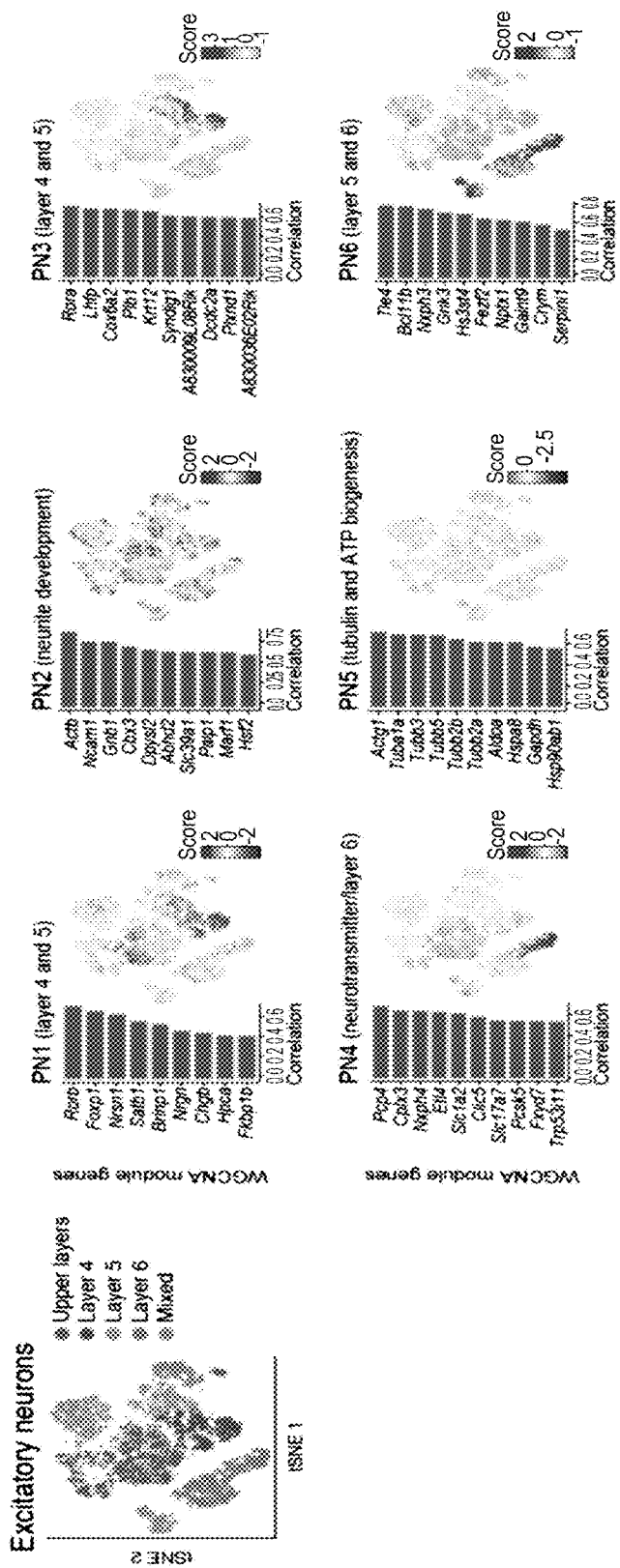
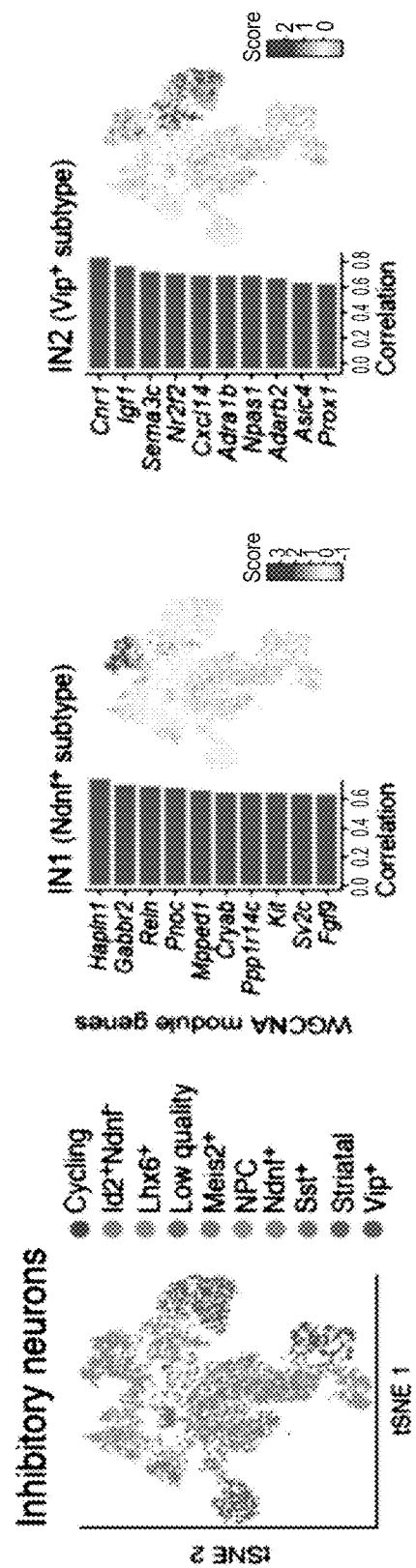
FIG. 10A
FIG. 10B

METHODS OF IN VIVO EVALUATION OF GENE FUNCTION

CROSS-REFERENCE TO RELATED APPLICATIONS

This application is a continuation of U.S. patent application Ser. No. 17/025,784, filed on Sep. 18, 2020, entitled "METHODS OF IN VIVO EVALUATION OF GENE FUNCTION," which claims the benefit of and priority to U.S. Provisional Patent Application No. 62/902,932, filed on Sep. 19, 2019 entitled "METHODS OF IN VIVO EVALUATION OF GENE FUNCTION," the contents of which are incorporated by reference herein in their entirety.

STATEMENT REGARDING FEDERALLY SPONSORED RESEARCH

This invention was made with government support under Grant No. MH15727, MH096066, MH094271, HG009761, MH110049, HL141201, and HG006193 awarded by National Institutes of Health. The government has certain rights in the invention.

SEQUENCE LISTING

This application contains a sequence listing filed in electronic form as an ASCII.txt file entitled BROD-4900US-CON_ST25.txt, created on Jan. 29, 2021 and having a size of 21,016 bytes (25 KB on disk). The content of the sequence listing is incorporated herein in its entirety.

TECHNICAL FIELD

The subject matter disclosed herein is generally directed to methods and uses thereof for in vivo evaluation of gene functions.

BACKGROUND

In the past decades, human genetics has uncovered strong links between genetic states and human diseases ranging from breast cancer to psychiatric disorders (1). Many risk-associated genes for a variety of diseases have been proposed. However, a major challenge remains for the identification of the point of action of these risk-associated genes, because each can affect any of a massive number of different tissues, cell types, and molecular pathways. High-resolution phenotyping methods to identify tissue- and cell-type specific effects of genetic perturbations are needed, as generating and analyzing individual knockout animal models for long lists of risk-associated genes is prohibitive as a first line of functional investigation.

Citation or identification of any document in this application is not an admission that such a document is available as prior art to the present invention.

SUMMARY

In certain example embodiments, methods are provided for in vivo evaluating a plurality of genes in parallel. The methods comprise introducing a plurality of genetic perturbations into a plurality of progenitor cells in an in vivo animal model. The genetic perturbation is achieved by introducing mutations into each gene of the plurality of genes in vivo. In some embodiments, the genetic perturbation is achieved by introducing mutations into each gene of the plurality of genes in utero. In the meantime, a reporter gene is also introduced together with each genetic perturbation. As the progenitor cells develop into diverse distinct types of progeny cells, the genomic, genetic, epigenetic, proteomic, or phenotypic profiles of distinct types of progeny cells are profiled, thus revealing the function of each gene in the plurality of genes in a cell type-specific manner.

In certain embodiments, methods and uses of preparing guide RNAs targeting the gene of interest are provided. Using these methods, one can effectively prepare a plurality of lentivirus-based genetic perturbations targeting a plurality of genes of interest in parallel.

In certain embodiments, methods of in utero genetic perturbation are provided. The methods allow one to specifically deliver genetic perturbations into desired progenitor cells in utero.

In certain embodiments, methods of preparing desired progeny cells are provided. These methods allow one to effectively obtain single progeny cells for subsequent analyses.

In certain embodiments, methods of analyzing perturbed progeny cells are provided. In some embodiments, progeny cells are subjected to single-cell RNA sequencing, wherein a transcriptome for each cell with single or multiplex genetic perturbation can be obtained.

In certain embodiments, methods and uses of evaluating gene functions based on the changes in gene expression programs, cell states, and other genomic and proteomic parameters are provided. Using these methods, the in vivo functions of multiple genes can be revealed in parallel in a cell type-specific manner.

Described in certain example embodiments herein are methods of identifying functions of a plurality of genes in parallel in vivo, comprising:
  a. introducing, in vivo, a plurality of genetic perturbations in each of a plurality of progenitor cells in a Cas animal model, wherein each genetic perturbation is operatively coupled to a reporter gene and a barcode;
  b. generating an enriched perturbed cell population by enriching for cells expressing the reporter;
  c. identifying cell types and corresponding perturbations via scRNA-seq in the enriched perturbed cell population; and
  d. detecting one or more gene modules that co-vary within a cell type in the enriched perturbed cell population.

In certain example embodiments, the enriched perturbed cell population comprises progenitor cell progeny.

In certain example embodiments, the plurality of genetic perturbations are introduced using two or more guide RNAs (gRNAs) for each target gene, wherein the two or more gRNAs each bind to s sequence of an exon, an intron, or both at the 5' end of a target gene.

In certain example embodiments, the two or more gRNAs each bind to a sequence of a coding exon at the 5' end of a target gene.

In certain example embodiments, each of the two or more gRNAs are controlled by a different pol III promoter.

In certain example embodiments, a first gRNA of the two or more gRNAs is controlled by a human pol III promoter and a second gRNA of the two or more gRNAs is controlled by a non-human pol III promoter.

In certain example embodiments, the human pol III promoter and the non-human pol III promoters are each independently selected from a U6, a 7SK, or an H1 promoter.

In certain example embodiments, one or more of the poll III promoters are constitutive.

In certain example embodiments, one or more of the pol III promoters are inducible.

In certain example embodiments, the barcode is polyadenylated.

In certain example embodiments, the reporter gene is controlled by a constitutive pol II promoter.

In certain example embodiments, introducing further comprises delivering to the plurality of progenitor cells a pool of engineered virus particles comprising equal genetic perturbation representation.

In certain example embodiments, the engineered virus particles are engineered lentiviral particles.

In certain example embodiments, introducing further comprises delivering the pool of engineered virus particles to a target tissue of a developing embryo of the Cas animal model in utero.

In certain example embodiments, the developing embryo is at stage between E5-E15 or an equivalent stage thereof.

In certain example embodiments, the reporter gene encodes an optically active protein.

In certain example embodiments, the reporter gene encodes a cell surface molecules selected from the group of: CD3, CD4, CD19, CD20, CD22, CD34, CD45, CD80, a cell surface receptor, a cluster differentiation (CD) molecule, or any combination thereof.

In certain example embodiments, the Cas animal model constitutively or inducibly expresses a Cas protein in one of, a plurality of, or all of its cells.

In certain example embodiments, the Cas protein is a Cas Type I, II, III, IV, or V protein.

In certain example embodiments, identifying further comprises a genomic analysis, an epigenomic analysis, a transcriptomic analysis, a proteomic analysis, or a combination thereof.

In certain example embodiments, the method further comprises a genomic analysis, an epigenomic analysis, a transcriptomic analysis, a proteomic analysis, or a combination thereof.

In certain example embodiments, the plurality of genes are autism spectrum disorder associated genes.

Described in certain example embodiments herein are methods of in vivo screening for therapeutic targets useful for developing treatment for a disease, comprising:
  a. performing a method as in any of paragraphs e.g. [0013]-[0034] and as further described elsewhere herein, wherein the plurality of genes are a plurality of candidate genes; and
  b. selecting one or more candidate genes that produce a change in one or more identified gene modules that are indicative of the disease status; whereby the selected one or more candidate genes are identified as therapeutic targets for disease treatment screening.

In certain example embodiments, the method further comprises using the selected candidate gene(s) as therapeutic targets in a disease treatment screen.

In certain example embodiments, the disease treatment screen is an autism spectrum disease treatment screen.

In certain example embodiments, the disease is an autism spectrum disease.

Described in certain example embodiments herein are therapeutic agents for treating a disease where the therapeutic agent is capable of modifying the function, activity, expression, or a combination thereof of identified therapeutic targets of any one of claims [0035]-[0038] and as further described elsewhere herein, one or more gene product(s) thereof, or both.

In certain exemplary embodiments, the disease is an autism spectrum disease.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 1A) Schematics of the in vivo Perturb-Seq platform, which introduces mutations in individual genes in utero at E12.5, followed by transcriptomic profiling of the cellular progeny of these perturbed cells at P7 via single-cell RNA sequencing (scRNA-seq). (FIG. 1B) tSNE of five major cell populations identified in the Perturb-Seq cells. (FIG. 1C) In vivo Perturb-Seq lentiviral vector carrying an mCherry reporter drives detectable expression within 24h, and can sparsely infect brain cells across many brain regions. Scale bar is 1000 μm. (FIG. 1D) Cell-type analysis of in vivo Perturb-Seq of ASD/ND de novo risk genes. Canonical marker genes were used to identify major cell clusters (left), and cell-type distribution in each perturbation group (right). Negative control (GFP) is highlighted by a black rectangle. (FIG. 1E) tSNEs showing the subclusters of each of the five major cell types, identified by re-clustering each cell type separately.

(FIG. 2A) Schematic illustration of the Perturb-Seq analysis pipeline. (FIG. 2B) ASD/ND risk gene perturbation effects in different WGCNA gene modules compared to GFP controls. Dot color corresponds to effect size, dot size corresponds to negative base 10 log(P-value). Module gene lists are presented in Table 4. P-values were calculated from linear modeling, Padj was calculated by Benjamini & Hochberg FDR correction. (FIG. 2C) The four cell types and five gene modules that were altered by ASD risk gene perturbations. Top row: subcluster tSNE of each cell class (repeated from FIG. 1E for ease of comparison). Bottom row: feature plots of gene module expression scores and the top correlated genes within each module across the relevant cell class.

(FIG. 3A) tSNE of oligodendrocyte subtypes from the Perturb-Seq data. (FIG. 3B) The ODC1 gene module expression score in each cell (left) and in each subcluster (right). (FIG. 3C) Average expression of genes in the ODC1 gene module (by row) in each perturbation group (by column), scaled by row. (FIG. 3D) Effect size of each perturbation on the ODC1 gene module compared to the control group. Note that the perturbation effects of the different genes present a continuous gradient. Error bars represent 95% confidence intervals. (FIG. 3E) In situ hybridization for Cspg4, a gene in module ODC1 that is a known marker of oligodendrocyte precursor cells (OPC), in the somatosensory cortex of P7 Chd8+/− and wild-type littermates. The bottom images of represent the higher magnifications of top images, and the right images represent higher magnifications for each cell. Right: quantification of Cspg4 expression in P7 cortex of Chd8+/− and wild-type littermates. Each dot represents the gene expression value from one cell; error bars represent standard error of the mean (n=3 animals per genotype). Scale bar is 1000 μm (left bottom panel), 100 μm (left top panel), and 10 μm (right panel), respectively. (FIG. 3F) Immunohistochemistry for PDGFRA and MBP (markers for immature OPC and mature oligodendrocytes, respectively), PDGFRA+ cell counts, and distribution of MBP expression, in the somatosensory cortex of P11 Chd8+/− animals and wild-type littermates. Scale bar is 1000 μm (left panel) and 250 μm (right panel), respectively.

(FIG. 4A) Percent of genes with a human orthologue expressed in >5% of cells of the associated cell type in scRNA-seq datasets from the human brain or human brain organoids. (FIG. 4B) Normalized average pairwise correlation of gene expression within each gene module in the human brain or human brain organoids. Correlation values were normalized to the mean correlation from the background distribution, and divided by the standard deviation of the background distribution. Correlations are shown for modules with at least 4 genes after filtering out genes expressed in less than 5% of cells. Bars represent 95% confidence intervals. Red color represents statistical significance (FDR<0.05). (FIG. 4C) Expression of module PN3 over developmental time in human brain tissues across regions (BrainSpan data). (FIG. 4D) Expression of each module over developmental time in human primary somatosensory cortex SiC (BrainSpan). (FIG. 4E) Distribution of the Spearman correlation of module expression with age in human brain data over various brain regions (BrainSpan). (FIG. 4F) Differential gene expression analysis of human prefrontal cortical samples from ASD donors and controls. Left: Expression of differentially expressed (DE) genes across cell types (color bars) from Velmeshev et al. (30) (rows) in the Perturb-Seq data across a panel of ASD/ND risk genes (columns). Right: DE gene expression changes in Perturb-Seq data (black dots; each dot represents an ASD/ND risk gene perturbation) compared to DE values for the 14 genes found to be DE in ASD patients in the Velmeshev et al dataset (30) (FDR<0.2) (red dots). The two highlighted genes, SST and NRN1, showed decreased expression in the Perturb-Seq data (FDR<0.1), consistent with the ASD patient dataset.

(FIGS. 5B-5D) Gene expression of a panel of selected ASD/ND de novo risk genes in human somatosensory cortex (S1C), striatum, and thalamus across the Allen Brain Atlas BrainSpan postmortem samples. Dendrogram indicates hierarchical clustering by rows.

(FIG. 6C) Expression of the 38 initially-selected risk-associated genes in the cell clusters from E18.5 and P7 wild-type cortex.

(FIG. 7C) The proportion of live cells after FACS purification is 78.2%, and <0.1% of total dissociated cortical cells are BFP+ (indicated by polygons). (FIGS. 7D-7E) Frameshift insertion/deletion rates of the targeted loci by CRISPR/Cas9 genome editing (FIG. 7D) in the infected cells in vivo, and (FIG. 7E) in mouse embryonic stem cells in vitro as a control, for each gRNA. (FIG. 7F) Distribution of the perturbed cells in the 5 major cell types, across 17 different libraries (independent experimental batches) (left) and 35 different perturbation groups (right). (FIG. 7G) Number of genes detected in each cell type in the Perturb-Seq single-cell RNA-seq data. Quality control cutoffs for each cell type are marked by black vertical bars.

(FIG. 8B) The distribution of cell numbers from each ASD/ND perturbation group. (FIG. 8C) Estimated doublet score in the Perturb-Seq data using the Scrublet package; the black vertical bar represents the cutoff above which a "cell" is declared as a doublet. (FIG. 8D) The distribution of the number of perturbation barcodes detected per cell. (FIG. 8E) BFP is one of the genes with the highest expression level, detected in all 5 cell types. (FIG. 8F) BFP expression level is correlated with the number of genes detected in each cell type. (FIG. 8G) Percentage of UMI from reads mapping to the mitochondrial genome in each cell type.

(FIG. 9B) Poisson regression for differences of cell type composition compared to the GFP control group. The size of the dots corresponds to base 10 log (P-value), the color to effect size. (FIG. 9C) Nonparametric ANOVA analysis shows that perturbation status overall (as opposed to the status of individual target genes) explains a significant portion of the variation in one glial module, ODC1.

FIGS. 10A-10F—(FIGS. 10A-10E) Subclusters of each major cell class and feature plots of scores of gene modules identified by WGCNA, labelled by associated cell subtypes or biological processes. (FIG. 10F) Expression of key cell type marker genes in each subtype.

(FIGS. 13B-13C) ASD/ND risk gene perturbation effects in different WGCNA gene modules compared to GFP controls, measured as FIG. 2B, with an alternative method for calculating P-values: instead of using the naive P-value output by the linear model (as FIG. 2B), they were calculated using a permutation test (FIG. 13B) or through a linear mixed model (FIG. 13C). Padj was calculated using Benjamini & Hochberg FDR correction. Dot color corresponds to effect size, dot size corresponds to base 10 log(P-value). (FIG. 13D) Correlation of the Perturb-Seq effect size measured by TPM (FIG. 13A) and those measured by scaled eigen score (in FIG. 2B). (FIG. 2E) Correlation of the reported P-values generated by a linear model (in FIG. 2B) and those measured by a permutation test (in FIG. 13B).

(FIG. 14B) Cell type clusters from P7 neocortical simplex Ank2 Perturb-Seq. (FIGS. 14C-14D) Subtype clusters of inhibitory neurons from the simplex Ank2 Perturb-Seq. (FIG. 14E) Simplex dataset expression of the gene module IN1 identified in the pooled Perturb-Seq analysis.

(FIGS. 15B-15C) In situ hybridization for Pdgfra, a marker of oligodendrocyte precursor cells, in the somatosensory cortex of P7 Chd8+/− animals and wild-type littermates. Dotted lines in FIG. 15C indicate individual Pdgfra-positive nuclei at higher magnification (white boxes in panel FIG. 15B). Scale bar is 100 m (panel FIG. 15B) and 10 m (panel FIG. 15C), respectively. (FIG. 15D) Quantification of Pdgfra expression in somatosensory cortex of Chd8+/− and wild-type littermates. Each dot represents the gene expression measurement from one cell; error bars represent standard error of the mean n=3 animals per genotype.

(FIGS. 16B-16C) Metrics used for human conservation analysis, repeated on mouse cells as a control (compare FIGS. 4A-4B). (FIG. 16B) Percent of genes in each gene module expressed in at least 5% of cells in the P7 mouse brain nuclei, Perturb-Seq dataset (whole cell), and simplex Perturb-Seq (whole cell) scRNA-seq datasets. (FIG. 16C) Normalized average pairwise correlation of gene expression within each gene module in each mouse dataset. Bars represent 95% confidence intervals. (FIGS. 16D-16E) Gene expression and modularity analyses analogous to FIGS. 4A-4B, performed on the non-associated cell types of each module as a control, shows a lower proportion of comparisons with significant correlation coefficients and a much lower strength of correlations than in the associated cell types (FIGS. 4A-4B).

Figure 1A:
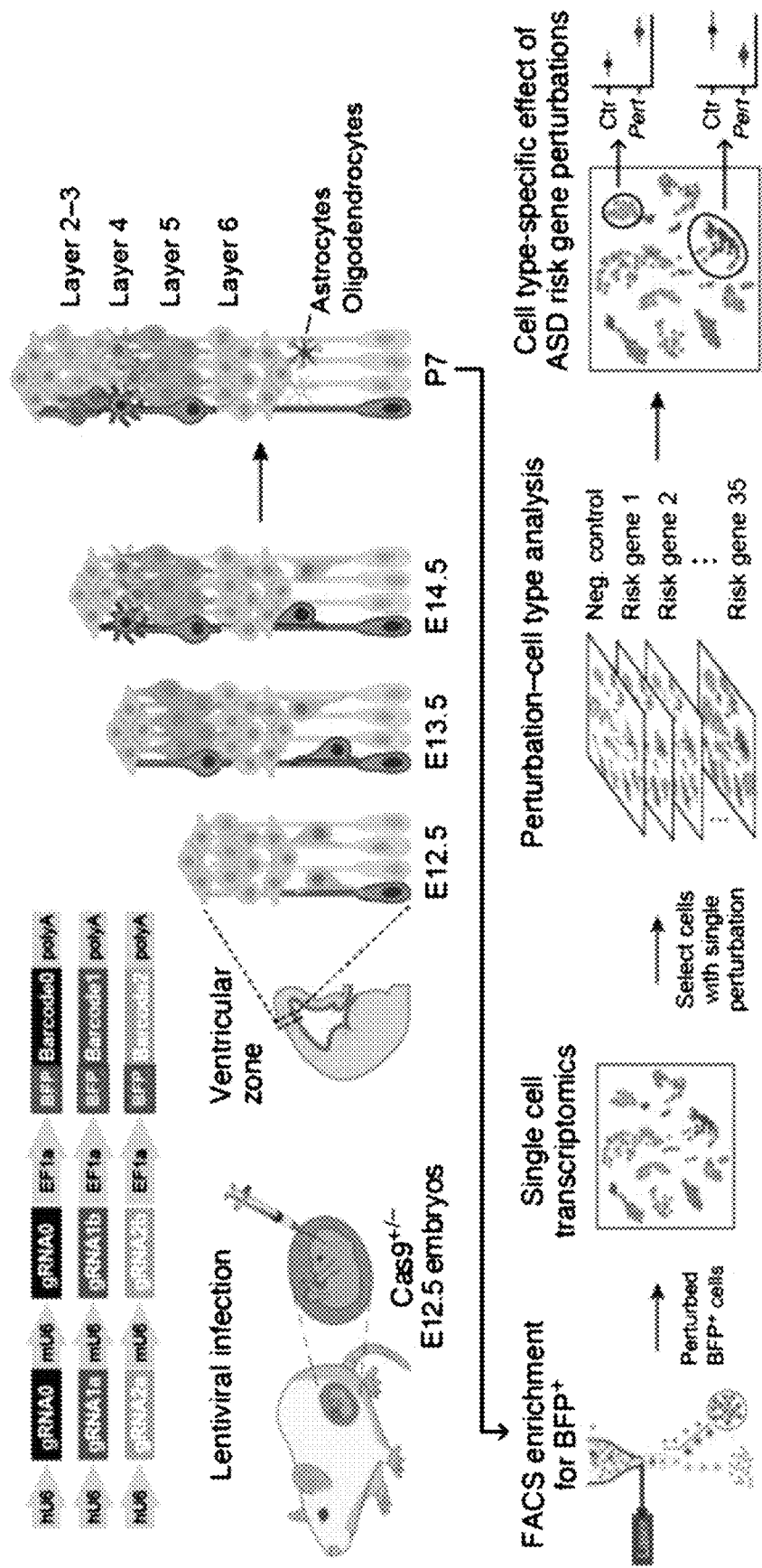
FIGS. 1A-1E—In vivo Perturb-Seq to investigate functions of a panel of ASD/ND risk genes harboring de novo variants.
Figure 1B:
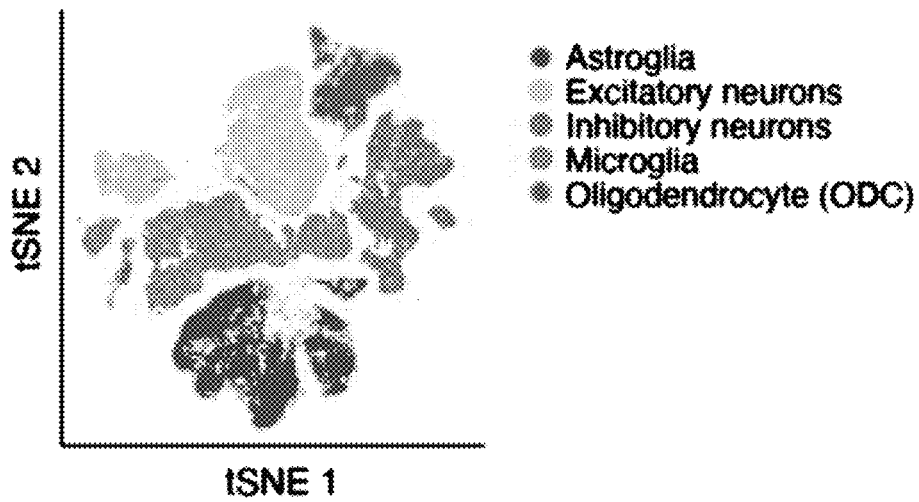
Figure 1C:
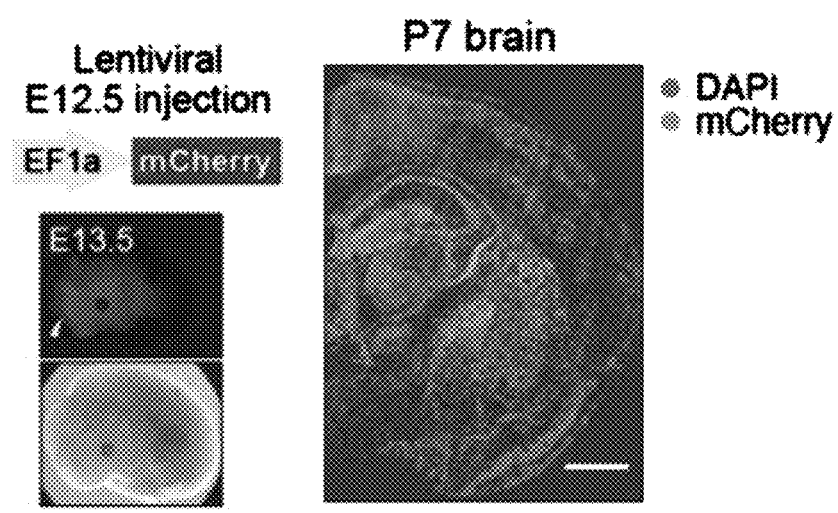

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/− 10% or less, +/− 5% or less, +/−1% or less, and +/− 0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and uses thereof for in vivo evaluation of functions for a plurality of genes in parallel in a cell type-specific manner. The invention used a combination of in vivo genetic perturbation of progenitor cells and single-cell transcriptomic profiling of distinct types of progeny cells to interrogate the functions of multiple genes simultaneously in an in vivo environment. One of the many advantages of the present invention is that multiple genes can be evaluated simultaneously for their functions. Another major advantage of the present invention is that the function of genes in different cell types can be analyzed and revealed. Using these methods, the inventors extracted cell type-specific gene signatures for autism spectrum disorders (ASD) risk-associated genes and surprisingly found that the developmental maturation of two broad glial classes, oligodendrocyte and astrocyte are affected by loss of function mutation of selected ASD risk-associated genes.

In some embodiments, methods for in vivo genetic perturbation in Cas animal model are disclosed. The in vivo genetic perturbation of multiple genes in parallel described herein provides an effective way for investigating the in vivo function of genes on a large scale with single-cell resolution. The methods disclosed herein include introduction and expression of two or more guide RNAs (gRNAs) for each target gene, where each gRNA is under the control of different promoters. In some embodiments, one gRNA is under the control of mouse pol III promoter (e.g., U6) and another is under the control of human pol III promoter (e.g., U6). Additionally, the perturbations introduced into each cell are linked to a constitutively expressed reporter gene and barcode via linking the two or more gRNAs used per target gene to the reporter gene and barcode. Generally, in some embodiments, after introducing perturbations into cells (e.g., progenitor cells), cells expressing the reporter gene (which is a proxy for the presence of the gRNAs and thus the corresponding perturbations) can be enriched using a suitable technique capable of detecting reporter gene expression and separating reporter gene expressing cells from non-expressing cells to obtain an enriched perturbed cell population. Suitable sequencing and/or other analytic techniques are used to identify cell types and gene modules in the perturbed cell population that covary within a cell type and are indicative of a disease or disease state.

In some embodiments, the method includes delivering a pool of engineered virus particles to cells of the Cas9 animal model. In some embodiments, delivery is in utero. The pool of virus particles contains equal representation of each gRNA combination used. In this way the pool of virus particles contains equal representation of each perturbation. In some embodiments, engineered virus particle pool is generated using a suitable viral vector system (e.g., lentiviral vector system) to generate engineered virus particles (e.g., lentiviral particles) containing packaged perturbation constructs for each set of gRNAs. After packaging and generating virus particles for each set of gRNAs (and thus each perturbation construct), equal amounts or titers of each different engineered virus are combined to for the pool of engineered virus particles to be delivered. The specific perturbation construct packaged in any specific virus particle or contained in any viral vector is, in some embodiments, verified using a suitable sequencing technique prior to pooling. In some embodiments, each target gene has equal representation in the virus particle pool. In some embodiments, the suitable viral vector system includes a vector containing a two or more gRNAs, each operatively coupled to a different pol III promoter; a reporter gene and a barcode, where the reporter gene, the barcode, or both are operatively coupled to the two or more gRNAs and a constitutive pol III promoter.

The design, preparation, and/or utilization of the perturbation constructs herein surprisingly provides substantial superiority over the conventional methods that use single gRNA for each target gene and/or generate viral delivery particles for delivering perturbation constructs by pooling the perturbation constructs prior to viral packaging and particle generation or using an array technique.

In some embodiments, methods for in vivo delivering genetic perturbation are disclosed. One of the main advantages of these methods is that the genetic perturbations are delivered in parallel into progenitor cells in vivo in an animal. The progenitor cells can develop into a diversity of distinct type of progeny cells. Therefore, the present invention provides a surprising unique avenue for evaluating gene functions in each of the cell types so that the function of each gene in a plurality of genes can be interrogated in multiple cell types in parallel.

In some embodiments, methods for evaluating disease risk-associated genes in vivo are disclosed. One of the main advantages of the present invention is that it provides methods that the point-of-action of a plurality of risk-associated genes for a disease can be interrogated in parallel and in a cell type-specific manner. A disease commonly involves malfunction of many distinct types of cells. Therefore, the capability of the methods disclosed herein in deciphering multiple risk-associated genes of a disease in parallel in different cell types provide an innovative and effective way for functional analysis of the point-of-action of multiple risk-associated genes in vivo.

In some embodiments, methods for identifying therapeutic targets for a disease are disclosed. The therapeutic targets identified using the methods provided herein can more reliably represent authentic changes in molecular machinery and the cell state, thus providing attractive modality for being used for screening and evaluating drugs that are capable of treating the disease through acting on the targets.

Methods and Uses for In Vivo Evaluation of Gene Function and Uses Thereof

In some embodiments, provided are methods and uses of evaluating the functions of a plurality of genes in vivo in parallel in an animal, in which the function for each gene of interest is analyzed in multiple distinct types of cells.

In some embodiments, the number of plurality of genes to be evaluated in the methods disclosed herein can be 1, 2, 3, 4, 5, 6, 7, 8, 9, 10, more than 10, more than 20, more than 30, more than 40, more than 50, or more than 100, more than 200, or more than 500.

In some embodiments, the progenitor cells that receive genetic perturbation can be 1, 2, 3, more than 3, more than 10, more than 100, more than 1000, more than 10,000, more than 100,000, more than 1 million, more than 10 million, more than 100 million, or more than 1 billion.

As used herein, a genetic perturbation is defined as an alteration of the structure and/or functions of a gene or gene expression products in a biological system including, but not limited to, a cell, a cell-free system, an organism, a plant, an animal, or a human.

Described in certain example embodiments herein are methods of identifying functions of a plurality of genes in parallel in vivo, comprising:
  a. introducing, in vivo, a plurality of genetic perturbations in each of a plurality of progenitor cells in a Cas animal model, wherein each genetic perturbation is operatively coupled to a reporter gene and a barcode;
  b. generating an enriched perturbed cell population by enriching for cells expressing the reporter;
  c. identifying cell types and corresponding perturbations via scRNA-seq in the enriched perturbed cell population; and
  d. detecting one or more gene modules that co-vary within a cell type in the enriched perturbed cell population.

In certain example embodiments, identifying further comprises a genomic analysis, an epigenomic analysis, a transcriptomic analysis, a proteomic analysis, or a combination thereof.

In certain example embodiments, the method further comprises a genomic analysis, an epigenomic analysis, a transcriptomic analysis, a proteomic analysis, or a combination thereof.

In certain example embodiments, the plurality of genes are autism spectrum disorder associated genes.

In some embodiments, the genetic perturbation can be achieved by RNA interference, by a CRISPR-Cas system, by zinc finger nucleases (ZFN) system, by transcription-activator-like effector nucleases (TALENs) system, by short-hairpin RNA method, by gene knock-out, or by any other technologies that can introduce insertion/deletion frameshift mutations into a gene. In some embodiments, the genetic perturbation disclosed herein employs a CRISPR-Cas system.

Cas Animal Models

In some embodiments, the animal model is a Cas animal model. As used herein, the term "Cas animal model" refers to transgenic animal models that are engineered to express, either constitutively or inducibly, in one or more of their cells. This term includes progeny (including embryos) of a Cas animal model and cells thereof. In some embodiments, all of the cells of a Cas animal model contain a Cas protein gene. In some embodiments, some of the cells of a Cas animal model contain a Cas protein gene. In some embodiments, all of the cells of a Cas animal model express a Cas protein. In some embodiments, some of the cells of a Cas animal model express a Cas protein. In certain example embodiments, the Cas animal model constitutively or inducibly expresses a Cas protein in one of, a plurality of, or all of its cells. In certain example embodiments, the Cas protein is a Cas Type I, II, III, IV, or V protein. The Cas protein can be functional within a CRISPR-Cas system, of which components thereof can be provided separate from the Cas protein expressing cell, such as by viral or other delivery. In some embodiments, gRNAs are provided to the Cas animal model so as to form a complete CRISPR-Cas system.

CRISPR-Cas Systems and Components Thereof

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

In some embodiments, the CRISPR-Cas system that can be used to modify a polynucleotide of the present invention described herein can be a Class 1 CRISPR-Cas system. Class 1 CRISPR-Cas systems are divided into types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin EV, Makarova KS. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasY(Cas12d), CasX (Cas12e), Cas14, and/or Cas (D.

Guide RNAs (gRNAs)

As previously described, when a CRISPR-Cas system is used to generate genetic perturbations, such as in the context of a Cas animal model, the gRNAs for the desired perturbations are subsequently delivered to cells containing a Cas protein or capable of expressing a Cas protein in the animal model. In some embodiments, a plurality of guide RNAs (gRNAs) are used for targeting a gene of interest. In certain example embodiments, the plurality of genetic perturbations are introduced using two or more guide RNAs (gRNAs) for each target gene. In some embodiments, the two or more gRNAs each bind to sequence of an exon, an intron, or both at the 5' end of a target gene. In some embodiments, the two or more gRNAs each bind to sequences of one or more coding exons at the 5' end of a target gene.

The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

A guide sequence, and hence a nucleic acid-targeting guide may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm, and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333]. which is incorporated herein by reference.

In some embodiments, the gRNAs are designed based on www.benchling.com. The gRNAs can also be designed using other technologies and strategies. In some embodiments, two gRNAs are used for targeting a gene of interest. In some embodiments, the two gRNAs have the same sequences. In some embodiments, the two gRNAs have different sequences. In some embodiments, the number of gRNAs for targeting a gene of interest can be 2, 3, more than 3, more than 5, or more than 10. In some embodiments, the sequences of gRNAs are the same. In some embodiments, the sequences of gRNAs are different from each other.

In certain example embodiments, each of the two or more gRNAs are controlled by a different pol III promoter. In some embodiments, the pol III promoters differ by organism optimization (e.g., human, mouse, chicken, dog, pig, fish, non-human primate, etc.). In some embodiments, the pol III promoters differ by type (e.g., H1, U6, 7SK, etc.). In some embodiments, the pol III promoters differ by organism optimization and type.

In certain example embodiments, a first gRNA of the two or more gRNAs is controlled by a human pol III promoter and a second gRNA of the two or more gRNAs is controlled by a non-human pol III promoter. In certain example embodiments, the human pol III promoter and the non-human pol III promoters are each independently selected from a U6, a 7SK, or an H1 promoter.

In some embodiments, the same promoter is used to control the expression of the gRNAs. In some embodiments, different promoter is used for controlling different gRNAs. In some embodiments, a mouse U6 promoter is used for controlling one gRNA expression, and a human U6 promoter is used for controlling another gRNA expression. In some embodiments, all of the gRNAs' expressions are controlled by either a mouse U6 promoter or a human U6 promoter.

In certain example embodiments, one or more of the poll II promoters are constitutive. Thus, in any cell where the gRNAs are present, they will be expressed irrespective of temporal, spatial, and/or environmental control. When combined in a cell expressing a Cas protein, the gRNAs present can generate the genomic perturbations. It will be appreciated that when present in a cell that contains a Cas encoding sequence under control of an inducible promoter, perturbation can be controlled via control of the expression of the Cas protein in an inducible manner. Thus, in some of these embodiments, perturbation temporal and/or spatial incorporation can be controlled in vivo by controlling the on/off status of the Cas protein. This can be achieved a variety of ways and is dependent on the specific design of the inducible promoter and system. Inducible promoters are described in greater detail elsewhere herein.

In certain example embodiments, one or more of the pol III promoters are inducible. In some embodiments, two gRNAs are present and both are under control of inducible promoters. By inducible controlling expression of the two gRNAs present, even in cells where there is a Cas protein is present, perturbation can still be controlled such as temporally and spatially.

In some embodiments, the cells of the Cas animal model contains a constitutively expressed Cas protein and the gRNAs are both under the control of constitutive pol III promoters. In some embodiments, the cells of the Cas animal model contains a constitutively expressed Cas protein and the gRNAs are both under the control of inducible pol III promoters. In some embodiments, the cells of the Cas animal model contains a constitutively expressed Cas protein and one gRNAs is under the control of a constitutive pol III promoter and one or more gRNAs are under the control of an inducible promoter.

In some embodiments, the cells of the Cas animal model contains an inducibly expressed Cas protein and the gRNAs are both under the control of constitutive pol III promoters. In some embodiments, the cells of the Cas animal model contains an inducibly expressed Cas protein and the gRNAs are both under the control of inducible pol III promoters. In some embodiments, the cells of the Cas animal model contains an inducibly expressed Cas protein and one gRNAs is under the control of a constitutive pol III promoter and one or more gRNAs are under the control of an inducible promoter.

In some embodiments, the animal model (e.g., a Cas animal model) is a mouse, a rat, or a rabbit, a non-human primate, a pig, another mammal, or avian. In some embodiments, a mouse is used. In some embodiments the animal model (e.g., a Cas animal model) is a pregnant animal model.

The Cas animal model may comprise a cell in a model non-human organism, a model non-human mammal that expresses a Cas protein, a mouse that expresses a Cas protein, a mouse that expresses Cpf1, a cell in vivo or a cell ex vivo or a cell in vitro (see e.g., WO 2014/093622 (PCT/US13/074667); US Patent Publication Nos. 20120017290 and 20110265198 assigned to Sangamo BioSciences, Inc.; US Patent Publication No. 20130236946 assigned to Cellectis; Platt et al., "CRISPR-Cas9 Knockin Mice for Genome Editing and Cancer Modeling" Cell (2014), 159(2): 440-455; "Oncogenic models based on delivery and use of the crispr-cas systems, vectors and compositions" WO2014204723A1 "Delivery and use of the crispr-cas systems, vectors and compositions for hepatic targeting and therapy" WO2014204726A1; "Delivery, use and therapeutic applications of the crispr-cas systems and compositions for modeling mutations in leukocytes" WO2016049251; and Chen et al., "Genome-wide CRISPR Screen in a Mouse Model of Tumor Growth and Metastasis" 2015, Cell 160, 1246-1260).

Target Sequences, PAMs, and PFSs

In some embodiments, the two or more gRNAs each bind to sequence (e.g., a target sequence) in an exon, an intron, or both at the 5' end of a target gene. In some embodiments, the two or more gRNAs each bind to sequences of one or more coding exons at the 5' end of a target gene.

As used herein, "target gene" refers to a pre-selected and non-random gene or gene product whose sequence, function, expression, activity and the like are to be modified or modulated. Target genes can be objectively chosen amongst any known genes by a set of criteria. It will be appreciated that the set of criteria will be appreciated by those of ordinary skill in the art based on many factors including, but not limited to, a disease or condition being studied, a biological pathway being studied, the age of an organism being studied, the cell type, cell state, and/or tissue being studied. Target genes can be selected from personal knowledge of a person performing a method described herein, the literature, publicly accessible databases, which can be generic (e.g., NCBI's GenBank) or be focused (such as on a specific cell type, pathway, disease, and the like) (e.g., FaCD Online, DriverDBv3, BRCA Public Database, DisGeNET, MalaCards, Gene Disease Database, eDGAR, mitoMAP, Human Variome Project, Human Gene Mutation Database, and the like), and combinations thereof. Other considerations for choosing target genes for a desired disease, condition, or state, will be appreciated by those of ordinary skill in the art. Thus, in view of the description herein it is possible for one of ordinary skill in the art to choose a target gene based on their specific interests and then implement the perturbation methods described herein by objectively determining which target genes are. Thus, it will be appreciated that the methods described herein can be applied to any target gene, whether a gene has been given such a designation as of the filing date and/or priority date of this application or not. In short, a target gene can be objectively identified by one of ordinary skill in the art at a future date and perturbed using the methods described herein. The fact that a target gene is designated as such in the future does not impede the method from being operational, enabled, or fully described as to those yet-to-be designated target genes.

In some embodiments, target genes are defined by a gene signature or module and can be used to generate a focused gRNA library that can be used to introduce the perturbations as described elsewhere herein. In some embodiments, systematic perturbation of target genes can be performed, such as those relevant to a particular disease, cell state, or condition. Gene expression profiling can be used to define the target genes of interest as well as perform follow-up single cell and population RNA-seq analysis.

In some embodiments, the target genes are autism spectrum disease associated genes. In some embodiments, the target genes are autism spectrum disease risk-associated genes.

Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table 1 below shows several Cas polypeptides and the PAM sequence they recognize.

TABLE 1

Example PAM Sequences

| Cas Protein | PAM Sequence |
|---|---|
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cas12a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein HisA, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature14592. As further detailed herein, the skilled person will understand that Cas13 proteins may be modified analogously. Gao et al, "Engineered Cpf1 Enzymes with Altered PAM Specificities," bioRxiv 091611; doi: http://dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155(Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016.Mol. Cell. 16:253), and negative screening (Zetsche et al. 2015. Cell. 163:759-771).

As previously mentioned, CRISPR-Cas systems that target RNA do not typically rely on PAM sequences. Instead, such systems typically recognize protospacer flanking sites (PFSs) instead of PAMs. Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3' end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Delivery

The present disclosure also provides delivery systems for introducing exogenous perturbation construction herein to cells in the animal model, such as Cas animal model. A delivery system may comprise one or more delivery vehicles and/or cargos. Exemplary delivery systems and methods include those described in paragraphs [00117] to [00278] of Feng Zhang et al., (WO2016106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties. In some embodiments the cargos are one or more components of the perturbation constructs described herein such as the two or more gRNAs, reporter gene, and barcode.

Transduction

The cargos, e.g., nucleic acids and/or polypeptides, can be introduced to cells by transduction by a viral or pseudoviral particle. Methods of packaging the cargos in viral particles can be accomplished using any suitable viral vector or vector systems. Such viral vector and vector systems are described in greater detail elsewhere herein. As used in this context herein "transduction" refers to the process by which foreign nucleic acids and/or proteins are introduced to a cell (prokaryote or eukaryote) by a viral or pseudo viral particle. After packaging in a viral particle or pseudo viral particle, the viral particles can be exposed to cells (e.g., in vitro, ex vivo, or in vivo) where the viral or pseudoviral particle infects the cell and delivers the cargo to the cell via transduction. Viral and pseudoviral particles can be optionally concentrated prior to exposure to target cells. In some embodiments, the virus titer of a composition containing viral and/or pseudoviral particles can be obtained and a specific titer be used to transduce cells.

Vectors and Vector Systems

Also provided herein are vectors that can contain one or more of the perturbation constructs or components thereof described herein, such as the two or more gRNAs, reporter gene and barcode. In certain embodiments, the vector can contain one or more polynucleotides encoding one or more elements of a perturbation construct described herein. The vectors can be useful in producing bacterial, fungal, yeast, plant cells, animal cells, and transgenic animals that can express one or more components of the perturbation construct described herein. Within the scope of this disclosure are vectors containing one or more of the polynucleotide sequences described herein. One or more of the polynucleotides that are part of the perturbation construct described herein can be included in a vector or vector system. The vectors and/or vector systems can be used, for example, to express one or more of the polynucleotides in a cell, such as a producer cell, to produce perturbation construct system containing virus particles described elsewhere herein. Other uses for the vectors and vector systems described herein are also within the scope of this disclosure. In general, and throughout this specification, the term "vector" refers to a tool that allows or facilitates the transfer of an entity from one environment to another. In some contexts which will be appreciated by those of ordinary skill in the art, "vector" can be a term of art to refer to a nucleic acid molecule capable of transporting another nucleic acid to which it has been linked. A vector can be a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can be composed of a nucleic acid (e.g., a polynucleotide) of the invention in a form suitable for expression of the nucleic acid in a host cell, which means that the recombinant expression vectors include one or more regulatory elements, which can be selected on the basis of the host cells to be used for expression, that is operatively-linked to the nucleic acid sequence to be expressed. Within a recombinant expression vector, "operably linked" and "operatively-linked" are used interchangeably herein and further defined elsewhere herein. In the context of a vector, the term "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells. These and other embodiments of the vectors and vector systems are described elsewhere herein.

In some embodiments, the vector can be a bicistronic vector. In some embodiments, a bicistronic vector can be used for one or more elements of the perturbation construct described herein. In some embodiments, expression of elements of the perturbation construct described herein can be driven by a ubiquitous promoter, constitutive, cell-specific promoter, inducible promoter or any permissible combination thereof. In some embodiments, expression of elements of the perturbation construct described herein can be driven by a cell-specific and/or inducible promoter. Where the element of the perturbation construct system is an RNA, its expression can be driven by a Pol III promoter, such as a U6 promoter. In some embodiments, the reporter gene expression is driven by a pol II promoter, such as EF1a, beta actin, CAG, and the like.

In some embodiments, a vector capable of delivering a perturbation construct or component thereof to a cell can be composed of or contain a minimal promoter operably linked to a first gRNA, and/or a second gRNA, and a second minimal promoter operably linked to a first gRNA and/or a second gRNA, and a third minimal promoter operably linked to a reporter gene and, optionally, a barcode, wherein the length of the vector sequence comprising the minimal promoters and polynucleotide sequences is less than 4.4Kb. In an embodiment, the vector can be a viral vector. In certain embodiments, the viral vector is an is an adeno-associated virus (AAV) or an adenovirus vector.

In one embodiment, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas enzyme complexed with the one or more guide sequence(s) that is hybridized to the one or more target sequence(s); and (b) a second regulatory element operably linked to an enzyme-coding sequence encoding said Cas enzyme, preferably comprising at least one nuclear localization sequence and/or at least one NES; wherein components (a) and (b) are located on the same or different vectors of the system. Where applicable, a tracr sequence may also be provided. In some embodiments, component (a) further comprises two or more guide sequences operably linked to the first regulatory element, wherein when expressed, each of the two or more guide sequences direct sequence specific binding of a Cas CRISPR complex to a different target sequence in a eukaryotic cell. In some embodiments, the CRISPR complex comprises one or more nuclear localization sequences and/or one or more NES of sufficient strength to drive accumulation of said Cas CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Cell-Based Vector Amplification and Expression

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g., amplifying a plasmid as part of a viral vector packaging system). The vectors can be viral-based or non-viral based. In some embodiments, a prokaryote is used to amplify copies of a vector and express one or more nucleic acids, such as to provide a source of one or more proteins for delivery to a host cell or host organism.

Vectors can be designed for expression of one or more elements of the perturbation construct described herein (e.g., nucleic acids, transcripts, proteins, enzymes, and combinations thereof) in a suitable host cell. In some embodiments, the suitable host cell is a prokaryotic cell. Suitable host cells include, but are not limited to, bacterial cells, yeast cells, insect cells, and mammalian cells. In some embodiments, the suitable host cell is a eukaryotic cell.

In some embodiments, the suitable host cell is a suitable bacterial cell. Suitable bacterial cells include, but are not limited to, bacterial cells from the bacteria of the species *Escherichia coli*. Many suitable strains of *E. coli* are known in the art for expression of vectors. These include, but are not limited to Pir1, Stbl2, Stbl3, Stbl4, TOP10, XL1 Blue, and XL10 Gold. In some embodiments, the host cell is a suitable insect cell. Suitable insect cells include those from *Spodoptera frugiperda*. Suitable strains of *S. frugiperda* cells include, but are not limited to, Sf9 and Sf21. In some embodiments, the host cell is a suitable yeast cell. In some embodiments, the yeast cell can be from *Saccharomyces cerevisiae*. In some embodiments, the host cell is a suitable mammalian cell. Many types of mammalian cells have been developed to express vectors. Suitable mammalian cells include, but are not limited to, HEK293, Chinese Hamster Ovary Cells (CHOs), mouse myeloma cells, HeLa, U20S, A549, HT1080, CAD, P19, NIH 3T3, L929, N2a, MCF-7, Y79, SO-Rb50, HepG G2, DIKX-X11, J558L, Baby hamster kidney cells (BHK), and chicken embryo fibroblasts (CEFs). Suitable host cells are discussed further in Goeddel, GENE EXPRESSION TECHNOLOGY: METHODS IN ENZYMOLOGY 185, Academic Press, San Diego, Calif. (1990).

In some embodiments, the vector can be a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (Invitrogen Corp, San Diego, Calif.). As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors can contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

In some embodiments, the vector is a baculovirus vector or expression vector and can be suitable for expression of polynucleotides and/or proteins in insect cells. In some embodiments, the suitable host cell is an insect cell. Baculovirus vectors available for expression of proteins in cultured insect cells (e.g., SF9 cells) include the pAc series (Smith, et al., 1983. Mol. Cell. Biol. 3: 2156-2165) and the pVL series (Lucknow and Summers, 1989. Virology 170: 31-39). rAAV (recombinant Adeno-associated viral) vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, the vector is a mammalian expression vector. In some embodiments, the mammalian expression vector is capable of expressing one or more polynucleotides and/or polypeptides in a mammalian cell. Examples of mammalian expression vectors include, but are not limited to, pCDM8 (Seed, 1987. Nature 329: 840) and pMT2PC (Kaufman, et al., 1987. EMBO J. 6: 187-195). The mammalian expression vector can include one or more suitable regulatory elements capable of controlling expression of the one or more polynucleotides and/or proteins in the mammalian cell. For example, commonly used promoters are derived from polyoma, adenovirus 2, cytomegalovirus, simian virus 40, and others disclosed herein and known in the art. More detail on suitable regulatory elements are described elsewhere herein.

For other suitable expression vectors and vector systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campus and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments can utilize viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element can be operably linked to one or more elements of a perturbation construct described herein so as to drive expression of the one or more elements of the perturbation construct described herein.

In some embodiments, the vector can be a fusion vector or fusion expression vector. In some embodiments, fusion vectors add a number of amino acids to a protein encoded therein, such as to the amino terminus, carboxy terminus, or both of a recombinant protein. Such fusion vectors can serve one or more purposes, such as: (i) to increase expression of recombinant protein; (ii) to increase the solubility of the recombinant protein; and (iii) to aid in the purification of the recombinant protein by acting as a ligand in affinity purification. In some embodiments, expression of polynucleotides (such as non-coding polynucleotides) and proteins in prokaryotes can be carried out in *Escherichia coli* with vectors containing constitutive or inducible promoters directing the expression of either fusion or non-fusion polynucleotides and/or proteins. In some embodiments, the fusion expression vector can include a proteolytic cleavage site, which can be introduced at the junction of the fusion vector backbone or other fusion moiety and the recombinant polynucleotide or protein to enable separation of the recombinant polynucleotide or protein from the fusion vector backbone or other fusion moiety subsequent to purification of the fusion polynucleotide or protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89).

In some embodiments, one or more vectors driving expression of one or more elements of a perturbation construct described herein are introduced into a host cell, such as in an animal model (e.g., a Cas animal model) such that expression of the elements of the engineered delivery system described herein direct formation a CRISPR-Cas complex at one or more target sites. For example, a CRISPR-Cas effector protein described herein can be provided in the host cell and a nucleic acid component (e.g., a guide polynucleotide) can be operably linked to a regulatory elements on separate vectors. Different or all elements of perturbation construct described herein can be delivered to an animal, plant, microorganism or cell thereof to produce an animal (e.g., a mammal, reptile, avian, etc.), plant, microorganism or cell thereof that constitutively, inducibly, or conditionally expresses all or different elements of the perturbation construct described herein. As previously described the host cell can express or be capable of expressing a Cas protein, such that when gRNAs present in the perturbation construct are expressed in the same host cell, a CRISPR-Cas system is generated, and genetic perturbations can be introduced in that cell.

In some embodiments, two or more of the elements expressed from the same or different regulatory element(s), can be combined in a single vector, with one or more additional vectors providing any components of the system not included in the first vector perturbation construct polynucleotides that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element and oriented in the same or opposite direction.

Vector Features

The vectors can include additional features that can confer one or more functionalities to the vector, the polynucleotide to be delivered, a virus particle produced there from, or polypeptide expressed thereof. Such features include, but are not limited to, regulatory elements, selectable markers, molecular identifiers (e.g., molecular barcodes), stabilizing elements, and the like. It will be appreciated by those skilled in the art that the design of the expression vector and additional features included can depend on such factors as the choice of the host cell to be transformed, the level of expression desired, etc.

Regulatory Elements

In certain embodiments, the polynucleotides and/or vectors thereof described herein (such as the perturbation construct of the present invention) can include one or more regulatory elements that can be operatively linked to the polynucleotide. The term "regulatory element" is intended to include promoters, enhancers, internal ribosomal entry sites (IRES), other expression control elements (e.g., transcription termination signals, such as polyadenylation signals and poly-U sequences) and cellular localization signals (e.g., nuclear localization signals). Such regulatory elements are described, for example, in Goeddel, GENE EXPRESSION TECHNOLOGY: METHODS IN ENZYMOLOGY 185, Academic Press, San Diego, Calif (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter can direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6, 7SK, and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). Specific configurations of the gRNAs, reporter gene and pol II and pol III promoters in the context of the present invention are described in greater detail elsewhere herein.

In some embodiments, the regulatory sequence can be a regulatory sequence described in U.S. Pat. No. 7,776,321, U.S. Pat. Pub. No. 2011/0027239, and International Patent Publication No. WO 2011/028929, the contents of which are incorporated by reference herein in their entirety. In some embodiments, the vector can contain a minimal promoter. In some embodiments, the minimal promoter is the Mecp2 promoter, tRNA promoter, or U6. In a further embodiment, the minimal promoter is tissue specific. In some embodiments, the length of the vector polynucleotide the minimal promoters and polynucleotide sequences is less than 4.4Kb.

To express a polynucleotide, the vector can include one or more transcriptional and/or translational initiation regulatory sequences, e.g., promoters, that direct the transcription of the gene and/or translation of the encoded protein in a cell. In some embodiments a constitutive promoter may be employed. Suitable constitutive promoters for mammalian cells are generally known in the art and include, but are not limited to SV40, CAG, CMV, EF-1α, β-actin, RSV, and PGK. Suitable constitutive promoters for bacterial cells, yeast cells, and fungal cells are generally known in the art, such as a T-7 promoter for bacterial expression and an alcohol dehydrogenase promoter for expression in yeast.

In some embodiments, the regulatory element can be a regulated promoter. "Regulated promoter" refers to promoters that direct gene expression not constitutively, but in a temporally- and/or spatially-regulated manner, and includes tissue-specific, tissue-preferred and inducible promoters. Regulated promoters include conditional promoters and inducible promoters. In some embodiments, conditional promoters can be employed to direct expression of a polynucleotide in a specific cell type, under certain environmental conditions, and/or during a specific state of development. Suitable tissue specific promoters can include, but are not limited to, liver specific promoters (e.g. APOA2, SERPIN A1 (hAAT), CYP3A4, and MIR122), pancreatic cell promoters (e.g. INS, IRS2, Pdx1, Alx3, Ppy), cardiac specific promoters (e.g. Myh6 (alpha MHC), MYL2 (MLC-2v), TNI3 (cTnI), NPPA (ANF), Slc8al (Ncx1)), central nervous system cell promoters (SYN1, GFAP, INA, NES, MOBP, MBP, TH, FOXA2 (HNF3 beta)), skin cell specific promoters (e.g. FLG, K14, TGM3), immune cell specific promoters, (e.g. ITGAM, CD43 promoter, CD14 promoter, CD45 promoter, CD68 promoter), urogenital cell specific promoters (e.g. Pbsn, Upk2, Sbp, Ferl14), endothelial cell specific promoters (e.g. ENG), pluripotent and embryonic germ layer cell specific promoters (e.g. Oct4, NANOG, Synthetic Oct4, T brachyury, NES, SOX17, FOXA2, MIR122), and muscle cell specific promoter (e.g. Desmin). Other tissue and/or cell specific promoters are generally known in the art and are within the scope of this disclosure.

Inducible/conditional promoters can be positively inducible/conditional promoters (e.g. a promoter that activates transcription of the polynucleotide upon appropriate interaction with an activated activator, or an inducer (compound, environmental condition, or other stimulus) or a negative/conditional inducible promoter (e.g. a promoter that is repressed (e.g. bound by a repressor) until the repressor condition of the promotor is removed (e.g. inducer binds a repressor bound to the promoter stimulating release of the promoter by the repressor or removal of a chemical repressor from the promoter environment). The inducer can be a compound, environmental condition, or other stimulus. Thus, inducible/conditional promoters can be responsive to any suitable stimuli such as chemical, biological, or other molecular agents, temperature, light, and/or pH. Suitable inducible/conditional promoters include, but are not limited to, Tet-On, Tet-Off, Lac promoter, pBad, AlcA, LexA, Hsp70 promoter, Hsp90 promoter, pDawn, XVE/OlexA, GVG, and pOp/LhGR.

Examples of promoters that are inducible and that can allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome)., such as a Light Inducible Transcriptional Effector (LITE) that direct changes in transcriptional activity in a sequence-specific manner. The components of a light inducible system may include one or more elements of the CRISPR-Cas system described herein, a light-responsive cytochrome heterodimer (e.g., from *Arabidopsis thaliana*), and a transcriptional activation/repression domain. In some embodiments, the vector can include one or more of the inducible DNA binding proteins provided in International Patent Publication No. WO 2014/018423 and US Patent Publication Nos., 2015/0291966, 2017/0166903, 2019/0203212, which describe e.g., embodiments of inducible DNA binding proteins and methods of use and can be adapted for use with the present invention.

In some embodiments, transient or inducible expression can be achieved by including, for example, chemical-regulated promoters, i.e., whereby the application of an exogenous chemical induces gene expression. Modulation of gene expression can also be obtained by including a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some embodiments, the polynucleotide, vector or system thereof can include one or more elements capable of translocating and/or expressing a one or more elements of a perturbation construct described herein to/in a specific cell component or organelle. Such organelles can include, but are not limited to, nucleus, ribosome, endoplasmic reticulum, Golgi apparatus, chloroplast, mitochondria, vacuole, lysosome, cytoskeleton, plasma membrane, cell wall, peroxisome, centrioles, etc. Such regulatory elements can include, but are not limited to, nuclear localization signals (examples of which are described in greater detail elsewhere herein), any such as those that are annotated in the LocSigDB database (see e.g., http://genome.unmc.edu/LocSigDB/ and Negi et al., 2015. Database. 2015: bav003; doi: 10.1093/database/bav003), nuclear export signals, endoplasmic reticulum localization/retention signals (see e.g., Liu et al. 2007 Mol. Biol. Cell. 18(3):1073-1082 and Gorleku et al., 2011. J. Biol. Chem. 286:39573-39584), mitochondria (see e.g., Cell Reports. 22:2818-2826, particularly at FIG. 2; Doyle et al. 2013. PLoS ONE 8, e67938; Funes et al. 2002. J. Biol. Chem. 277:6051-6058; Matouschek et al. 1997. PNAS USA 85:2091-2095; Oca-Cossio et al., 2003. 165: 707-720; Waltner et al., 1996. J. Biol. Chem. 271:21226-21230; Wilcox et al., 2005. PNAS USA 102:15435-15440; Galanis et al., 1991. FEBS Lett 282:425-430, peroxisome (e.g. (S/A/C)-(K/R/H)-(L/A), SLK, (R/K)-(L/V/I)-XXXXX-(H/Q)-(L/A/F). Suitable protein targeting motifs can also be designed or identified using any suitable database or prediction tool, including but not limited to Minimotif Miner (http:minimotifminer.org, http://mitominer.mrc-mbu.cam.ac.uk/release-4.0/embodiment.do?name=Protein %20MTS), LocDB (see above), PTSs predictor ( ), TargetP-2.0 (http://www.cbs.dtu.dk/services/TargetP/), ChloroP (http://www.cbs.dtu.dk/services/ChloroP/); NetNES (http://www.cbs.dtu.dk/services/NetNES/), Predotar (https://urgi.versailles.inra.fr/predotar/), and SignalP (http://www.cbs.dtu.dk/services/SignalP/).

Reporter Genes, Selectable Markers, and Tags

In some embodiments, one or more of the gRNAs and/or barcodes of the perturbation construct described herein is operably linked, fused to, or otherwise modified to include a polynucleotide that encodes or is a selectable marker or tag, which can be a polynucleotide or polypeptide. Such configurations are described in greater detail elsewhere herein.

It will be appreciated that the polynucleotide encoding such selectable markers or tags can be incorporated into a polynucleotide encoding one or more components of the CRISPR-Cas system described herein in an appropriate manner to allow expression of the selectable marker or tag. Such techniques and methods are described elsewhere herein and will be instantly appreciated by one of ordinary skill in the art in view of this disclosure. Many such selectable markers and tags are generally known in the art and are intended to be within the scope of this disclosure.

Reporter genes/proteins, selectable markers and tags include, but are not limited to, affinity tags, such as chitin binding protein (CBP), maltose binding protein (MBP), glutathione-S-transferase (GST), poly(His) tag; solubilization tags such as thioredoxin (TRX) and poly(NANP), MBP, and GST; chromatography tags such as those consisting of polyanionic amino acids, such as FLAG-tag; epitope tags such as V5-tag, Myc-tag, HA-tag and NE-tag; protein tags that can allow specific enzymatic modification (such as biotinylation by biotin ligase) or chemical modification (such as reaction with FlAsH-EDT2 for fluorescence imaging), DNA and/or RNA segments that contain restriction enzyme or other enzyme cleavage sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as P-galactosidase, GUS; optically active proteins (e.g. fluorescent proteins such as a green fluorescent protein (GFP), cyan (CFP), yellow (YFP), red (RFP), blue (BFP) luciferase, and cell surface proteins); polynucleotides that can generate one or more new primer sites for PCR (e.g., the juxtaposition of two DNA sequences not previously juxtaposed), DNA sequences not acted upon or acted upon by a restriction endonuclease or other DNA modifying enzyme, chemical, etc.; epitope tags (e.g. GFP, FLAG- and His-tags), and, DNA sequences that make a molecular barcode or unique molecular identifier (UMI), DNA sequences required for a specific modification (e.g., methylation) that allows its identification. Other suitable markers will be appreciated by those of skill in the art.

In some embodiments, the reporter gene can be a gene coding for a cluster of differentiation (CD) molecule or CD molecules. The CD molecules that can be used as a reporter herein include, but are not limited to, CD3, CD4, CD8, CD19, CD20, CD22, CD27, CD29, CD30, CD33, CD34, CD44, CD45, CD47, CD48, CD58, CD66, CD70, CD79, CD80, CD82, CD86, CD101, and CD156. In some embodiments, the reporter gene can be a gene coding for a cell surface receptor that include, but are not limited to, EGFR, FGFR, HER2, and HER3. In certain example embodiments, the reporter gene encodes a cell surface molecules selected from the group of: CD3, CD4, CD19, CD20, CD22, CD34, CD45, CD80, a cell surface receptor, a cluster differentiation (CD) molecule, or any combination thereof.

Reporter genes, selectable markers, and tags can be operably linked to one or more components of the perturbation construct described herein via suitable linker, such as a glycine or glycine serine linkers, which are generally known in the art. Other suitable linkers are described elsewhere herein and generally known in the art.

The vector or vector system can include one or more polynucleotides encoding one or more targeting moieties. In some embodiments, the targeting moiety encoding polynucleotides can be included in the vector or vector system, such as a viral vector system, such that they are expressed within and/or on the virus particle(s) produced such that the virus particles can be targeted to specific cells, tissues, organs, etc. In some embodiments, the targeting moiety encoding polynucleotides can be included in the vector or vector system such that the perturbation construct described herein and/or products expressed therefrom include the targeting moiety and can be targeted to specific cells, tissues, organs, etc. In some embodiments, such as non-viral carriers, the targeting moiety can be attached to the carrier (e.g., polymer, lipid, inorganic molecule etc.) and can be capable of targeting the carrier and any attached or associated perturbation construct or component thereof described herein to specific cells, tissues, organs, etc.

Codon Optimization of Vector Polynucleotides

As described elsewhere herein, the polynucleotide encoding one or more embodiments of the perturbation construct described herein can be codon optimized. In some embodiments, one or more polynucleotides contained in a vector ("vector polynucleotides") described herein that are in addition to an optionally codon optimized polynucleotide encoding embodiments of the perturbation construct described herein can be codon optimized. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or *Codon selection in yeast*, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11.; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

The vector polynucleotide can be codon optimized for expression in a specific cell-type, tissue type, organ type, and/or subject type. In some embodiments, a codon optimized sequence is a sequence optimized for expression in a eukaryote, e.g., humans (i.e., being optimized for expression in a human or human cell), or for another eukaryote, such as another animal (e.g., a mammal or avian) as is described elsewhere herein. Such codon optimized sequences are within the ambit of the ordinary skilled artisan in view of the description herein. In some embodiments, the polynucleotide is codon optimized for a specific cell type. Such cell types can include, but are not limited to, epithelial cells (including skin cells, cells lining the gastrointestinal tract, cells lining other hollow organs), nerve cells (nerves, brain cells, spinal column cells, nerve support cells (e.g. astrocytes, glial cells, Schwann cells etc.), muscle cells (e.g. cardiac muscle, smooth muscle cells, and skeletal muscle cells), connective tissue cells (fat and other soft tissue padding cells, bone cells, tendon cells, cartilage cells), blood cells, stem cells and other progenitor cells, immune system cells, germ cells, and combinations thereof. Such codon optimized sequences are within the ambit of the ordinary skilled artisan in view of the description herein. In some embodiments, the polynucleotide is codon optimized for a specific tissue type. Such tissue types can include, but are not limited to, muscle tissue, connective tissue, connective tissue, nervous tissue, and epithelial tissue. Such codon optimized sequences are within the ambit of the ordinary skilled artisan in view of the description herein. In some embodiments, the polynucleotide is codon optimized for a specific organ. Such organs include, but are not limited to, muscles, skin, intestines, liver, spleen, brain, lungs, stomach, heart, kidneys, gallbladder, pancreas, bladder, thyroid, bone, blood vessels, blood, and combinations thereof. Such codon optimized sequences are within the ambit of the ordinary skilled artisan in view of the description herein.

In some embodiments, a vector polynucleotide is codon optimized for expression in particular cells, such as prokaryotic or eukaryotic cells. The eukaryotic cells may be those of or derived from a particular organism, such as a plant or a mammal, including but not limited to human, or non-human eukaryote or animal or mammal as discussed herein, e.g., mouse, rat, rabbit, dog, livestock, or non-human mammal or primate.

Vector Construction

The vectors described herein can be constructed using any suitable process or technique. In some embodiments, one or more suitable recombination and/or cloning methods or techniques can be used to the vector(s) described herein. Suitable recombination and/or cloning techniques and/or methods can include, but not limited to, those described in U.S. Patent Publication No. US 2004/0171156 A1. Other suitable methods and techniques are described elsewhere herein.

Construction of recombinant AAV vectors are described in a number of publications, including U.S. Pat. No. 5,173, 414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Any of the techniques and/or methods can be used and/or adapted for constructing an AAV or other vector described herein. nAAV vectors are discussed elsewhere herein.

In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. When multiple different guide polynucleotides are used, a single expression construct may be used to target nucleic acid-targeting activity to multiple different, corresponding target sequences within a cell. For example, a single vector may comprise about or more than about 1, 2, 3, 4, 5, 6, 7, 8, 9, 10, 15, 20, or more guide s polynucleotides. In some embodiments, about or more than about 1, 2, 3, 4, 5, 6, 7, 8, 9, 10, or more such guide-polynucleotide-containing vectors may be provided, and optionally delivered to a cell.

Delivery vehicles, vectors, particles, nanoparticles, formulations and components thereof for expression of one or more elements of a CRISPR-Cas system described herein are as used in the foregoing documents, such as International Patent Publication No. WO 2014/093622 (PCT/US2013/074667) and are discussed in greater detail herein.

Viral Vectors

In some embodiments, the vector is a viral vector. The term of art "viral vector" and as used herein in this context refers to polynucleotide based vectors that contain one or more elements from or based upon one or more elements of a virus that can be capable of expressing and packaging a polynucleotide, such as a perturbation construct of the present invention, into a virus particle and producing said virus particle when used alone or with one or more other viral vectors (such as in a viral vector system). Viral vectors and systems thereof can be used for producing viral particles for delivery of and/or expression of one or more components of the perturbation construct described herein. The viral vector can be part of a viral vector system involving multiple vectors. In some embodiments, systems incorporating multiple viral vectors can increase the safety of these systems. Suitable viral vectors can include retroviral-based vectors, lentiviral-based vectors, adenoviral-based vectors, adeno associated vectors, helper-dependent adenoviral (HdAd) vectors, hybrid adenoviral vectors, herpes simplex virus-based vectors, poxvirus-based vectors, and Epstein-Barr virus-based vectors. Other embodiments of viral vectors and viral particles produce therefrom are described elsewhere herein. In some embodiments, the viral vectors are configured to produce replication incompetent viral particles for improved safety of these systems.

In certain embodiments, the virus structural component, which can be encoded by one or more polynucleotides in a viral vector or vector system, comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, VP2, and VP3, thus delivery systems of the invention can comprise one or more of VP1, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8(1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned elsewhere herein, the teachings herein as to modifying adenovirus and AAV, respectively, can be applied to those viruses without undue experimentation from this disclosure and the knowledge in the art.

In some embodiments, the viral vector is configured such that when the cargo is packaged the cargo(s) (e.g., one or more components of the perturbation construct including but not limited to the two or more gRNAs, is/are external to the capsid or virus particle. In the sense that it is not inside the capsid (enveloped or encompassed with the capsid) but is externally exposed so that it can contact the target genomic DNA. In some embodiments, the viral vector is configured such that all the cargo(s) are contained within the capsid after packaging.

Retroviral and Lentiviral Vectors

Retroviral vectors can be composed of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Suitable retroviral vectors for the perturbation construct described herein can include those based upon murine leukemia virus (MuLV), gibbon ape leukemia virus (GaLV), Simian immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). Selection of a retroviral gene transfer system may therefore depend on the target tissue.

The tropism of a retrovirus can be altered by incorporating foreign envelope proteins, expanding the potential target population of target cells. Lentiviral vectors are retroviral vectors that are able to transduce or infect non-dividing cells and are described in greater detail elsewhere herein. A retrovirus can also be engineered to allow for conditional expression of the inserted transgene, such that only certain cell types are infected by the lentivirus.

Lentiviruses are complex retroviruses that have the ability to infect and express their genes in both mitotic and post-mitotic cells. Advantages of using a lentiviral approach can include the ability to transduce or infect non-dividing cells and their ability to typically produce high viral titers, which can increase efficiency or efficacy of production and delivery. Suitable lentiviral vectors include, but are not limited to, human immunodeficiency virus (HIV)-based lentiviral vectors, feline immunodeficiency virus (FIV)-based lentiviral vectors, simian immunodeficiency virus (SIV)-based lentiviral vectors, Moloney Murine Leukaemia Virus (Mo-HLV), Visna.maedi virus (VMV)-based lentiviral vector, caprine arthritis-encephalitis virus (CAEV)-based lentiviral vector, bovine immune deficiency virus (BIV)-based lentiviral vector, and Equine infectious anemia (EIAV)-based lentiviral vector. In some embodiments, an HIV-based lentiviral vector system can be used. In some embodiments, a FIV-based lentiviral vector system can be used.

In some embodiments, the lentiviral vector is an EIAV-based lentiviral vector or vector system. EIAV vectors have been used to mediate expression, packaging, and/or delivery in other contexts, such as for ocular gene therapy (see, e.g., Balagaan, J Gene Med 2006; 8: 275-285). In another embodiment, RetinoStat®, (see, e.g., Binley et al., HUMAN GENE THERAPY 23:980-991 (September 2012)), which describes RetinoStat®, an equine infectious anemia virus-based lentiviral gene therapy vector that expresses angiostatic proteins endostatin and angiostatin that is delivered via a subretinal injection for the treatment of the wet form of age-related macular degeneration. Any of these vectors described in these publications can be modified for the elements of the perturbation construct described herein.

In some embodiments, the lentiviral vector or vector system thereof can be a first-generation lentiviral vector or vector system thereof. First-generation lentiviral vectors can contain a large portion of the lentivirus genome, including the gag and pol genes, other additional viral proteins (e.g., VSV-G) and other accessory genes (e.g., vif, vprm vpu, nef, and combinations thereof), regulatory genes (e.g., tat and/or rev) as well as the gene of interest between the LTRs. First generation lentiviral vectors can result in the production of virus particles that can be capable of replication in vivo, which may not be appropriate for some instances or applications.

In some embodiments, the lentiviral vector or vector system thereof can be a second-generation lentiviral vector or vector system thereof. Second-generation lentiviral vectors do not contain one or more accessory virulence factors and do not contain all components necessary for virus particle production on the same lentiviral vector. This can result in the production of a replication-incompetent virus particle and thus increase the safety of these systems over first-generation lentiviral vectors. In some embodiments, the second-generation vector lacks one or more accessory virulence factors (e.g., vif, vprm, vpu, nef, and combinations thereof). Unlike the first-generation lentiviral vectors, no single second generation lentiviral vector includes all features necessary to express and package a polynucleotide into a virus particle. In some embodiments, the envelope and packaging components are split between two different vectors with the gag, pol, rev, and tat genes being contained on one vector and the envelope protein (e.g., VSV-G) are contained on a second vector. The gene of interest, its promoter, and LTRs can be included on a third vector that can be used in conjunction with the other two vectors (packaging and envelope vectors) to generate a replication-incompetent virus particle.

In some embodiments, the lentiviral vector or vector system thereof can be a third-generation lentiviral vector or vector system thereof. Third-generation lentiviral vectors and vector systems thereof have increased safety over first- and second-generation lentiviral vectors and systems thereof because, for example, the various components of the viral genome are split between two or more different vectors but used together in vitro to make virus particles, they can lack the tat gene (when a constitutively active promoter is included up-stream of the LTRs), and they can include one or more deletions in the 3'LTR to create self-inactivating (SIN) vectors having disrupted promoter/enhancer activity of the LTR. In some embodiments, a third-generation lentiviral vector system can include (i) a vector plasmid that contains the polynucleotide of interest and upstream promoter that are flanked by the 5' and 3' LTRs, which can optionally include one or more deletions present in one or both of the LTRs to render the vector self-inactivating; (ii) a "packaging vector(s)" that can contain one or more genes involved in packaging a polynucleotide into a virus particle that is produced by the system (e.g. gag, pol, and rev) and upstream regulatory sequences (e.g. promoter(s)) to drive expression of the features present on the packaging vector, and (iii) an "envelope vector" that contains one or more envelope protein genes and upstream promoters. In certain embodiments, the third-generation lentiviral vector system can include at least two packaging vectors, with the gag-pol being present on a different vector than the rev gene.

In some embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) can be used/and or adapted to the perturbation construct of the present invention.

In some embodiments, the pseudotype and infectivity or tropism of a lentivirus particle can be tuned by altering the type of envelope protein(s) included in the lentiviral vector or system thereof. As used herein, an "envelope protein" or "outer protein" means a protein exposed at the surface of a viral particle that is not a capsid protein. For example, envelope or outer proteins typically comprise proteins embedded in the envelope of the virus. In some embodiments, a lentiviral vector or vector system thereof can include a VSV-G envelope protein. VSV-G mediates viral attachment to an LDL receptor (LDLR) or an LDLR family member present on a host cell, which triggers endocytosis of the viral particle by the host cell. Because LDLR is expressed by a wide variety of cells, viral particles expressing the VSV-G envelope protein can infect or transduce a wide variety of cell types. Other suitable envelope proteins can be incorporated based on the host cell that a user desires to be infected by a virus particle produced from a lentiviral vector or system thereof described herein and can include, but are not limited to, feline endogenous virus envelope protein (RD 114) (see e.g., Hanawa et al. Molec. Ther. 2002 5(3) 242-251), modified Sindbis virus envelope proteins (see e.g., Morizono et al. 2010. J. Virol. 84(14) 6923-6934; Morizono et al. 2001. J. Virol. 75:8016-8020; Morizono et al. 2009. J. Gene Med. 11:549-558; Morizono et al. 2006 Virology 355:71-81; Morizono et al J. Gene Med. 11:655-663, Morizono et al. 2005 Nat. Med. 11:346-352), baboon retroviral envelope protein (see e.g., Girard-Gagnepain et al. 2014. Blood. 124: 1221-1231); Tupaia paramyxovirus glycoproteins (see e.g., Enkirch T. et al., 2013. Gene Ther. 20:16-23); measles virus glycoproteins (see e.g., Funke et al. 2008. Molec. Ther. 16(8): 1427-1436), rabies virus envelope proteins, MLV envelope proteins, Ebola envelope proteins, baculovirus envelope proteins, filovirus envelope proteins, hepatitis E1 and E2 envelope proteins, gp41 and gp120 of HIV, hemagglutinin, neuraminidase, M2 proteins of influenza virus, and combinations thereof.

In some embodiments, the tropism of the resulting lentiviral particle can be tuned by incorporating cell targeting peptides into a lentiviral vector such that the cell targeting peptides are expressed on the surface of the resulting lentiviral particle. In some embodiments, a lentiviral vector can contain an envelope protein that is fused to a cell targeting protein (see e.g., Buchholz et al. 2015. Trends Biotechnol. 33:777-790; Bender et al. 2016. PLoS Pathog. 12(e1005461); and Friedrich et al. 2013. Mol. Ther. 2013. 21: 849-859.

In some embodiments, a split-intein-mediated approach to target lentiviral particles to a specific cell type can be used (see e.g., Chamoun-Emaneulli et al. 2015. Biotechnol. Bioeng. 112:2611-2617, Ramirez et al. 2013. Protein. Eng. Des. Sel. 26:215-233. In these embodiments, a lentiviral vector can contain one half of a splicing-deficient variant of the naturally split intein from *Nostoc punctiforme* fused to a cell targeting peptide and the same or different lentiviral vector can contain the other half of the split intein fused to an envelope protein, such as a binding-deficient, fusion-competent virus envelope protein. This can result in production of a virus particle from the lentiviral vector or vector system that includes a split intein that can function as a molecular Velcro linker to link the cell-binding protein to the pseudotyped lentivirus particle. This approach can be advantageous for use where surface-incompatibilities can restrict the use of, e.g., cell targeting peptides.

In some embodiments, a covalent-bond-forming protein-peptide pair can be incorporated into one or more of the lentiviral vectors described herein to conjugate a cell targeting peptide to the virus particle (see e.g., Kasaraneni et al. 2018. Sci. Reports (8) No. 10990). In some embodiments, a lentiviral vector can include an N-terminal PDZ domain of InaD protein (PDZ1) and its pentapeptide ligand (TEFCA) from NorpA, which can conjugate the cell targeting peptide to the virus particle via a covalent bond (e.g., a disulfide bond). In some embodiments, the PDZ1 protein can be fused to an envelope protein, which can optionally be binding deficient and/or fusion competent virus envelope protein and included in a lentiviral vector. In some embodiments, the TEFCA can be fused to a cell targeting peptide and the TEFCA-CPT fusion construct can be incorporated into the same or a different lentiviral vector as the PDZ 1-envelope protein construct. During virus production, specific interaction between the PDZ1 and TEFCA facilitates producing virus particles covalently functionalized with the cell targeting peptide and thus capable of targeting a specific cell-type based upon a specific interaction between the cell targeting peptide and cells expressing its binding partner. This approach can be advantageous for use where surface-incompatibilities can restrict the use of, e.g., cell targeting peptides.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015. Any of these systems or a variant thereof can be used to deliver a perturbation construct described herein to a cell.

In some embodiments, a lentiviral vector system can include one or more transfer plasmids. Transfer plasmids can be generated from various other vector backbones and can include one or more features that can work with other retroviral and/or lentiviral vectors in the system that can, for example, improve safety of the vector and/or vector system, increase virial titers, and/or increase or otherwise enhance expression of the desired insert to be expressed and/or packaged into the viral particle. Suitable features that can be included in a transfer plasmid can include, but are not limited to, 5'LTR, 3'LTR, SIN/LTR, origin of replication (Ori), selectable marker genes (e.g., antibiotic resistance genes), Psi ($\Psi$), RRE (rev response element), cPPT (central polypurine tract), promoters, WPRE (woodchuck hepatitis post-transcriptional regulatory element), SV40 polyadenylation signal, pUC origin, SV40 origin, F1 origin, and combinations thereof.

In another embodiment, Cocal vesiculovirus envelope pseudotyped retroviral or lentiviral vector particles are contemplated (see, e.g., US Patent Publication No. 20120164118 assigned to the Fred Hutchinson Cancer Research Center). Cocal virus is in the Vesiculovirus genus and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. In certain embodiments of these embodiments, the Gag, Pol, and accessory proteins are lentiviral and/or gammaretroviral. In some embodiments, a retroviral vector can contain encoding polypeptides for one or more Cocal vesiculovirus envelope proteins such that the resulting viral or pseudoviral particles are Cocal vesiculovirus envelope pseudotyped.

Adenoviral Vectors, Helper-Dependent Adenoviral Vectors, and Hybrid Adenoviral Vectors In some embodiments, the vector can be an adenoviral vector. In some embodiments, the adenoviral vector can include elements such that the virus particle produced using the vector or system thereof can be serotype 2 or serotype 5. In some embodiments, the polynucleotide to be delivered via the adenoviral particle can be up to about 8 kb. Thus, in some embodiments, an adenoviral vector can include a DNA polynucleotide to be delivered that can range in size from about 0.001 kb to about 8 kb. Adenoviral vectors have been used successfully in several contexts (see e.g., Teramato et al. 2000. Lancet. 355:1911-1912; Lai et al. 2002. DNA Cell. Biol. 21:895-913; Flotte et al., 1996. Hum. Gene. Ther. 7:1145-1159; and Kay et al. 2000. Nat. Genet. 24:257-261.

In some embodiments the vector can be a helper-dependent adenoviral vector or system thereof. These are also referred to in the art as "gutless" or "gutted" vectors and are a modified generation of adenoviral vectors (see e.g., Thrasher et al. 2006. Nature. 443:E5-7). In certain embodiments of the helper-dependent adenoviral vector system one vector (the helper) can contain all the viral genes required for replication but contains a conditional gene defect in the packaging domain. The second vector of the system can contain only the ends of the viral genome, one or more CRISPR-Cas polynucleotides, and the native packaging recognition signal, which can allow selective packaged release from the cells (see e.g., Cideciyan et al. 2009. N Engl J Med. 361:725-727). Helper-dependent adenoviral vector systems have been successful for gene delivery in several contexts (see e.g., Simonelli et al. 2010. J Am Soc Gene Ther. 18:643-650; Cideciyan et al. 2009. N Engl J Med. 361:725-727; Crane et al. 2012. Gene Ther. 19(4):443-452; Alba et al. 2005. Gene Ther. 12:18-S27; Croyle et al. 2005. Gene Ther. 12:579-587; Amalfitano et al. 1998. J. Virol. 72:926-933; and Morral et al. 1999. PNAS. 96:12816-12821). The techniques and vectors described in these publications can be adapted for inclusion and delivery of the CRISPR-Cas system polynucleotides described herein. In some embodiments, the polynucleotide to be delivered via the viral particle produced from a helper-dependent adenoviral vector or system thereof can be up to about 37 kb. Thus, in some embodiments, an adenoviral vector can include a DNA polynucleotide to be delivered that can range in size from about 0.001 kb to about 37 kb (see e.g., Rosewell et al. 2011. J. Genet. Syndr. Gene Ther. Suppl. 5:001).

In some embodiments, the vector is a hybrid-adenoviral vector or system thereof. Hybrid adenoviral vectors are composed of the high transduction efficiency of a gene-deleted adenoviral vector and the long-term genome-integrating potential of adeno-associated, retroviruses, lentivirus, and transposon based-gene transfer. In some embodiments, such hybrid vector systems can result in stable transduction and limited integration site. See e.g., Balague et al. 2000. Blood. 95:820-828; Morral et al. 1998. Hum. Gene Ther. 9:2709-2716; Kubo and Mitani. 2003. J. Virol. 77(5): 2964-2971; Zhang et al. 2013. PloS One. 8(10) e76771; and Cooney et al. 2015. Mol. Ther. 23(4):667-674), whose techniques and vectors described therein can be modified and adapted for use in the CRISPR-Cas system of the present invention. In some embodiments, a hybrid-adenoviral vector can include one or more features of a retrovirus and/or an adeno-associated virus. In some embodiments the hybrid-adenoviral vector can include one or more features of a spuma retrovirus or foamy virus (FV). See e.g., Ehrhardt et al. 2007. Mol. Ther. 15:146-156 and Liu et al. 2007. Mol. Ther. 15:1834-1841, whose techniques and vectors described therein can be modified and adapted for use in the CRISPR-Cas system of the present invention. Advantages of using one or more features from the FVs in the hybrid-adenoviral vector or system thereof can include the ability of the viral particles produced therefrom to infect a broad range of cells, a large packaging capacity as compared to other retroviruses, and the ability to persist in quiescent (non-dividing) cells. See also e.g., Ehrhardt et al. 2007. Mol. Ther. 156:146-156 and Shuji et al. 2011. Mol. Ther. 19:76-82, whose techniques and vectors described therein can be modified and adapted for use in the perturbation construct of the present invention. Adeno Associated Viral (AAV) Vectors In an embodiment, the vector can be an adeno-associated virus (AAV) vector. See, e.g., West et al., Virology 160:38-47 (1987); U.S. Pat. No. 4,797,368; WO 93/24641; Kotin, Human Gene Therapy 5:793-801 (1994); and Muzyczka, J. Clin. Invest. 94:1351 (1994). Although similar to adenoviral vectors in some of their features, AAVs have some deficiency in their replication and/or pathogenicity and thus can be safer that adenoviral vectors. In some embodiments the AAV can integrate into a specific site on chromosome 19 of a human cell with no observable side effects. In some embodiments, the capacity of the AAV vector, system thereof, and/or AAV particles can be up to about 4.7 kb. The AAV vector or system thereof can include one or more regulatory molecules. In some embodiments the regulatory molecules can be promoters, enhancers, repressors and the like, which are described in greater detail elsewhere herein. In some embodiments, the AAV vector or system thereof can include one or more polynucleotides that can encode one or more regulatory proteins. In some embodiments, the one or more regulatory proteins can be selected from Rep78, Rep68, Rep52, Rep40, variants thereof, and combinations thereof.

The AAV vector or system thereof can include one or more polynucleotides that can encode one or more capsid proteins. The capsid proteins can be selected from VP1, VP2, VP3, and combinations thereof. The capsid proteins can be capable of assembling into a protein shell of the AAV virus particle. In some embodiments, the AAV capsid can contain 60 capsid proteins. In some embodiments, the ratio of VP1:VP2:VP3 in a capsid can be about 1:1:10.

In some embodiments, the AAV vector or system thereof can include one or more adenovirus helper factors or polynucleotides that can encode one or more adenovirus helper factors. Such adenovirus helper factors can include, but are not limited, E1A, E1B, E2A, E40RF6, and VA RNAs. In some embodiments, a producing host cell line expresses one or more of the adenovirus helper factors.

The AAV vector or system thereof can be configured to produce AAV particles having a specific serotype. In some embodiments, the serotype can be AAV-1, AAV-2, AAV-3, AAV-4, AAV-5, AAV-6, AAV-8, AAV-9 or any combinations thereof. In some embodiments, the AAV can be AAV1, AAV-2, AAV-5 or any combination thereof. One can select the AAV of the AAV with regard to the cells to be targeted, e.g., one can select AAV serotypes 1, 2, 5 or a hybrid capsid AAV-1, AAV-2, AAV-5 or any combination thereof for targeting brain and/or neuronal cells; and one can select AAV-4 for targeting cardiac tissue; and one can select AAV8 for delivery to the liver. Thus, in some embodiments, an AAV vector or system thereof capable of producing AAV particles capable of targeting the brain and/or neuronal cells can be configured to generate AAV particles having serotypes 1, 2, 5 or a hybrid capsid AAV-1, AAV-2, AAV-5 or any combination thereof. In some embodiments, an AAV vector or system thereof capable of producing AAV particles capable of targeting cardiac tissue can be configured to generate an AAV particle having an AAV-4 serotype. In some embodiments, an AAV vector or system thereof capable of producing AAV particles capable of targeting the liver can be configured to generate an AAV having an AAV-8 serotype. In some embodiments, the AAV vector is a hybrid AAV vector or system thereof. Hybrid AAVs are AAVs that include genomes with elements from one serotype that are packaged into a capsid derived from at least one different serotype. For example, if it is the rAAV2/5 that is to be produced, and if the production method is based on the helper-free, transient transfection method discussed above, the 1st plasmid and the 3rd plasmid (the adeno helper plasmid) will be the same as discussed for rAAV2 production. However, the second plasmid, the pRepCap will be different. In this plasmid, called pRep2/Cap5, the Rep gene is still derived from AAV2, while the Cap gene is derived from AAV5. The production scheme is the same as the above-mentioned approach for AAV2 production. The resulting rAAV is called rAAV2/5, in which the genome is based on recombinant AAV2, while the capsid is based on AAV5. It is assumed the cell or tissue-tropism displayed by this AAV2/5 hybrid virus should be the same as that of AAV5.

A tabulation of certain AAV serotypes as to these cells can be found in Grimm, D. et al, J. Virol. 82: 5887-5911 (2008).

In some embodiments, the AAV vector or system thereof is configured as a "gutless" vector, similar to that described in connection with a retroviral vector. In some embodiments, the "gutless" AAV vector or system thereof can have the cis-acting viral DNA elements involved in genome amplification and packaging in linkage with the heterologous sequences of interest (e.g., the perturbation construct (s)).

In some embodiments, the AAV vectors are produced in in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

In some embodiments, an AAV vector or vector system can contain or consists essentially of one or more polynucleotides encoding one or more components of a perturbation construct described herein. In some embodiments, the AAV vector or vector system can contain a plurality of cassettes comprising or consisting a first cassette comprising or consisting essentially of a two or more gRNAs (or their encoding polynucleotides), reporter gene, barcode, and a terminator, advantageously up to the packaging size limit of the vector, e.g., in total.

In one embodiment, the invention provides a non-naturally occurring or engineered composition comprising a perturbation construct, which is part of or tethered to an AAV capsid domain, i.e., VP1, VP2, or VP3 domain of Adeno-Associated Virus (AAV) capsid. In some embodiments, part of or tethered to an AAV capsid domain includes associated with associated with an AAV capsid domain. In some embodiments, the perturbation construct may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, VP2 and VP3 domains of AAV are alternative splices of the same RNA and so a C-terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C-terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the perturbation construct or component thereof fused to the end of one of the branches. This allows for some degree of spatial separation between the capsid and the perturbation construct or component thereof. In this way, the perturbation construct or component thereof is part of (or fused to) the AAV capsid domain.

In other embodiments, the perturbation construct or component thereof may be fused in frame within, i.e., internal to, the AAV capsid domain. Thus, in some embodiments, the AAV capsid domain again preferably retains its N-terminal and C-terminal ends. In this case, a linker is preferred, in some embodiments, either at one or both ends of the perturbation construct. In this way, the perturbation construct or component thereof is again part of (or fused to) the AAV capsid domain. In certain embodiments, the positioning of the perturbation construct or component thereof is such that the perturbation construct or component thereof is at the external surface of the viral capsid once formed. In one embodiment, the invention provides a non-naturally occurring or engineered composition comprising a perturbation construct or component thereof associated with a AAV capsid domain of Adeno-Associated Virus (AAV) capsid. Here, associated may mean in some embodiments fused, or in some embodiments bound to, or in some embodiments tethered to. The perturbation construct or component thereof may, in some embodiments, be tethered to the VP1, VP2, or VP3 domain. This may be via a connector protein or tethering system such as the biotin-streptavidin system. In one example, a biotinylation sequence (15 amino acids) could therefore be fused to the perturbation construct or component thereof. When a fusion of the AAV capsid domain, especially the N-terminus of the AAV AAV capsid domain, with streptavidin is also provided, the two will therefore associate with very high affinity. Thus, in some embodiments, provided is a composition or system comprising a perturbation construct or component thereof—biotin fusion and a streptavidin-AAV capsid domain arrangement, such as a fusion. The perturbation construct or component thereof—biotin and streptavidin-AAV capsid domain forms a single complex when the two parts are brought together. NLSs may also be incorporated between the perturbation construct or component thereof and the biotin; and/or between the streptavidin and the AAV capsid domain.

As such, provided is a fusion of a perturbation construct or component thereof with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the perturbation construct or component thereof to the AAV VP2 domain. The reverse arrangement is also possible. In some embodiments, a biotinylation sequence (15 amino acids) could therefore be fused to the AAV VP2 domain, especially the N-terminus of the AAV VP2 domain. A fusion of the perturbation construct or component thereof with streptavidin is also preferred, in some embodiments. In some embodiments, the biotinylated AAV capsids with streptavidin-perturbation construct or component thereof are assembled in vitro. This way the AAV capsids should assemble in a straightforward manner and the perturbation construct or component thereof—streptavidin fusion can be added after assembly of the capsid. In other embodiments a biotinylation sequence (15 amino acids) could therefore be fused to the perturbation construct or component thereof, together with a fusion of the AAV VP2 domain, especially the N-terminus of the AAV VP2 domain, with streptavidin. For simplicity, a fusion of the perturbation construct or component thereof and the AAV VP2 domain is preferred in some embodiments. In some embodiments, the fusion may be to the N-terminal end of the perturbation construct or component thereof. In other words, in some embodiments, the AAV and perturbation construct or component thereof are associated via fusion. In some embodiments, the AAV and perturbation construct or component thereof are associated via fusion including a linker. Suitable linkers are discussed herein include, but are not limited to, GlySer linkers. Fusion to the N-term of AAV VP2 domain is preferred, in some embodiments. In some embodiments, the perturbation construct or component thereof comprises at least one Nuclear Localization Signal (NLS). In a further embodiment, the present invention provides compositions comprising the perturbation construct or component thereof and associated AAV VP2 domain or the polynucleotides or vectors described herein. Such compositions and formulations are discussed elsewhere herein.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the perturbation construct or component thereof may, in some embodiments, be tethered to the adaptor protein of the AAV capsid domain. The perturbation construct or component thereof may, in some embodiments, be tethered to the adaptor protein of the AAV capsid domain via the C perturbation construct or component thereof being in a complex with a modified guide, see Konermann et al. The modified guide is, in some embodiments, a sgRNA. In some embodiments, the modified guide comprises a distinct RNA sequence; see, e.g., International Patent Application No. PCT/US14/70175, incorporated herein by reference.

In some embodiments, distinct RNA sequence is an aptamer. Thus, corresponding aptamer-adaptor protein systems are preferred. One or more functional domains may also be associated with the adaptor protein. An example of a preferred arrangement would be: [AAV AAV capsid domain-adaptor protein]-[modified guide-perturbation construct or component thereof].

In certain embodiments, the positioning of the perturbation construct or component thereof is such that the perturbation construct or component thereof is at the internal surface of the viral capsid once formed. In one embodiment, the invention provides a non-naturally occurring or engineered composition comprising a perturbation construct or component thereof associated with an internal surface of an AAV capsid domain. Here again, associated may mean in some embodiments fused, or in some embodiments bound to, or in some embodiments tethered to. The perturbation construct or component thereof may, in some embodiments, be tethered to the VP1, VP2, or VP3 domain such that it locates to the internal surface of the viral capsid once formed. This may be via a connector protein or tethering system such as the biotin-streptavidin system as described above and/or elsewhere herein.

Herpes Simplex Viral Vectors

In some embodiments, the vector can be a Herpes Simplex Viral (HSV)-based vector or system thereof. HSV systems can include the disabled infections single copy (DISC) viruses, which are composed of a glycoprotein H defective mutant HSV genome. When the defective HSV is propagated in complementing cells, virus particles can be generated that are capable of infecting subsequent cells permanently replicating their own genome but are not capable of producing more infectious particles. See e.g., 2009. Trobridge. Exp. Opin. Biol. Ther. 9:1427-1436, whose techniques and vectors described therein can be modified and adapted for use in the CRISPR-Cas system of the present invention. In some embodiments where an HSV vector or system thereof is utilized, the host cell can be a complementing cell. In some embodiments, HSV vector or system thereof can be capable of producing virus particles capable of delivering a polynucleotide cargo of up to 150 kb. Thus, in some embodiment the CRISPR-Cas system polynucleotide(s) included in the HSV-based viral vector or system thereof can sum from about 0.001 to about 150 kb. HSV-based vectors and systems thereof have been successfully used in several contexts including various models of neurologic disorders. See e.g., Cockrell et al. 2007. Mol. Biotechnol. 36:184-204; Kafri T. 2004. Mol. Biol. 246:367-390; Balaggan and Ali. 2012. Gene Ther. 19:145-153; Wong et al. 2006. Hum. Gen. Ther. 2002. 17:1-9; Azzouz et al. J. Neurosci. 22L10302-10312; and Betchen and Kaplitt. 2003. Curr. Opin. Neurol. 16:487-493, whose techniques and vectors described therein can be modified and adapted for use in the CRISPR-Cas system of the present invention.

Poxvirus Vectors

In some embodiments, the vector can be a poxvirus vector or system thereof. In some embodiments, the poxvirus vector can result in cytoplasmic expression of perturbation construct or component thereof the present invention. In some embodiments the capacity of a poxvirus vector or system thereof can be about 25 kb or more. In some embodiments, a poxvirus vector or system thereof can include one or more perturbation constructs or component thereof described herein.

Virus Particle Production from Viral Vectors

Retroviral Production

In some embodiments, one or more viral vectors and/or system thereof can be delivered to a suitable cell line for production of virus particles containing the polynucleotide or other payload to be delivered to a host cell. Suitable host cells for virus production from viral vectors and systems thereof described herein are known in the art and are commercially available. For example, suitable host cells include HEK 293 cells and its variants (HEK 293T and HEK 293TN cells). In some embodiments, the suitable host cell for virus production from viral vectors and systems thereof described herein can stably express one or more genes involved in packaging (e.g., pol, gag, and/or VSV-G) and/or other supporting genes.

In some embodiments, after delivery of one or more viral vectors to the suitable host cells for or virus production from viral vectors and systems thereof, the cells are incubated for an appropriate length of time to allow for viral gene expression from the vectors, packaging of the polynucleotide to be delivered (e.g., a perturbation construct or component thereof), and virus particle assembly, and secretion of mature virus particles into the culture media. Various other methods and techniques are generally known to those of ordinary skill in the art.

Mature virus particles can be collected from the culture media by a suitable method. In some embodiments, this can involve centrifugation to concentrate the virus. The titer of the composition containing the collected virus particles can be obtained using a suitable method. Such methods can include transducing a suitable cell line (e.g., NIH 3T3 cells) and determining transduction efficiency, infectivity in that cell line by a suitable method. Suitable methods include PCR-based methods, flow cytometry, and antibiotic selection-based methods. Various other methods and techniques are generally known to those of ordinary skill in the art. The concentration of virus particle can be adjusted as needed. In some embodiments, the resulting composition containing virus particles can contain $1\times10^1$-$1\times10^{20}$ particles/mL.

Lentiviruses may be prepared from any lentiviral vector or vector system described herein. In one example embodiment, after cloning pCasES10 (which contains a lentiviral transfer plasmid backbone), HEK293FT at low passage (p=5) can be seeded in a T-75 flask to 50% confluence the day before transfection in DMEM with 10% fetal bovine serum and without antibiotics. After 20 hours, the media can be changed to OptiMEM (serum-free) media and transfection of the lentiviral vectors can done 4 hours later. Cells can be transfected with 10 μg of lentiviral transfer plasmid (pCasES10) and the appropriate packaging plasmids (e.g., 5 μg of pMD2.G (VSV-g pseudotype), and 7.5ug of psPAX2 (gag/pol/rev/tat)). Transfection can be carried out in 4 mL OptiMEM with a cationic lipid delivery agent (50 uL Lipofectamine 2000 and 100ul Plus reagent). After 6 hours, the media can be changed to antibiotic-free DMEM with 10% fetal bovine serum. These methods can use serum during cell culture, but serum-free methods are preferred.

Following transfection and allowing the producing cells (also referred to as packaging cells) to package and produce virus particles with packaged cargo, the lentiviral particles can be purified. In an exemplary embodiment, virus-containing supernatants can be harvested after 48 hours. Collected virus-containing supernatants can first be cleared of debris and filtered through a 0.45 um low protein binding (PVDF) filter. They can then be spun in an ultracentrifuge for 2 hours at 24,000 rpm. The resulting virus-containing pellets can be resuspended in 50ul of DMEM overnight at 4 degrees C. They can be then aliquoted and used immediately or immediately frozen at −80 degrees C. for storage.

Pooling of Virus Particles

In some embodiments, the virus particles (e.g., lentiviral particles) containing the gRNAs, the reporter gene, and the barcode is packaged individually for each perturbation construct and/or each target gene. In some embodiments, the lentiviruses containing the gRNAs, the reporter gene, and the barcode for multiple targets are packaged in a pool or in an array manner.

In some embodiments, the virus particles (e.g., lentiviral particles containing gRNAs for each target gene are pooled with equal titer to minimize vector recombination so that each individual type of lentiviruses that representing each individual type of gRNA for a target gene has an equal representation in the pool.

In some embodiments, the pool of lentiviruses is delivered by injection into an anatomic site or anatomic sites in vivo that contain the desired progenitor cells. As a result, one or more progenitor cells are transduced with the viruses delivered, and the gRNAs together with reporter(s) and barcode are expressed in the transduced progenitor cells.

AAV Particle Production

There are two main strategies for producing AAV particles from AAV vectors and systems thereof, such as those described herein, which depend on how the adenovirus helper factors are provided (helper v. helper free). In some embodiments, a method of producing AAV particles from AAV vectors and systems thereof can include adenovirus infection into cell lines that stably harbor AAV replication and capsid encoding polynucleotides along with AAV vector containing the polynucleotide to be packaged and delivered by the resulting AAV particle (e.g., the perturbation construct or component thereof (s)). In some embodiments, a method of producing AAV particles from AAV vectors and systems thereof can be a "helper free" method, which includes co-transfection of an appropriate producing cell line with three vectors (e.g., plasmid vectors): (1) an AAV vector that contains a polynucleotide of interest (e.g., the perturbation construct or component thereof (s)) between 2 ITRs; (2) a vector that carries the AAV Rep-Cap encoding polynucleotides; and (helper polynucleotides. One of skill in the art will appreciate various methods and variations thereof that are both helper and -helper free and as well as the different advantages of each system.

Barcodes

As described elsewhere herein the perturbation construct includes a barcode that can be operably linked to the reporter gene and gRNAs. In certain example embodiments, the barcode is polyadenylated.

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMIs are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

In some embodiments, the expression of reporter gene and barcode is controlled by a separate promoter from those used for controlling the expression of gRNAs. Configuration of the barcode within the perturbation construct is described in greater detail elsewhere herein.

Barcode with Cleavage Sites

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such an endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang)

capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments, the specific binding agent has been immobilized for example on a solid support, thereby isolating the origin-specific barcode.

Other Barcoding Embodiments

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

Delivery of a Perturbation Construct to Animal Model Cells

In some embodiments, the method includes introducing a plurality of genetic perturbations in a plurality of cells in an animal model, such as a Cas animal model. In some embodiments, introduction of a plurality of genetic perturbations includes delivering a pool of engineered virus particles to the animal model such that one or more of the cells in the animal model are transduced. In some embodiments, introducing a plurality of genetic perturbations in a plurality of cells in an animal model occurs at one or more timepoints during embryonic development. In some embodiments, introducing a plurality of genetic perturbations occurs at one or more time points post-partum. In some embodiments, introducing a plurality of genetic perturbations is induced by triggering an inducible promoter of the perturbation construct and/or Cas protein in the Cas animal model such that the gRNAs and/or Cas protein are expressed at the same time. This can allow for both spatial and temporal control over the perturbations. In some embodiments, introduction is cell or tissue specific, which can be controlled by various methods such as spatially controlling delivery a pool of engineered virus particles only to a specific cell or cell population, tissue or other spatial region.

In some embodiments, a delivery is to the heart, kidney, lung, skin, pancreas, intestine, bone, bone marrow, fat, spleen, bursa of Fabricius, bladder, blood, placenta, thymus, brain or other central nervous system cell, peripheral nervous system cell, liver, muscle, any other organ, soft tissue, or any combination thereof.

In some embodiments, delivery is to one or more progenitor cells. As used herein, "progenitor cell" refers to cells that are early descendants of stem cells that are capable of a limited number of cell divisions and are capable of differentiating to form one or more types of cells. In some embodiment, the progenitor cells are neural progenitor cells, myeloid progenitor cells, multipotent progenitor cells, and/or hematopoietic progenitor cells. It will be appreciated that there is overlap between multi-potent stem cells and progenitor cells. As used herein, "neural progenitor" refers to a progenitor cell of the central nervous system (CNS) that give rise to many, if not all, of the glial and neuronal cell types that populate the CNS (see e.g., Martinez-Cerdeno and Noctor. Front. Neuroanat., 6 Dec. 2018 | https://doi.org/10.3389/fnana.2018.00104).

In some embodiments, delivery is to a progenitor cell such that progeny carry the perturbation as the progenitor cell divides and/or differentiates. In some embodiments, subsequent steps of the methods described herein (such as enrichment and/or sc-RNA seq) occur after division and/or differentiation of a transduced and/or perturbed cell.

In some embodiments, the progenitor cells infected with the lentiviruses develop into a plurality of distinct types of progeny cells. In some embodiments, the neural progenitor cells infected with the lentiviruses develop into a plurality of distinct types of progeny cells. In some embodiments, the progeny cells arise from the lentivirus-infected neural progenitor cells include, but are not limited, projection neurons, interneurons, astroglia, and oligodendrocytes. In some embodiments, the neural progeny cells are located in diverse brain regions.

In some embodiments, the progeny cells are collected from the targeted tissue or tissues in the newborn mouse at any time of P1, P2, P3, P4, P5, P6, P7, P8, P9, P10, or after P10. In some embodiments, the progeny cells are collected from the targeted tissue or tissues in the newborn mouse on P7.

In some embodiments, the rate of frameshifted insertion/deletion for each gRNA target among the lentiviral infected cells is at least 30%, at least 40%, at least 50%, at least 60%, at least 70%, or at least 80%.

In certain example embodiments, introducing further comprises delivering to the plurality of progenitor cells a pool of engineered virus particles comprising equal genetic perturbation representation.

In certain example embodiments, the engineered virus particles are engineered lentiviral particles.

In certain example embodiments, introducing further comprises delivering the pool of engineered virus particles to a target tissue of a developing embryo of the Cas animal model in utero.

In certain example embodiments, the developing embryo is at stage between E5-E17 or an equivalent stage thereof, such as E5, E6, E7, E8, E9, E10, E11, E12, E13, E14, E15, E16, or E17 or an equivalent stage thereof. In some embodiments, the developing embryo is at stage 12.5 or equivalent thereof In some embodiments, the lentiviruses are injected into the lateral ventricular zone in a developing embryo in utero at a stage of E5, E6, E7, E8, E9, E10, E11, E12, E13, E14, E15, E16, or E17. In some aspect, the lentiviruses are injected at a stage of E12.5.

Enrichment of Perturbed Cells

In embodiments, the method includes generating and enriched perturbed and/or reporter gene expressing cell population. As previously discussed, a reporter gene is operably linked and to at least the two or more gRNAs of the perturbation construct. Thus, by identifying, separating and/or isolating the cells expressing the reporter, the result is also an enrichment of perturbed cells. In certain example embodiments, the enriched perturbed cell population comprises progenitor cell progeny.

In some embodiments, identification and separation of reporter expressing cells includes FACS. FACS can be performed directly, such as by detecting expression of an optically active reporter, or indirectly by using one or more immunological detection methods to apply an optically active label to reporter expressing cells and performing FACS based on detection of the optically active label. Other methods of detecting, separating, isolating, and thus enriching live cells based on detection of expression of a reporter gene are known and can be used to enrich the population of perturbed cells.

In some embodiments, enrichment includes dissecting out a tissue or cell population prior to or alternative to FACS or other separation/isolation method. In some embodiments, dissecting includes microdissection. In some embodiments, transduced progeny cells can be dissected out. In some embodiments, the cell survival rate after FACS is at least 40%, at least 50%, at least 60%, at least 70%, at least 80%, or at least 90%.

Analysis of the Enriched Perturbed Cell Population

The method includes phenotypic evaluation or a proxy therefor of the perturbed cells. Such analysis includes the identification of cell types within the enriched perturbed population and determination of gene modules that covary within a cell type. In some embodiments, scRNA-seq is used to identify cell types within the enriched perturbed population. In some embodiments, additional phenotypic analyses are performed.

ScRNA-Seq

Generally, and as previously described, the gene signatures and gene modules are screened by perturbation of target genes within said signatures and modules. Methods and tools for genome-scale screening of perturbations in single cells using CRISPR-Cas9 have been described, and are generally referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; Feldman et al., Lentiviral co-packaging mitigates the effects of intermolecular recombination and multiple integrations in pooled genetic screens, bioRxiv 262121, doi: doi.org/10.1101/262121; Datlinger, et al., 2017, Pooled CRISPR screening with single-cell transcriptome readout. Nature Methods. Vol. 14 No. 3 DOI: 10.1038/nmeth.4177; Hill et al., On the design of CRISPR-based single cell molecular screens, Nat Methods. 2018 April; 15(4): 271-274; Replogle, et al., "Combinatorial single-cell CRISPR screens by direct guide RNA capture and targeted sequencing" Nat Biotechnol (2020). doi.org/10.1038/s41587-020-0470-y; and International publication serial number WO/2017/075294). It will be appreciated as discussed elsewhere herein that the present disclosure relates to such methods but differs as discussed elsewhere herein. The present invention is compatible with perturb-seq, such that signature genes may be perturbed, and the perturbation may be identified and assigned to the proteomic and gene expression readouts of single cells and can be capable of doing so with greater efficiency. In certain embodiments, a plurality of target genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a cancer. Thus, in certain embodiments, perturb-seq is used to discover novel gene and drug targets to allow treatment of various diseases in which the target genes are involved.

The perturbation methods and tools allow reconstructing of a cellular network or circuit. In one embodiment, the method comprises (1) introducing combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10X genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

In some embodiments, the method includes identifying cell types and corresponding perturbations via single cell RNA sequencing of the enriched perturbed cell population (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-

667, 2017; Gierahn et al., "Seq-Well: portable, low-cost RNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International patent application number PCT/US2016/059239, published as WO2017164936 on Sep. 28, 2017; International patent application number PCT/US2018/060860, published as WO/2019/094984 on May 16, 2019; International patent application number PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi: 10.1126/science.aab1601. Epub 2015 May 7; US20160208323A1; US20160060691A1; and WO2017156336A1).

In some embodiments, the scRNA-Seq produces a transcriptome of the different types of progeny cells. In some embodiments, the scRNA-Seq produces a gene program or module information of the different types of progeny cells. In some embodiments, the scRNA-Seq produces information about cell states for the progeny cells.

Additional Phenotypic Analyses

In some embodiments additional analyses are performed. In some embodiments, the enriched progeny cells are subjected to proteomic analysis, genomic analysis, phenotypic analysis, and/or any other relevant biological analyses. In some embodiments, the tissues that contain the progeny cells are subjected to immunohistochemistry analysis to show the expression of proteins.

Identification of Gene Modules that Covary in a Cell Type

As used herein, a "gene module" is defined as a set of genes within each cell type that co-varied as a group across most cells within a given cell-type cluster. Within each module, the expression of the group of genes is highly correlated with one another. In some embodiments, the modules are used to reflect common biological processes. These common biological processes can be cell cycle, cell differentiation, cell identity, cell death, apoptosis, or any other biological cellular events.

In some embodiments, a gene module can be established using a variety of algorithms. In some embodiments, a module can be established using Weighted Gene Correlation Network Analysis (WGCNA). In some other embodiments, a module can be established using Structural Topic Modeling (STM). In some embodiments, a module can be established using other algorithms.

In some embodiments, the modules selected using WGCNA is highly correlated with those selected using STM. In some embodiments, modules selected using either WGCNA or STM can be used for subsequent analysis.

In some embodiments, a number of WGCNA modules can be used for subsequent analysis. The number of modules can be 1, 2, 3, more than 3, more than 10, more than 15, or more than 50.

In some embodiments, a number of modules are extracted from all of relevant cell types. In some embodiments, a number of modules are extracted from major cell types.

In some embodiments, some modules are specific to one subcluster within a cell type. In some embodiments, some modules are across cells in multiple subclusters.

In some embodiments, the modules are used for testing the association with the perturbation of genes under interrogation. In some embodiments, a linear model is developed to estimate the effect size of each genetic perturbation on that module. As such, the function of each gene perturbed in each cell type can be evaluated using the modules selected.

Focusing on gene modules as opposed to individual genes can provide more statistical power to detect biologically meaningful perturbation effects while using fewer cells. In some embodiments, the method includes a determination of gene modules that covary with cell type and/or state.

In some embodiments, gene expression modules are generated using WGCNA or STP algorithms. In some embodiments, the modules selected using WGCNA is highly correlated with those selected using STM. In some embodiments, modules selected using either WGCNA or STM can be used for subsequent analysis.

In some embodiments, a number of WGCNA modules can be used for subsequent analysis. The number of modules can be 1, 2, 3, more than 3, more than 10, more than 15, or more than 50.

In some embodiments, a number of modules are extracted from all of relevant neural cell types. In some embodiments, a number of modules are extracted from major neural cell types.

In some embodiments, some modules are specific to one subcluster within a cell type. In some embodiments, some modules are across cells in multiple subclusters.

In some embodiments, the modules are used for testing the association with the perturbation of ASD risk-associated genes under interrogation. In some embodiments, a linear model is developed to estimate the effect size of each genetic perturbation of the ASD risk-associated genes on that module. As such, the effect of each ASD risk-associated gene perturbed in each progeny cell type can be evaluated using the modules selected.

In vivo Screening for Therapeutic Targets and Therapeutic Agents

In some embodiments, methods for identifying therapeutic targets are disclosed. The targets identified using these methods represent faithfully authentic changes in molecular machinery and the cell states induced the disease.

In some embodiments, candidate genes for therapeutic targets can be selected from the literature, from the database, from experiments, or from bioinformatics means.

In some embodiments, perturbation of the candidate genes in desired embryonic tissues containing a desired group of progenitor cells is performed using methods as described in above sections.

In some embodiments, the effect of candidate genes on the physiological and/or pathological status of the animal are evaluated. The perturbed candidate genes that produce a desired pathological condition or conditions therefore can be used as therapeutic targets.

In some embodiments, the effects of candidate genes on the progeny cells are measured based on the genomic, proteomic, genetic, epigenetic and/or phenotypic changes. In some embodiments, the effect of candidate genes on the progeny cells are measured using scRNA-Seq, and the changes in transcriptomic profile are evaluated against the candidate genes. The genes produce significant changes in gene expression programs that are pathologically relevant to the onset or status of the disease of interest therefore can be used as therapeutic targets.

In some embodiments, an experiment can be set up to test agents or compounds for their ability to modify the expression of the selected therapeutic target genes. In some embodiments, the agents of compounds can be antibodies, small molecules, peptides, or proteins.

Described in certain example embodiments herein are methods of in vivo screening for therapeutic targets useful for developing treatment for a disease, comprising:
a. performing a of in vivo gene function analysis as further described elsewhere herein, wherein the plurality of genes are a plurality of candidate genes; and
b. selecting one or more candidate genes that produce a change in one or more identified gene modules that are indicative of the disease status; whereby the selected one or more candidate genes are identified as therapeutic targets for disease treatment screening.

In certain example embodiments, the method further comprises using the selected candidate gene(s) as therapeutic targets in a disease treatment screen. The term "candidate gene" refers to any gene that is being examined for the ability to modulate one or more phenotypic aspects of a cell or cell population as disclosed herein in a method performing an in vivo gene function analysis of the present invention and observing whether a modulation associated with particular cell state and/or disease takes place.

In certain example embodiments, the disease treatment screen is an autism spectrum disease treatment screen.

In certain example embodiments, the disease is an autism spectrum disease.

Described in certain example embodiments herein are therapeutic agents for treating a disease where the therapeutic agent is capable of modifying the function, activity, expression, or a combination thereof of identified therapeutic targets identified using a method described elsewhere herein, one or more gene product(s) thereof, or both.

In certain exemplary embodiments, the disease is an autism spectrum disease.

Exemplary Therapies

The present invention also contemplates the uses of the in vivo genetic perturbation, in particular the in utero genetic perturbation described herein, for treatment in a variety of diseases and disorders.

In some embodiments, the invention described herein relates to a method for therapy in which a genetic abnormality or genetic abnormalities of an embryo can be corrected by in utero genetic perturbation described herein. The correction of genetic abnormality or abnormalities can be performed on 1, 2, 3, 4, 5, 6, 7, 8, 9, 10, more than 10, more than 20, or more than 50 genes in parallel as described herein. In some embodiments, the correction can be performed on multiple abnormalities on a single gene. For example, 1, 2, 3, 4, 5, 6, 7, 8, 9, 10, or more than 10 abnormalities on a single gene can be corrected using the methods described herein.

In embodiments, the treatment is for disease/disorder of an organ, including brain diseases, liver disease, eye disease, muscle disease, heart disease, blood disease, kidney disease, or may comprise treatment for an autoimmune disease, central nervous system disease, cancer and other proliferative diseases, neurodegenerative disorders, inflammatory disease, metabolic disorder, musculoskeletal disorder and the like.

EXAMPLES

The following examples are included for illustrative purposes only and are not intended to limit the scope of the invention.

Figure 5A:
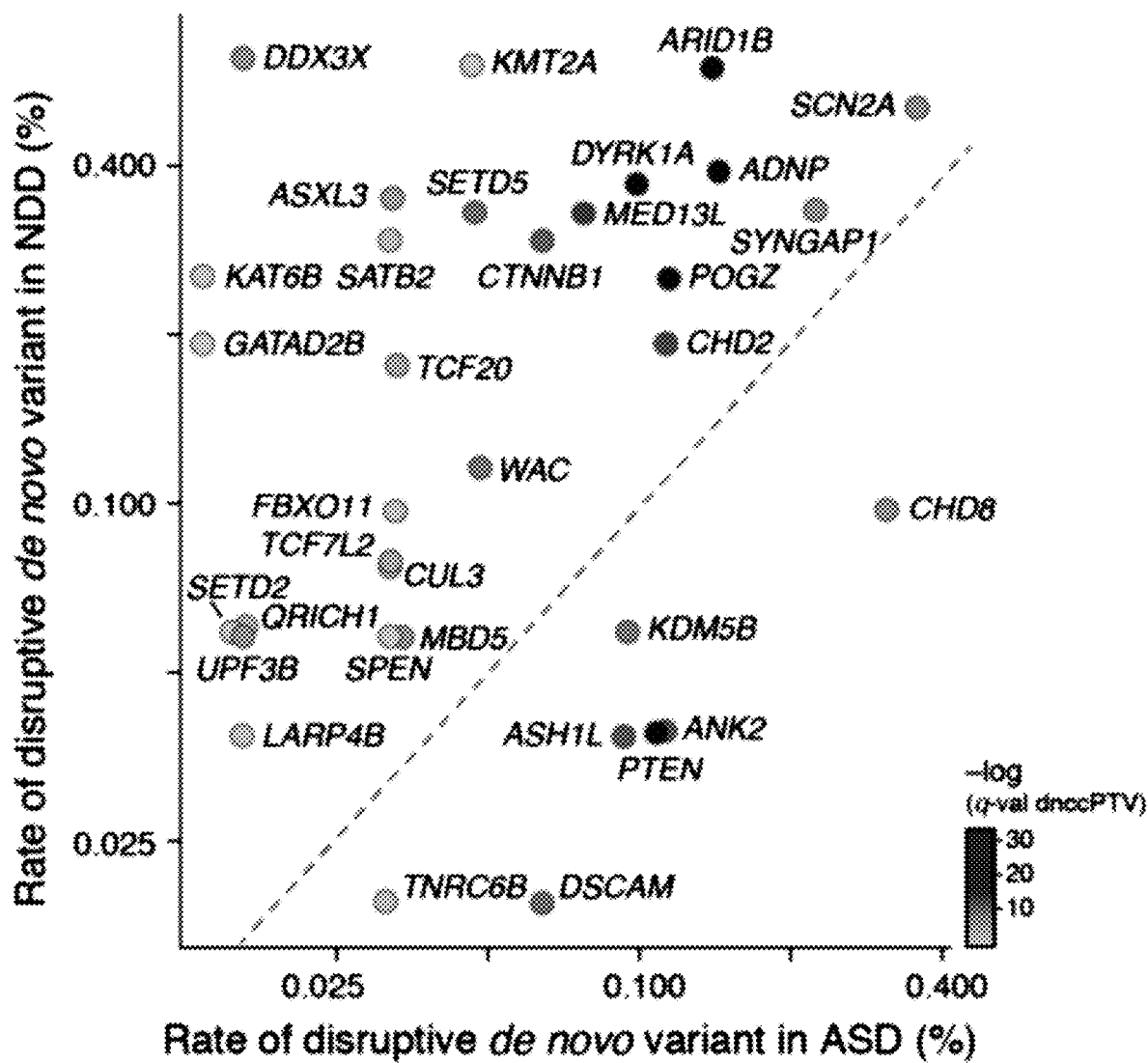
FIGS. 5A-5D—(FIG. 5A) The frequency of de novo loss-of-function variants in ascertained Autism Spectrum Disorders (ASD) and neurodevelopmental delay (NDD) cases for the 35 risk-associated genes included the Perturb-Seq analysis. Q-value was calculated based on the de novo and case control (dncc) data. This data comes from Satterstrom et al (30).
Figure 5B:
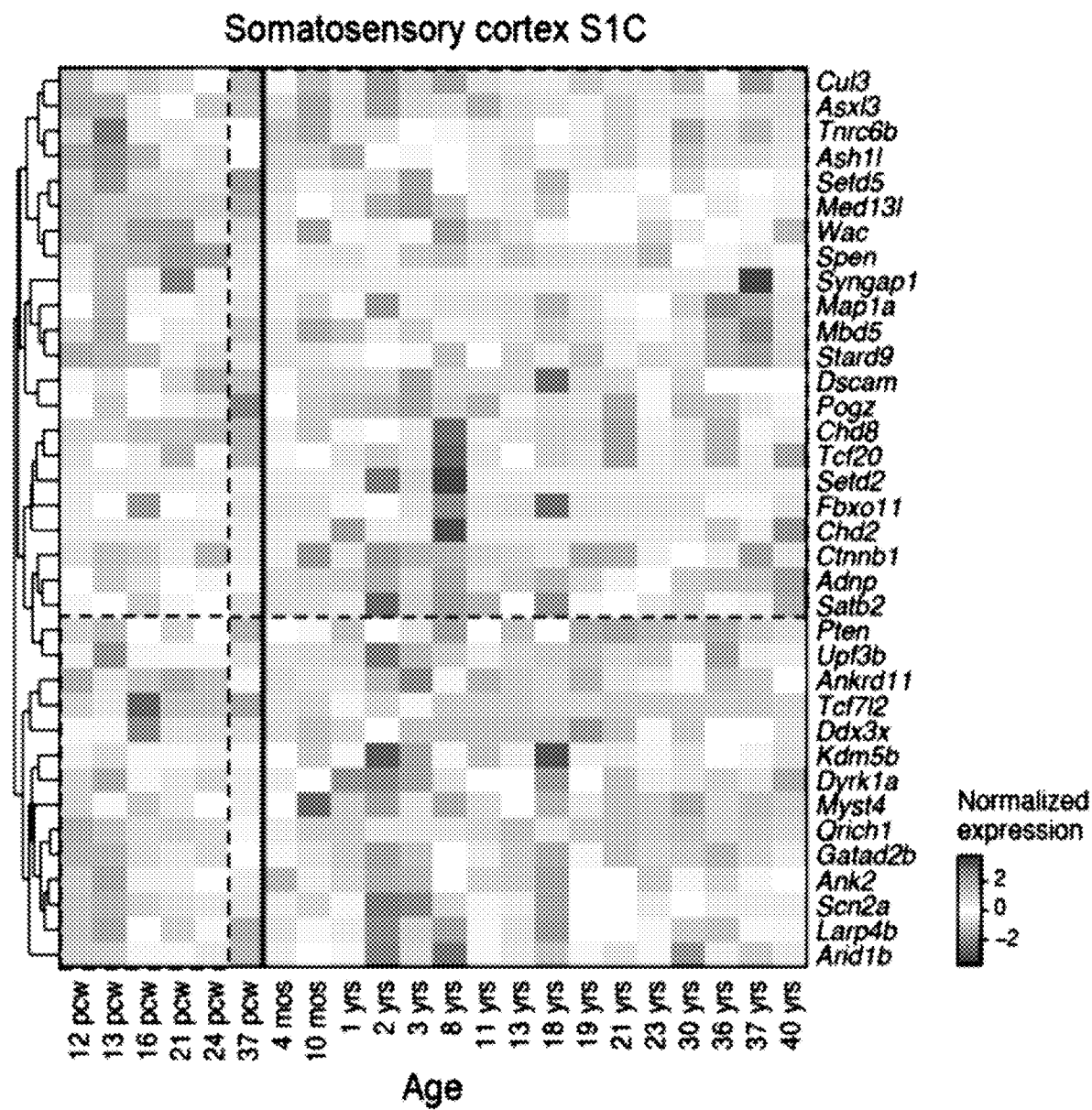
Figure 5D:
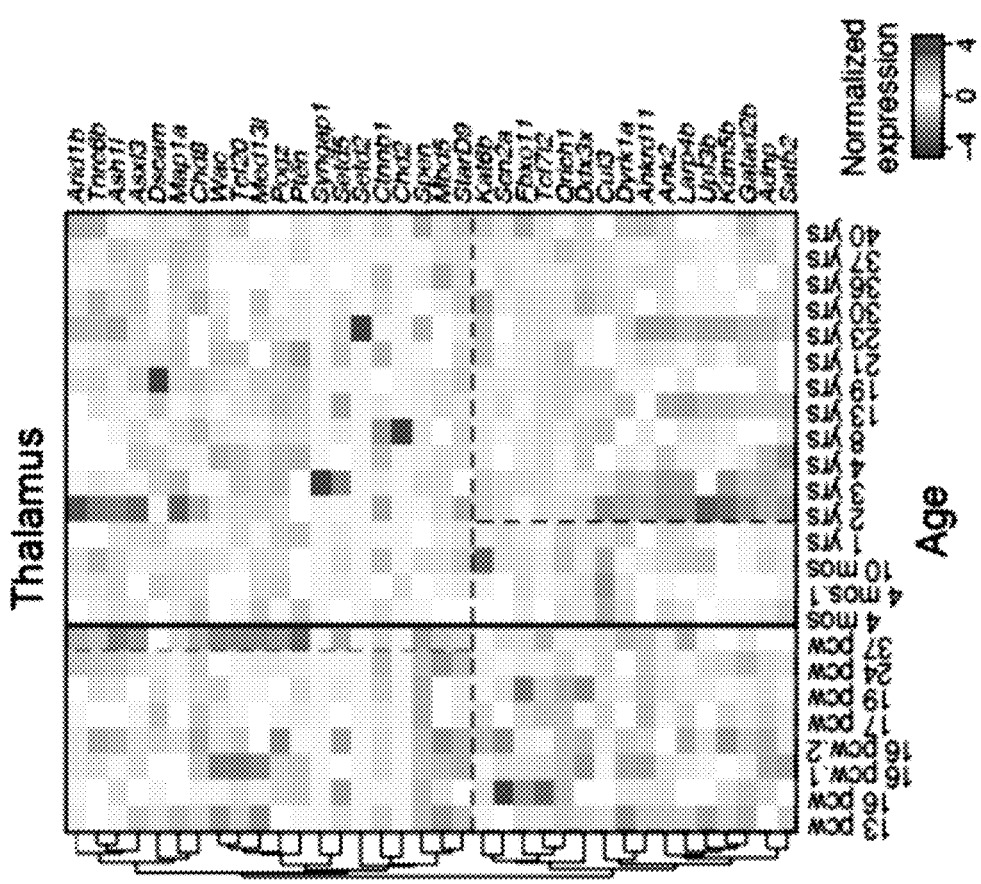
Figure 5C:
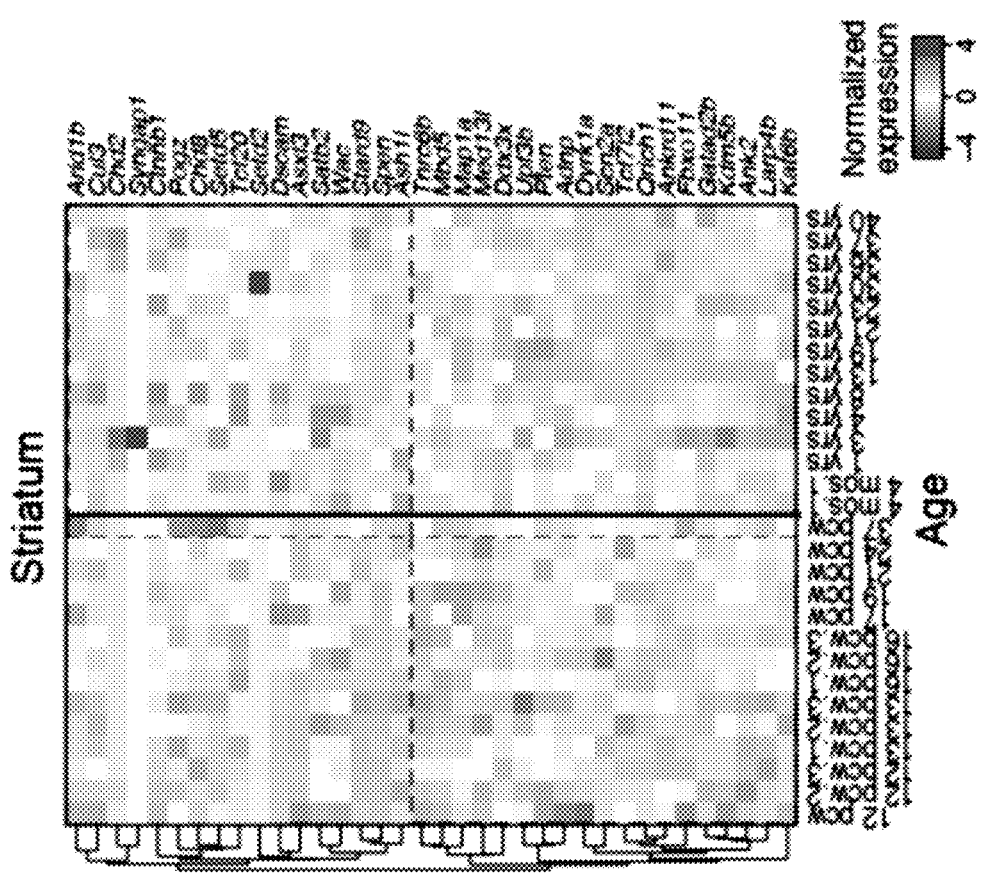
Figure 6A:
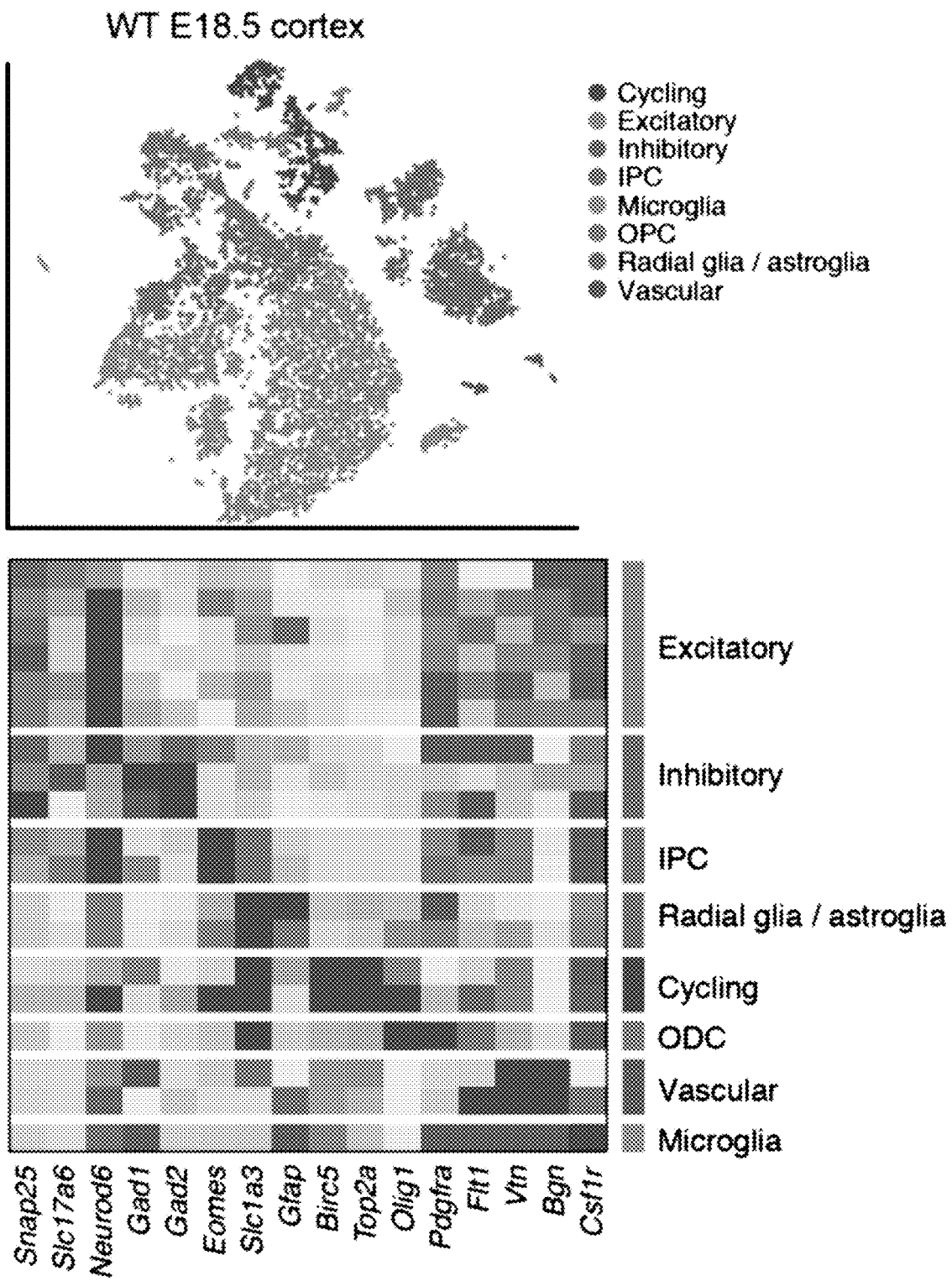
FIGS. 6A-6C—(FIGS. 6A-6B) Cell type clusters from E18.5 (public data from 10× Genomics) and WT P7 (data generated from this work) neocortex, as well as expression of cell-type marker genes across identified cell clusters.
Figure 6B:
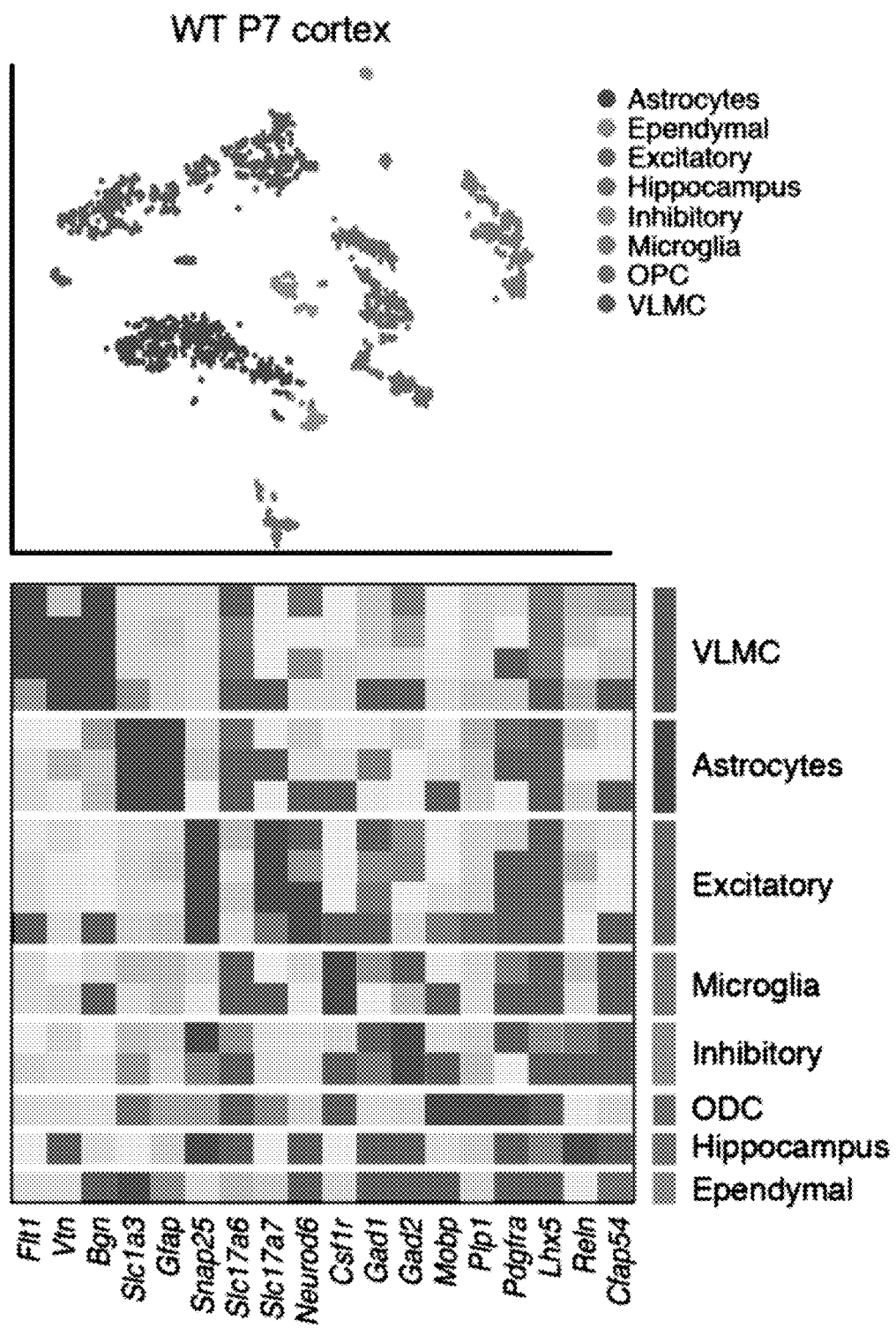
Figure 6C:
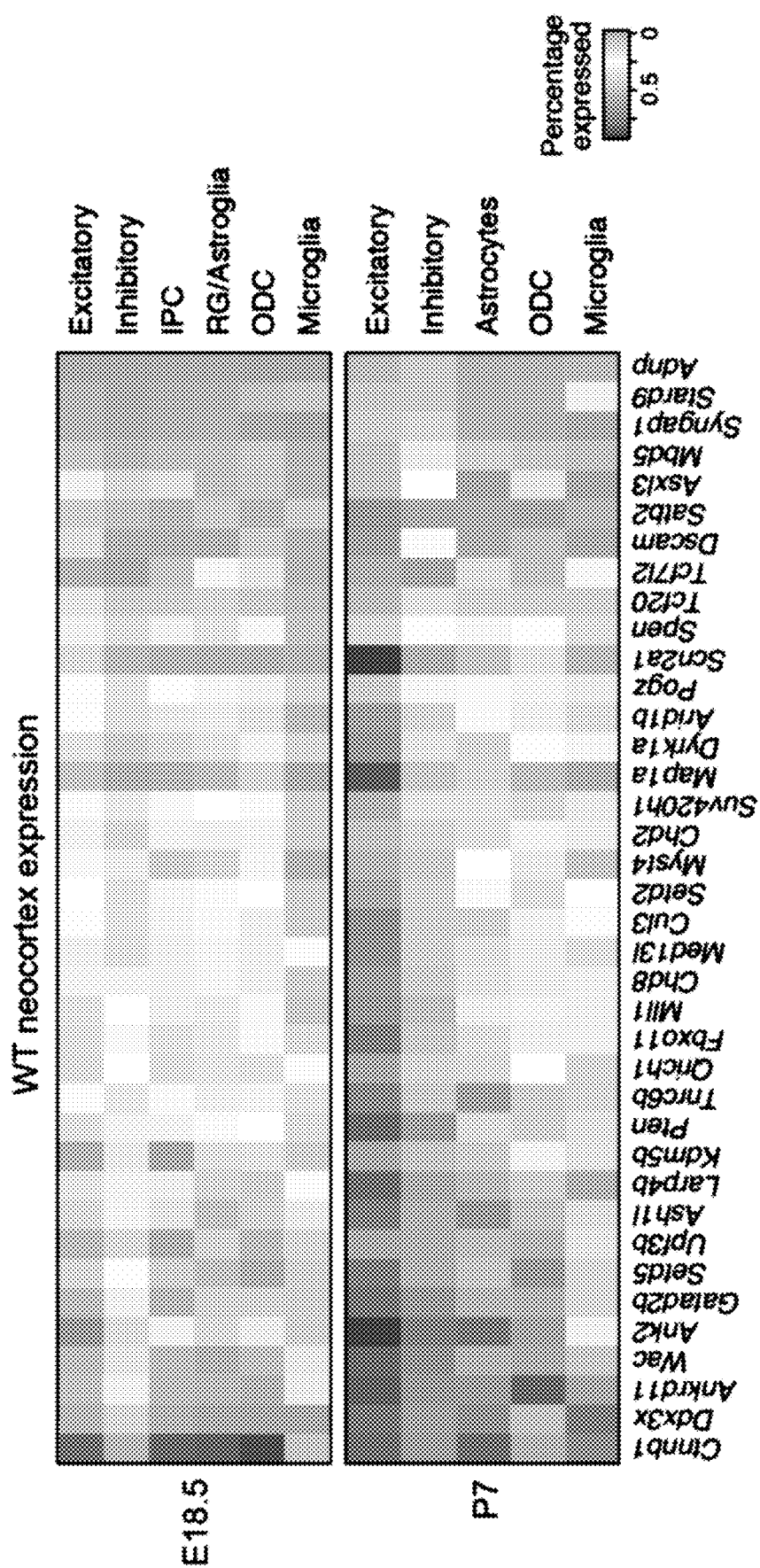

Example 1—In Vivo Perturb -Seq to Assess the Function of ASD Risk-Associated Genes ASD/ND candidate genes from a recently published WES study of 11,986 cases with 6,430 ASD/ND probands were chosen (8) (Table 2). 38 candidate genes were initially prioritized (of which 35 were retained in the final analysis, Table 2) that harbor de novo variants specific to ASD/ND patients within the broader class of neurodevelopmental disability (FIG. 5A, Table 2). These ASD/ND risk genes are expressed in human brain tissue, as assessed by the BrainSpan bulk RNA-seq dataset (9); some are highly expressed at embryonic stages, and others highly expressed from early postnatal to adult stages (FIGS. 5B-5D). Based on mouse cortical single-cell RNA sequencing (scRNA-seq) data, the orthologs of these ASD/ND risk genes are expressed in diverse cell types (FIGS. 6A-6C) (E18.5 data from the 10x Genomics public dataset (10); P7 data from this work). Thus, these ASD/ND genes could, in principle, act in many different cell types and temporal frames, requiring scalable methods to test gene function across a range of cell types and developmental events.

TABLE 2

| ASD/ND risk gene list and their effect in the patient cohort. | | | | |
|---|---|---|---|---|
| gene | asd_rate_dn | ddid_rate_dn | qval_dnccPTV | Alt_name_or_note |
| ADNP | 0.001399689 | 0.003799392 | 8.52E−15 | |
| ANK2 | 0.001088647 | 0.000379939 | 1.43E−05 | |
| ANKRD11 | 0.000622084 | 0.006079027 | 9.55E−06 | Dropout in screen |
| ARID1B | 0.001399689 | 0.005889058 | 2.58E−10 | |

TABLE 2-continued

ASD/ND risk gene list and their effect in the patient cohort.

| gene | asd_rate_dn | ddid_rate_dn | qval_dnccPTV | Alt_name_or_note |
|---|---|---|---|---|
| ASH1L | 0.000933126 | 0.000379939 | 2.04E-05 | |
| ASXL3 | 0.000311042 | 0.003419453 | 0.019950532 | |
| CHD2 | 0.001088647 | 0.001899696 | 5.47E-06 | |
| CHD8 | 0.002954899 | 0.000949848 | 0 | |
| CTNNB1 | 0.000622084 | 0.002849544 | 3.98E-05 | |
| CUL3 | 0.000311042 | 0.000759878 | 0.301166206 | |
| DDX3X | 0.000155521 | 0.006079027 | 0 | |
| DSCAM | 0.000622084 | 0.00018997 | 0.000134664 | |
| DYRK1A | 0.000933126 | 0.003609422 | 8.22E-10 | |
| FBXO11 | 0.000311042 | 0.000949848 | 0.530919852 | |
| FOXP1 | 0.001399689 | 0.002659574 | 1.77E-12 | |
| GATAD2B | 0 | 0.001899696 | 0.923047848 | |
| KDM5B | 0.000933126 | 0.000569909 | 0.000345432 | |
| LARP4B | 0.000155521 | 0.000379939 | 0.514242847 | |
| MAP1A | 0 | 0.00018997 | 0.009309407 | Dropout in screen |
| MBD5 | 0.000311042 | 0.000569909 | 0.008457933 | |
| MED13L | 0.000777605 | 0.003229483 | 1.84E-06 | |
| MLL1 | 0.000466563 | 0.005889058 | 0.754464152 | KMT2A |
| MYST4 | 0 | 0.002469605 | 0.698791831 | KAT6B |
| POGZ | 0.001088647 | 0.002469605 | 1.09E-10 | |
| PTEN | 0.001088647 | 0.000379939 | 5.26E-08 | |
| QRICH1 | 0.000155521 | 0.000569909 | 0.103038387 | |
| SATB2 | 0.000311042 | 0.002849544 | 0.323451606 | |
| SCN2A | 0.003421462 | 0.00493921 | 0 | |
| SETD2 | 0.000155521 | 0.000569909 | 0.704208112 | |
| SETD5 | 0.000466563 | 0.003229483 | 0.000184044 | |
| SPEN | 0.000311042 | 0.000569909 | 0.758446035 | |
| SUV420H1 | 0.001088647 | 0.000569909 | 5.48E-10 | Dropout in screen |
| SYNGAP1 | 0.002177294 | 0.003229483 | 0 | |
| TCF20 | 0.000311042 | 0.001709726 | 0.029926217 | |
| TCF7L2 | 0.000311042 | 0.000759878 | 0.033914706 | |
| TNRC6B | 0.000311042 | 0.00018997 | 0.3063045 | |
| UPF3B | 0.000155521 | 0.000569909 | 0 | |
| WAC | 0.000466563 | 0.001139818 | 0.000408636 | |

For in vivo Perturb-Seq, Cas9-mediated genome editing was used (11-13) in a pooled approach to introduce mutations in each of the ASD/ND risk genes within progenitor cells of the mouse developing forebrain in utero, followed by scRNA-seq at P7 to read out both a barcode identifying the perturbation and the expression profile of the perturbed cells (FIG. 1A). Specifically, a transgenic mouse line that constitutively expresses Cas9 (14) was used and pools of gRNAs targeting the different risk genes were delivered by lentiviral infection into the lateral ventricles of the developing embryo in utero. Each lentiviral vector contained two different gRNAs targeting the 5'-end coding exons of one ASD/ND gene (to enhance knockout efficiency), and a blue fluorescent protein (BFP) reporter with a unique barcode corresponding to the perturbation identity (11-13). To minimize vector recombination, packaged each lentivirus was packaged separately and then pooled viruses at equal titers.

A pool of lentiviruses with equal gRNA representation was injected into the ventricles of the developing forebrain at E12.5 (FIG. 1A). In this approach, lentiviral injection leads to infection of neural progenitors lining the lateral ventricle of the developing forebrain, including progenitors of the neocortex and the ganglionic eminences. Since lentiviral vectors integrate into the genome, the progeny of the infected progenitors are labeled by BFP and carry a perturbation barcode corresponding to the target ASD/ND gene.

Figure 7A:
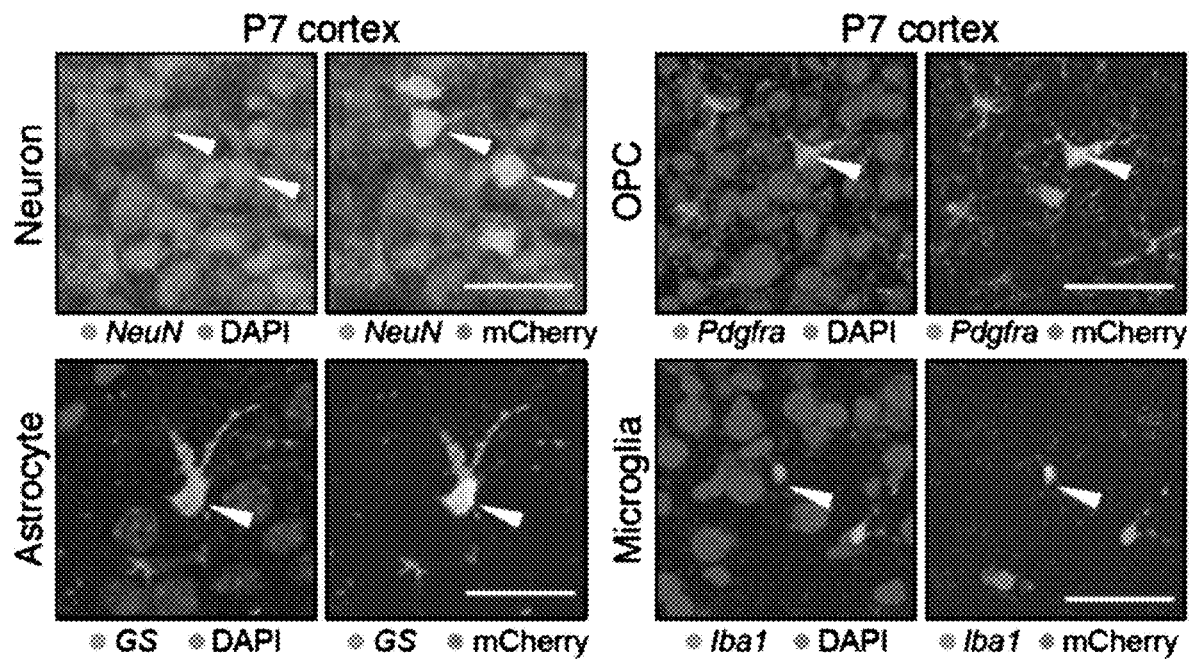
FIGS. 7A-7G—(FIGS. 7A-7B) Lentiviral injection at E12.5 sparsely infects neurons (NeuN+), astrocytes (Glutamine Synthase [GS]+), oligodendrocyte precursor cells (PDGFRA+), and microglia and macrophages (IBA1+) in the P7 neocortex (indicated by white arrows). Scale bar is 50 μm. In vivo Perturb-Seq lentiviral vector with an mCherry expression cassette allows immunohistochemical identification of the targeted cell types. Lentiviral vector expression, indicated by BFP expression as well as perturbation barcode expression, was present in microglia (and likewise in all cell types included in this study, FIGS. 8E-8F).
Figure 7B:
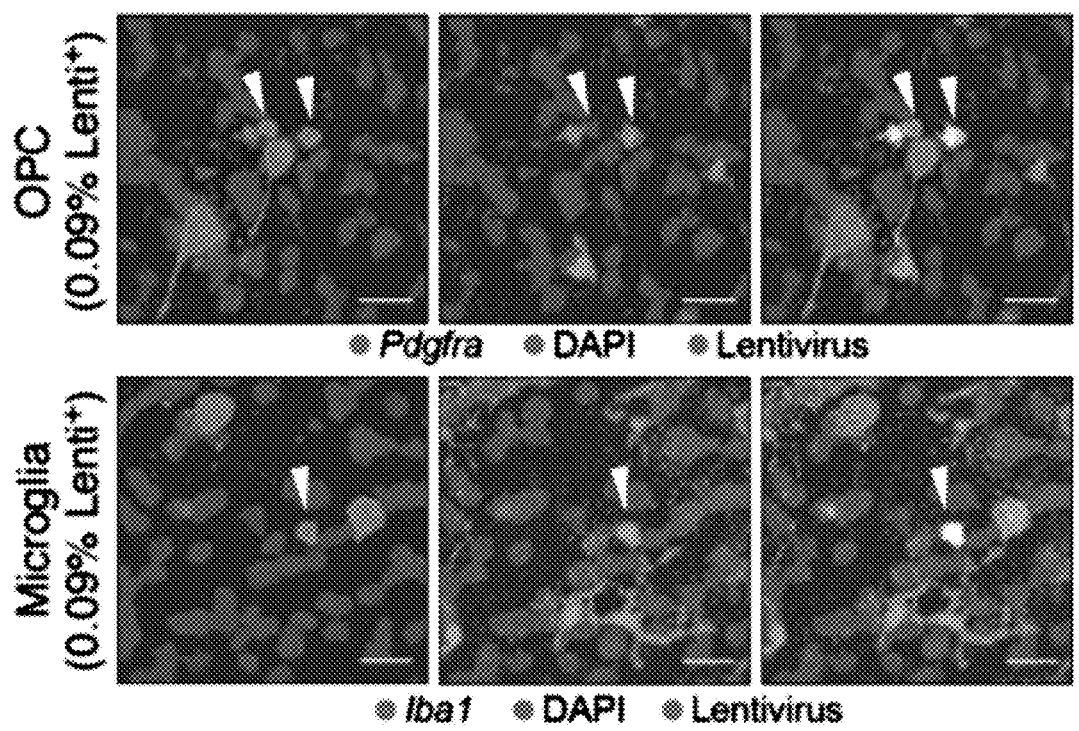
Figure 7C:
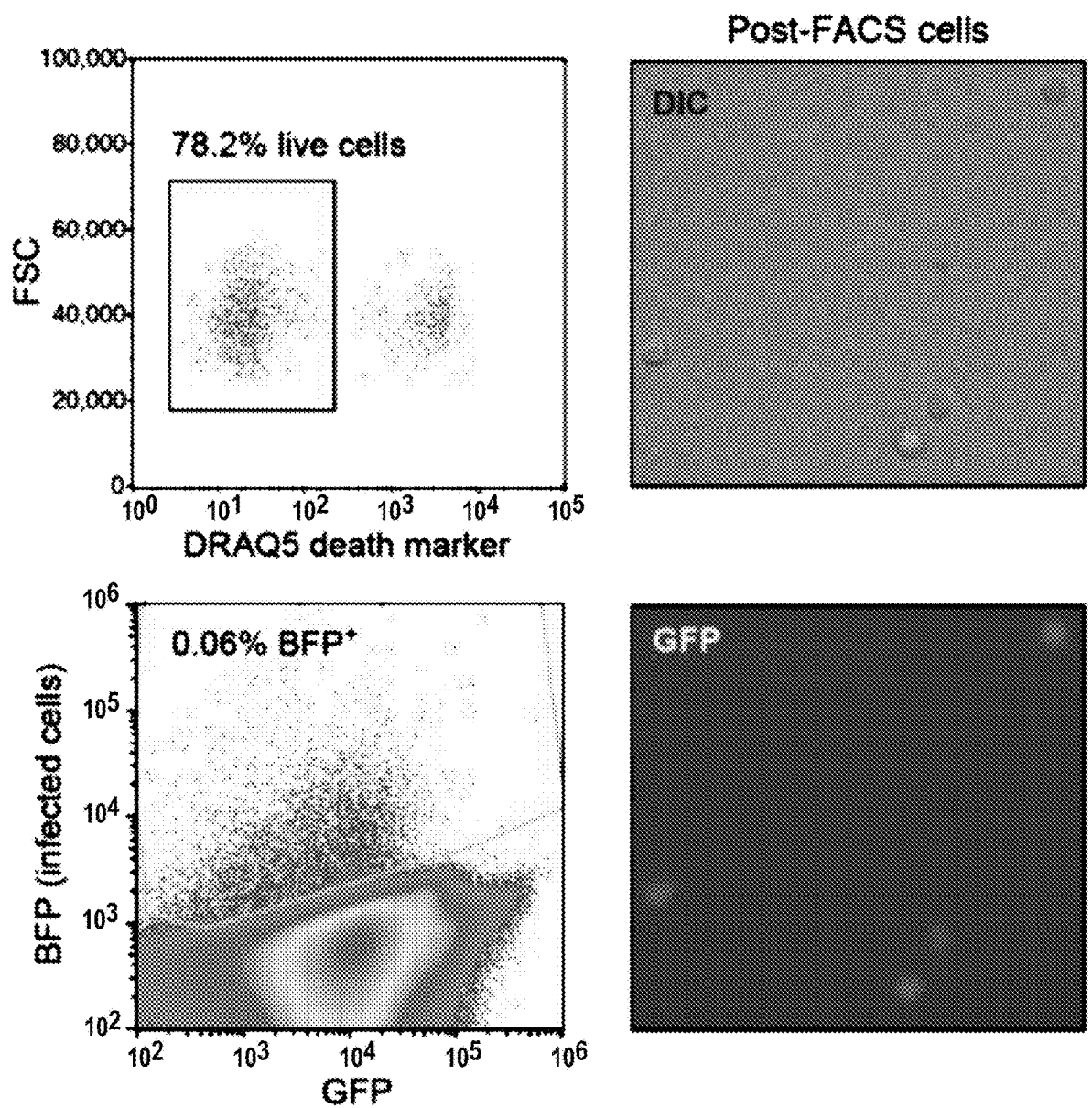

Both immunohistochemical analysis and scRNA-seq of BFP+cells at P7 showed that the Perturb-Seq vectors were expressed across a variety of neuronal and glial cell types in the cortex (FIGS. 1B-1C and 7A-7B). While microglia originate mostly from outside the targeted germinal zones, lentiviral vector expression was detected in cortical microglia, indicated by the presence of BFP as well as perturbation barcode expression, across multiple individual experiments (FIGS. 8E-8F). Without being bound by theory, it is possible that the in utero injection could have led to either local lesions that recruited and expanded the number of microglia along the injection tract, or that microglia were labeled within the parenchyma along the same tract. Overall, this approach allowed examination of the effects of each perturbation across a wide range of cell types from distinct brain regions (i.e., cortical projection neurons, interneurons, astroglia, oligodendroglia, etc.), and, importantly, under sparse labeling conditions where less than 0.1% of cells in the cortex were perturbed, and thus development of individual perturbed cells is highly unlikely to be affected by perturbed neighbors (FIGS. 7A-7C).

Figure 7D:
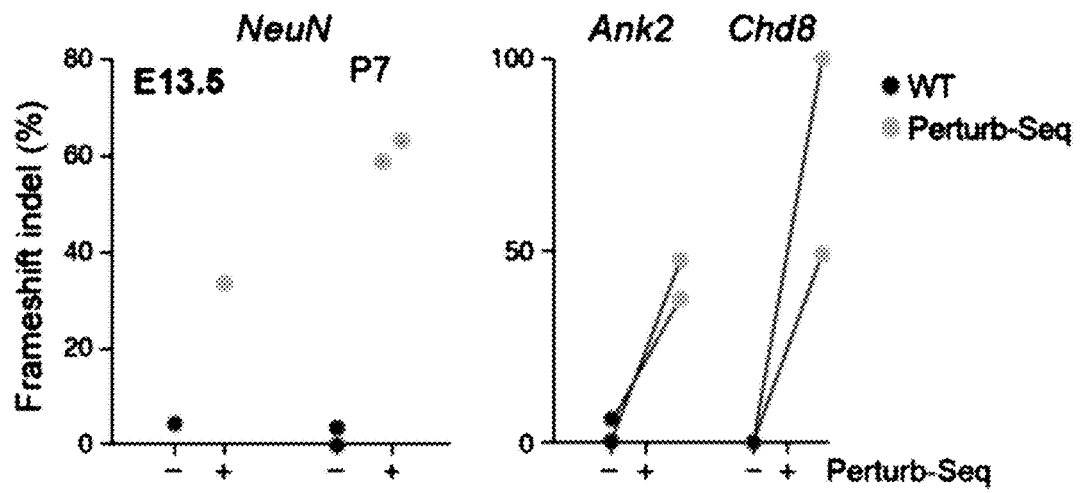
Figure 7E:
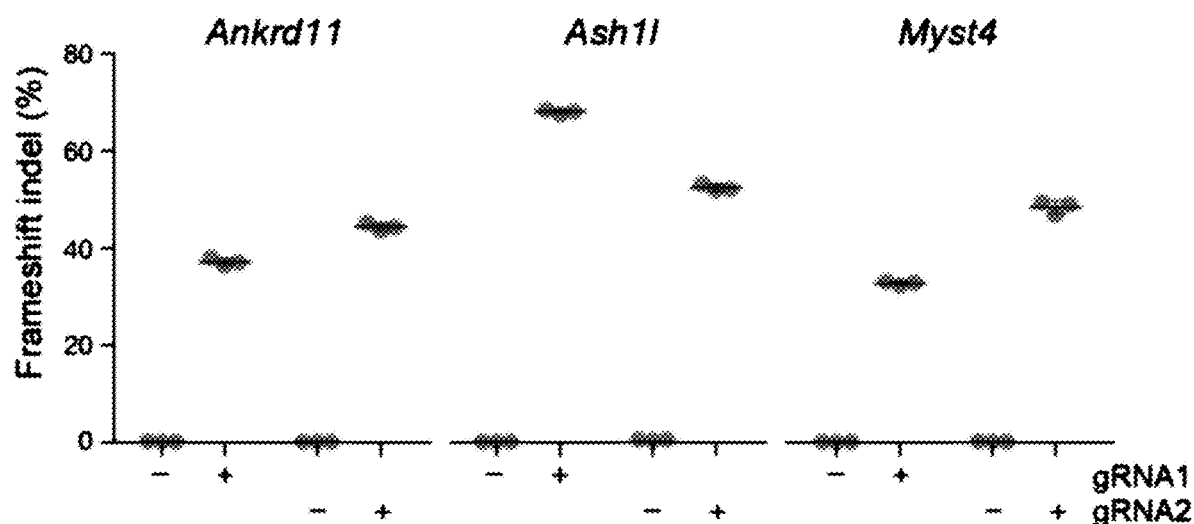

Example 2—In Vivo Perturb-Seq Targets Diverse Cell Types without Affecting Overall Cell Type Composition The experiment was performed with 18 different cohorts of pregnant mice, for a total of 163 embryos, each subjected to the entire pool of perturbations. The cortical tissues were micro-dissected and dissociated separately at P7, FACS-enriched the perturbed cells by selecting for BFP expression and droplet-based scRNA-seq was used to obtain each cell's expression profile along with its perturbation barcode. The cell survival rate after FACS was 78%, and a 40-70% frameshift insertion/deletion for each gRNA target among the infected cells was confirmed (FIGS. 7D-7E).

Figure 1D:
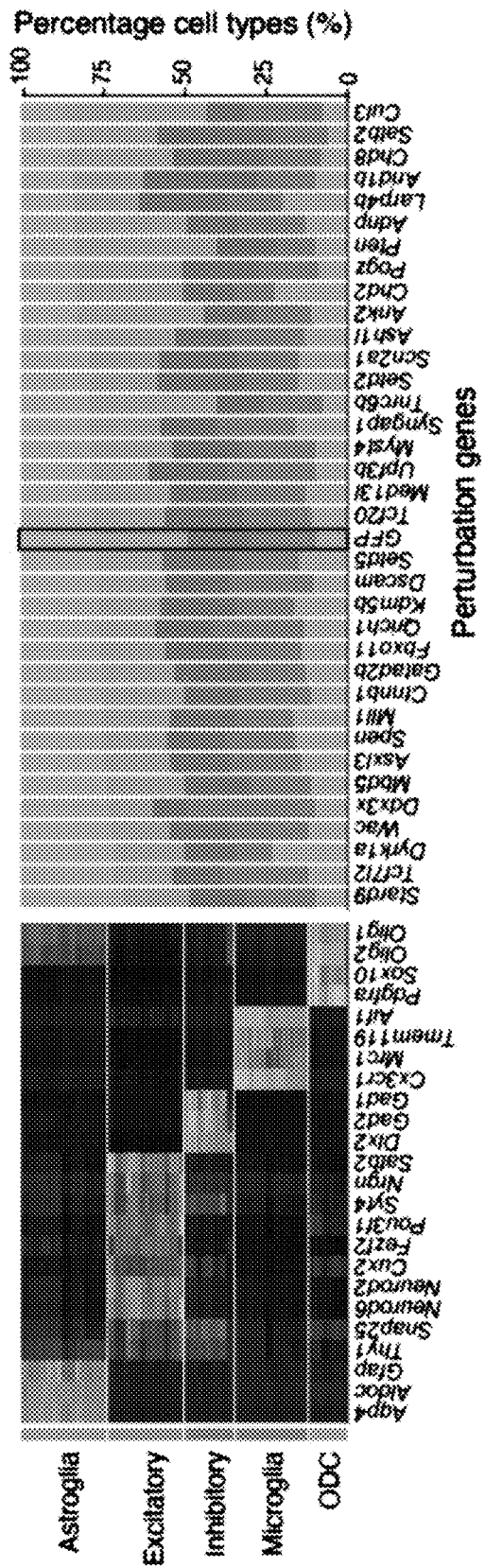
Figure 1E:
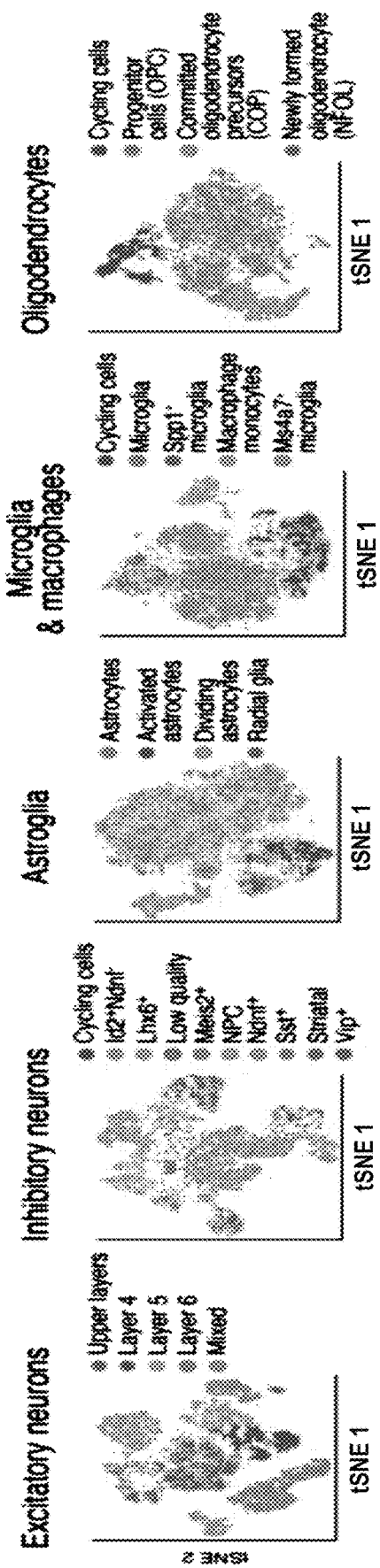
Figure 7F:
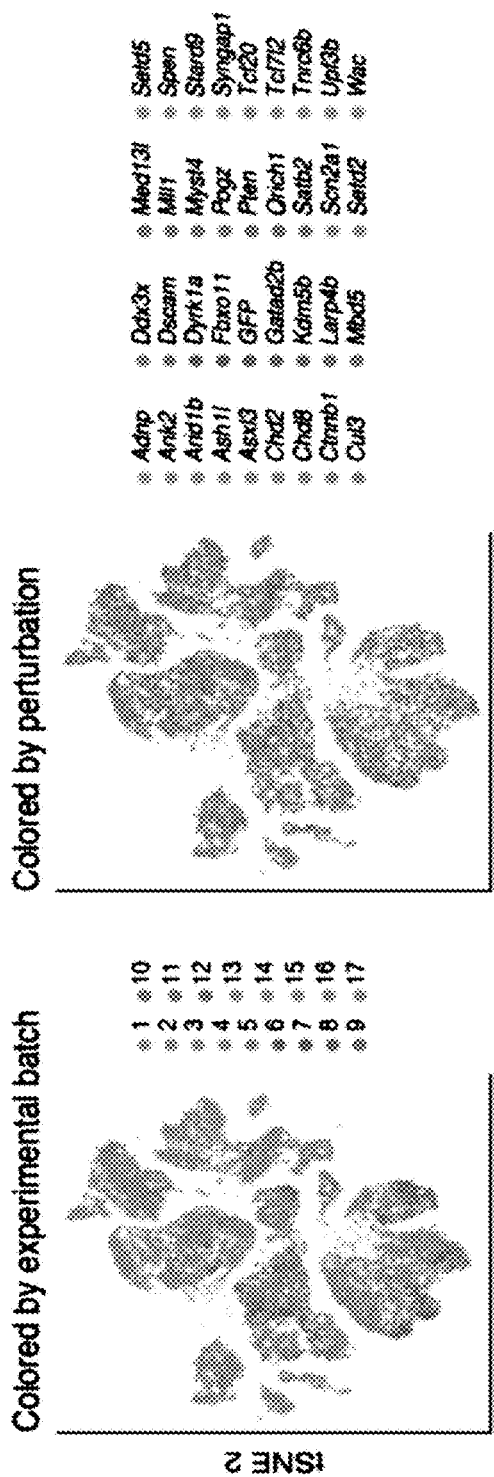

This multiplexed experimental design allowed testing of the cell-autonomous effect of all perturbations against the effect of a negative control construct targeting the endogenous GFP in the Rosa26 locus, thus controlling for effects related to viral infection, among other confounders. To minimize batch-dependent variation, the control construct was included in the same pool as the perturbation vectors (FIG. 7F). After quality control, a total of 46,770 neocortical cells across 17 high-quality experimental batches was retained for further analysis. Cells were partitioned into major cell classes using Louvain clustering (15) and were annotated by known marker gene expression (16, 54) (FIG. 1D).

Figure 7G:
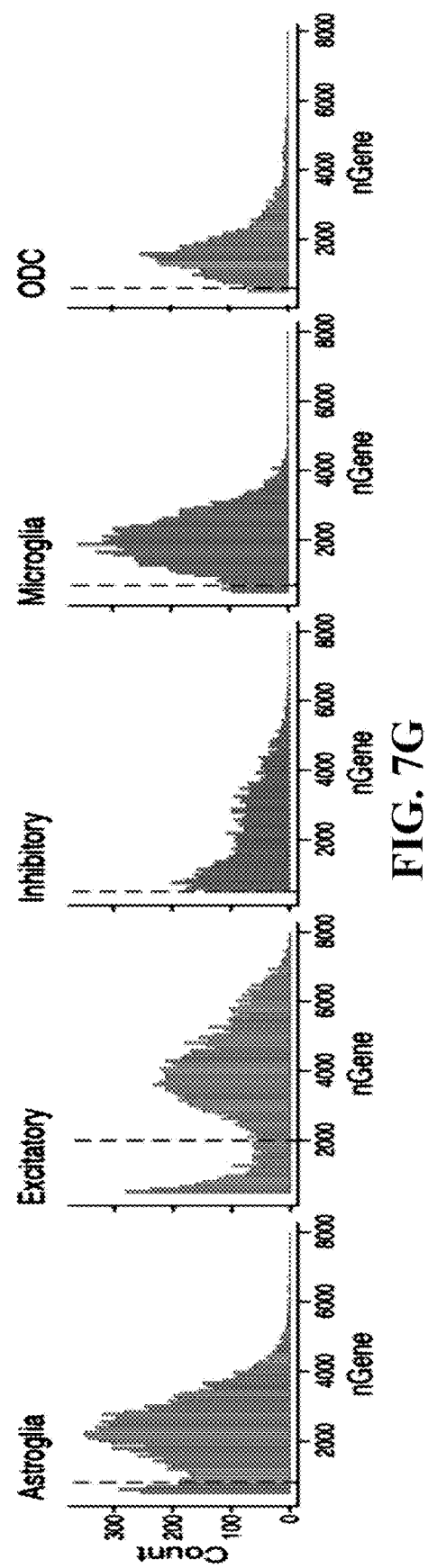

Five broad cell populations from this cortical dataset were focused on for downstream analysis: cortical projection neurons (8,450 cells), cortical inhibitory neurons (5,532 cells), astrocytes (9,526 cells), oligodendrocytes (4,279 cells), and microglia/macrophages (8,070 cells) (thus excluding vascular, endothelial, and contaminant hippocampal and striatal cells). Some remaining low-quality cells in these five major cell classes were further filtered out, retaining 35,857 high-quality cells (median of 2,436 detected genes per cell overall, and median of 4,084 genes in the projection neuron cluster, as expected from their large size and known high RNA content (FIG. 7G)). Each of the five major cell types were subclustered separately and annotated biologically meaningful subclusters (FIGS. 1E and 10A-10F).

Figure 8A:
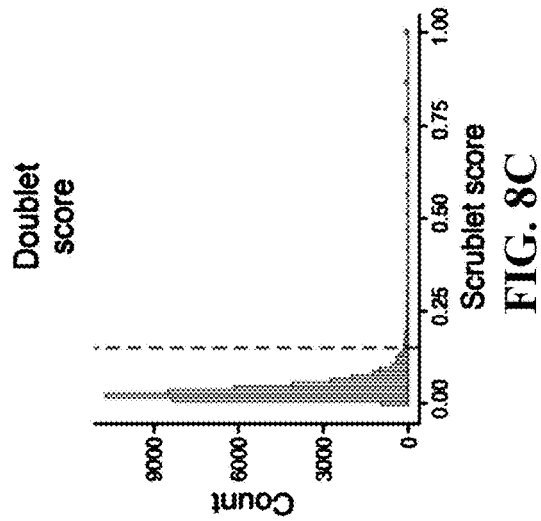
FIGS. 8A-8G—(FIG. 8A) The distribution of each perturbation vector in the lentiviral pool.
Figure 8B:
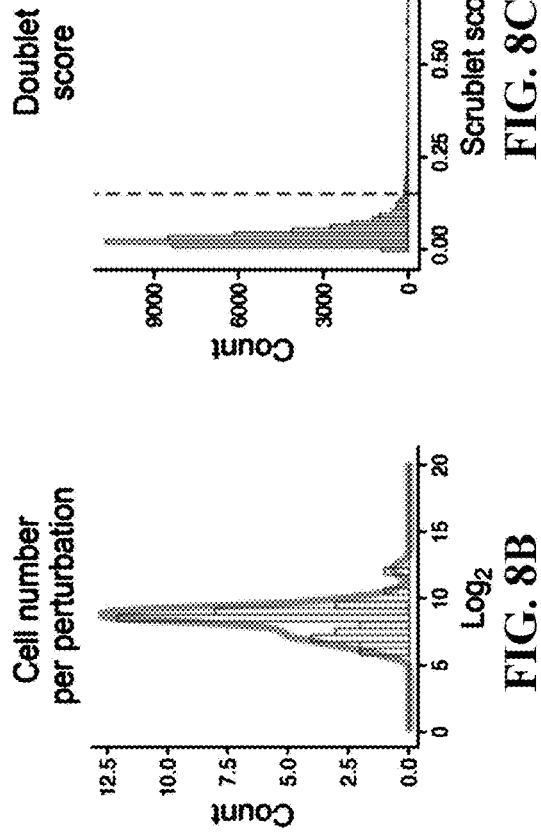
Figure 8C:
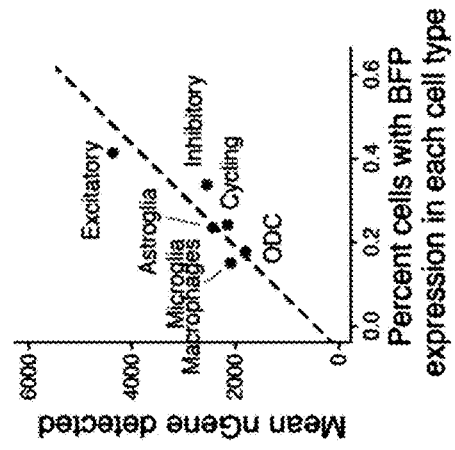
Figure 8D:
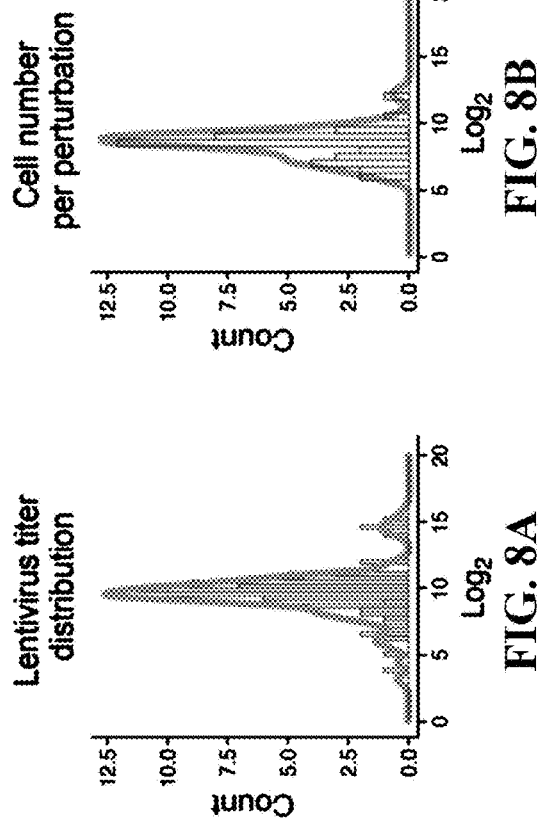
Figure 8E:
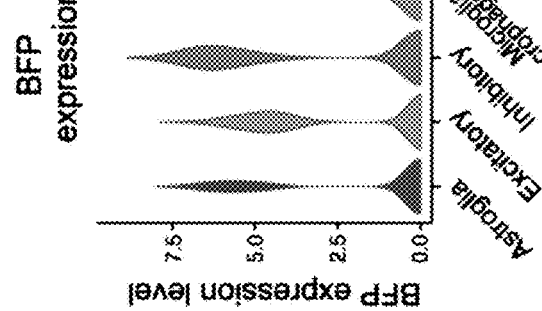
Figure 8F:
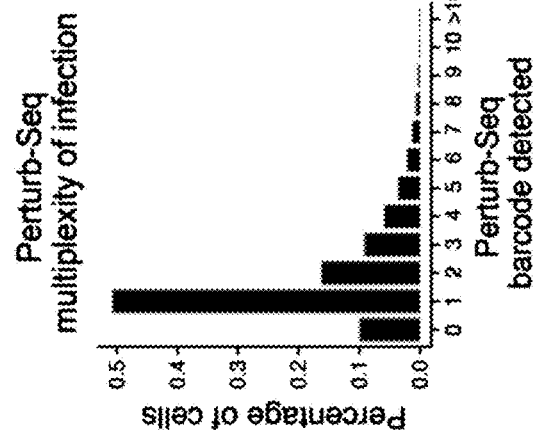
Figure 8G:
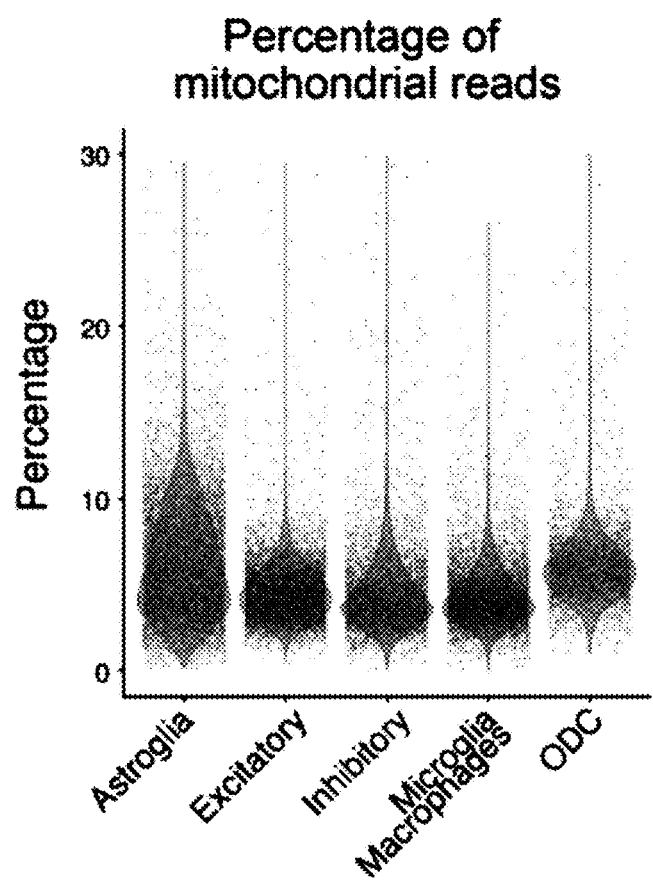
Figure 9A:
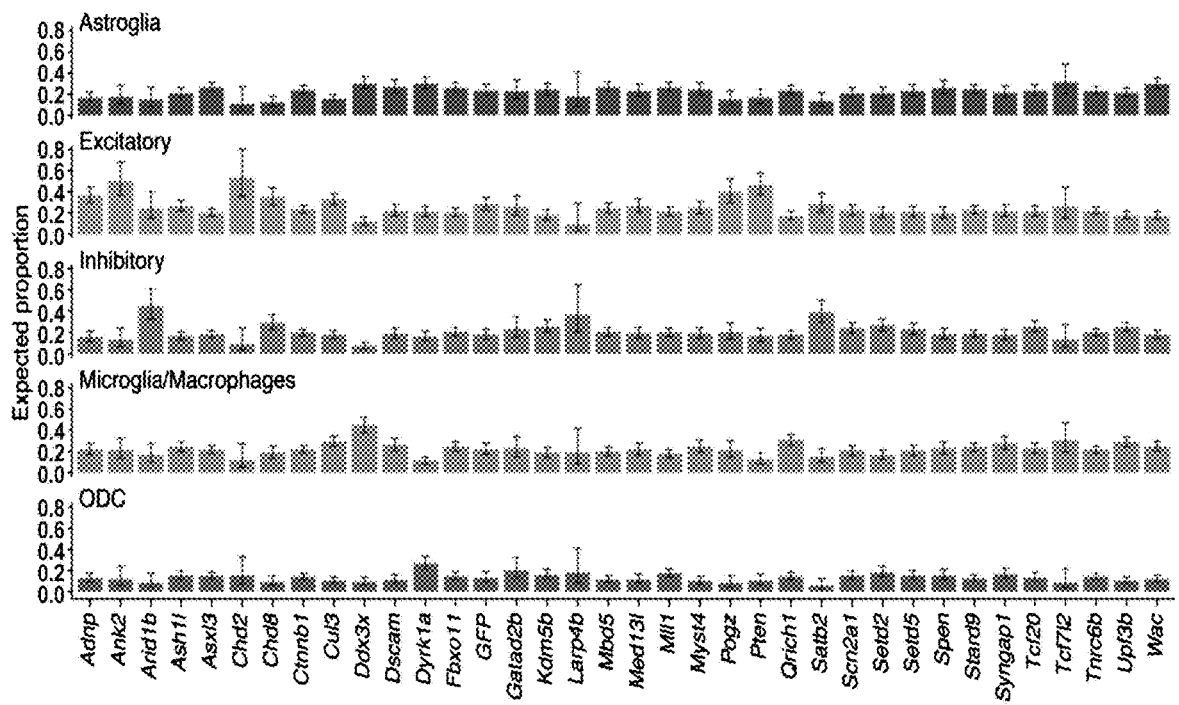
FIGS. 9A-9C—(FIG. 9A) Proportion of the 5 major cell types in each perturbation group.
Figure 9B:
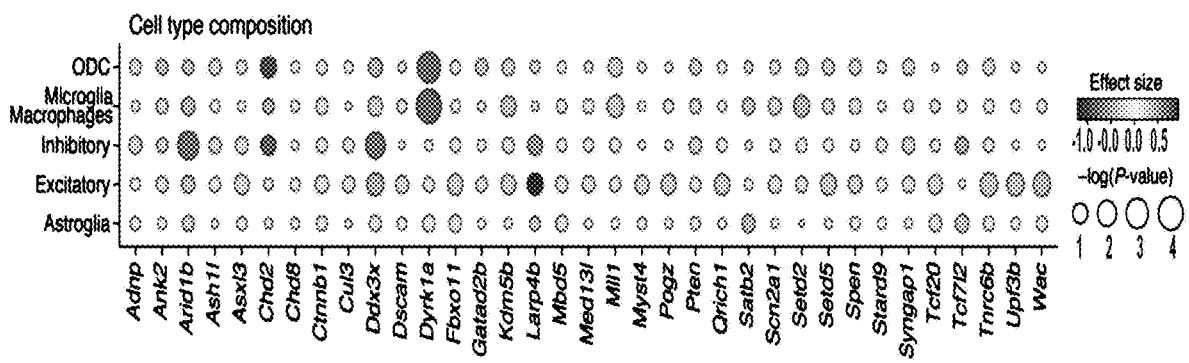
Figure 9C:
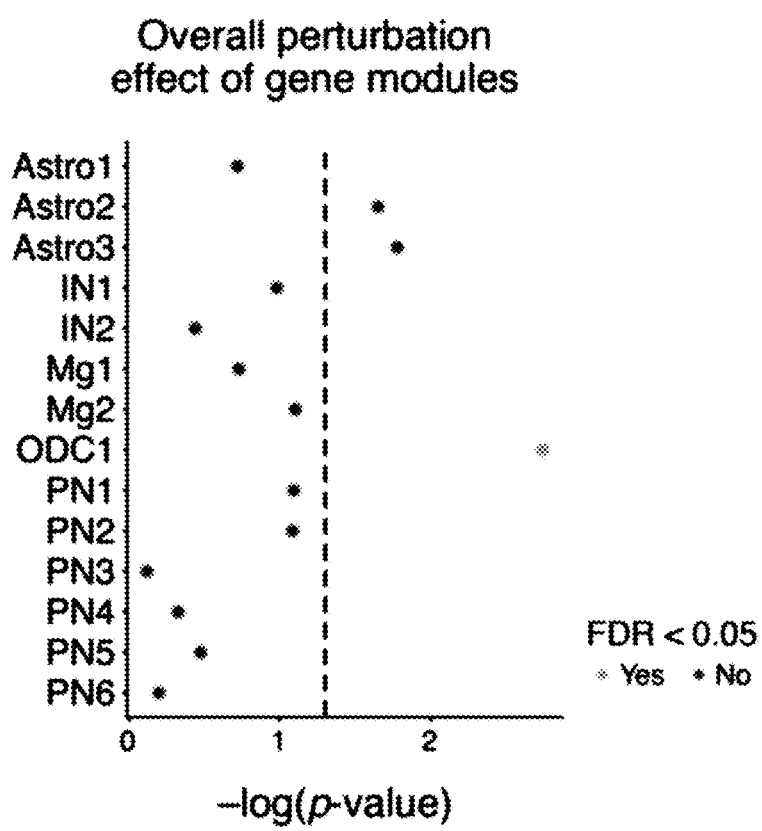
Figure 10C:
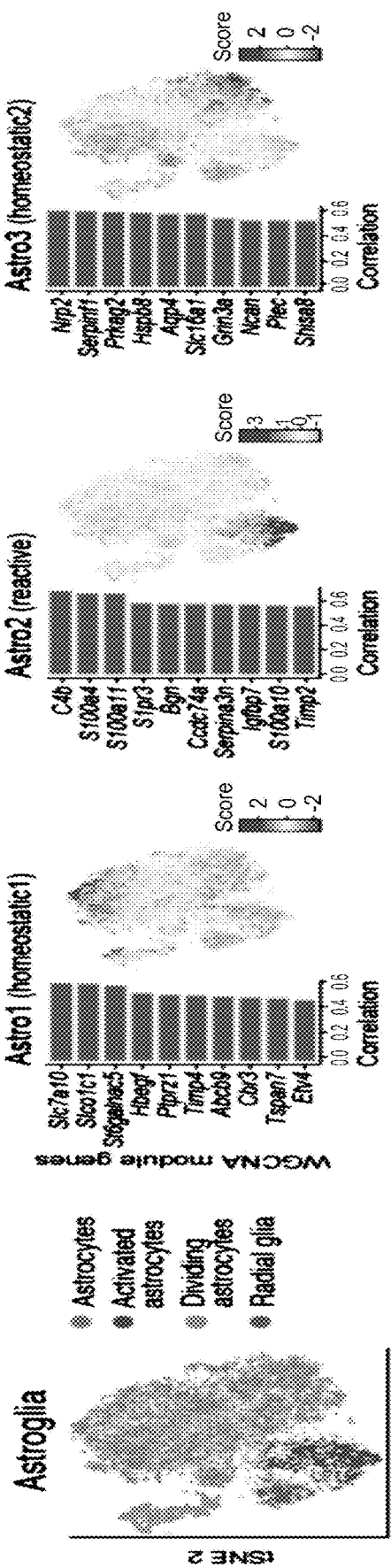
Figure 10D:
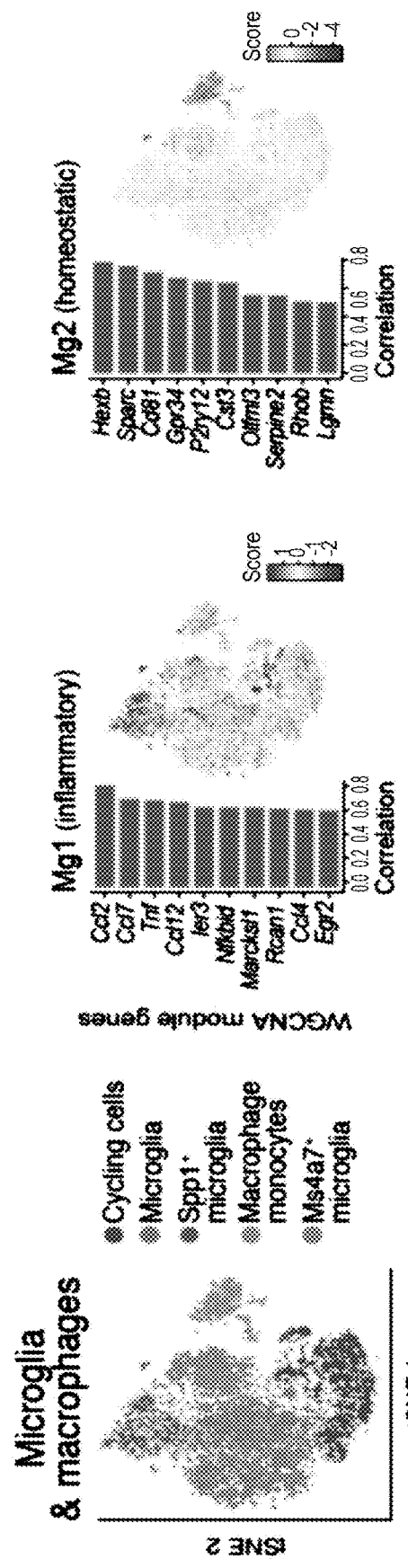
Figure 10E:
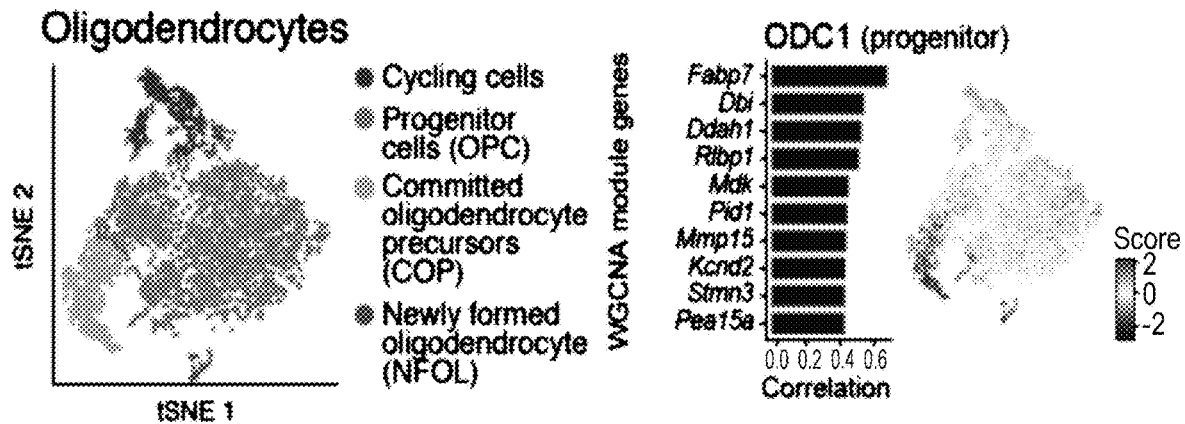
Figure 10F:
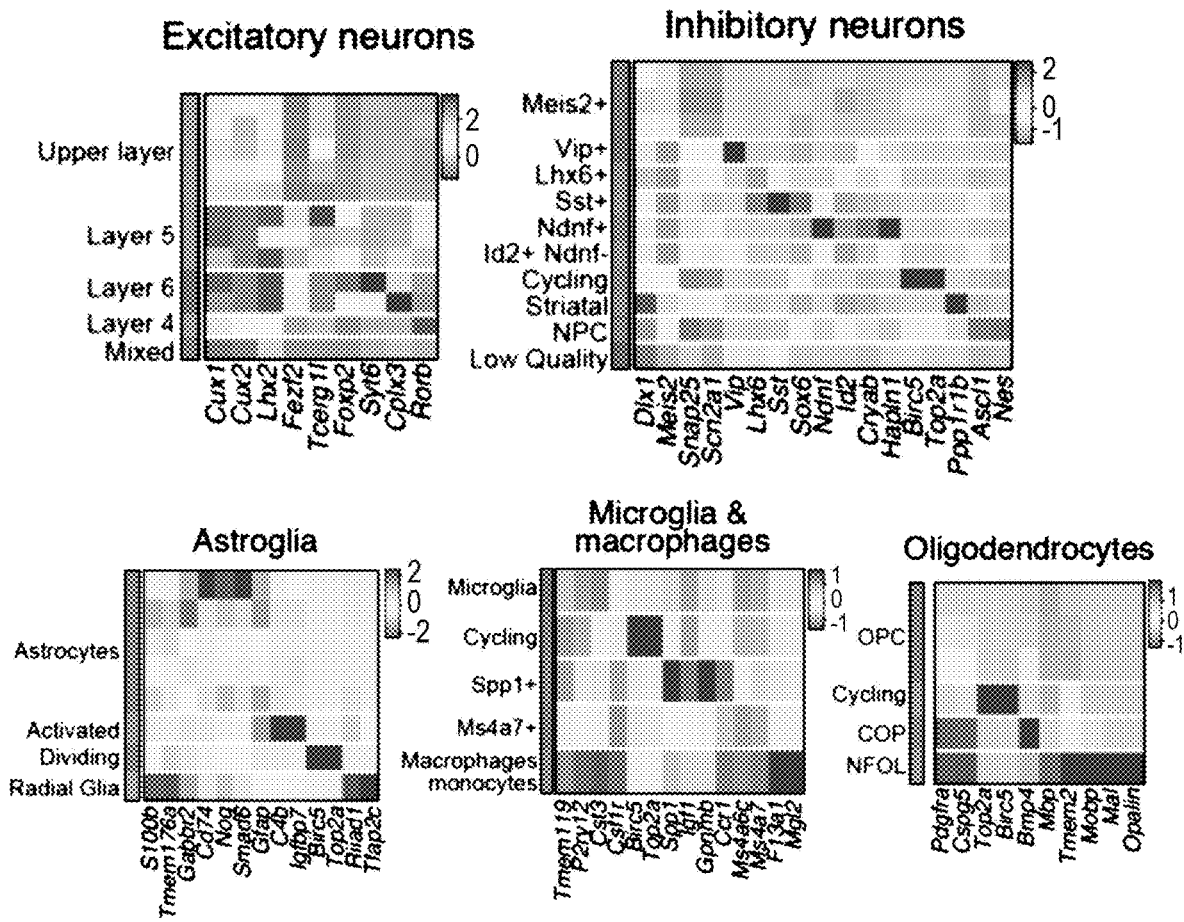
Figure 11A:
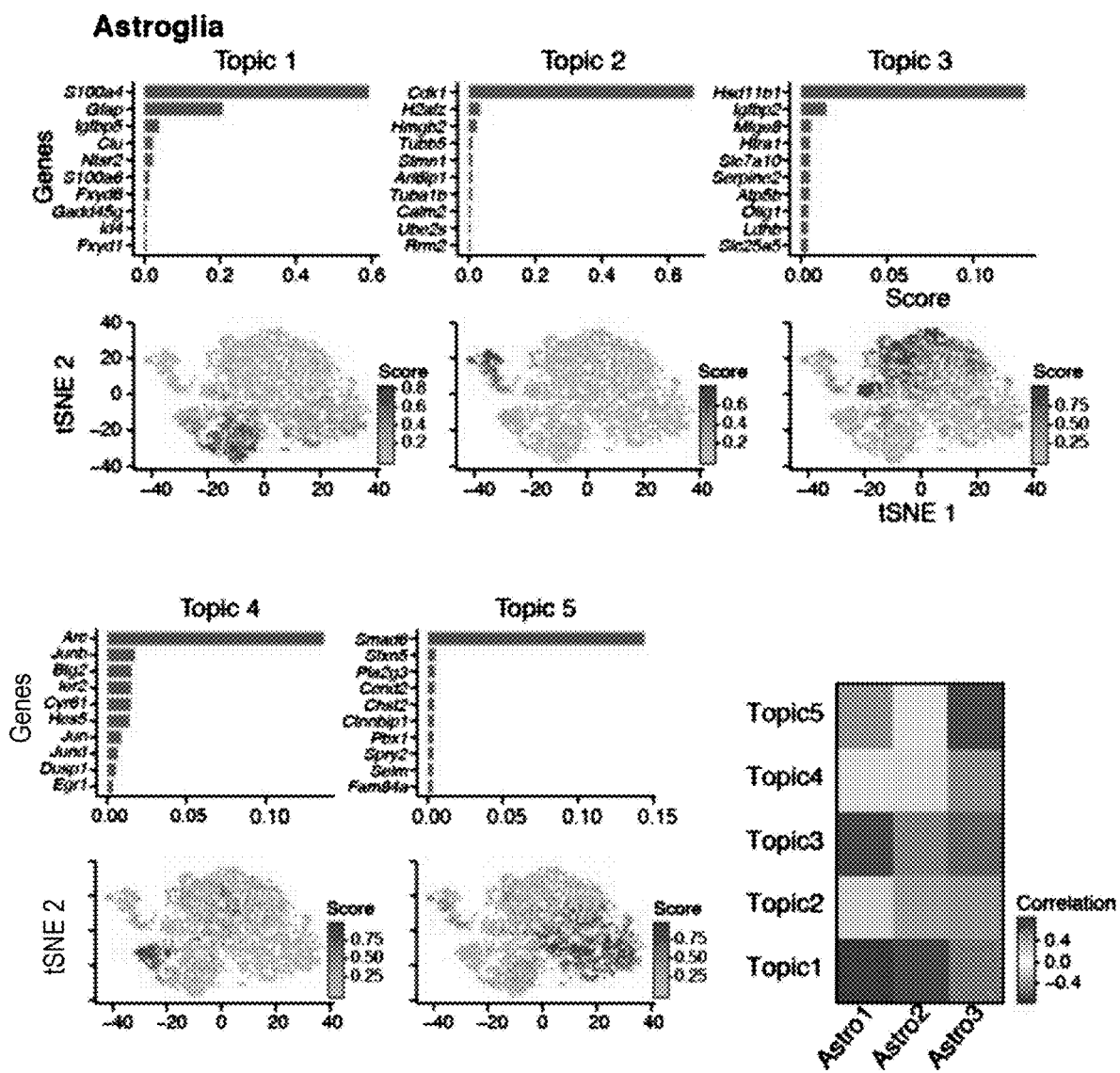
FIGS. 11A-11E—Topics identified by structural topic modeling (STM) and their correlation with WGCNA modules. Gene score indicates the lift score from STM analysis; a gene with high gene score is highly representative of the given topic.
Figure 11B:
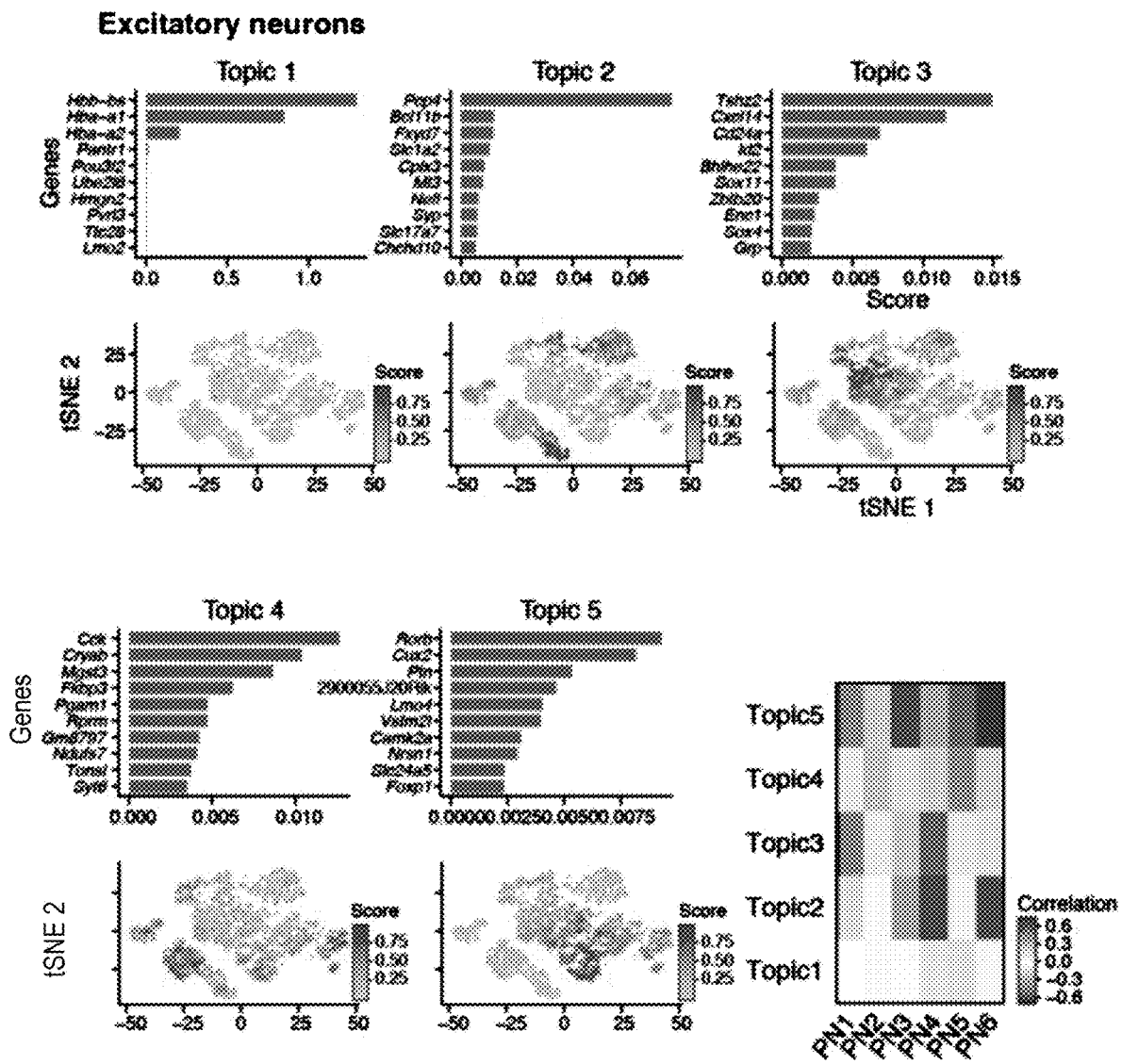
Figure 11C:
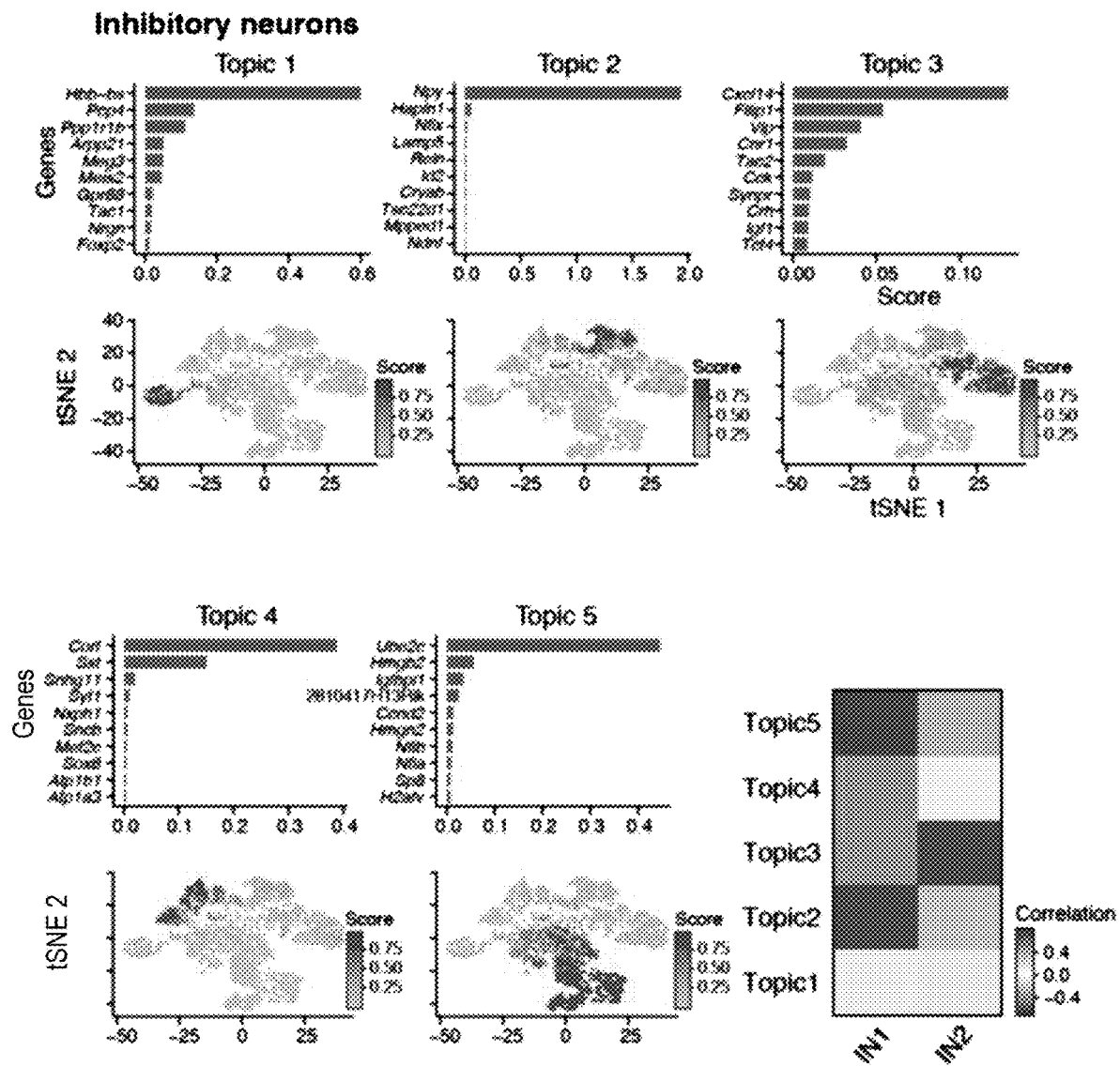
Figure 11D:
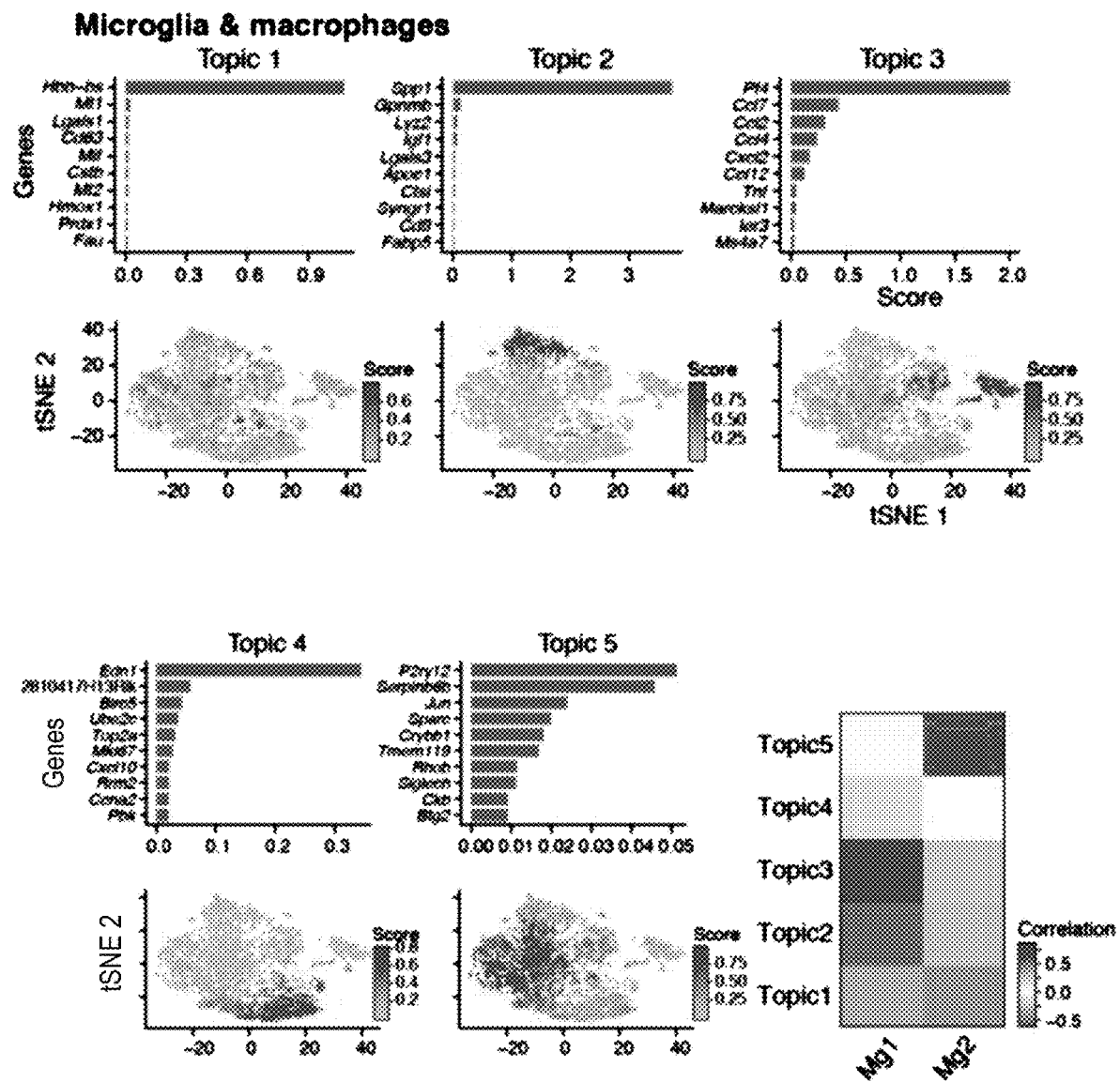
Figure 11E:
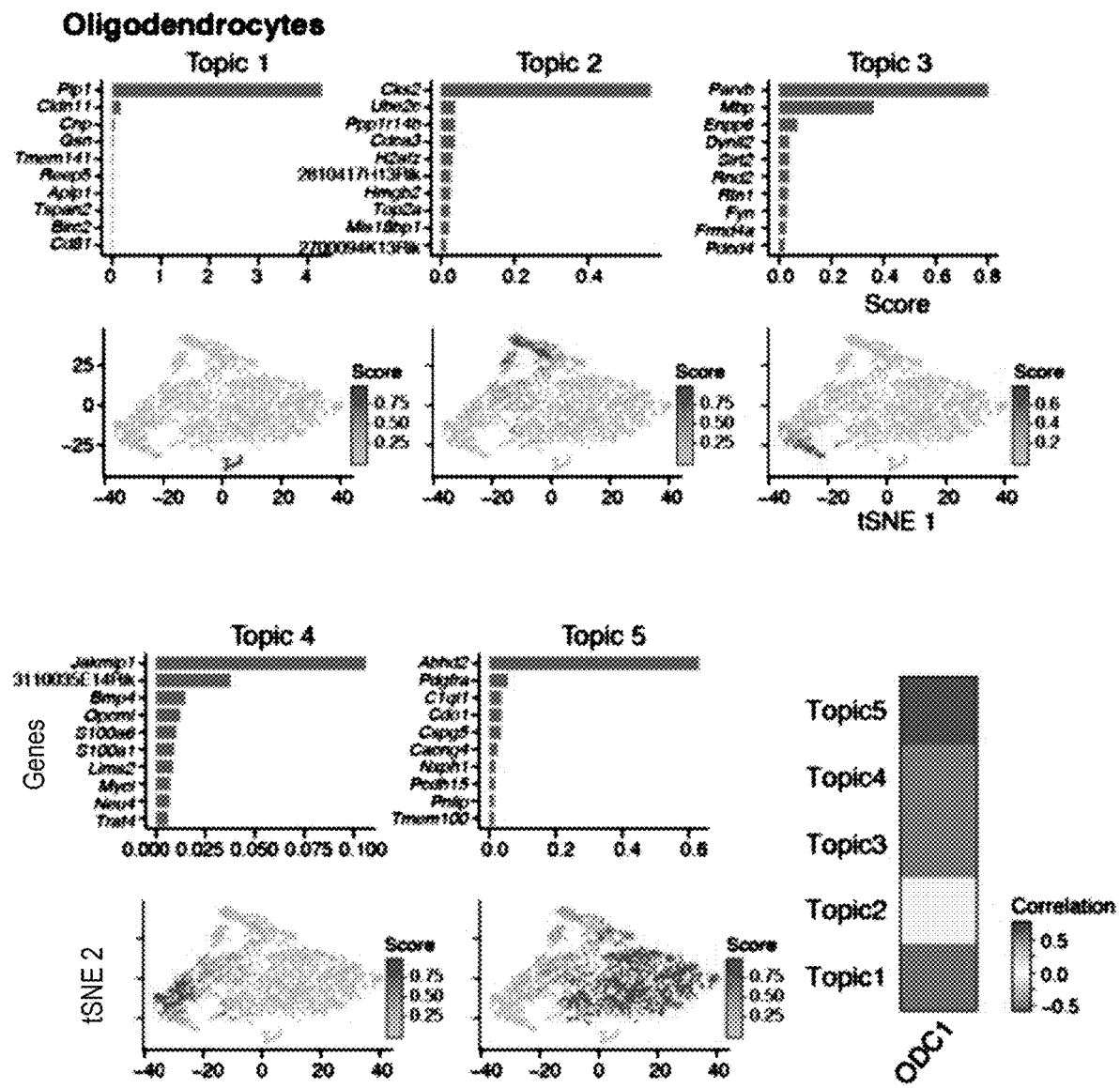
Figure 12A:
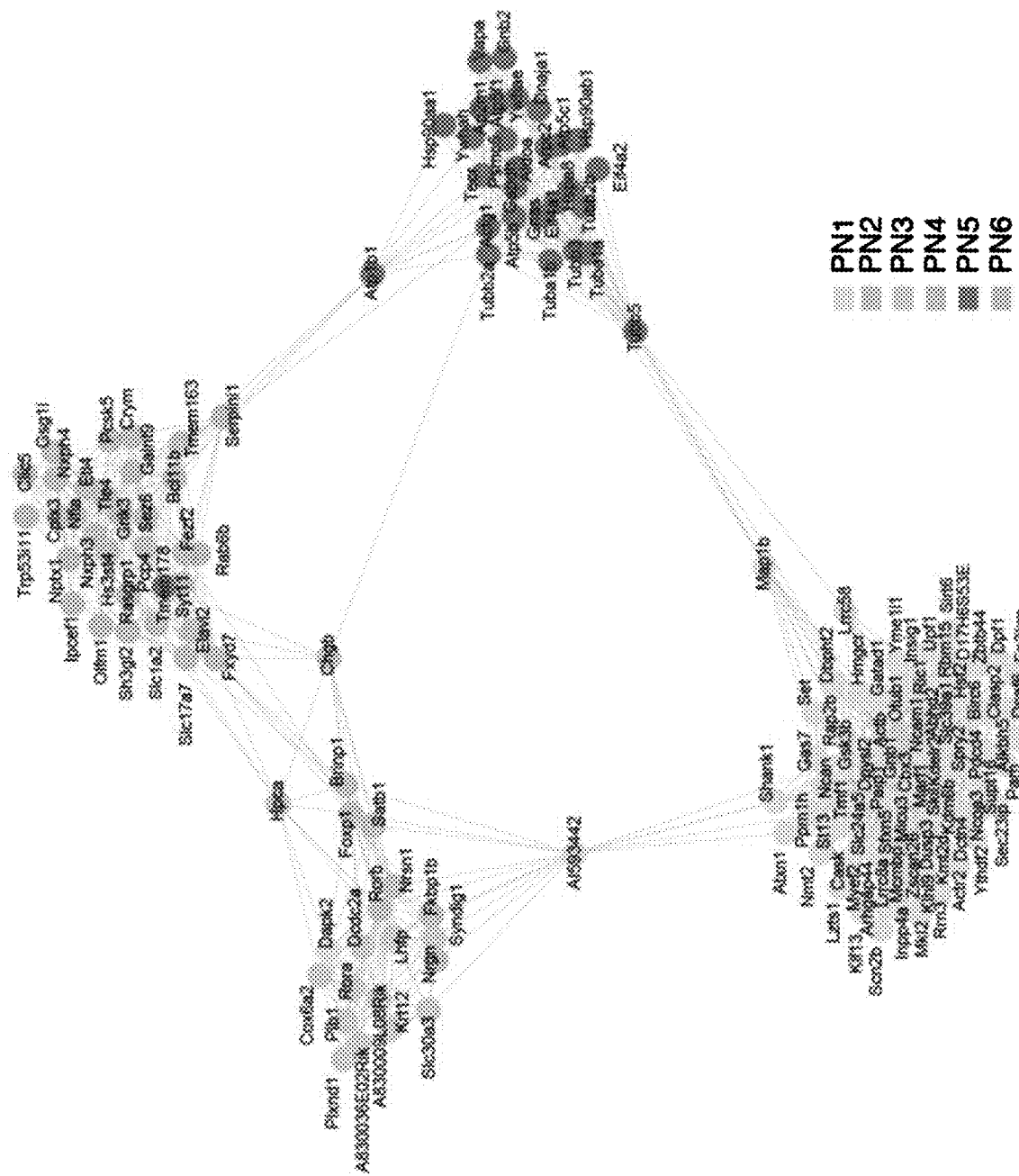
FIGS. 12A-12E—Graph visualization of the 14 WGCNA network modules in 5 major cell types. Pairwise correlation was computed between each two genes, and a directed 11 nearest neighbor graph was generated and plotted with igraph.
Figure 12B:
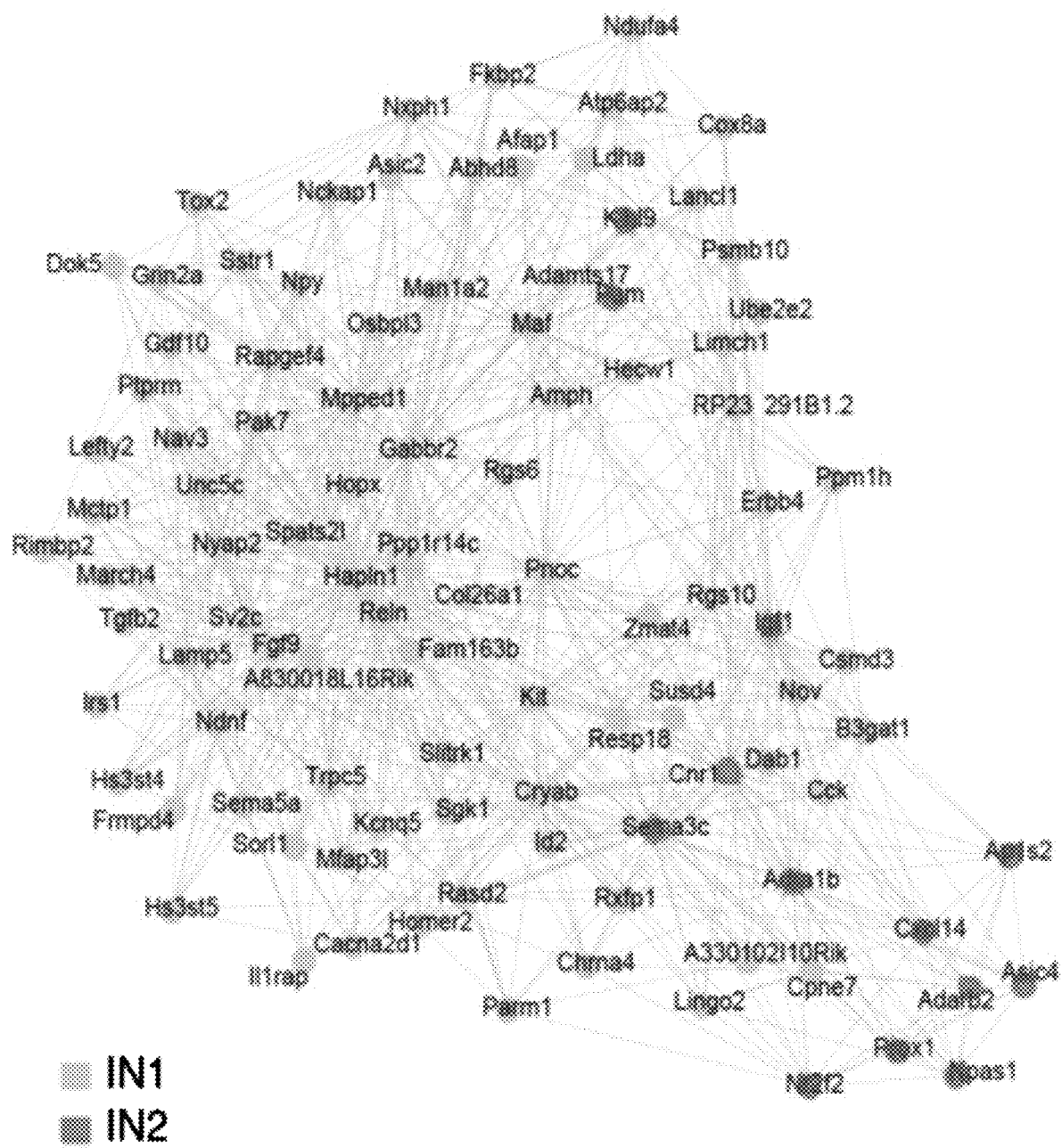
Figure 12C:
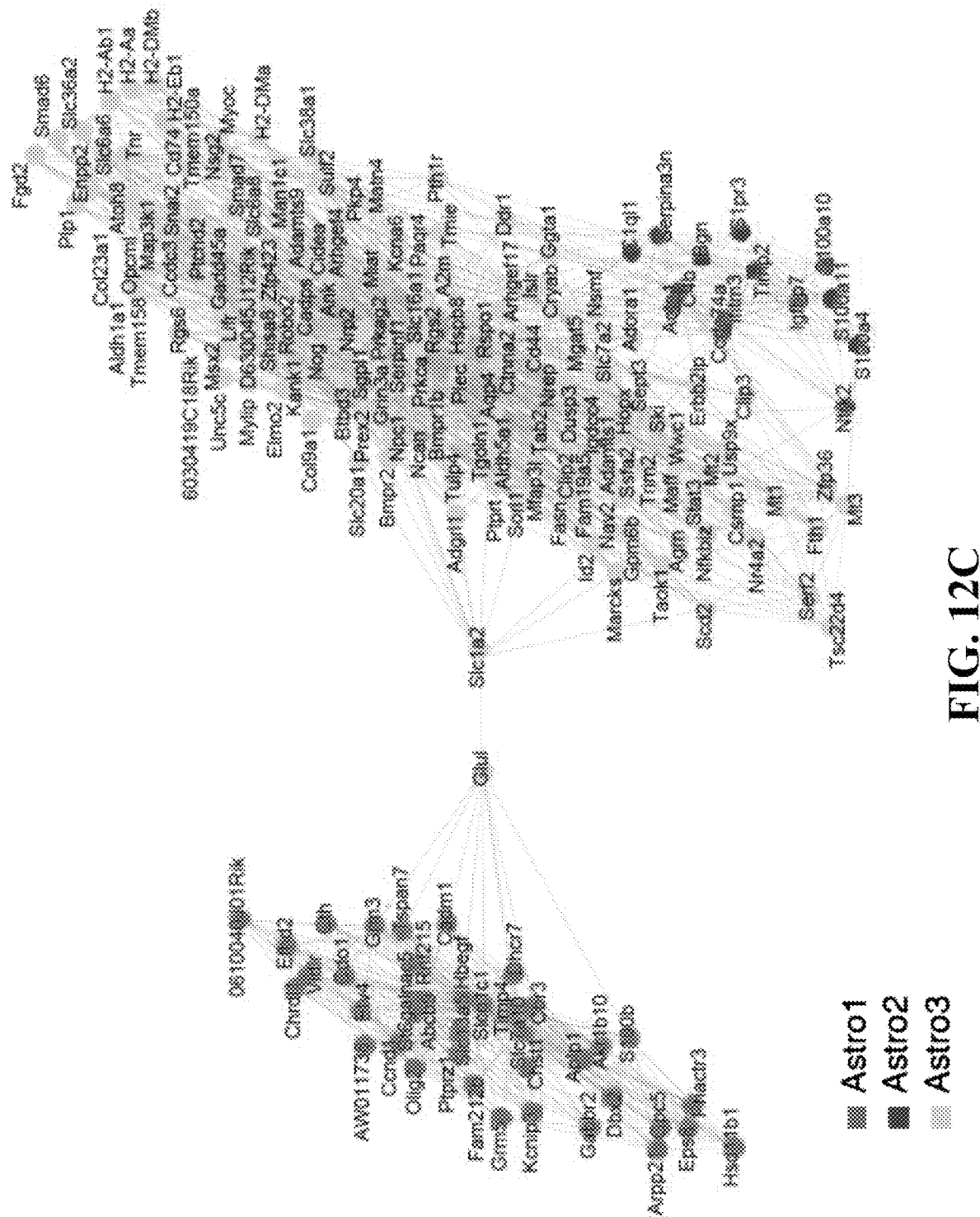
Figure 12D:
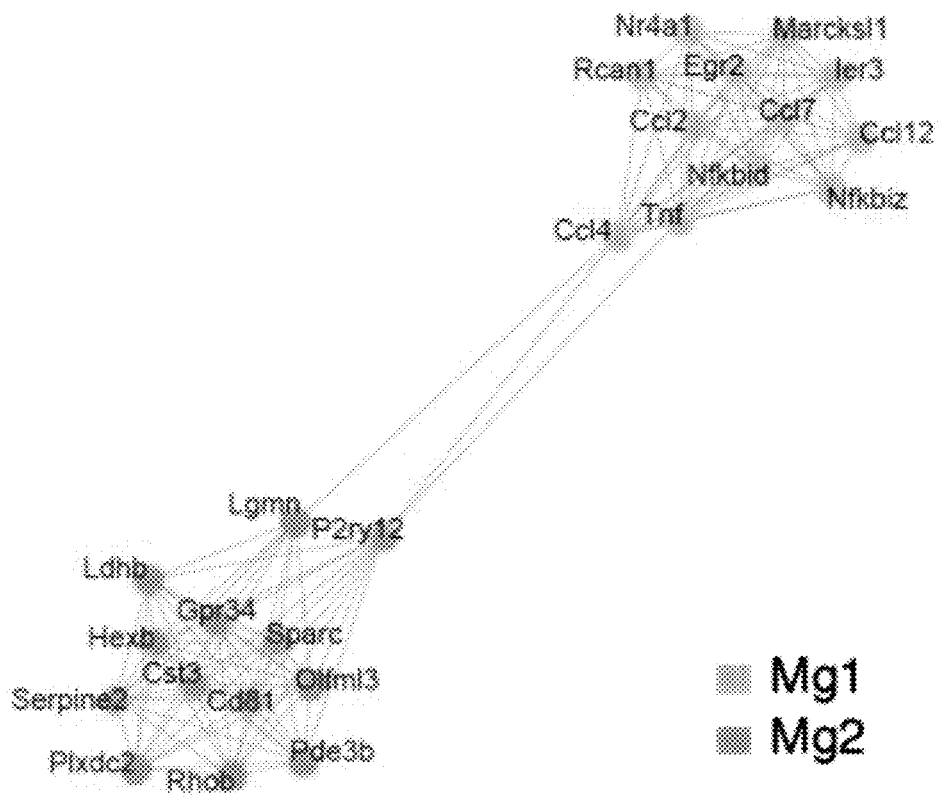
Figure 12E:
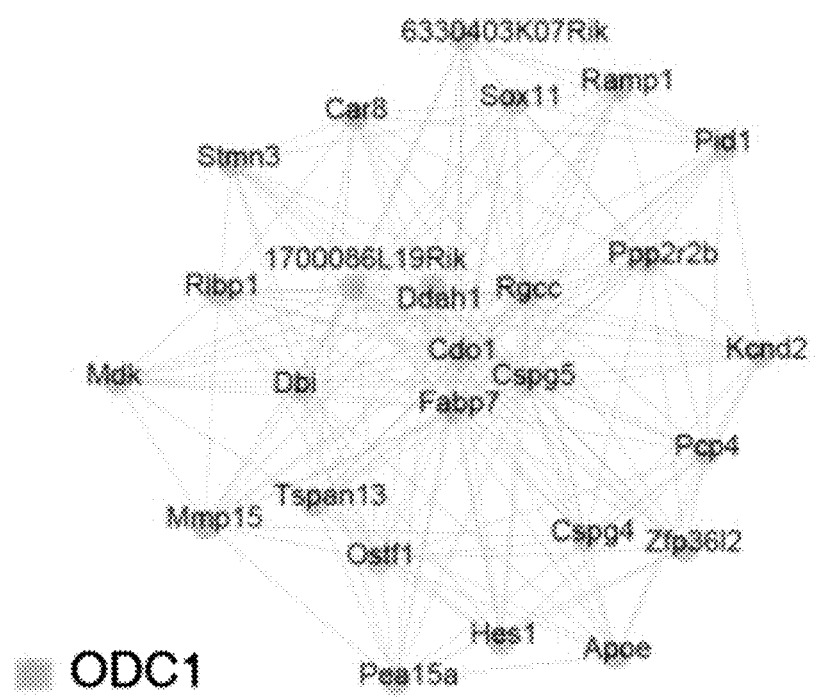
Figure 13A:
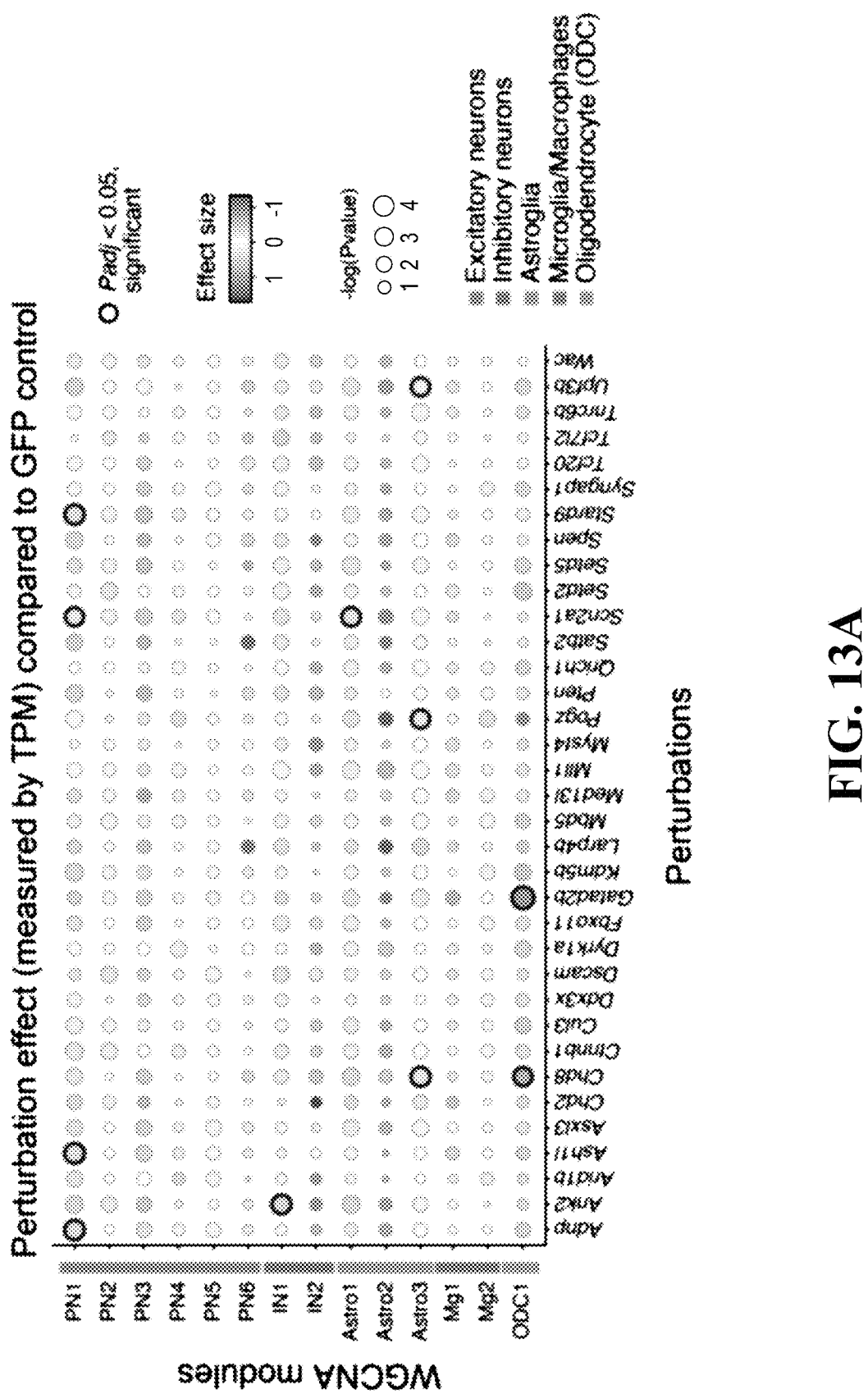
FIGS. 13A-13E—(FIG. 13A) ASD/ND risk gene perturbation effects in different WGCNA gene modules compared to GFP controls, measured by TPM. Dot color corresponds to effect size, dot size corresponds to base 10 log(P-value). P-values were extracted from the analysis in FIGS. 3A-3F; Padj was calculated using Benjamini & Hochberg FDR correction.
Figure 13B:
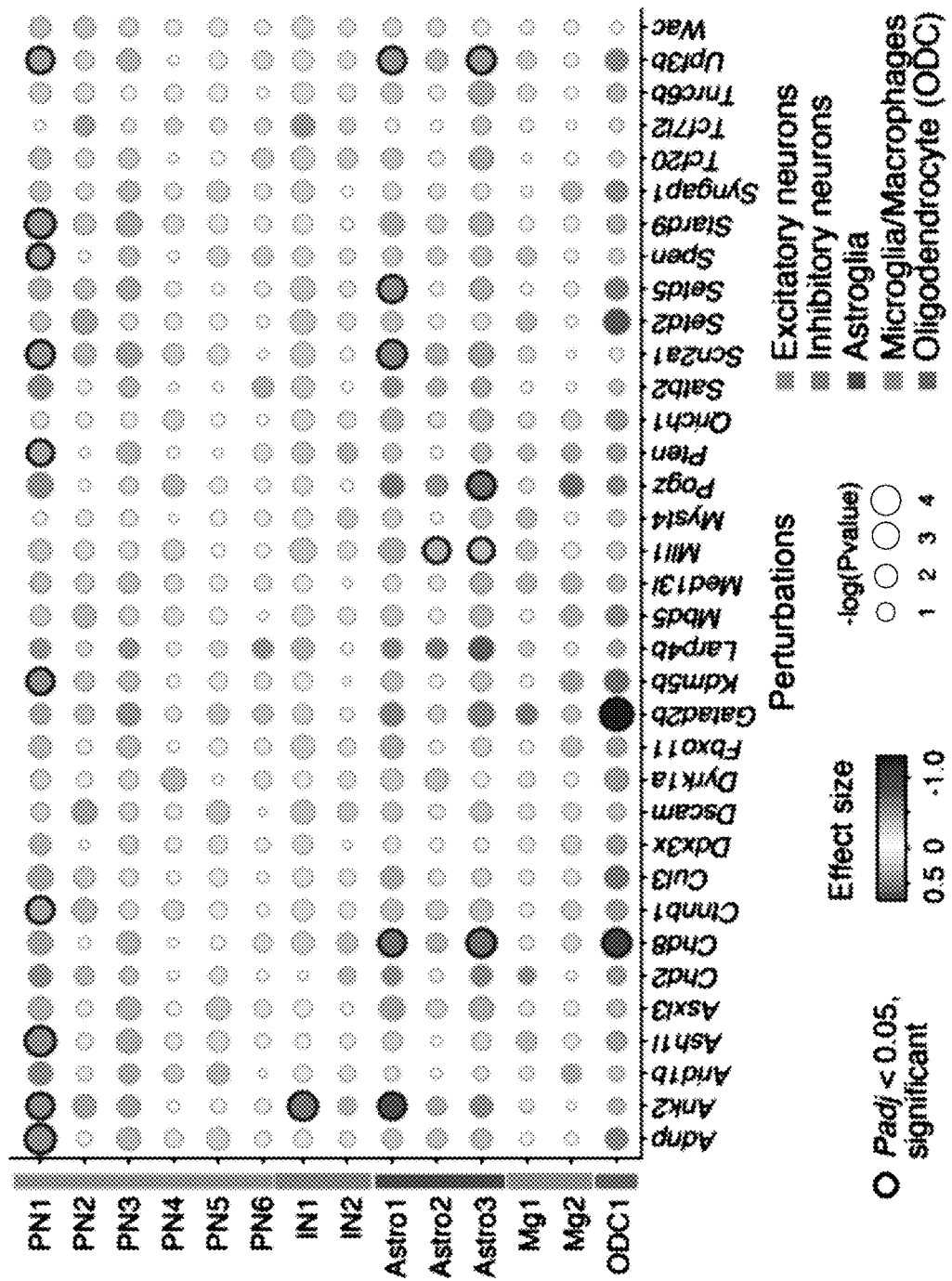
Figure 13C:
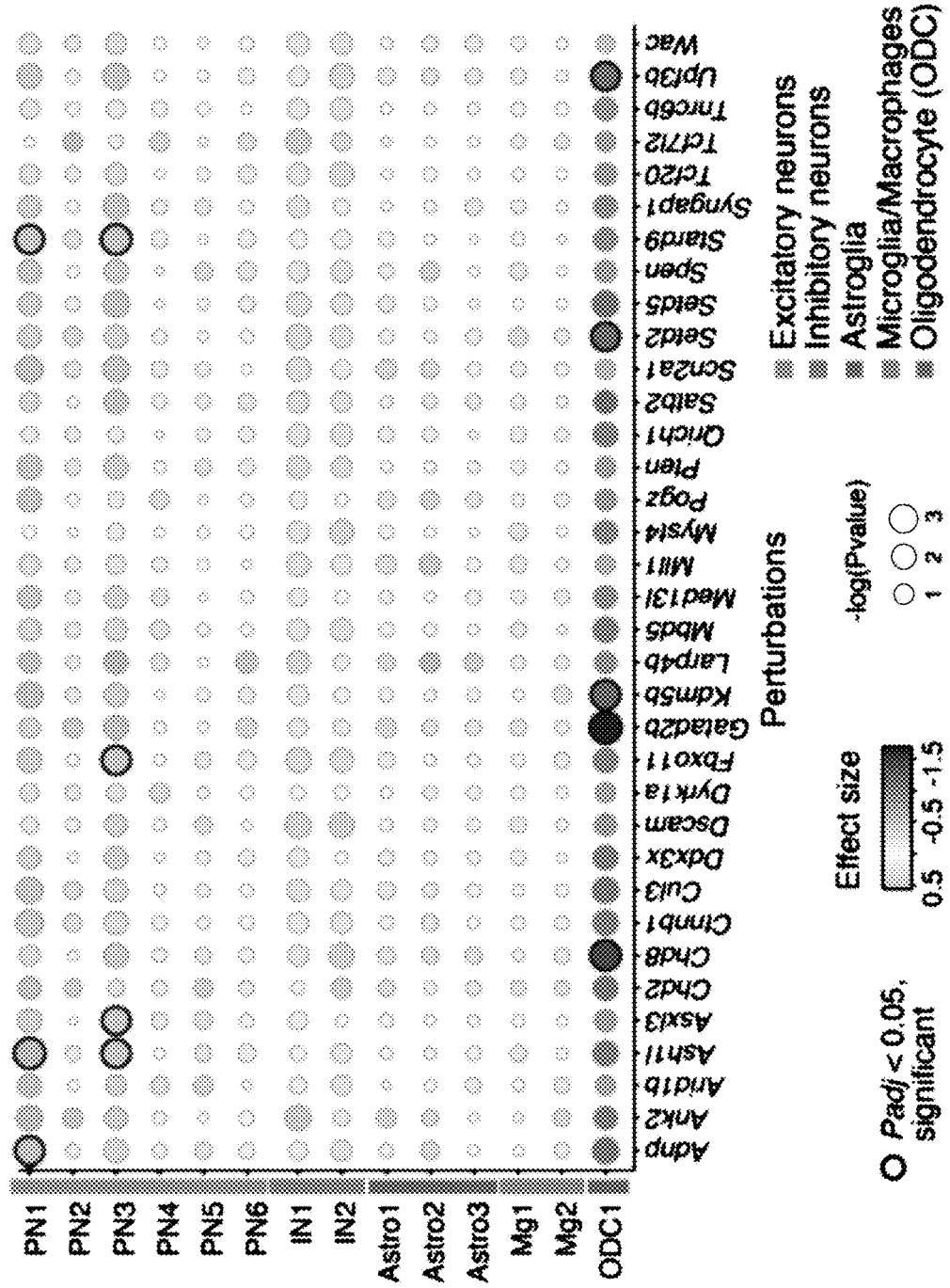
Figure 13D:
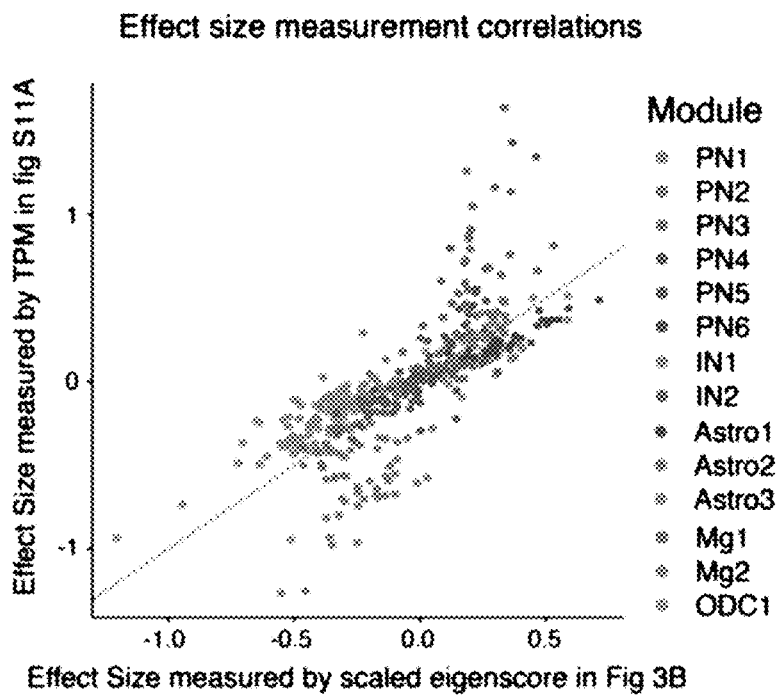
Figure 13E:
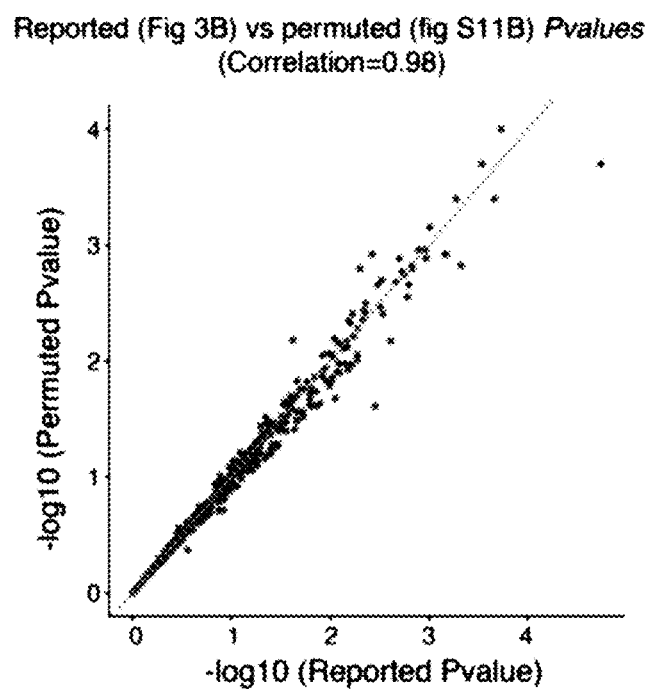

From inspecting the perturbation barcodes from the lentiviral constructs, 92% (33,231 cells) of the cells in these five major cell classes had at least one perturbation read assigned to them, and 50% had barcodes for a single gene (FIGS. 8A-8C, 18,044 cells), reflecting the low multiplicity of infection (FIG. 8D). As it is rare for multiple ASD/ND loss-of-function risk gene mutations to co-occur in patients, the 18,044 cells that carried a single perturbation were focused on. A median of 338 cells per perturbation was found: after excluding perturbations with <70 perturbed cells, 35 ASD/ND risk gene perturbations were retained. BFP from the lentiviral vector was robustly detected as one of the most highly expressed genes in all retained cells (FIG. 8E). The BFP detection rate in each cell type correlated with the average number of genes detected (FIG. 8F), further supporting the reliability of the readout.

ASD/ND risk gene perturbations had a very modest effect on the presence and proportions of these five major cell types relative to the negative control (targeting the GFP gene). Only loss of Dyrk1a had a significant effect on cell type composition, increasing the proportion of oligodendrocytes and reducing the proportion of microglia/macrophages [FDR-corrected P<0.05 using Poisson regression (17)] (FIGS. 1D and 9A-9C).

Example 3—Co-Varying Gene Modules Associate with Cell States

To assess whether ASD/ND genetic perturbations caused molecular changes and alterations in cell states, it was first sought to define gene modules that co-vary within each of the five broad cell classes. As previous work has shown (11-13, 18), focusing on gene modules instead of individual genes provides more statistical power to detect biologically-meaningful perturbation effects using fewer cells than would be required for single gene-level analysis, and can capture diversity both within and across cell types.

It was first tested if the expression of known Gene Ontology (GO) gene sets (19) was affected by calculating a gene-set expression score for each cell and fitting a linear regression model to this score. After correcting for multiple hypothesis testing, no GO terms were significantly altered by any perturbation (Table 3). However, this approach is limited by the large number of tests performed (one test per GO term per cell type per perturbation, for a total of 510,265 tests), as well as the limited number of GO terms relevant to the developing cortex.

TABLE 3

Analysis of ASD/ND risk gene perturbation effect for GO term gene signatures.

| Estimate | Std..Error | t.value | pval | Pert | Name | CellType |
|---|---|---|---|---|---|---|
| −1.150003746 | 0.226873197 | −5.068927323 | 4.25E−07 | Pogz | GO:0008528 | Astroglia |
| −0.503415553 | 0.101940391 | −4.938332582 | 8.32E−07 | Cul3 | GO:0002026 | Astroglia |
| −0.904979089 | 0.19384124 | −4.668661265 | 3.17E−06 | Chd8 | GO:0002162 | Astroglia |
| −0.769374175 | 0.165937695 | −4.63652442 | 3.7E−06 | Upf3b | GO:0008528 | Astroglia |
| −0.737836571 | 0.164941317 | −4.473327417 | 7.99E−06 | Mbd5 | GO:0008528 | Astroglia |
| −0.710936059 | 0.159069379 | −4.469345775 | 8.14E−06 | Tnrc6b | GO:0008528 | Astroglia |
| −0.389500932 | 0.088034757 | −4.424399443 | 1E−05 | Dyrk1a | GO:0035082 | Astroglia |
| 0.913664946 | 0.206578584 | 4.422844472 | 1.01E−05 | Larp4b | GO:0010575 | Inhibitory |
| −0.703224665 | 0.159830257 | −4.39982191 | 1.12E−05 | Stard9 | GO:0008528 | Astroglia |
| −0.78708216 | 0.179162272 | −4.393124476 | 1.16E−05 | Dscam | GO:0008528 | Astroglia |
| 0.713169269 | 0.162340549 | 4.393044591 | 1.16E−05 | Tcf20 | GO:0043267 | Inhibitory |
| −0.858063812 | 0.196754612 | −4.361086136 | 1.37E−05 | Myst4 | GO:0010524 | ODC |
| 0.418061159 | 0.096423708 | 4.335667709 | 1.5E−05 | Arid1b | GO:0017048 | Astroglia |
| 0.703614964 | 0.16320145 | 4.311327888 | 1.68E−05 | Setd2 | GO:0008066 | Astroglia |
| −0.403639559 | 0.094133654 | −4.287941039 | 1.86E−05 | Tnrc6b | GO:0017134 | Microglia |
| −0.456309221 | 0.106709917 | −4.27616506 | 1.96E−05 | Mll1 | GO:0002063 | Astroglia |
| 0.889502918 | 0.208065792 | 4.275104083 | 1.97E−05 | Arid1b | GO:0031681 | Microglia |
| 0.63742574 | 0.150278773 | 4.241621948 | 2.29E−05 | Qrich1 | GO:0008066 | Astroglia |
| −0.218032138 | 0.051449362 | −4.237800626 | 2.32E−05 | Kdm5b | GO:0060021 | Excitatory |
| −0.49174702 | 0.11610971 | −4.235192907 | 2.35E−05 | Kdm5b | GO:0071498 | Astroglia |
| −0.396324073 | 0.093986743 | −4.216808261 | 2.56E−05 | Ctnnb1 | GO:0017134 | Microglia |
| 0.384372831 | 0.091194469 | 4.214869977 | 2.58E−05 | Arid1b | GO:0030879 | Inhibitory |
| −0.625053759 | 0.148372438 | −4.212734986 | 2.6E−05 | Stard9 | GO:0071385 | Astroglia |
| 0.711724638 | 0.169879385 | 4.18958802 | 2.89E−05 | Chd2 | GO:0070886 | Inhibitory |
| 0.379939422 | 0.09076425 | 4.186002969 | 2.93E−05 | Tcf20 | GO:0048468 | Inhibitory |
| −0.72411368 | 0.173909667 | −4.163734501 | 3.22E−05 | Scn2a1 | GO:0008528 | Astroglia |
| −0.587684917 | 0.141005483 | −4.167816059 | 3.23E−05 | Cul3 | GO:0016032 | ODC |
| −0.601382071 | 0.145300561 | −4.138883344 | 3.59E−05 | Pogz | GO:0004181 | Astroglia |
| 0.844335978 | 0.204051793 | 4.137851298 | 3.61E−05 | Chd2 | GO:0008209 | Inhibitory |

TABLE 3-continued

Analysis of ASD/ND risk gene perturbation effect for GO term gene signatures.

| | | | | | | |
|---|---|---|---|---|---|---|
| −0.448797514 | 0.108955995 | −4.119071322 | 3.91E−05 | Upf3b | GO:0071498 | Astroglia |
| −0.74032323 | 0.179596902 | −4.122138092 | 3.93E−05 | Gatad2b | GO:0050839 | ODC |
| −0.45384813 | 0.110388521 | −4.111370692 | 4.04E−05 | Setd5 | GO:0051279 | Excitatory |
| 0.561042332 | 0.136548137 | 4.108751279 | 4.1E−05 | Satb2 | GO:0042551 | Inhibitory |
| 0.353490322 | 0.086213991 | 4.100150295 | 4.25E−05 | Adnp | GO:0051018 | Inhibitory |
| −0.252153048 | 0.061682102 | −4.087945102 | 4.46E−05 | Dyrk1a | GO:0008047 | Excitatory |
| −0.371646 | 0.091206712 | −4.0747659 | 4.73E−05 | Mll1 | GO:1904754 | Astroglia |
| −0.18937733 | 0.046497596 | −4.072841321 | 4.76E−05 | Qrich1 | GO:0001889 | Excitatory |
| −0.720056743 | 0.176832653 | −4.07196709 | 4.78E−05 | Kdm5b | GO:0008528 | Astroglia |
| −0.306595637 | 0.075296366 | −4.071851707 | 4.8E−05 | Mbd5 | GO:0006672 | Inhibitory |
| −0.393088161 | 0.096674939 | −4.066081309 | 4.91E−05 | Mbd5 | GO:0002026 | Astroglia |
| −0.501863493 | 0.123590147 | −4.060707966 | 5.03E−05 | Scn2a1 | GO:0097242 | Microglia |
| −0.653181741 | 0.161028176 | −4.056319564 | 5.11E−05 | Asxl3 | GO:0008528 | Astroglia |
| −0.375025774 | 0.092542372 | −4.052476348 | 5.21E−05 | Stard9 | GO:0030574 | Inhibitory |
| 0.45351895 | 0.112147648 | 4.043945256 | 5.49E−05 | Dyrk1a | GO:0006497 | ODC |
| 0.816094633 | 0.202349586 | 4.033092675 | 5.64E−05 | Chd8 | GO:0043117 | Astroglia |
| −0.388595264 | 0.096415712 | −4.030414307 | 5.71E−05 | Qrich1 | GO:0002026 | Astroglia |
| −0.657359474 | 0.163293172 | −4.025639681 | 5.82E−05 | Wac | GO:0008528 | Astroglia |
| −0.374604107 | 0.093225279 | −4.018267468 | 6E−05 | Setd5 | GO:0097340 | Excitatory |
| −1.161386124 | 0.288841924 | −4.020836407 | 6.05E−05 | Chd2 | GO:0032331 | ODC |
| −0.458089532 | 0.114200479 | −4.011275046 | 6.19E−05 | Cul3 | GO:0071498 | Astroglia |
| 0.408514717 | 0.101910067 | 4.008580585 | 6.28E−05 | Upf3b | GO:2001171 | Inhibitory |
| 0.448587134 | 0.111993288 | 4.005482316 | 6.36E−05 | Ctnnb1 | GO:0042551 | Inhibitory |
| −0.343810608 | 0.08597691 | −3.998871406 | 6.52E−05 | Qrich1 | GO:0050807 | Astroglia |
| −0.435745835 | 0.109004224 | −3.997513302 | 6.56E−05 | Setd2 | GO:0017134 | Microglia |
| −0.462944572 | 0.115859149 | −3.995753273 | 6.72E−05 | Dyrk1a | GO:0006672 | ODC |
| −0.45795955 | 0.114990881 | −3.982572752 | 6.99E−05 | Ddx3x | GO:0097242 | Microglia |
| −0.2180048 | 0.054831282 | −3.975920192 | 7.17E−05 | Scn2a1 | GO:0035176 | Excitatory |
| −0.570264328 | 0.143566213 | −3.972134638 | 7.3E−05 | Asxl3 | GO:0031994 | Microglia |
| −0.385986815 | 0.097258933 | −3.968651562 | 7.4E−05 | Upf3b | GO:0002026 | Astroglia |
| 0.396038929 | 0.099806908 | 3.96805127 | 7.44E−05 | Myst4 | GO:0048468 | Inhibitory |
| −0.557465429 | 0.140629082 | −3.964083551 | 7.55E−05 | Chd8 | GO:0097242 | Microglia |
| 0.430904319 | 0.108896342 | 3.95701371 | 7.76E−05 | Kdm5b | GO:0048535 | Excitatory |
| 0.495000995 | 0.125188699 | 3.954038961 | 7.88E−05 | Ash1l | GO:0042551 | Inhibitory |
| −0.751987856 | 0.190390415 | −3.949714888 | 8.14E−05 | Ddx3x | GO:0010524 | ODC |
| 0.331910936 | 0.084179193 | 3.942909445 | 8.26E−05 | Mbd5 | GO:0072593 | Inhibitory |
| 0.270262663 | 0.068750953 | 3.931038802 | 8.65E−05 | Med13l | GO:0003746 | Excitatory |
| −0.234093922 | 0.059555666 | −3.930674216 | 8.67E−05 | Ash1l | GO:0030544 | Astroglia |
| −0.299704412 | 0.076342005 | −3.925812694 | 8.84E−05 | Cul3 | GO:0010595 | Astroglia |
| −0.491394061 | 0.125404209 | −3.918481419 | 9.12E−05 | Setd2 | GO:0007131 | Microglia |
| −0.669874783 | 0.170990817 | −3.917606783 | 9.15E−05 | Ash1l | GO:0008528 | Astroglia |
| 0.396104422 | 0.101071583 | 3.919048381 | 9.23E−05 | Dyrk1a | GO:0034497 | ODC |
| 0.356736465 | 0.091158447 | 3.913367086 | 9.33E−05 | Scn2a1 | GO:0048468 | Inhibitory |
| −0.484062687 | 0.123771514 | −3.910937753 | 9.41E−05 | Spen | GO:0042129 | Microglia |
| −0.662279697 | 0.169396602 | −3.909639808 | 9.6E−05 | Qrich1 | GO:0006851 | ODC |
| −0.642420487 | 0.164499039 | −3.905314522 | 9.62E−05 | Qrich1 | GO:0008528 | Astroglia |
| −0.34428546 | 0.088275881 | −3.900107891 | 9.83E−05 | Mll1 | GO:0046716 | Astroglia |
| −0.979339536 | 0.250883752 | −3.903559037 | 9.84E−05 | Mbd5 | GO:2000279 | Astroglia |
| −0.725737149 | 0.186025221 | −3.901283627 | 9.93E−05 | Tcf20 | GO:0010524 | ODC |
| −0.335068585 | 0.086068728 | −3.893035151 | 0.000101186 | Asxl3 | GO:0004180 | Astroglia |
| 0.589982601 | 0.151593062 | 3.89188391 | 0.000101665 | Upf3b | GO:0008066 | Astroglia |
| 0.260763399 | 0.067011696 | 3.891311747 | 0.00010194 | Ash1l | GO:0000462 | Astroglia |
| −0.28301018 | 0.072753561 | −3.889983903 | 0.00010246 | Mll1 | GO:0099645 | Astroglia |
| −0.547951825 | 0.140991211 | −3.886425413 | 0.000104067 | Ctnnb1 | GO:0031994 | Microglia |
| 0.314413201 | 0.080900692 | 3.886409291 | 0.000104213 | Med13l | GO:0045739 | Inhibitory |
| 0.701726011 | 0.180653534 | 3.884374673 | 0.000105085 | Dscam | GO:0043267 | Inhibitory |
| −0.294382572 | 0.075800842 | −3.883631963 | 0.000105161 | Ddx3x | GO:0051019 | Astroglia |
| −0.436520866 | 0.112419901 | −3.88295011 | 0.000105455 | Upf3b | GO:0006959 | Astroglia |
| −0.524930341 | 0.13525899 | −3.880927542 | 0.000106332 | Setd2 | GO:0060384 | Astroglia |
| 0.517783133 | 0.13359741 | 3.87569739 | 0.00010863 | Dyrk1a | GO:0043117 | Astroglia |
| 0.675503912 | 0.174185958 | 3.878061818 | 0.000109202 | Mll1 | GO:0034383 | ODC |
| −0.487435767 | 0.125859896 | −3.87284418 | 0.000109904 | Larp4b | GO:0010595 | Astroglia |
| −0.436328921 | 0.112686892 | −3.872046822 | 0.000110369 | Ddx3x | GO:0032753 | Microglia |
| −0.297908578 | 0.076947207 | −3.871597022 | 0.000110465 | Setd2 | GO:0043531 | Astroglia |
| −0.943774819 | 0.243567018 | −3.874805489 | 0.00011066 | Qrich1 | GO:2000279 | ODC |
| 0.70157529 | 0.181294661 | 3.869806683 | 0.000111529 | Pten | GO:0005184 | Inhibitory |
| −0.365114531 | 0.094381379 | −3.868501754 | 0.000111869 | Asxl3 | GO:0002026 | Astroglia |
| −0.388885262 | 0.100692524 | −3.862106598 | 0.000115084 | Chd8 | GO:0050718 | Inhibitory |

| padj | Ont | Description |
|---|---|---|
| 0.183522816 | Molecular Function | G protein-coupled peptide receptor activity |
| 0.183522816 | Biological Process | regulation of the force of heart contraction |
| 0.407867534 | Molecular Function | dystroglycan binding |
| 0.407667534 | Molecular Function | G protein-coupled peptide receptor activity |
| 0.465913758 | Molecular Function | G protein-coupled peptide receptor activity |
| 0.465913758 | Molecular Function | G protein-coupled peptide receptor activity |
| 0.465913758 | Biological Process | axoneme assembly |

TABLE 3-continued

Analysis of ASD/ND risk gene perturbation effect for GO term gene signatures.

| | | |
|---|---|---|
| 0.465913758 | Biological Process | positive regulation of vascular endothelial growth factor production |
| 0.465913758 | Molecular Function | G protein-coupled peptide receptor activity |
| 0.465913758 | Molecular Function | G protein-coupled peptide receptor activity |
| 0.465913758 | Biological Process | negative regulation of potassium ion transport |
| 0.498574515 | Biological Process | positive regulation of calcium ion transport into cytosol |
| 0.498574515 | Molecular Function | Rho GTPase binding |
| 0.498574515 | Molecular Function | glutamate receptor activity |
| 0.498574515 | Molecular Function | fibroblast growth factor binding |
| 0.498574515 | Biological Process | chondrocyte development |
| 0.498574515 | Molecular Function | G-protein beta-subunit binding |
| 0.498574515 | Molecular Function | glutamate receptor activity |
| 0.498574515 | Biological Process | roof of mouth development |
| 0.498574515 | Biological Process | cellular response to fluid shear stress |
| 0.498574515 | Molecular Function | fibroblast growth factor binding |
| 0.498574515 | Biological Process | mammary gland development |
| 0.498574515 | Biological Process | cellular response to glucocorticoid stimulus |
| 0.514265412 | Biological Process | positive regulation of calcineurin-NFAT signaling cascade |
| 0.514265412 | Biological Process | cell development |
| 0.514265412 | Molecular Function | G protein-coupled peptide receptor activity |
| 0.514265412 | Biological Process | viral process |
| 0.514265412 | Molecular Function | metallocarboxypeptidase activity |
| 0.514265412 | Biological Process | androgen metabolic process |
| 0.514265412 | Biological Process | cellular response to fluid shear stress |
| 0.514265412 | Molecular Function | cell adhesion molecule binding |
| 0.514265412 | Biological Process | regulation of release of sequestered calcium ion into cytosol |
| 0.514265412 | Biological Process | neuron maturation |
| 0.514265412 | Molecular Function | protein kinase A binding |
| 0.514265412 | Molecular Function | enzyme activator activity |
| 0.514265412 | Biological Process | positive regulation of vascular associated smooth muscle cell migration |
| 0.514265412 | Biological Process | liver development |
| 0.514265412 | Molecular Function | G protein-coupled peptide receptor activity |
| 0.514265412 | Biological Process | ceramide metabolic process |
| 0.514265412 | Biological Process | regulation of the force of heart contraction |
| 0.514265412 | Biological Process | amyloid-beta clearance |
| 0.514265412 | Molecular Function | G protein-coupled peptide receptor activity |
| 0.514265412 | Biological Process | collagen catabolic process |
| 0.514265412 | Biological Process | protein lipidation |
| 0.514265412 | Biological Process | positive regulation of vascular permeability |
| 0.514265412 | Biological Process | regulation of the force of heart contraction |
| 0.514265412 | Molecular Function | G protein-coupled peptide receptor activity |
| 0.514265412 | Biological Process | acrosome reaction |
| 0.514265412 | Biological Process | negative regulation of chondrocyte differentiation |
| 0.514265412 | Biological Process | cellular response to fluid shear stress |
| 0.514265412 | Biological Process | positive regulation of ATP biosynthetic process |
| 0.514265412 | Biological Process | neuron maturation |
| 0.514265412 | Biological Process | regulation of synapse organization |
| 0.514265412 | Molecular Function | fibroblast growth factor binding |
| 0.514265412 | Biological Process | ceramide metabolic process |
| 0.514265412 | Biological Process | amyloid-beta clearance |
| 0.514265412 | Biological Process | social behavior |
| 0.514265412 | Molecular Function | insulin-like growth factor I binding |
| 0.514265412 | Biological Process | regulation of the force of heart contraction |
| 0.514265412 | Biological Process | cell development |
| 0.514265412 | Biological Process | amyloid-beta clearance |
| 0.514265412 | Biological Process | lymph node development |
| 0.514265412 | Biological Process | neuron maturation |
| 0.514265412 | Biological Process | positive regulation of calcium ion transport into cytosol |
| 0.514265412 | Biological Process | reactive oxygen species metabolic process |
| 0.514265412 | Molecular Function | translation elongation factor activity |
| 0.514265412 | Molecular Function | Hsp70 protein binding |
| 0.514265412 | Biological Process | positive regulation of endothelial cell migration |
| 0.514265412 | Biological Process | reciprocal meiotic recombination |
| 0.514265412 | Molecular Function | G protein-coupled peptide receptor activity |
| 0.514265412 | Biological Process | protein localization to phagophore assembly site |
| 0.514265412 | Biological Process | cell development |
| 0.514265412 | Biological Process | regulation of T cell proliferation |
| 0.514265412 | Biological Process | mitochondrial calcium ion transmembrane transport |
| 0.514265412 | Molecular Function | G protein-coupled peptide receptor activity |
| 0.514265412 | Biological Process | muscle cell cellular homeostasis |
| 0.514265412 | Biological Process | negative regulation of DNA biosynthetic process |
| 0.514265412 | Biological Process | positive regulation of calcium ion transport into cytosol |
| 0.514265412 | Molecular Function | carboxypeptidase activity |
| 0.514265412 | Molecular Function | glutamate receptor activity |
| 0.514265412 | Biological Process | maturation of SSU-rRNA from tricistronic rRNA transcript (SSU-rRNA, 5.8S rRNA, LSU-rRNA) |

TABLE 3-continued

Analysis of ASD/ND risk gene perturbation effect for GO term gene signatures.

| | | |
|---|---|---|
| 0.514265412 | Biological Process | neurotransmitter receptor localization to postsynaptic specialization membrane |
| 0.514265412 | Molecular Function | insulin-like growth factor I binding |
| 0.514265412 | Biological Process | positive regulation of DNA repair |
| 0.514265412 | Biological Process | negative regulation of potassium ion transport |
| 0.514265412 | Molecular Function | mitogen-activated protein kinase binding |
| 0.514265412 | Biological Process | humoral immune response |
| 0.514265412 | Biological Process | innervation |
| 0.514265412 | Biological Process | positive regulation of vascular permeability |
| 0.514265412 | Biological Process | low-density lipoprotein particle clearance |
| 0.514265412 | Biological Process | positive regulation of endothelial cell migration |
| 0.514265412 | Biological Process | positive regulation of interleukin-4 production |
| 0.514265412 | Molecular Function | ADP binding |
| 0.514265412 | Biological Process | negative regulation of DNA biosynthetic process |
| 0.514265412 | Molecular Function | neuropeptide hormone activity |
| 0.514265412 | Biological Process | regulation of the force of heart contraction |
| 0.523591478 | Biological Process | positive regulation of interleukin-1 beta secretion |

It was therefore sought to identify gene modules de novo in this data using two approaches: Weighted Gene Correlation Network Analysis (WGCNA), which identifies "modules" of genes with correlated expression, and structural topic modeling (STM), which attempts to reduce the dimensionality of the gene expression matrix and returns "topics" corresponding to the components of this representation (FIGS. 2A, 10A-10F, 11A-11E, and 12A-12E and Table 4) (20, 21). These analyses were performed for each of the five major cell clusters separately, to better identify effects associated with specific cell types; the nomenclature used here for the modules incorporates the cell cluster analysis it is derived from (e.g., PN1 represents a module identified by analysis of projection neurons). Each of these analyses used the full set of perturbations in order to identify effects shared across multiple perturbations. The subsequent analysis focused on the 14 modules identified by WGCNA, because they were highly correlated with one or more topics returned by STM (FIGS. 11A-11E).

TABLE 4

WGCNA gene module gene lists.

| Module name in paper | ODC1 | Mg1 | Mg2 | PN1 | PN2 |
|---|---|---|---|---|---|
| Note | Progenitor | Inflammatory | Homeostatic | Layer 4-5 | Neurite development |
| Module name from WGCNA | OPC_turquoise | Mg_brown | Mg_blue | PN_greenyellow | PN_brown |
| | Pid1 | Marcksl1 | Serpine2 | Chgb | Inpp4a |
| | Ramp1 | Nfkbid | Plxdc2 | Brinp1 | Pam |
| | Dbi | Egr2 | Cst3 | Hpca | Dcaf6 |
| | Mdk | Ccl2 | Gpr34 | Foxp1 | Nmt2 |
| | Stmn3 | Ccl7 | P2ry12 | Nrgn | Ymel1l |
| | Fabp7 | Ccl12 | Olfml3 | Nrsn1 | Set |
| | Pea15a | Ccl4 | Ldhb | Fkbp1b | Lrrc8a |
| | Ddah1 | Nr4a1 | Pde3b | Satb1 | Slc24a5 |
| | Car8 | Nfkbiz | Cd81 | Rorb | Myef2 |
| | Kcnd2 | Rcan1 | Sparc | | Ncoa3 |
| | Apoe | Tnf | Hexb | | Cask |
| | Rlbp1 | Ier3 | Rhob | | Skil |
| | Mmp15 | | Lgmn | | Rap2b |
| | Cspg5 | | | | Slc39a1 |
| | Rgcc | | | | Rbm15 |
| | 6330403K07Rik | | | | Klhl9 |
| | Sox11 | | | | Ythdf2 |
| | Tspan13 | | | | Gnb1 |
| | Zfp36l2 | | | | Gatad1 |
| | 1700086L19Rik | | | | Insig1 |
| | Hes1 | | | | Actb |
| | Pcp4 | | | | Kdelr2 |
| | Ppp2r2b | | | | Cbx3 |
| | Cdo1 | | | | Sfxn5 |
| | Cspg4 | | | | Iqsec1 |
| | Ostf1 | | | | Tmf1 |
| | | | | | Dpf1 |
| | | | | | Shank1 |
| | | | | | Klf13 |
| | | | | | Abhd2 |
| | | | | | Mcmbp |
| | | | | | Sec23ip |
| | | | | | Hsf2 |
| | | | | | Sirt6 |
| | | | | | Ppm1h |
| | | | | | Micu3 |
| | | | | | Lzts1 |
| | | | | | Ncan |

TABLE 4-continued

WGCNA gene module gene lists.

|  |  |  |  |  | Upf1 |  |
|  |  |  |  |  | Supt16 |  |
|  |  |  |  |  | Dpysl2 |  |
|  |  |  |  |  | Spry2 |  |
|  |  |  |  |  | Zbtb44 |  |
|  |  |  |  |  | Scn2b |  |
|  |  |  |  |  | Ncam1 |  |
|  |  |  |  |  | AI593442 |  |
|  |  |  |  |  | Dapk2 |  |
|  |  |  |  |  | Clasp2 |  |
|  |  |  |  |  | Actr2 |  |
|  |  |  |  |  | Alkbh5 |  |
|  |  |  |  |  | Arhgap44 |  |
|  |  |  |  |  | Gas7 |  |
|  |  |  |  |  | Kdm6b |  |
|  |  |  |  |  | Dusp3 |  |
|  |  |  |  |  | Fn3krp |  |
|  |  |  |  |  | Zscan26 |  |
|  |  |  |  |  | Atxn1 |  |
|  |  |  |  |  | Hmgcr |  |
|  |  |  |  |  | Map1b |  |
|  |  |  |  |  | Paip1 |  |
|  |  |  |  |  | Dbpht2 |  |
|  |  |  |  |  | St13 |  |
|  |  |  |  |  | Kmt2d |  |
|  |  |  |  |  | Mkl2 |  |
|  |  |  |  |  | Rrn3 |  |
|  |  |  |  |  | Marf1 |  |
|  |  |  |  |  | Lrrc58 |  |
|  |  |  |  |  | Gsk3b |  |
|  |  |  |  |  | Tmem181a |  |
|  |  |  |  |  | D17H6S53E |  |
|  |  |  |  |  | Birc6 |  |
|  |  |  |  |  | Dctn4 |  |
|  |  |  |  |  | Otub1 |  |
|  |  |  |  |  | Ric1 |  |
|  |  |  |  |  | Pdcd4 |  |

| Module name in paper | PN3 | PN4 | PN5 | PN6 | IN1 |
| --- | --- | --- | --- | --- | --- |
| Note | Layer 4-5 | Neurotransmitter/Layer 6 | Tubulin and ATP biogenesis | Layer 5-6 | Ndnf+ |
| Module name from WGCNA | PN_purple | PN_red | PN_yellow | PN_magenta | IN_blue |
|  | Syndig1 | Etl4 | Arpc2 | Tmem163 | A830018L16Rik |
|  | Lhfp | Olfm1 | Atp1b1 | Serpini1 | Kcnq5 |
|  | Slc30a3 | Trp53i11 | Atp5c1 | Grik3 | Spats2l |
|  | Plb1 | Slc1a2 | Gnas | Galnt9 | Lancl1 |
|  | Plxnd1 | Rasgrp1 | Atp5f1 | Crym | Erbb4 |
|  | Cox6a2 | Syt11 | Dnaja1 | Hs3st4 | 43894 |
|  | Rora | Sh3gl2 | Ywhah | Fezf2 | Resp18 |
|  | Krt12 | Elavl2 | Gnb2 | Nxph3 | Nyap2 |
|  | A830036E02Rik | Nfia | Gapdh | Nptx1 | Irs1 |
|  | Dcdc2a | Fxyd7 | Aldoa | Bcl11b | Lefty2 |
|  | A830009L08Rik | Slc17a7 | Atp5b | Tle4 | Susd4 |
|  |  | Gsg1l | Tecr |  | Tgfb2 |
|  |  | Ipcef1 | Tubb3 |  | Fam163b |
|  |  | Nxph4 | Hspa8 |  | Rapgef4 |
|  |  | Cplx3 | Eif4a1 |  | Nckap1 |
|  |  | Rab6b | Ywhae |  | Lamp5 |
|  |  | Sez6 | Psmc5 |  | Pak7 |
|  |  | Pcp4 | Actg1 |  | Tox2 |
|  |  | Clic5 | Tubb2a |  | Dok5 |
|  |  | Pcsk5 | Tubb2b |  | Chrna4 |
|  |  |  | Hsp90aa1 |  | Atp6ap2 |
|  |  |  | Tuba1b |  | Trpc5 |
|  |  |  | Tuba1a |  | Frmpd4 |
|  |  |  | Ap2m1 |  | Rxfp1 |
|  |  |  | Eif4a2 |  | Man1a2 |
|  |  |  | Tubb5 |  | Unc5c |
|  |  |  | Hsp90ab1 |  | Lingo2 |
|  |  |  | Vapa |  | Gabbr2 |
|  |  |  | Tmem178 |  | Dab1 |
|  |  |  |  |  | Cacna2d1 |
|  |  |  |  |  | Reln |
|  |  |  |  |  | Afap1 |
|  |  |  |  |  | Limch1 |
|  |  |  |  |  | Kit |
|  |  |  |  |  | Hopx |
|  |  |  |  |  | Parm1 |
|  |  |  |  |  | Rimbp2 |

TABLE 4-continued

WGCNA gene module gene lists.

Col26a1
Nxph1
Ndufa4
Npy
Osbpl3
Ndnf
RP23-291B1.2
Ldha
Adamts17
Homer2
Hs3st4
Rgs10
Ppp1r14c
Sgk1
Hs3st5
Nav3
Ppm1h
Zmat4
Mfap3l
Abhd8
Rasd2
Psmb10
Maf
Cpne7
Ube2e2
Gdf10
Fgf9
Pnoc
Slitrk1
B3gat1
Sorl1
Cryab
Cck
Asic2
Hecw1
Amph
A330102I10Rik
Mctp1
Hapln1
Sv2c
Id2
Sstr1
Rgs6
Sema5a
Csmd3
Nov
Mpped1
Grin2a
Il1rap
Ptprm
Fkbp2
Cox8a

| | | | | |
|---|---|---|---|---|
| Module name in paper | IN2 | Astro1 | Astro2 | Astro3 |
| Note | Vip+ | Homeostatic1 | Activation | Homeostatic2 |
| Module name from WGCNA | IN_green | Astro_blue | Astro_green | Astro_turquoise |
| | Asic4 | Hsd11b1 | Bgn | Prex2 |
| | Pam | Chst1 | S100a4 | Col9a1 |
| | Prox1 | Kcnip3 | S100a11 | Arhgef4 |
| | Ap1s2 | Phactr3 | S100a10 | Bmpr2 |
| | Cnr1 | Tspan7 | Igfbp7 | Nrp2 |
| | Klhl9 | Chrdl1 | Ifitm3 | Mgat5 |
| | Sema3c | Fam212b | C1ql1 | Adora1 |
| | Npas1 | St6galnac5 | Timp2 | Rgs2 |
| | Nr2f2 | Cth | S1pr3 | Glul |
| | Igf1 | Gabbr2 | Ntrk2 | Tnr |
| | Adra1b | Efhd2 | Actn1 | Myoc |
| | Adarb2 | AW011738 | Serpina3n | Ccdc3 |
| | Cxcl14 | Grm3 | Ccdc74a | Nsmf |
| | | 0610040J01Rik | C4b | Ggta1 |
| | | Abcb9 | | Nr4a2 |
| | | Ptprz1 | | Pkp4 |
| | | Akr1b10 | | Ssfa2 |
| | | Timp4 | | Slc1a2 |
| | | Eps8 | | Cd44 |
| | | Slco1c1 | | Serf2 |
| | | Aplp1 | | Slc20a1 |
| | | Slc7a10 | | Btbd3 |

TABLE 4-continued

WGCNA gene module gene lists.

| | |
|---|---|
| Grm5 | Ptprt |
| Dhcr7 | Matn4 |
| Ccnd1 | Elmo2 |
| S100b | Sulf2 |
| Gpc5 | Usp9x |
| Cadm1 | Slc6a8 |
| Arpp21 | Plp1 |
| Rnf215 | Gpm6b |
| Slc13a5 | Trim2 |
| Etv4 | Slc16a1 |
| Dbx2 | Unc5c |
| Olig2 | Bmpr1b |
| Cbr3 | Grin3a |
| Hbegf | Rspo1 |
| Cdo1 | Man1c1 |
| Vldlr | Ptchd2 |
| | Ski |
| | Agrn |
| | Prkag2 |
| | Hopx |
| | Miat |
| | Hspb8 |
| | Clip2 |
| | Tsc22d4 |
| | D630045J12Rik |
| | Gadd45a |
| | Atoh8 |
| | Tmem150a |
| | Tgoln1 |
| | Ctnna2 |
| | Slc6a6 |
| | Adamts9 |
| | A2m |
| | Kcna6 |
| | Zfp36 |
| | Clip3 |
| | Nav2 |
| | Arhgef17 |
| | Tab2 |
| | Marcks |
| | Sgpl1 |
| | Slc7a2 |
| | Mfap3l |
| | Ncan |
| | Adgrl1 |
| | Zfp423 |
| | Mt3 |
| | Mt2 |
| | Mt1 |
| | Cadps |
| | Opcml |
| | Sorl1 |
| | Cryab |
| | Islr |
| | 6030419C18Rik |
| | Smad6 |
| | Igdcc4 |
| | Pth1r |
| | Tmie |
| | Csrnp1 |
| | Tmem158 |
| | Nsg2 |
| | Wwc1 |
| | Col23a1 |
| | Slc36a2 |
| | Serpinf1 |
| | Taok1 |
| | Nog |
| | Stat3 |
| | Dusp3 |
| | Prkca |
| | Fasn |
| | Aldh5a1 |
| | Mylip |
| | Msx2 |
| | Erbb2ip |
| | Map3k1 |
| | Id2 |

TABLE 4-continued

WGCNA gene module gene lists.

Rgs6
Lifr
Ank
Enpp2
Plec
Maff
Shisa8
3-Sep
Fam19a5
Slc38a1
Snai2
Nfkbiz
Robo2
Adamts1
Tulp4
Paqr4
Fgd2
H2-DMa
H2-DMb1
H2-Ab1
H2-Aa
H2-Eb1
Ddr1
Npc1
Aqp4
Nrep
Cd74
Cidea
Smad7
Fth1
Aldh1a1
Kank1
Scd2

The 14 WGCNA modules comprised two broad categories. Some reflect common biological processes and were present across multiple cell subsets (e.g., cell cycle, differentiation, maturation). For example, module PN2 is associated with genes involved in neurite development and varied across cells in multiple projection neuron subclusters (FIG. 10A). Others represent cell type-specific features unique to only some subsets (e.g., sub cluster-specific features of a neuronal sub-type). For example, module PN1 is a module associated with two defined subclusters of projection neurons of Layer 4 and Layer 5 (FIG. 10A).

Example 4—ASD/ND Gene Perturbations Affect Cell States in Multiple Cell Classes

Figure 2A:
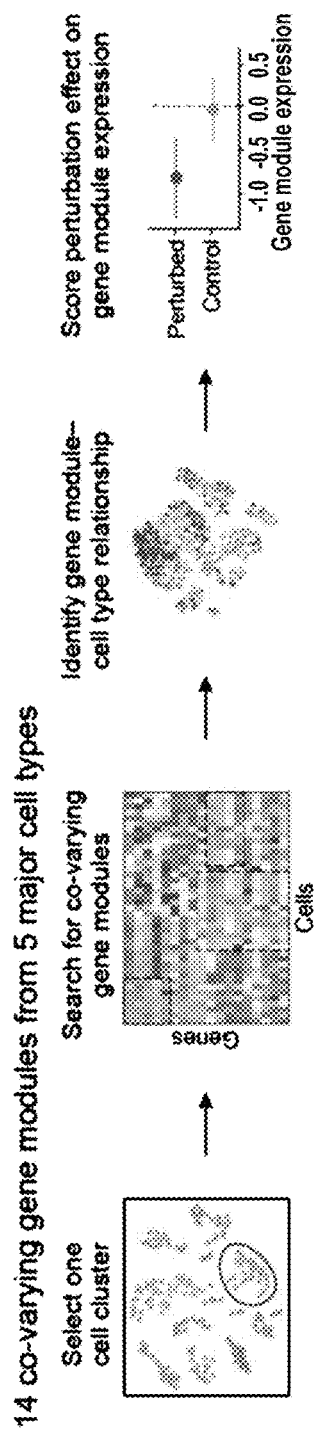
FIGS. 2A-2C—In vivo Perturb-Seq reveals cell-type specific effects of ASD/ND risk gene perturbations.
Figure 2B:
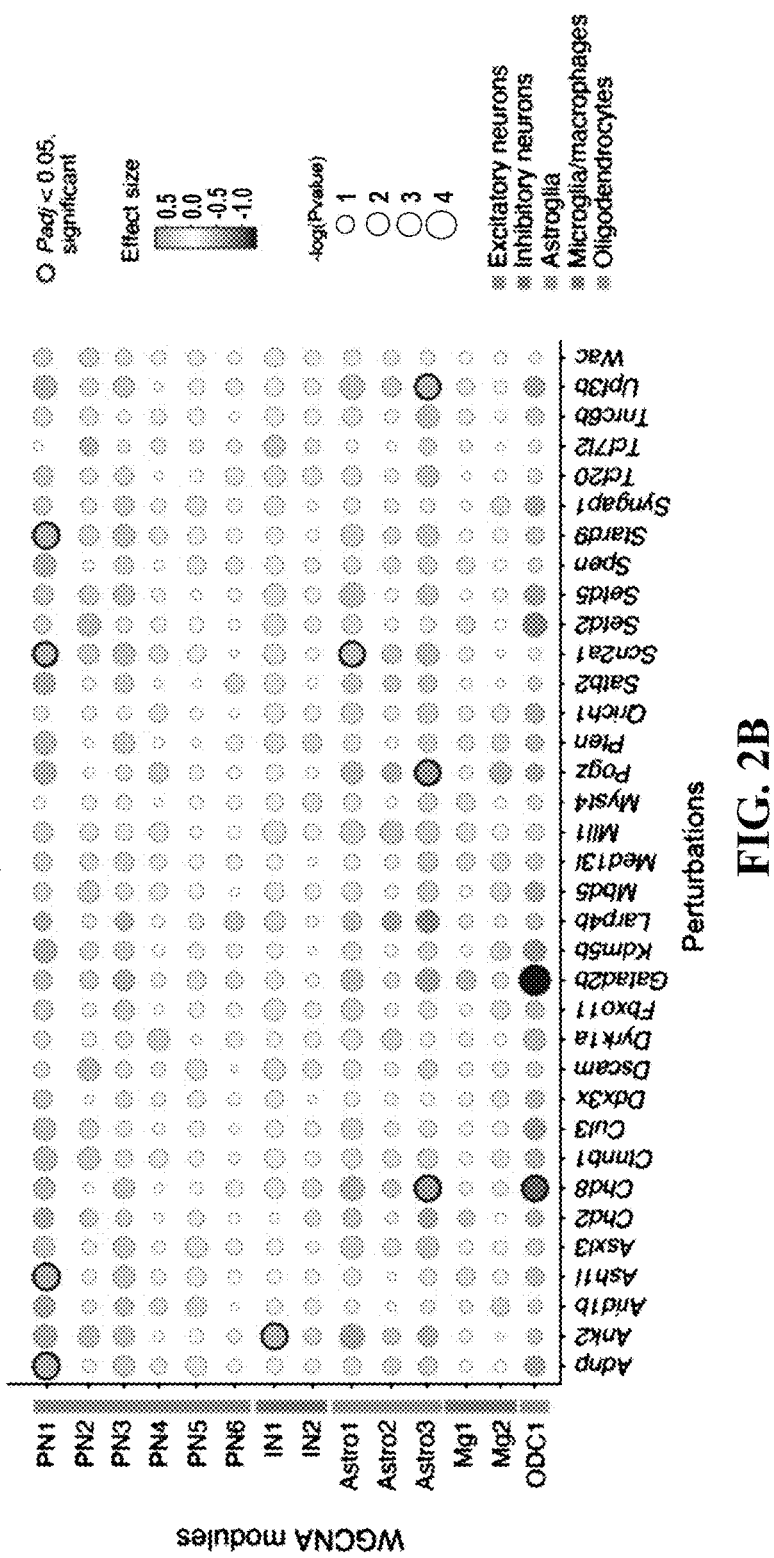
Figure 2C:
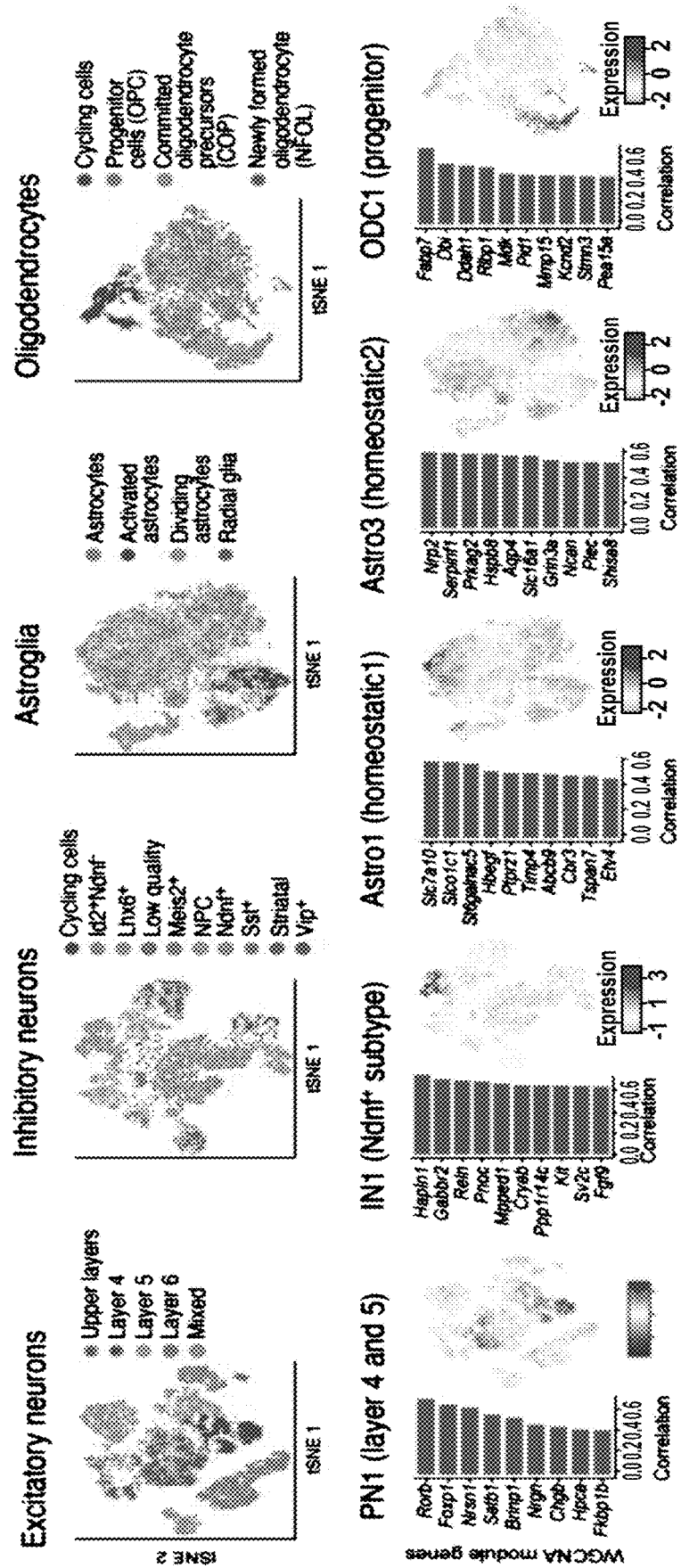

As the WGCNA analysis is expected to recover gene modules associated with many kinds of variation across the data, the association of each risk gene perturbation with the 14 individual WGCNA gene modules was tested next. It was estimated the effect size of each perturbation on each gene module by fitting a joint linear regression model, estimating how module gene expression in cells from each perturbation group deviated from the GFP control cells (FIG. 2A-2B). To ensure that no single perturbation or batch dominated the linear model, the cells in each cell category were downsampled such that no perturbation had more than two times the median number of cells over all perturbations. This linear regression analysis was performed on mean-centered and standard deviation-scaled module scores, so effect sizes can be interpreted in terms of standard deviations from the population mean (FIG. 2B). This modeling approach assumes that module expression in individual cells is independent after conditioning on the experimental batch, and that noise is normally distributed. To evaluate the effects of these assumptions, alternative approaches were also compared, including a linear mixed model-based approach and a permutation-based approach (FIGS. 13A-13E and Table 5).

TABLE 5

Alternative effect size and statistical measurements of Perturb-Seq.

| perturbation | Module | pval | padj | Estimate | SE | df | t.value |
| --- | --- | --- | --- | --- | --- | --- | --- |
| Gatad2b | ODC1 | 0.00019929 | 0.09148041 | −1.6392731 | 0.43402622 | 245.473281 | −3.7768988 |
| Ash1l | PN1 | 0.00040956 | 0.09148041 | −0.5702511 | 0.15798048 | 160.261013 | −3.6096302 |
| Chd8 | ODC1 | 0.00061256 | 0.09148041 | −1.4433344 | 0.4157381 | 241.328595 | −3.4717395 |
| Stard9 | PN3 | 0.00074678 | 0.09148041 | −0.4945026 | 0.14236812 | 105.399114 | −3.4734084 |
| Kdm5b | ODC1 | 0.00105686 | 0.0947702 | −1.2177755 | 0.36673854 | 213.093268 | −3.320555 |
| Adnp | PN1 | 0.00174366 | 0.0947702 | −0.5197172 | 0.16287405 | 142.956625 | −3.1909144 |
| Ash1l | PN3 | 0.0017729 | 0.0947702 | −0.4682456 | 0.14676601 | 132.809402 | −3.1904225 |
| Fbxo11 | PN3 | 0.00183349 | 0.0947702 | −0.4707365 | 0.14841361 | 151.862298 | −3.171788 |
| Setd2 | ODC1 | 0.00192802 | 0.0947702 | −1.1736475 | 0.37333025 | 195.532048 | −3.1437246 |
| Upf3b | ODC1 | 0.00193409 | 0.0947702 | −1.1332804 | 0.36093759 | 209.827187 | −3.1398237 |
| Stard9 | PN1 | 0.002176 | 0.09693093 | −0.4832762 | 0.15463063 | 134.549616 | −3.1253587 |

TABLE 5-continued

Alternative effect size and statistical measurements of Perturb-Seq.

| perturbation | Module | pval | padj | Estimate | SE | df | t.value |
|---|---|---|---|---|---|---|---|
| Asxl3 | PN3 | 0.0024178 | 0.09872663 | −0.4535802 | 0.14641887 | 122.498726 | −3.0978265 |
| Setd5 | ODC1 | 0.00374726 | 0.14124293 | −1.0649438 | 0.3633284 | 212.539974 | −2.9310778 |
| Cul3 | ODC1 | 0.00470021 | 0.14418933 | −1.03766 | 0.36318713 | 212.478167 | −2.8570945 |
| Adnp | ODC1 | 0.0047499 | 0.14418933 | −1.0526633 | 0.36915875 | 228.302171 | −2.8515192 |
| Ctnnb1 | PN1 | 0.00481414 | 0.14418933 | −0.4243003 | 0.14816893 | 144.072277 | −2.8636256 |
| Scn2a1 | PN1 | 0.0055001 | 0.14418933 | −0.4711114 | 0.16753867 | 170.957327 | −2.811956 |
| Upf3b | PN3 | 0.00556665 | 0.14418933 | −0.4351463 | 0.15448305 | 137.233728 | −2.8167896 |
| Setd5 | PN3 | 0.00585783 | 0.14418933 | −0.4603121 | 0.16512846 | 187.205554 | −2.7876001 |
| Scn2a1 | PN3 | 0.00588528 | 0.14418933 | −0.4364571 | 0.15614299 | 145.694403 | −2.7952399 |
| Kdm5b | PN1 | 0.00685531 | 0.14996152 | −0.4831399 | 0.17729142 | 265.365193 | −2.725117 |
| Cul3 | PN1 | 0.00716729 | 0.14996152 | −0.4419764 | 0.16134234 | 111.695992 | −2.73937 |
| Ctnnb1 | ODC1 | 0.00735312 | 0.14996152 | −0.9658219 | 0.35653152 | 194.185047 | −2.7089383 |
| Ank2 | PN1 | 0.00763061 | 0.14996152 | −0.5417298 | 0.20070335 | 175.6413 | −2.699157 |
| Ash1l | ODC1 | 0.00825021 | 0.14996152 | −0.9879851 | 0.37022521 | 197.370732 | −2.6686057 |
| Ank2 | IN1 | 0.00838415 | 0.14996152 | 0.50499251 | 0.19081393 | 509.391877 | 2.64651802 |
| Dscam | IN1 | 0.00849347 | 0.14996152 | 0.39991241 | 0.15054164 | 213.047921 | 2.65649027 |
| Syngap1 | PN3 | 0.00860101 | 0.14996152 | −0.4422123 | 0.16644951 | 179.551063 | −2.6567356 |
| Mbd5 | ODC1 | 0.00887527 | 0.14996152 | −0.9667204 | 0.36602191 | 212.830324 | −2.6411544 |
| Fbxo11 | ODC1 | 0.01045343 | 0.16238522 | −0.9275589 | 0.35889412 | 203.02041 | −2.5844919 |
| Chd8 | IN2 | 0.01054444 | 0.16238522 | 0.43024856 | 0.16587328 | 134.240663 | 2.59383876 |
| Ddx3x | ODC1 | 0.01088716 | 0.16238522 | −0.9653681 | 0.37586225 | 217.228987 | −2.5684094 |
| Dscam | IN2 | 0.01093615 | 0.16238522 | 0.4258342 | 0.16578804 | 201.473159 | 2.56854602 |
| Qrich1 | ODC1 | 0.01173012 | 0.16458641 | −0.9313837 | 0.36624599 | 204.035693 | −2.543055 |
| Chd2 | ODC1 | 0.01175617 | 0.16458641 | −1.0281392 | 0.40542834 | 281.292453 | −2.5359333 |
| Tcf7l2 | IN1 | 0.01339322 | 0.17724723 | 0.49096525 | 0.19782395 | 507.977987 | 2.48182912 |
| Gatad2b | PN3 | 0.0136635 | 0.17724723 | −0.4987271 | 0.20136181 | 406.623917 | −2.4767708 |
| Upf3b | IN2 | 0.01414945 | 0.17724723 | 0.36447251 | 0.14626047 | 113.504038 | 2.49194125 |
| Fbxo11 | IN1 | 0.01458943 | 0.17724723 | 0.3383005 | 0.13719383 | 183.060255 | 2.4658579 |
| Setd2 | IN1 | 0.01510976 | 0.17724723 | 0.34155837 | 0.13932971 | 194.86751 | 2.45143958 |
| Myst4 | IN2 | 0.01515849 | 0.17724723 | 0.39493793 | 0.16148755 | 247.205754 | 2.44562457 |
| Upf3b | PN1 | 0.01519262 | 0.17724723 | −0.4070623 | 0.16597076 | 169.947113 | −2.4526144 |
| Tcf20 | IN2 | 0.0161103 | 0.18068554 | 0.36449713 | 0.14978219 | 152.321615 | 2.43351449 |
| Chd8 | PN3 | 0.01622482 | 0.18068554 | −0.3964885 | 0.16263137 | 120.925541 | −2.4379583 |
| Pten | PN1 | 0.01664414 | 0.18123622 | −0.4317364 | 0.17778026 | 120.124443 | −2.4284835 |
| Fbxo11 | PN1 | 0.01737135 | 0.18504266 | −0.3819204 | 0.15903035 | 175.220643 | −2.4015567 |
| Myst4 | ODC1 | 0.01836352 | 0.19144941 | −0.9060429 | 0.38157756 | 239.451657 | −2.374466 |
| Pogz | PN1 | 0.02004044 | 0.19725751 | −0.4485723 | 0.19115805 | 178.826794 | −2.3466043 |
| Stard9 | ODC1 | 0.020834 | 0.19725751 | −0.8580433 | 0.3682325 | 192.429626 | −2.3301674 |
| Pten | PN3 | 0.02105492 | 0.19725751 | −0.3818055 | 0.16250732 | 87.3692069 | −2.3494663 |
| Asxl3 | PN1 | 0.02109219 | 0.19725751 | −0.3682935 | 0.15803759 | 152.774857 | −2.3304172 |
| Tnrc6b | ODC1 | 0.02122581 | 0.19725751 | −0.8052107 | 0.34670495 | 197.666663 | −2.3224665 |
| Satb2 | PN3 | 0.02133602 | 0.19725751 | −0.4528999 | 0.19376672 | 104.021141 | −2.3373463 |
| Scn2a1 | IN1 | 0.0230174 | 0.19966279 | 0.31470458 | 0.13735074 | 195.086726 | 2.2912478 |
| Fbxo11 | IN2 | 0.02372589 | 0.19966279 | 0.337944433 | 0.14810503 | 172.194808 | 2.28178825 |
| Spen | PN1 | 0.0238842 | 0.19966279 | −0.4196992 | 0.18426972 | 186.285964 | −2.2776354 |
| Spen | PN3 | 0.02390832 | 0.19966279 | −0.3931063 | 0.17243082 | 164.025561 | −2.2797916 |
| Satb2 | ODC1 | 0.02433803 | 0.19966279 | −1.0825085 | 0.47795154 | 261.500448 | −2.2648918 |
| Ank2 | ODC1 | 0.02442785 | 0.19966279 | −0.9707684 | 0.42933031 | 317.630567 | −2.2611224 |
| Adnp | PN3 | 0.0244485 | 0.19966279 | −0.343116 | 0.15053245 | 117.67566 | −2.279349 |
| Setd5 | IN1 | 0.02532973 | 0.20346835 | 0.32065153 | 0.14233776 | 205.847053 | 2.25275093 |
| Med13l | ODC1 | 0.02633977 | 0.20648176 | −0.8484613 | 0.37959847 | 236.953357 | −2.2351548 |
| Syngap1 | ODC1 | 0.02686339 | 0.20648176 | −0.8432233 | 0.37830387 | 212.582942 | −2.2289577 |
| Larp4b | PN3 | 0.0271183 | 0.20648176 | −0.5524442 | 0.24962064 | 979.063936 | −2.2131352 |
| Arid1b | PN1 | 0.02739044 | 0.20648176 | −0.4848622 | 0.21897869 | 349.197284 | −2.2152098 |
| Med13l | PN1 | 0.02833533 | 0.21036833 | −0.4221952 | 0.19034411 | 126.482012 | −2.2180628 |
| Ctnnb1 | PN3 | 0.02930188 | 0.2142973 | −0.3023499 | 0.13712463 | 124.112709 | −2.2049277 |
| Kdm5b | PN3 | 0.03022414 | 0.21657 | −0.3666168 | 0.16820822 | 250.250501 | −2.1795415 |
| Setd5 | PN1 | 0.03059615 | 0.21657 | −0.3825701 | 0.17570488 | 205.104462 | −2.1773448 |
| Cul3 | PN3 | 0.03110538 | 0.21657 | −0.3222806 | 0.14670126 | 75.3611305 | −2.1968495 |
| Mll1 | IN1 | 0.03138055 | 0.21657 | 0.31105438 | 0.14346563 | 191.562139 | 2.16814569 |
| Setd2 | PN3 | 0.03412606 | 0.22799966 | −0.3428662 | 0.16077114 | 208.133476 | −2.1326353 |
| Larp4b | IN1 | 0.03430065 | 0.22799966 | 0.37874849 | 0.17834605 | 406.716022 | 2.12367182 |
| Ddx3x | PN3 | 0.0344326 | 0.22799966 | −0.3771746 | 0.17743034 | 269.461882 | −2.1257614 |
| Syngap1 | PN1 | 0.03640184 | 0.23782535 | −0.3736477 | 0.17736193 | 198.239023 | −2.106696 |
| Pten | IN1 | 0.03802571 | 0.24297605 | 0.34718755 | 0.1665048 | 261.467272 | 2.08515043 |
| Med13l | PN3 | 0.03818195 | 0.24297605 | −0.3667481 | 0.17429104 | 88.8959415 | −2.104228 |
| Asxl3 | ODC1 | 0.04022464 | 0.24640322 | −0.742785 | 0.35968264 | 196.5631 | −2.0651123 |
| Tcf20 | ODC1 | 0.04045543 | 0.24640322 | −0.7731876 | 0.37499938 | 209.835499 | −2.0618369 |
| Setd2 | PN1 | 0.04115977 | 0.24640322 | −0.3500251 | 0.17044045 | 226.158301 | −2.0536507 |
| Dscam | ODC1 | 0.04130123 | 0.24640322 | −0.7904061 | 0.385021 | 213.722084 | −2.052891 |
| Mbd5 | IN2 | 0.04174905 | 0.24640322 | 0.30979166 | 0.15103144 | 174.007298 | 2.0511734 |
| Ank2 | PN3 | 0.04204699 | 0.24640322 | −0.3842745 | 0.18749879 | 160.123748 | −2.0494773 |
| Larp4b | ODC1 | 0.04329398 | 0.24640322 | −0.8450975 | 0.41615916 | 262.141864 | −2.0307073 |
| Cul3 | IN1 | 0.04334757 | 0.24640322 | 0.2939761 | 0.14459491 | 202.462117 | 2.03310131 |
| Mbd5 | PN3 | 0.04337062 | 0.24640322 | −0.3026135 | 0.14832803 | 129.280204 | −2.0401637 |
| Spen | ODC1 | 0.04386743 | 0.24640322 | −0.7421949 | 0.36617305 | 222.205812 | −2.0268966 |

TABLE 5-continued

Alternative effect size and statistical measurements of Perturb-Seq.

| perturbation | Module | pval | padj | Estimate | SE | df | t.value |
|---|---|---|---|---|---|---|---|
| Chd2 | PN1 | 0.04425201 | 0.24640322 | −0.4768338 | 0.23572346 | 228.742435 | −2.0228524 |
| Dscam | PN3 | 0.04793083 | 0.26388884 | −0.3410084 | 0.17074224 | 127.520632 | −1.9972118 |
| Tnrc6b | IN2 | 0.04879687 | 0.26567187 | 0.27910155 | 0.14062215 | 168.207503 | 1.9847624 |
| Qrich1 | IN1 | 0.04935811 | 0.26577441 | 0.27966809 | 0.14139027 | 192.337987 | 1.97798673 |
| Setd2 | IN2 | 0.05033431 | 0.26754815 | 0.29806063 | 0.15124956 | 175.698077 | 1.9706545 |
| Wac | IN1 | 0.05089802 | 0.26754815 | 0.27734145 | 0.14118309 | 195.732876 | 1.9644098 |
| Larp4b | PN6 | 0.05132556 | 0.26754815 | 0.50145802 | 0.25690778 | 742.902409 | 1.95189892 |
| Ddx3x | PN1 | 0.05237953 | 0.26839548 | −0.3634946 | 0.18658399 | 284.500854 | −1.9481556 |
| Mbd5 | PN1 | 0.0525836 | 0.26839548 | −0.3123583 | 0.15990287 | 153.826324 | −1.9534253 |
| Qrich1 | IN2 | 0.05350982 | 0.26877191 | 0.29827949 | 0.15346176 | 178.217697 | 1.94367306 |
| Wac | IN2 | 0.05375438 | 0.26877191 | 0.29903955 | 0.15408196 | 191.287276 | 1.94078235 |
| Tcf20 | IN1 | 0.0560518 | 0.27742809 | 0.26772604 | 0.13926607 | 189.81 | 1.92240682 |
| Satb2 | IN1 | 0.05704571 | 0.27952395 | 0.33435664 | 0.17448217 | 166.202049 | 1.9162797 |
| Pogz | ODC1 | 0.05839363 | 0.28329584 | −0.7904375 | 0.41609539 | 314.322084 | −1.8996545 |
| Syngap1 | IN1 | 0.05910231 | 0.28392285 | 0.2917968 | 0.15382473 | 227.453888 | 1.89694341 |
| Spen | IN2 | 0.06475702 | 0.30563812 | 0.31586545 | 0.17012955 | 211.386758 | 1.8566172 |
| Larp4b | PN1 | 0.06487013 | 0.30563812 | −0.4707516 | 0.25468242 | 911.604736 | −1.8483866 |
| Myst4 | IN1 | 0.0655383 | 0.30584539 | 0.26702444 | 0.14430914 | 230.948808 | 1.850364 |
| Tcf20 | PN3 | 0.06653463 | 0.30756576 | −0.2880181 | 0.15571213 | 135.70089 | −1.8496831 |
| Setd5 | IN2 | 0.06864764 | 0.3143677 | 0.28647332 | 0.15651066 | 204.734493 | 1.8303758 |
| Mbd5 | IN1 | 0.07279319 | 0.3302654 | 0.25212592 | 0.1397305 | 185.704142 | 1.80437291 |
| Ctnnb1 | IN2 | 0.07694194 | 0.34405266 | 0.25215923 | 0.14156716 | 147.221051 | 1.78119869 |
| Wac | PN3 | 0.07723631 | 0.34405266 | −0.2810658 | 0.15806527 | 163.442956 | −1.778163 |
| Pten | ODC1 | 0.07912183 | 0.34927652 | −0.7234123 | 0.41032923 | 249.921845 | −1.7630046 |
| Chd8 | IN1 | 0.08190038 | 0.35831416 | 0.27098887 | 0.15495404 | 194.118724 | 1.74883382 |
| Dyrk1a | ODC1 | 0.08457922 | 0.36675946 | −0.6877839 | 0.39675887 | 195.89186 | −1.7335061 |
| Arid1b | PN3 | 0.08847035 | 0.37446275 | −0.3579273 | 0.20950736 | 340.051858 | −1.7084233 |
| Ctnnb1 | IN1 | 0.08867228 | 0.37446275 | 0.22821284 | 0.13326931 | 167.304807 | 1.71241854 |
| Tnrc6b | IN1 | 0.09036519 | 0.37446275 | 0.22254693 | 0.130697 | 177.13054 | 1.70277002 |
| Scn2a1 | Astro1 | 0.09069609 | 0.37446275 | 0.36728677 | 0.21628943 | 256.616648 | 1.69812627 |
| Tcf7l2 | ODC1 | 0.09112832 | 0.37446275 | −0.7269746 | 0.42898237 | 315.640752 | −1.6946491 |
| Adnp | IN2 | 0.09120538 | 0.37446275 | 0.29642386 | 0.17484412 | 259.731956 | 1.69536076 |
| Mll1 | Astro2 | 0.09229944 | 0.37446275 | −0.425959 | 0.25202661 | 240.202703 | −1.6901349 |
| Spen | IN1 | 0.09246937 | 0.37446275 | 0.25992735 | 0.15381146 | 218.837373 | 1.68990891 |
| Gatad2b | PN1 | 0.09387819 | 0.37550282 | −0.3517088 | 0.2094425 | 401.927081 | −1.6792618 |
| Mll1 | PN1 | 0.09488777 | 0.37550282 | −0.2709321 | 0.16121128 | 152.462455 | −1.6806027 |
| Pten | IN2 | 0.09516184 | 0.37550282 | 0.31611869 | 0.1887937 | 281.031211 | 1.67441336 |
| Cul3 | IN2 | 0.09579154 | 0.37550282 | 0.262326 | 0.15651377 | 151.35227 | 1.676057 |
| Gatad2b | PN6 | 0.09829932 | 0.37751721 | 0.35363523 | 0.21330513 | 327.153359 | 1.6578843 |
| Chd8 | PN1 | 0.0983165 | 0.37751721 | −0.2925584 | 0.17583348 | 144.199437 | −1.6638381 |
| Satb2 | IN2 | 0.09861674 | 0.37751721 | 0.29580301 | 0.17680564 | 72.7126278 | 1.67304062 |
| Chd2 | IN2 | 0.09965973 | 0.37855246 | 0.44078116 | 0.26747441 | 1067.50326 | 1.6479277 |
| Wac | PN1 | 0.10168008 | 0.38325568 | −0.2777584 | 0.16887424 | 189.056758 | −1.6447645 |
| Arid1b | IN2 | 0.10301147 | 0.38531008 | 0.28408311 | 0.17369228 | 291.711235 | 1.63555399 |
| Arid1b | ODC1 | 0.10732648 | 0.39840892 | −0.6707221 | 0.41541466 | 340.657567 | −1.6145846 |
| Ank2 | PN2 | 0.10908119 | 0.40187805 | −0.4488767 | 0.2792997 | 297.746012 | −1.6071508 |
| Larp4b | Astro2 | 0.11160355 | 0.40810254 | −0.5305859 | 0.33297246 | 572.812177 | −1.5934827 |
| Dyrk1a | PN4 | 0.11450881 | 0.41562458 | −0.3197754 | 0.20166014 | 185.336932 | −1.5857144 |
| Kdm5b | IN1 | 0.11580458 | 0.41723709 | 0.23104577 | 0.14623668 | 187.565094 | 1.57994405 |
| Scn2a1 | ODC1 | 0.11710172 | 0.41883099 | −0.5656767 | 0.35946557 | 207.494277 | −1.5736676 |
| Mll1 | ODC1 | 0.11860514 | 0.4211342 | −0.5759361 | 0.36747017 | 202.58449 | −1.5673004 |
| Ash1l | IN2 | 0.12198562 | 0.4295698 | 0.24484961 | 0.15774639 | 231.723531 | 1.55217257 |
| Gatad2b | PN2 | 0.12273423 | 0.4295698 | −0.408516 | 0.26417443 | 437.390081 | −1.5463874 |
| Tcf7l2 | PN2 | 0.12414421 | 0.43142314 | −0.4964536 | 0.32236115 | 529.78759 | −1.5400541 |
| Satb2 | PN1 | 0.12763907 | 0.4402084 | −0.3223574 | 0.21033944 | 140.145731 | −1.5325581 |
| Tcf20 | PN1 | 0.12846898 | 0.4402084 | −0.2559473 | 0.16750743 | 161.972018 | −1.527976 |
| Mll1 | IN2 | 0.13081046 | 0.44511892 | 0.23098876 | 0.15171294 | 107.502688 | 1.52253831 |
| Tnrc6b | PN1 | 0.13535824 | 0.45441243 | −0.2179682 | 0.14526049 | 167.556762 | −1.500533 |
| Gatad2b | Astro1 | 0.13539636 | 0.45441243 | 0.35804573 | 0.23928536 | 382.716897 | 1.49631272 |
| Tcf7l2 | IN2 | 0.14036834 | 0.46785855 | 0.35824741 | 0.24273829 | 814.431287 | 1.47585866 |
| Tcf7l2 | PN4 | 0.14168645 | 0.46785855 | 0.40320111 | 0.27385936 | 422.459172 | 1.47229261 |
| Upf3b | IN1 | 0.14226719 | 0.46785855 | 0.20435692 | 0.13864556 | 177.358286 | 1.47395212 |
| Ddx3x | IN1 | 0.14617494 | 0.47750481 | 0.22821809 | 0.15665778 | 313.248231 | 1.45679382 |
| Ank2 | Astro1 | 0.14781237 | 0.47965605 | 0.39956277 | 0.27564342 | 495.801747 | 1.44956397 |
| Arid1b | PN5 | 0.15332592 | 0.49427435 | 0.42590913 | 0.29779043 | 462.49406 | 1.43023109 |
| Mll1 | PN3 | 0.15854256 | 0.50487174 | −0.2117959 | 0.14926807 | 119.024155 | −1.4188965 |
| Mll1 | Astro1 | 0.15867398 | 0.50487174 | 0.31307698 | 0.22144227 | 247.642878 | 1.41380856 |
| Setd2 | PN2 | 0.16024002 | 0.50656522 | −0.3222111 | 0.22894474 | 336.199893 | −1.4073752 |
| Spen | Astro2 | 0.16305787 | 0.51216895 | −0.3612308 | 0.25814225 | 229.672039 | −1.3993477 |
| Chd2 | PN5 | 0.17046605 | 0.5320278 | 0.4730862 | 0.34454298 | 416.031804 | 1.37308327 |
| Dyrk1a | PN1 | 0.17268329 | 0.53285394 | −0.2413247 | 0.17599866 | 129.993509 | −1.3711736 |
| Gatad2b | IN1 | 0.17290567 | 0.53285394 | 0.22695208 | 0.16611379 | 294.16276 | 1.36624469 |
| Pogz | PN4 | 0.17530734 | 0.53595644 | −0.2911766 | 0.21412822 | 215.406937 | −1.3598236 |
| Scn2a1 | IN2 | 0.17655489 | 0.53595644 | 0.2022653 | 0.14904597 | 170.403836 | 1.35706653 |
| Tnrc6b | PN3 | 0.17827442 | 0.53595644 | −0.1830557 | 0.13533739 | 146.286231 | −1.3525876 |
| Mbd5 | PN4 | 0.17828755 | 0.53595644 | −0.2444733 | 0.18098711 | 200.732389 | −1.3507771 |

TABLE 5-continued

Alternative effect size and statistical measurements of Perturb-Seq.

| perturbation | Module | pval | padj | Estimate | SE | df | t.value |
|---|---|---|---|---|---|---|---|
| Spen | PN6 | 0.18015818 | 0.53760242 | 0.25570565 | 0.18995218 | 159.791863 | 1.34615799 |
| Setd2 | Mg1 | 0.18102938 | 0.53760242 | 0.33240861 | 0.24760798 | 191.556783 | 1.34247939 |
| Dyrk1a | PN3 | 0.19094242 | 0.5636252 | −0.2129695 | 0.16175276 | 100.934316 | −1.3166361 |
| Adnp | IN1 | 0.19405063 | 0.56937013 | 0.20259153 | 0.15556103 | 240.369577 | 1.30232834 |
| Stard9 | IN2 | 0.19661319 | 0.57102142 | 0.1876929 | 0.14470956 | 149.890689 | 1.29703178 |
| Pogz | Astro2 | 0.19787668 | 0.57102142 | −0.3658267 | 0.28362491 | 389.407962 | −1.2898256 |
| Larp4b | Astro3 | 0.19810947 | 0.57102142 | −0.3927733 | 0.30489005 | 663.604701 | −1.2882456 |
| Cul3 | PN2 | 0.20144859 | 0.57725033 | −0.2981748 | 0.23287074 | 281.30109 | −1.2804304 |
| Scn2a1 | Astro2 | 0.20428102 | 0.58030982 | −0.313115 | 0.24598862 | 241.920131 | −1.2728842 |
| Asxl3 | IN1 | 0.20776789 | 0.58030982 | 0.17703497 | 0.14002279 | 177.659476 | 1.26432973 |
| Spen | PN5 | 0.2082352 | 0.58030982 | 0.35063143 | 0.27814934 | 378.030407 | 1.26058696 |
| Asxl3 | PN5 | 0.2099462 | 0.58030982 | 0.31132952 | 0.24785403 | 338.36755 | 1.25610026 |
| Wac | ODC1 | 0.21020503 | 0.58030982 | −0.4557558 | 0.36261097 | 208.64131 | −1.2568726 |
| Adnp | Astro2 | 0.21063655 | 0.58030982 | −0.3244788 | 0.25862885 | 288.123197 | −1.2546116 |
| Med13l | IN1 | 0.21080643 | 0.58030982 | 0.18733757 | 0.14928667 | 227.813488 | 1.25488472 |
| Chd2 | PN2 | 0.22092133 | 0.6020548 | −0.3866106 | 0.31528882 | 359.762296 | −1.2262108 |
| Tcf20 | PN6 | 0.22258013 | 0.6020548 | 0.21208773 | 0.17312114 | 141.449581 | 1.22508282 |
| Arid1b | PN4 | 0.22302392 | 0.6020548 | −0.2848739 | 0.23337412 | 353.029407 | −1.2206746 |
| Ctnnb1 | PN2 | 0.22362035 | 0.6020548 | −0.2589992 | 0.21231357 | 258.045902 | −1.2198899 |
| Tcf7l2 | PN6 | 0.22538342 | 0.60348565 | 0.32174365 | 0.26492906 | 354.528615 | 1.21445211 |
| Fbxo11 | PN6 | 0.22927125 | 0.6105593 | 0.1981227 | 0.16412604 | 150.640324 | 1.2071375 |
| Dscam | PN5 | 0.23567737 | 0.62422655 | 0.3388436 | 0.2852651 | 364.675847 | 1.18782003 |
| Myst4 | Mg1 | 0.23944631 | 0.63079943 | 0.2880371 | 0.24401789 | 174.937035 | 1.18039337 |
| Ash1l | PN6 | 0.24139533 | 0.63253321 | 0.19213456 | 0.16331081 | 139.848033 | 1.17649626 |
| Kdm5b | Mg2 | 0.24812997 | 0.64331493 | 0.29832927 | 0.25769887 | 244.491088 | 1.15766619 |
| Stard9 | PN2 | 0.24813576 | 0.64331493 | −0.2539718 | 0.2194641 | 287.680254 | −1.1572364 |
| Satb2 | PN6 | 0.25535028 | 0.65853493 | 0.24898471 | 0.21792608 | 129.252133 | 1.14251914 |
| Myst4 | PN3 | 0.2591674 | 0.66135943 | −0.1766618 | 0.15613455 | 206.747668 | −1.1314715 |
| Stard9 | IN1 | 0.26111036 | 0.66135943 | 0.1526452 | 0.13540113 | 177.913794 | 1.12735543 |
| Upf3b | Astro1 | 0.26418265 | 0.66135943 | 0.2334001 | 0.2085591 | 246.693216 | 1.11910773 |
| Larp4b | PN4 | 0.26424021 | 0.66135943 | 0.28779177 | 0.25757705 | 714.248177 | 1.11730363 |
| Pogz | IN1 | 0.26468335 | 0.66135943 | 0.17946308 | 0.16058219 | 286.598732 | 1.1175777 |
| Cul3 | Astro1 | 0.26499079 | 0.66135943 | 0.23993624 | 0.2148091 | 272.058753 | 1.11697427 |
| Chd8 | Astro1 | 0.266346 | 0.66135943 | 0.27128152 | 0.24371321 | 388.536817 | 1.11311783 |
| Chd2 | PN3 | 0.2672432 | 0.66135943 | −0.2475013 | 0.22250899 | 214.888311 | −1.1123205 |
| Dscam | PN1 | 0.26864254 | 0.66148163 | −0.2043485 | 0.18407066 | 155.491677 | −1.1101633 |
| Setd5 | Astro1 | 0.27564986 | 0.66902663 | 0.23497015 | 0.21510798 | 272.623952 | 1.09233583 |
| Pogz | Astro1 | 0.27917651 | 0.66902663 | 0.27448439 | 0.25332964 | 440.294827 | 1.08350561 |
| Adnp | PN5 | 0.28088284 | 0.66902663 | 0.27805976 | 0.25746749 | 355.667461 | 1.0799801 |
| Med13l | PN4 | 0.28150917 | 0.66902663 | −0.233994 | 0.2167198 | 210.305599 | −1.0797075 |
| Chd8 | Astro3 | 0.28292114 | 0.66902663 | −0.2694012 | 0.25056023 | 409.011186 | −1.0751953 |
| Stard9 | PN6 | 0.28442829 | 0.66902663 | 0.17247437 | 0.16040737 | 120.103158 | 1.07522723 |
| Larp4b | Astro1 | 0.28457803 | 0.66902663 | 0.32182506 | 0.30050641 | 675.092649 | 1.07094243 |
| Arid1b | IN1 | 0.28621596 | 0.66902663 | 0.16376974 | 0.15323487 | 249.34702 | 1.06874984 |
| Wac | Astro3 | 0.28742399 | 0.66902663 | 0.23149657 | 0.21715918 | 254.435602 | 1.06602248 |
| Spen | Mg1 | 0.28953893 | 0.66902663 | 0.26375857 | 0.24826578 | 172.318778 | 1.06240404 |
| Syngap1 | Astro3 | 0.2896817 | 0.66902663 | 0.25161088 | 0.2372046 | 293.96531 | 1.06073359 |
| Chd2 | Astro1 | 0.2909498 | 0.66902663 | 0.315637 | 0.298662 | 701.645834 | 1.05683682 |
| Ank2 | Mg2 | 0.29118172 | 0.66902663 | −0.3375746 | 0.31927558 | 313.72542 | −1.0573141 |
| Chd8 | Astro2 | 0.29237098 | 0.66902663 | −0.2886983 | 0.27376993 | 348.684426 | −1.0545289 |
| Gatad2b | IN2 | 0.2928021 | 0.66902663 | 0.20273642 | 0.19244871 | 379.384305 | 1.05345689 |
| Qrich1 | PN1 | 0.29449286 | 0.66902663 | −0.1798966 | 0.17107267 | 169.072756 | −1.0515802 |
| Ash1l | Mg1 | 0.29599175 | 0.66902663 | 0.24037313 | 0.2292543 | 159.773867 | 1.04850001 |
| Scn2a1 | PN2 | 0.29628322 | 0.66902663 | −0.2415428 | 0.23089106 | 322.398671 | −1.0461332 |
| Qrich1 | PN3 | 0.30382266 | 0.68290414 | −0.164423 | 0.15932412 | 142.200743 | −1.0320031 |
| Upf3b | Astro2 | 0.3100974 | 0.69382524 | −0.2415959 | 0.23750378 | 233.429045 | −1.0172295 |
| Ank2 | Astro2 | 0.31487322 | 0.70130855 | −0.3096623 | 0.30774306 | 425.796538 | −1.0062366 |
| Ank2 | IN2 | 0.31867065 | 0.70487084 | 0.23280309 | 0.23330094 | 739.66078 | 0.99786605 |
| Pten | PN6 | 0.31934965 | 0.70487084 | 0.18489405 | 0.18483706 | 110.356334 | 1.00030833 |
| Ash1l | PN5 | 0.32164727 | 0.70675857 | 0.24582022 | 0.24766693 | 335.719445 | 0.99254357 |
| Kdm5b | PN6 | 0.32516408 | 0.70888746 | 0.17913211 | 0.18165818 | 221.218852 | 0.98609438 |
| Pten | PN5 | 0.32550955 | 0.70888746 | 0.27620477 | 0.2805569 | 375.622717 | 0.98448755 |
| Wac | PN2 | 0.3270718 | 0.70913798 | −0.2258634 | 0.23012409 | 330.278873 | −0.9814855 |
| Asxl3 | PN4 | 0.32996088 | 0.7098563 | −0.1743863 | 0.17858207 | 205.743627 | −0.9765053 |
| Setd5 | PN6 | 0.33139571 | 0.7098563 | 0.17612834 | 0.18082253 | 173.133399 | 0.97403978 |
| Mll1 | Mg1 | 0.33174917 | 0.7098563 | 0.2374933 | 0.24400752 | 174.593202 | 0.9733032 |
| Gatad2b | Mg1 | 0.33749307 | 0.71900697 | 0.28009141 | 0.29150708 | 269.895696 | 0.96083911 |
| Ctnnb1 | Astro2 | 0.34067901 | 0.72265244 | −0.2206167 | 0.23101178 | 209.17035 | −0.9550021 |
| Upf3b | Astro3 | 0.34842511 | 0.73345953 | −0.2040676 | 0.21726634 | 275.37402 | −0.9392508 |
| Upf3b | PN6 | 0.34876749 | 0.73345953 | 0.16104828 | 0.17134306 | 150.369691 | 0.93991712 |
| Syngap1 | PN5 | 0.3504851 | 0.73352679 | 0.24885976 | 0.26622046 | 383.858061 | 0.93478827 |
| Chd8 | PN5 | 0.35179346 | 0.73352679 | 0.25637813 | 0.27500442 | 377.407565 | 0.93226913 |
| Syngap1 | IN2 | 0.36003978 | 0.74566045 | 0.15707866 | 0.1712751 | 231.007428 | 0.91711322 |
| Pogz | PN3 | 0.36065618 | 0.74566045 | −0.1637614 | 0.1786314 | 159.318334 | −0.9167559 |
| Fbxo11 | PN5 | 0.36688302 | 0.75394336 | 0.22246052 | 0.24621665 | 344.919541 | 0.90351536 |
| Dscam | Mg1 | 0.3681958 | 0.75394336 | 0.21813876 | 0.24171844 | 157.528927 | 0.90244979 |

TABLE 5-continued

Alternative effect size and statistical measurements of Perturb-Seq.

| perturbation | Module | pval | padj | Estimate | SE | df | t.value |
|---|---|---|---|---|---|---|---|
| Scn2a1 | PN4 | 0.36967906 | 0.75394336 | −0.1688266 | 0.18781037 | 219.688342 | −0.8989208 |
| Stard9 | PN4 | 0.37105198 | 0.75394336 | −0.1583032 | 0.17655611 | 191.003632 | −0.896617 |
| Fbxo11 | Astro1 | 0.3723557 | 0.75394336 | 0.18327708 | 0.20507238 | 243.23343 | 0.89371897 |
| Qrich1 | PN6 | 0.37555445 | 0.75422956 | 0.15701344 | 0.17665595 | 147.333811 | 0.8888092 |
| Gatad2b | Astro2 | 0.3769287 | 0.75422956 | −0.2379749 | 0.26897894 | 338.090072 | −0.8847343 |
| Pten | PN2 | 0.37711478 | 0.75422956 | 0.22351457 | 0.25270279 | 309.686461 | 0.88449586 |
| Fbxo11 | Mg2 | 0.38077651 | 0.75600862 | 0.20595347 | 0.23447822 | 206.348898 | 0.87834796 |
| Qrich1 | Mg1 | 0.38109006 | 0.75600862 | 0.2023028 | 0.23023136 | 138.4375 | 0.8786935 |
| Mbd5 | Mg1 | 0.38452002 | 0.75973713 | −0.2074172 | 0.2378585 | 158.109345 | −0.8720195 |
| Adnp | PN6 | 0.3916382 | 0.77069365 | 0.14507442 | 0.16876601 | 125.508836 | 0.8596187 |
| Ddx3x | PN6 | 0.39395529 | 0.7710519 | 0.16308745 | 0.19096435 | 237.217842 | 0.85402038 |
| Upf3b | Mg1 | 0.3949674 | 0.7710519 | 0.19117885 | 0.22406111 | 141.355208 | 0.85324421 |
| Chd8 | Mg2 | 0.40271732 | 0.77865747 | 0.23435033 | 0.27957509 | 244.112695 | 0.83823752 |
| Kdm5b | IN2 | 0.40425802 | 0.77865747 | 0.13210385 | 0.15799775 | 171.084591 | 0.83611222 |
| Larp4b | IN2 | 0.40506004 | 0.77865747 | 0.17765399 | 0.21319973 | 537.138806 | 0.83327496 |
| Gatad2b | Astro3 | 0.40579256 | 0.77865747 | −0.2048621 | 0.2461673 | 397.05413 | −0.8322066 |
| Arid1b | Mg2 | 0.40820688 | 0.77865747 | 0.23667804 | 0.2858657 | 395.568839 | 0.82793439 |
| Qrich1 | Astro1 | 0.4087239 | 0.77865747 | 0.17267531 | 0.20866348 | 250.628231 | 0.8275301 |
| Pogz | Astro3 | 0.40998699 | 0.77865747 | −0.2140939 | 0.25960974 | 455.803816 | −0.8246759 |
| Chd2 | Mg1 | 0.41638789 | 0.78638047 | 0.2966353 | 0.36477984 | 694.380562 | 0.81318995 |
| Dyrk1a | PN2 | 0.41757393 | 0.78638047 | −0.2038823 | 0.25114365 | 285.450498 | −0.8118155 |
| Wac | Astro2 | 0.42177404 | 0.78638047 | −0.1910887 | 0.23741148 | 215.430757 | −0.804884 |
| Mll1 | PN2 | 0.42187371 | 0.78638047 | −0.1806247 | 0.22458766 | 307.494523 | −0.8042504 |
| Qrich1 | PN2 | 0.42207768 | 0.78638047 | −0.1896844 | 0.23596813 | 319.577823 | −0.803856 |
| Tcf20 | PN2 | 0.42484464 | 0.78804349 | −0.1854949 | 0.23213788 | 318.195808 | −0.7990721 |
| Mbd5 | PN2 | 0.4274668 | 0.78804349 | −0.1781251 | 0.22416408 | 298.318264 | −0.7946191 |
| Kdm5b | PN2 | 0.42897056 | 0.78804349 | −0.1849706 | 0.23359622 | 363.759655 | −0.7918391 |
| Ash1l | IN1 | 0.43171796 | 0.78804349 | 0.11173583 | 0.1418511 | 220.84089 | 0.78769805 |
| Tcf7l2 | Mg2 | 0.43473347 | 0.78804349 | −0.2276521 | 0.29126532 | 306.970019 | −0.7821679 |
| Tnrc6b | PN4 | 0.43546956 | 0.78804349 | −0.1279096 | 0.16368773 | 201.622095 | −0.7814243 |
| Syngap1 | PN4 | 0.43552485 | 0.78804349 | −0.1538676 | 0.19698378 | 233.295681 | −0.7811183 |
| Setd2 | Astro3 | 0.43855288 | 0.78804349 | 0.17318876 | 0.22328359 | 308.525557 | 0.77564479 |
| Med13l | Mg2 | 0.43970721 | 0.78804349 | 0.20049065 | 0.25900987 | 224.263012 | 0.77406567 |
| Ash1l | PN2 | 0.44039713 | 0.78804349 | −0.1702654 | 0.22039076 | 296.653756 | −0.7725613 |
| Arid1b | Astro3 | 0.44279077 | 0.78804349 | 0.20396356 | 0.26557561 | 590.635292 | 0.76800563 |
| Setd2 | Mg2 | 0.44381775 | 0.78804349 | −0.1968112 | 0.25660764 | 251.124337 | −0.7669735 |
| Chd2 | PN6 | 0.44387756 | 0.78804349 | 0.18577643 | 0.24213259 | 191.451237 | 0.76725082 |
| Scn2a1 | Mg1 | 0.44736969 | 0.79137598 | 0.18331282 | 0.24070888 | 171.909943 | 0.76155402 |
| Cul3 | Astro2 | 0.44945353 | 0.79220227 | −0.1846654 | 0.24378935 | 258.17649 | −0.7574793 |
| Chd2 | Mg2 | 0.45160892 | 0.79314829 | −0.272229 | 0.3614571 | 723.161063 | −0.7531433 |
| Stard9 | Astro1 | 0.45407697 | 0.79463469 | 0.15366866 | 0.20491197 | 226.792301 | 0.74992524 |
| Chd2 | PN4 | 0.45673308 | 0.79643846 | 0.19315679 | 0.25914134 | 255.017912 | 0.74537235 |
| Adnp | Mg2 | 0.4627929 | 0.80145772 | −0.1843535 | 0.25067379 | 240.528335 | −0.7354321 |
| Ddx3x | Astro1 | 0.46288273 | 0.80145772 | 0.17050738 | 0.23190372 | 247.57752 | 0.73525073 |
| Mll1 | PN4 | 0.47062201 | 0.81198868 | −0.131518 | 0.18196208 | 209.737801 | −0.7227771 |
| Chd8 | PN6 | 0.47398974 | 0.81492973 | 0.13082562 | 0.18216889 | 126.102563 | 0.71815567 |
| Ddx3x | Mg1 | 0.48148878 | 0.82492833 | 0.17117616 | 0.2425225 | 138.448024 | 0.70581559 |
| Spen | Astro1 | 0.48552364 | 0.82894279 | 0.15823059 | 0.22652187 | 241.157311 | 0.69852235 |
| Med13l | Astro3 | 0.49403453 | 0.83898255 | 0.16628257 | 0.24283471 | 295.490422 | 0.68475619 |
| Mbd5 | Astro3 | 0.49482849 | 0.83898255 | 0.14410931 | 0.2107764 | 236.859129 | 0.68370704 |
| Syngap1 | Mg1 | 0.50062396 | 0.84303519 | −0.1662291 | 0.24620909 | 149.014715 | −0.6751544 |
| Ank2 | PN6 | 0.50065967 | 0.84303519 | 0.13985675 | 0.20716272 | 148.316286 | 0.67510576 |
| Scn2a1 | PN5 | 0.50329224 | 0.84456574 | 0.17164133 | 0.25618965 | 368.015776 | 0.66997759 |
| Satb2 | Astro3 | 0.50632628 | 0.84675727 | −0.1923981 | 0.28920351 | 342.43014 | −0.665269 |
| Ctnnb1 | PN4 | 0.52047009 | 0.86135196 | −0.1090316 | 0.16933148 | 178.576245 | −0.6438943 |
| Ash1l | Astro3 | 0.5217733 | 0.86135196 | 0.14203405 | 0.2214452 | 289.294572 | 0.64139592 |
| Ctnnb1 | PN6 | 0.52331597 | 0.86135196 | 0.09827286 | 0.15353725 | 123.928037 | 0.64005877 |
| Setd5 | PN2 | 0.52339192 | 0.86135196 | −0.1524579 | 0.23865946 | 328.59415 | −0.6388094 |
| Med13l | Mg1 | 0.5262796 | 0.86135196 | 0.15777773 | 0.24846606 | 169.579268 | 0.63500716 |
| Chd2 | Astro3 | 0.52754343 | 0.86135196 | −0.1913779 | 0.30277335 | 685.018255 | −0.6320832 |
| Myst4 | Astro1 | 0.53112832 | 0.86135196 | 0.14132449 | 0.22535003 | 257.161689 | 0.62713319 |
| Adnp | PN4 | 0.53196255 | 0.86135196 | −0.1160729 | 0.18537929 | 193.584716 | −0.6261372 |
| Dyrk1a | Astro3 | 0.53240352 | 0.86135196 | 0.16104843 | 0.25761732 | 269.86513 | 0.62514595 |
| Wac | Mg1 | 0.53783051 | 0.86135196 | 0.14401672 | 0.23322791 | 152.450343 | 0.61749351 |
| Larp4b | Mg2 | 0.54422035 | 0.86135196 | −0.1985139 | 0.32711131 | 486.914242 | −0.6068695 |
| Dyrk1a | Astro2 | 0.54586796 | 0.86135196 | −0.1703421 | 0.2816204 | 229.085288 | −0.6048641 |
| Satb2 | PN5 | 0.54686475 | 0.86135196 | 0.18859822 | 0.31280172 | 439.56242 | 0.60293219 |
| Setd2 | PN4 | 0.54791453 | 0.86135196 | −0.1128338 | 0.18752318 | 250.238283 | −0.6017061 |
| Qrich1 | Astro2 | 0.54987616 | 0.86135196 | −0.1421928 | 0.23746419 | 238.726992 | −0.5987968 |
| Scn2a1 | Astro3 | 0.55026884 | 0.86135196 | −0.1345884 | 0.22503841 | 285.244517 | −0.5980684 |
| Syngap1 | PN6 | 0.55127237 | 0.86135196 | 0.10904432 | 0.18263618 | 168.073906 | 0.59705761 |
| Dyrk1a | IN2 | 0.55262344 | 0.86135196 | 0.10341475 | 0.17347381 | 87.3332077 | 0.59614042 |
| Setd2 | Astro1 | 0.55449914 | 0.86135196 | 0.12735678 | 0.21522526 | 282.926418 | 0.59173715 |
| Dyrk1a | IN1 | 0.55478947 | 0.86135196 | 0.09855809 | 0.16659089 | 195.723534 | 0.59161749 |
| Larp4b | PN2 | 0.55584971 | 0.86135196 | −0.1742242 | 0.29564826 | 713.162981 | −0.5892955 |
| Satb2 | Astro2 | 0.55965421 | 0.86135196 | −0.1845858 | 0.31605653 | 290.947684 | −0.5840277 |

TABLE 5-continued

Alternative effect size and statistical measurements of Perturb-Seq.

| perturbation | Module | pval | padj | Estimate | SE | df | t.value |
|---|---|---|---|---|---|---|---|
| Cul3 | Astro3 | 0.55985119 | 0.86135196 | 0.13019227 | 0.22304442 | 304.036422 | 0.58370557 |
| Tcf7l2 | Mg1 | 0.56051561 | 0.86135196 | −0.1655581 | 0.28405635 | 256.720203 | −0.5828355 |
| Wac | PN6 | 0.56178224 | 0.86135196 | 0.10117535 | 0.1740238 | 162.970282 | 0.581388 |
| Satb2 | PN4 | 0.56563382 | 0.86135196 | −0.1364787 | 0.23722424 | 232.832508 | −0.575315 |
| Qrich1 | Mg2 | 0.56733987 | 0.86135196 | 0.13881622 | 0.24227899 | 192.620497 | 0.57296022 |
| Larp4b | Mg1 | 0.56809241 | 0.86135196 | 0.18608693 | 0.3257364 | 453.398346 | 0.57128075 |
| Gatad2b | Mg2 | 0.56837789 | 0.86135196 | 0.17033486 | 0.29828393 | 311.509219 | 0.5710494 |
| Tcf7l2 | PN3 | 0.56951918 | 0.86135196 | −0.142731 | 0.25075881 | 431.192064 | −0.5691965 |
| Ctnnb1 | Mg2 | 0.56954701 | 0.86135196 | 0.13250051 | 0.23257154 | 188.330581 | 0.56971935 |
| Ctnnb1 | Astro1 | 0.57455161 | 0.86512256 | 0.11359232 | 0.20205047 | 220.784346 | 0.56219777 |
| Pten | Mg1 | 0.5768521 | 0.86512256 | 0.1629593 | 0.29172147 | 293.465331 | 0.55861262 |
| Cul3 | PN5 | 0.57733689 | 0.86512256 | 0.14607118 | 0.26186765 | 347.083799 | 0.55780536 |
| Satb2 | Mg1 | 0.58222715 | 0.86800741 | −0.1624275 | 0.29481467 | 220.577282 | −0.5509477 |
| Myst4 | PN6 | 0.58280498 | 0.86800741 | 0.09359714 | 0.17010295 | 189.214163 | 0.5502382 |
| Pogz | Mg2 | 0.58641234 | 0.87059053 | 0.16237169 | 0.29811671 | 286.508656 | 0.54465812 |
| Chd8 | PN4 | 0.58809279 | 0.87059053 | −0.1084953 | 0.19999306 | 196.281911 | −0.5424953 |
| Med13l | PN2 | 0.59108615 | 0.87238618 | −0.1432354 | 0.26634546 | 334.42624 | −0.5377807 |
| Tnrc6b | PN2 | 0.59464866 | 0.87500854 | −0.1082475 | 0.20319985 | 283.33694 | −0.5327147 |
| Upf3b | PN2 | 0.60065176 | 0.87725408 | −0.119003 | 0.22712249 | 336.350734 | −0.5239595 |
| Tnrc6b | Mg1 | 0.60172254 | 0.87725408 | 0.11253806 | 0.21517994 | 155.399848 | 0.52299513 |
| Adnp | Astro1 | 0.60239263 | 0.87725408 | 0.1193529 | 0.22887166 | 318.027345 | 0.52148396 |
| Dscam | PN2 | 0.60333597 | 0.87725408 | −0.1333459 | 0.25636602 | 311.905546 | −0.5201386 |
| Kdm5b | Astro1 | 0.60600222 | 0.87763361 | 0.11295833 | 0.21873998 | 265.164233 | 0.51640462 |
| Adnp | PN2 | 0.60870536 | 0.87763361 | −0.1179118 | 0.23008506 | 294.925026 | −0.5124705 |
| Dyrk1a | PN6 | 0.60897026 | 0.87763361 | −0.0937199 | 0.18271261 | 116.126084 | −0.5129363 |
| Asxl3 | PN6 | 0.61880858 | 0.88919707 | 0.08154144 | 0.16351083 | 134.967287 | 0.49869141 |
| Med13l | IN2 | 0.62153986 | 0.89051033 | 0.08171023 | 0.16526207 | 202.447606 | 0.49442824 |
| Tnrc6b | PN5 | 0.6265434 | 0.895062 | 0.11204978 | 0.23004831 | 318.408176 | 0.48707065 |
| Cul3 | PN6 | 0.63123618 | 0.89700953 | 0.08088299 | 0.16801111 | 103.705776 | 0.48141453 |
| Mll1 | Astro3 | 0.63242543 | 0.89700953 | −0.1104003 | 0.23055997 | 283.022482 | −0.4788354 |
| Asxl3 | Astro1 | 0.6344336 | 0.89700953 | 0.09974654 | 0.20947918 | 218.220173 | 0.47616445 |
| Mll1 | Mg2 | 0.63646092 | 0.89700953 | 0.11996149 | 0.25349095 | 247.358705 | 0.47323774 |
| Setd2 | PN6 | 0.63976352 | 0.89700953 | 0.08208423 | 0.17510165 | 190.161713 | 0.46878046 |
| Scn2a1 | Mg2 | 0.64115736 | 0.89700953 | −0.1169295 | 0.25061287 | 231.711082 | −0.4666939 |
| Dyrk1a | Mg1 | 0.64251645 | 0.89700953 | 0.12494974 | 0.26876967 | 198.337239 | 0.46489525 |
| Med13l | Astro1 | 0.64450909 | 0.89700953 | −0.1079165 | 0.23361691 | 262.137096 | −0.4619378 |
| Mbd5 | PN5 | 0.64504467 | 0.89700953 | 0.11567117 | 0.25088426 | 351.991713 | 0.46105392 |
| Pogz | PN6 | 0.64621299 | 0.89700953 | −0.0907106 | 0.19722163 | 152.42442 | −0.4599424 |
| Ddx3x | PN5 | 0.65236322 | 0.90298864 | 0.11957824 | 0.26524576 | 399.901176 | 0.45082056 |
| Ctnnb1 | Mg1 | 0.65623095 | 0.90578356 | 0.0985363 | 0.22089306 | 139.310648 | 0.44608147 |
| Med13l | PN6 | 0.66133229 | 0.90640058 | 0.0867966 | 0.19763163 | 117.896993 | 0.43918373 |
| Chd2 | IN1 | 0.66800797 | 0.90640058 | 0.09166642 | 0.21363732 | 663.530068 | 0.42907493 |
| Ctnnb1 | PN5 | 0.66818777 | 0.90640058 | 0.10429322 | 0.24307399 | 300.053246 | 0.42905956 |
| Ddx3x | Astro3 | 0.66858888 | 0.90640058 | 0.10348167 | 0.24147709 | 281.190545 | 0.42853619 |
| Mbd5 | Astro2 | 0.66971521 | 0.90640058 | −0.102649 | 0.24034109 | 225.978795 | −0.4270972 |
| Dscam | Astro3 | 0.67006192 | 0.90640058 | 0.10305578 | 0.24159754 | 253.592027 | 0.42655703 |
| Qrich1 | PN5 | 0.67177162 | 0.90640058 | −0.1111911 | 0.26220553 | 364.547589 | −0.4240608 |
| Ddx3x | Astro2 | 0.67280434 | 0.90640058 | −0.1116097 | 0.26396244 | 238.547527 | −0.4228243 |
| Dscam | Astro2 | 0.67659867 | 0.90640058 | −0.1103218 | 0.26413016 | 214.684019 | −0.4176798 |
| Kdm5b | Astro3 | 0.67934783 | 0.90640058 | 0.09406856 | 0.22734783 | 294.082361 | 0.41376496 |
| Kdm5b | PN5 | 0.6815008 | 0.90640058 | 0.10547744 | 0.25680384 | 380.140945 | 0.41073156 |
| Myst4 | PN1 | 0.68354758 | 0.90640058 | −0.0675741 | 0.16555972 | 224.952228 | −0.4081557 |
| Pogz | IN2 | 0.68372568 | 0.90640058 | 0.07536628 | 0.18484172 | 339.730585 | 0.40773415 |
| Fbxo11 | Mg1 | 0.6839919 | 0.90640058 | 0.09129236 | 0.22386815 | 153.59168 | 0.40779521 |
| Fbxo11 | Astro3 | 0.68671096 | 0.90640058 | 0.08629283 | 0.21372663 | 272.358662 | 0.4037533 |
| Tnrc6b | Mg2 | 0.68779724 | 0.90640058 | −0.0906462 | 0.22525947 | 207.88535 | −0.402408 |
| Tcf20 | Astro2 | 0.68959274 | 0.90640058 | −0.0990169 | 0.24762088 | 249.048775 | −0.3998731 |
| Mbd5 | PN6 | 0.69098843 | 0.90640058 | −0.0659083 | 0.16544303 | 133.966542 | −0.3983744 |
| Cul3 | Mg2 | 0.69182412 | 0.90640058 | 0.0950299 | 0.23939421 | 198.211022 | 0.3969599 |
| Ank2 | PN4 | 0.69734773 | 0.91120103 | −0.0878675 | 0.22561975 | 205.179341 | −0.3894493 |
| Dscam | PN4 | 0.70903855 | 0.9167956 | −0.0776347 | 0.20776957 | 208.593979 | −0.3736576 |
| Setd5 | Astro2 | 0.71013169 | 0.9167956 | 0.09084722 | 0.24415238 | 256.216899 | 0.37209231 |
| Stard9 | Mg1 | 0.71209934 | 0.9167956 | 0.08370061 | 0.226341 | 138.003543 | 0.36979872 |
| Ash1l | Astro1 | 0.71328325 | 0.9167956 | 0.07833232 | 0.21294633 | 260.945394 | 0.36785004 |
| Syngap1 | PN2 | 0.71548619 | 0.9167956 | −0.0879997 | 0.24122314 | 334.934804 | −0.3648064 |
| Syngap1 | Astro2 | 0.7172316 | 0.9167956 | −0.0940068 | 0.25927755 | 249.375994 | −0.3625722 |
| Fbxo11 | PN2 | 0.71756593 | 0.9167956 | −0.0796295 | 0.21994111 | 305.007541 | −0.3620493 |
| Ddx3x | IN2 | 0.71941685 | 0.9167956 | 0.06568625 | 0.182721 | 404.077655 | 0.35948933 |
| Tcf20 | PN5 | 0.7200799 | 0.9167956 | 0.0924377 | 0.2577549 | 368.696866 | 0.35862634 |
| Pogz | PN2 | 0.72119512 | 0.9167956 | 0.0942598 | 0.26389691 | 312.385529 | 0.35718416 |
| Dscam | Astro1 | 0.72351893 | 0.9167956 | 0.08191233 | 0.23126227 | 227.946785 | 0.35419666 |
| Setd2 | Astro2 | 0.72513759 | 0.9167956 | −0.0858991 | 0.24404647 | 261.827255 | −0.3519784 |
| Pogz | Mg1 | 0.7274751 | 0.9167956 | −0.1010476 | 0.28959765 | 223.229836 | −0.3489242 |
| Pten | PN4 | 0.73349971 | 0.9167956 | −0.0695849 | 0.2040802 | 192.15918 | −0.3409686 |
| Arid1b | Mg1 | 0.73758274 | 0.9167956 | 0.09462441 | 0.28218697 | 346.414793 | 0.33532522 |
| Upf3b | Mg2 | 0.73872172 | 0.9167956 | −0.0787076 | 0.23563277 | 193.231544 | −0.3340266 |

TABLE 5-continued

Alternative effect size and statistical measurements of Perturb-Seq.

| perturbation | Module | pval | padj | Estimate | SE | df | t.value |
| --- | --- | --- | --- | --- | --- | --- | --- |
| Chd8 | Mg1 | 0.73880366 | 0.9167956 | 0.08996248 | 0.26940114 | 186.541823 | 0.33393506 |
| Dyrk1a | PN5 | 0.74045839 | 0.9167956 | −0.093554 | 0.28220407 | 346.217573 | −0.331512 |
| Dscam | Mg2 | 0.74374681 | 0.9167956 | 0.08272345 | 0.25273207 | 214.973777 | 0.32731678 |
| Pten | Astro2 | 0.7455054 | 0.9167956 | −0.0918636 | 0.28277339 | 304.232644 | −0.3248665 |
| Chd2 | Astro2 | 0.74629465 | 0.9167956 | −0.1070252 | 0.33065137 | 591.870171 | −0.32368 |
| Tcf20 | Mg1 | 0.7463485 | 0.9167956 | 0.07778108 | 0.24006884 | 166.511803 | 0.3239949 |
| Asxl3 | Mg1 | 0.7469197 | 0.9167956 | 0.07281877 | 0.2252342 | 148.931113 | 0.32330246 |
| Pten | Astro3 | 0.74731023 | 0.9167956 | 0.08343418 | 0.25876148 | 357.843947 | 0.32243664 |
| Ash1l | Astro2 | 0.74892947 | 0.9167956 | 0.07755759 | 0.24205656 | 245.383042 | 0.320411 |
| Pten | Mg2 | 0.75275795 | 0.9167956 | 0.09378185 | 0.29747301 | 337.236655 | 0.31526171 |
| Gatad2b | PN4 | 0.7548976 | 0.9167956 | −0.0693027 | 0.22182515 | 368.763737 | −0.3124204 |
| Myst4 | PN5 | 0.75635715 | 0.9167956 | 0.07666198 | 0.24689496 | 359.868385 | 0.31050442 |
| Cul3 | PN4 | 0.75735 | 0.9167956 | −0.0577253 | 0.18654884 | 178.049098 | −0.3094383 |
| Wac | PN4 | 0.75775963 | 0.9167956 | −0.0580044 | 0.1878465 | 233.23846 | −0.3087864 |
| Satb2 | Astro1 | 0.76275127 | 0.92056187 | 0.08453173 | 0.27979041 | 322.676134 | 0.3021252 |
| Dyrk1a | Mg2 | 0.76773544 | 0.9237563 | −0.082192 | 0.27800914 | 261.812296 | −0.2956451 |
| Tnrc6b | Astro3 | 0.76936486 | 0.9237563 | −0.0600881 | 0.20472193 | 260.9451 | −0.293511 |
| Asxl3 | IN2 | 0.77105372 | 0.9237563 | 0.04328453 | 0.14843471 | 129.602102 | 0.2916065 |
| Satb2 | Mg2 | 0.77491926 | 0.92422814 | −0.0869077 | 0.30364009 | 283.412765 | −0.2862193 |
| Ash1l | Mg2 | 0.77521993 | 0.92422814 | 0.06850153 | 0.23958931 | 215.524747 | 0.28591227 |
| Spen | PN2 | 0.78005988 | 0.92774112 | 0.07033394 | 0.25167145 | 332.734371 | 0.27946728 |
| Asxl3 | Astro3 | 0.79373424 | 0.93930409 | −0.0573414 | 0.21907376 | 249.416172 | −0.2617448 |
| Ctnnb1 | Astro3 | 0.79481235 | 0.93930409 | 0.05501071 | 0.21129706 | 247.11846 | 0.26034774 |
| Kdm5b | Astro2 | 0.79579423 | 0.93930409 | −0.06438 | 0.24850342 | 249.518977 | −0.2590708 |
| Syngap1 | Mg2 | 0.79745 | 0.93930409 | 0.06640512 | 0.25839134 | 197.979635 | 0.25699438 |
| Dyrk1a | Astro1 | 0.80100366 | 0.94033681 | 0.06230379 | 0.24690301 | 229.077577 | 0.25234114 |
| Cul3 | Mg1 | 0.80216487 | 0.94033681 | 0.05717643 | 0.22777634 | 140.678597 | 0.25102006 |
| Wac | Mg2 | 0.80926443 | 0.94435396 | 0.05900248 | 0.24413841 | 212.124696 | 0.24167635 |
| Wac | Astro1 | 0.8138117 | 0.94435396 | 0.0490153 | 0.20788182 | 227.884321 | 0.23578445 |
| Fbxo11 | Astro2 | 0.81490116 | 0.94435396 | −0.054759 | 0.23363769 | 230.864646 | −0.2343756 |
| Tcf20 | Astro3 | 0.81502562 | 0.94435396 | −0.0530461 | 0.22653983 | 293.399521 | −0.234158 |
| Arid1b | Astro2 | 0.81583699 | 0.94435396 | 0.06759268 | 0.29006806 | 508.015379 | 0.23302353 |
| Upf3b | PN5 | 0.81799039 | 0.94435396 | 0.05782534 | 0.25109455 | 372.627703 | 0.23029311 |
| Kdm5b | Mg1 | 0.81908252 | 0.94435396 | −0.0568919 | 0.24838644 | 187.799217 | −0.2290459 |
| Setd5 | PN5 | 0.82287605 | 0.94650062 | −0.0592266 | 0.26439819 | 372.088306 | −0.2240054 |
| Fbxo11 | PN4 | 0.83293853 | 0.95439023 | −0.037647 | 0.1782601 | 214.55213 | −0.2111912 |
| Gatad2b | PN5 | 0.8342434 | 0.95439023 | 0.05970686 | 0.285145 | 424.120169 | 0.20939121 |
| Tnrc6b | Astro2 | 0.83811874 | 0.95439023 | −0.0457778 | 0.2238068 | 220.938769 | −0.2045414 |
| Pten | Astro1 | 0.83839476 | 0.95439023 | 0.05116742 | 0.25069269 | 338.496032 | 0.20410417 |
| Mll1 | PN5 | 0.84016055 | 0.95439023 | 0.05065626 | 0.25097432 | 349.219732 | 0.20183844 |
| Satb2 | PN2 | 0.84142159 | 0.95439023 | −0.0578021 | 0.28870393 | 379.751005 | −0.2002125 |
| Tnrc6b | Astro1 | 0.85088185 | 0.9628917 | 0.03692198 | 0.19618528 | 236.127794 | 0.18819956 |
| Myst4 | Astro2 | 0.86832382 | 0.97488347 | −0.0425353 | 0.25629171 | 241.569514 | −0.1659644 |
| Mbd5 | Astro3 | 0.86874708 | 0.97488347 | −0.0363657 | 0.21985265 | 266.629192 | −0.1654094 |
| Arid1b | PN2 | 0.87010778 | 0.97488347 | −0.0454905 | 0.27803367 | 449.574964 | −0.163615 |
| Chd8 | PN2 | 0.87215093 | 0.97488347 | 0.03987962 | 0.24760521 | 307.360431 | 0.1610613 |
| Tcf7l2 | Astro3 | 0.87223368 | 0.97488347 | 0.04157664 | 0.25835202 | 381.015737 | 0.16093018 |
| Wac | PN5 | 0.87525192 | 0.97488347 | 0.04007667 | 0.25510151 | 366.220707 | 0.15710088 |
| Ash1l | PN4 | 0.87540557 | 0.97488347 | −0.0279633 | 0.17812059 | 206.349643 | −0.1569908 |
| Setd2 | PN5 | 0.88565354 | 0.97691898 | 0.03652111 | 0.25378204 | 362.715728 | 0.14390736 |
| Myst4 | Mg2 | 0.88831642 | 0.97691898 | 0.03565465 | 0.25362142 | 243.19471 | 0.14058215 |
| Tcf20 | Astro1 | 0.89292861 | 0.97691898 | 0.02935694 | 0.21789295 | 260.417272 | 0.13473103 |
| Dscam | PN6 | 0.89594773 | 0.97691898 | 0.02494567 | 0.19038756 | 136.592904 | 0.13102574 |
| Ank2 | PN5 | 0.89801554 | 0.97691898 | 0.04006933 | 0.3124074 | 357.055839 | 0.12825985 |
| Adnp | Astro3 | 0.89866209 | 0.97691898 | 0.03016065 | 0.23665236 | 339.176039 | 0.12744707 |
| Tnrc6b | PN6 | 0.90146418 | 0.97691898 | 0.01861151 | 0.15005507 | 143.46784 | 0.12403119 |
| Adnp | Mg1 | 0.90243232 | 0.97691898 | −0.0296441 | 0.24148852 | 186.845529 | −0.1227559 |
| Upf3b | PN4 | 0.90251466 | 0.97691898 | −0.0227481 | 0.18551679 | 230.999492 | −0.12262 |
| Med13l | Astro2 | 0.90329684 | 0.97691898 | −0.0322817 | 0.26542972 | 250.873452 | −0.1216206 |
| Myst4 | PN4 | 0.90451212 | 0.97691898 | −0.0218829 | 0.18222761 | 249.200966 | −0.1200856 |
| Setd5 | Mg1 | 0.90597949 | 0.97691898 | −0.0283612 | 0.23979317 | 184.750567 | −0.1182734 |
| Stard9 | Astro2 | 0.90681803 | 0.97691898 | −0.027422 | 0.23399677 | 217.539235 | −0.1171895 |
| Tcf20 | Mg2 | 0.9069012 | 0.97691898 | −0.029289 | 0.250169 | 230.547513 | −0.1170767 |
| Asxl3 | Astro2 | 0.90762753 | 0.97691898 | −0.0278242 | 0.23951093 | 211.302912 | −0.1161708 |
| Spen | Astro3 | 0.91209925 | 0.97691898 | 0.02609224 | 0.23614125 | 270.913982 | 0.11049421 |
| Ddx3x | PN2 | 0.91216931 | 0.97691898 | 0.026839 | 0.24316283 | 388.453514 | 0.11037458 |
| Asxl3 | Mg2 | 0.91312019 | 0.97691898 | −0.0257891 | 0.23608315 | 206.896159 | −0.1092373 |
| Tcf20 | PN4 | 0.91616662 | 0.9780428 | −0.0198659 | 0.1885025 | 213.790192 | −0.1053882 |
| Tcf7l2 | PN1 | 0.91906827 | 0.97900751 | 0.02647334 | 0.26039243 | 430.460985 | 0.10166708 |
| Setd5 | Mg2 | 0.92324484 | 0.97981268 | 0.02401188 | 0.24896202 | 241.33821 | 0.09644797 |
| Syngap1 | Astro1 | 0.92382339 | 0.97981268 | −0.0218443 | 0.22823569 | 266.088466 | −0.0957094 |
| Scn2a1 | PN6 | 0.92854312 | 0.98151797 | 0.01553852 | 0.17297604 | 148.338353 | 0.08983045 |
| Ddx3x | PN4 | 0.92943743 | 0.98151797 | 0.01788263 | 0.20177379 | 299.739093 | 0.08862713 |
| Mbd5 | Mg2 | 0.93457445 | 0.98482039 | 0.02043943 | 0.24869287 | 214.06079 | 0.08218745 |
| Tcf7l2 | Astro2 | 0.93725549 | 0.98552616 | 0.02224033 | 0.28230588 | 323.973359 | 0.07878095 |
| Setd5 | Astro3 | 0.94408912 | 0.98649408 | 0.0156786 | 0.22337452 | 301.863442 | 0.07018973 |

TABLE 5-continued

Alternative effect size and statistical measurements of Perturb-Seq.

| perturbation | Module | pval | padj | Estimate | SE | df | t.value |
|---|---|---|---|---|---|---|---|
| Ank2 | Astro3 | 0.94420207 | 0.98649408 | −0.0197268 | 0.28171107 | 497.705054 | −0.0700248 |
| Larp4b | PN5 | 0.94421577 | 0.98649408 | 0.02136092 | 0.30514278 | 570.959429 | 0.07000302 |
| Tcf7l2 | Astro1 | 0.94811979 | 0.98829569 | −0.0163352 | 0.25087837 | 372.234954 | −0.065112 |
| Mll1 | PN6 | 0.95214938 | 0.98829569 | 0.01002708 | 0.16678757 | 135.720847 | 0.06011889 |
| Setd5 | PN4 | 0.95504745 | 0.98829569 | 0.01099067 | 0.1947672 | 234.675057 | 0.05642978 |
| Tcf7l2 | PN5 | 0.95601699 | 0.98829569 | 0.01872843 | 0.33941191 | 520.43967 | 0.05517906 |
| Kdm5b | PN4 | 0.95859711 | 0.98829569 | 0.01001849 | 0.19280908 | 279.895275 | 0.05196066 |
| Ddx3x | Mg2 | 0.96062219 | 0.98829569 | 0.01260716 | 0.25502181 | 197.183768 | 0.04943561 |
| Spen | Mg2 | 0.96215406 | 0.98829569 | 0.01228317 | 0.25857764 | 227.964511 | 0.04750283 |
| Arid1b | PN6 | 0.96284218 | 0.98829569 | 0.01041347 | 0.22333249 | 289.065857 | 0.04662766 |
| Ank2 | Mg1 | 0.9649606 | 0.98829569 | −0.0137277 | 0.31221077 | 276.183992 | −0.0439694 |
| Myst4 | PN2 | 0.96610946 | 0.98829569 | −0.0094631 | 0.22255594 | 334.756277 | −0.0425201 |
| Qrich1 | Astro3 | 0.97462951 | 0.9925345 | −0.0069148 | 0.21723629 | 281.456446 | −0.0318308 |
| Myst4 | Astro3 | 0.97585756 | 0.9925345 | −0.0071017 | 0.2344636 | 284.865655 | −0.0302893 |
| Stard9 | Mg2 | 0.97632985 | 0.9925345 | −0.0070777 | 0.23823155 | 191.969124 | −0.0297092 |
| Pogz | PN5 | 0.98551667 | 0.99755377 | −0.0053377 | 0.29383165 | 361.796228 | −0.0181657 |
| Med13l | PN5 | 0.98599396 | 0.99755377 | 0.00515119 | 0.2932471 | 393.983741 | 0.01756602 |
| Arid1b | Astro1 | 0.98737465 | 0.99755377 | −0.0041315 | 0.26097358 | 588.124274 | −0.0158309 |
| Spen | PN4 | 0.98983057 | 0.99791738 | −0.0026202 | 0.2053524 | 229.506518 | −0.0127597 |
| Stard9 | PN5 | 0.99180769 | 0.99791738 | 0.00253996 | 0.24718726 | 333.270175 | 0.01027543 |
| Qrich1 | PN4 | 0.99425614 | 0.99833096 | 0.0013827 | 0.19185089 | 219.186257 | 0.00720714 |
| Stard9 | Astro3 | 0.99788991 | 0.99956811 | 0.0005666 | 0.21403846 | 256.769662 | 0.00264718 |
| Asxl3 | PN2 | 0.99956811 | 0.99956811 | −0.0001197 | 0.22086453 | 299.528783 | −0.0005417 |

*Used FindVariableGenes with x.low.cutoff = 1, x.high.cutoff = 5 on the combined dataset
**Used FindVariableGenes separately on each batch (with x.low.cutoff = 1, x.high.cutoff = 5), then only kept those that occurred in al least a certain number of batches (specified in column E). So. if this column = 4, means that variable genes have to be variable in at least 4 batches.
***For those datasets where calculated variable genes on each batch were calculated and combined, this column has the number of batches required to have a genes as variable for it to be kept Perturbations in 9 ASD/ND genes (Adnp, Ank2, Ash11, Chd8, Gatad2b, Pogz, Scn2a1, Stard9, and Upf3b) had significant effects across 5 modules (FIG. 2B, highlighted circles, compared to the GFP control, FDR corrected P<0.05): a module associated with projection neurons of Layer 4 and 5 (PN1, affected by perturbations in Adnp, Ash11, Scn2a1, and Stard9); modules representing two distinct homeostatic signatures in astrocytes (Astro1 affected by perturbation of Scn2a1, and Astro3 affected by perturbations of Chd8, Pogz, and Upf3b); a module associated with oligodendrocyte progenitor cells (ODC1, Chd8 and Gatad2b); and a module associated with Ndnf+ interneurons (IN1, Ank2) (FIGS. 2C and 10A-10F).

Notably, the oligodendrocyte progenitor module (ODC1) also had a significant amount of its variation across the oligodendrocyte cell cluster explained by the perturbation state overall (van der Waerden test, a non-parametric alternative to ANOVA analysis, FDR corrected P<0.05) (FIG. 9C), suggesting that this module represents convergent effects across different perturbed genes. Collectively, the data indicate that a selected group of perturbations was able to affect recurrent gene modules with cell-type specificity and point to some convergent effects across diverse ASD/ND risk genes.

Example 5—Single Perturbation of Ank2 Confirms Perturb-Seq Effect on an Interneuron Gene Expression Module In the multiplex in vivo Perturb-Seq results, Ank2 perturbation led to increased expression of an interneuron module (IN1) (FDR corrected P<0.05, FIGS. 14A-14E). This module was strongly correlated with a subcluster of inhibitory interneurons expressing Ndnf (FIGS. 14C-14D) and contains genes such as Kcnq5 (a voltage-gated potassium channel) and Gabbr2 (GABA receptor subunit) (FIG. 10B and Table 4). To validate the finding from the pooled, Perturb-Seq experiment, performed a single perturbation targeting either Ank2 or GFP (control) was performed, followed by scRNA-seq of neocortical cells at P7, resulting in 2,943 and 1,716 high-quality cells, respectively.

Figure 14A:
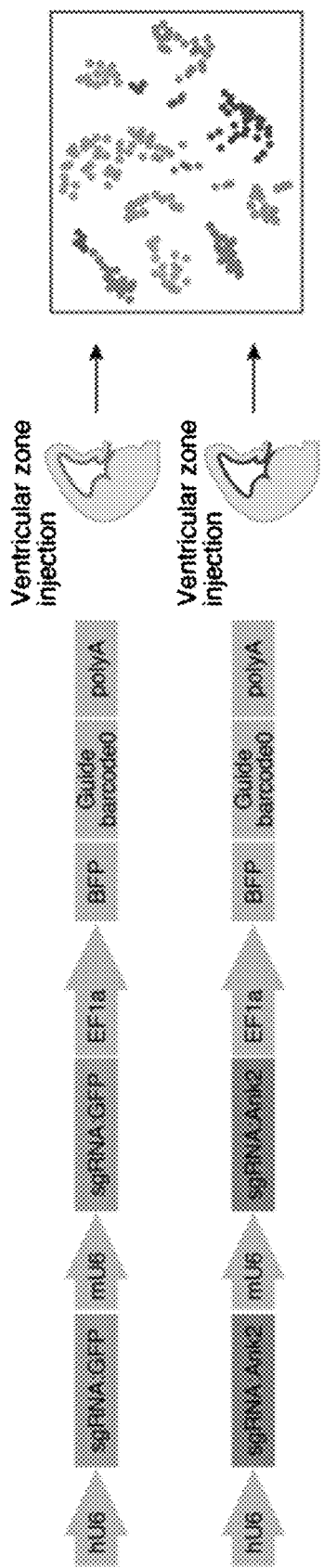
FIGS. 14A-14E—(FIG. 14A) Schematics of simplex Perturb-Seq of the ASD/ND risk gene Ank2 and a GFP control.
Figure 14B:
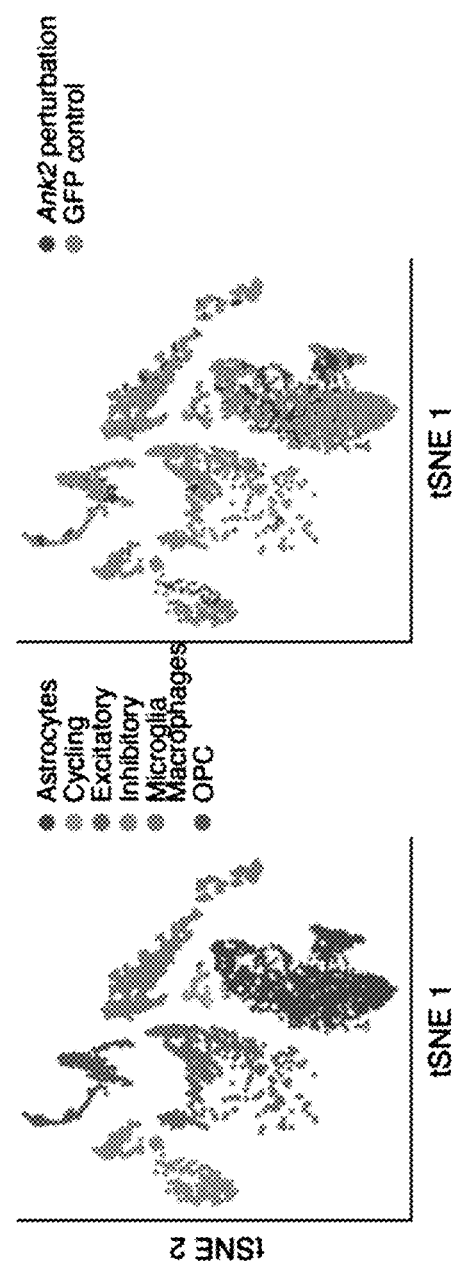
Figure 14C:
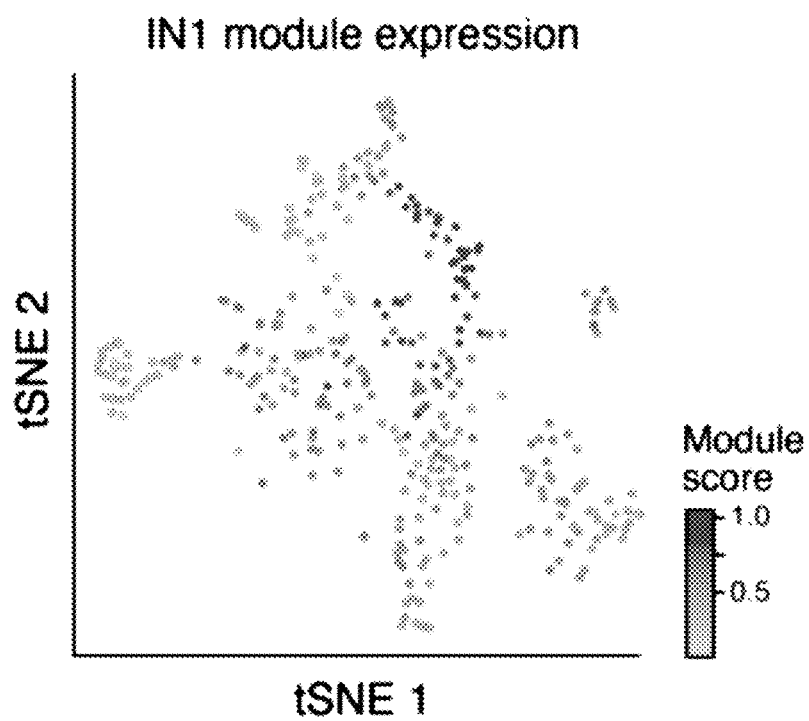
Figure 14D:
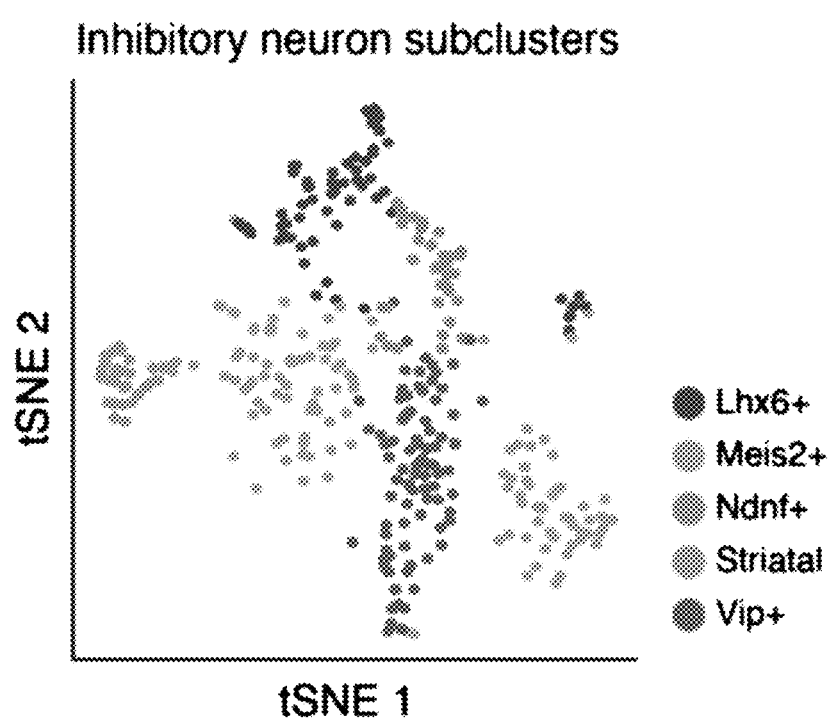
Figure 14E:
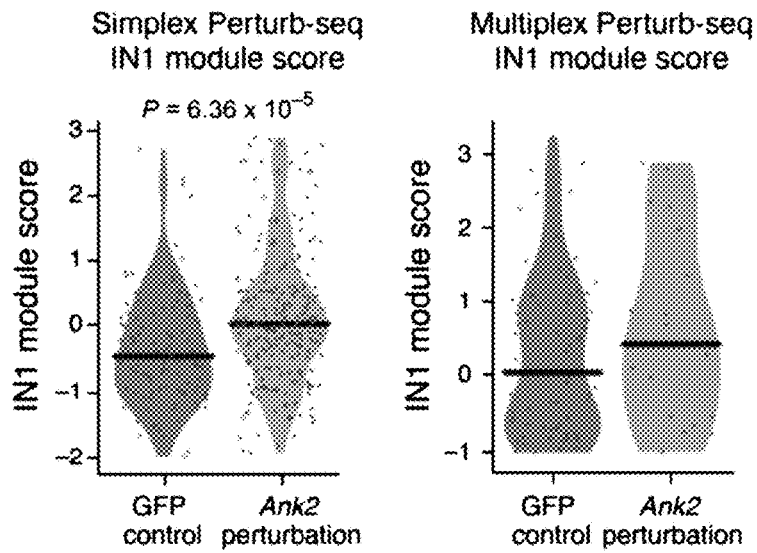

The individual perturbation experiment confirmed the results from the pooled Perturb-Seq screen. Ank2-perturbed cells were present across all cell types and overall proportions of cells were not significantly changed (FIG. 14B). Within the Ndnf+interneurons, Ank2 perturbation led to upregulation of the IN1 module (FDR corrected P<0.05, FIG. 14E), confirming the Perturb-Seq result. This finding indicates that multiplexing perturbations in the pooled approach does not significantly distort the results observed for an individually perturbed gene.

Ank2 encodes an ankyrin protein and is expressed broadly in excitatory and inhibitory neurons as well as glial cells in the brain (22). Studies examining Ank2 loss-of-function suggest that it is involved in axonal morphology, connectivity, and calcium signaling in excitatory neurons (23-26). This Perturb-Seq data suggests a role of Ank2 in the Ndnf+ interneuron subtype during cortical development, in addition to its known roles in excitatory neurons.

Figure 15A:
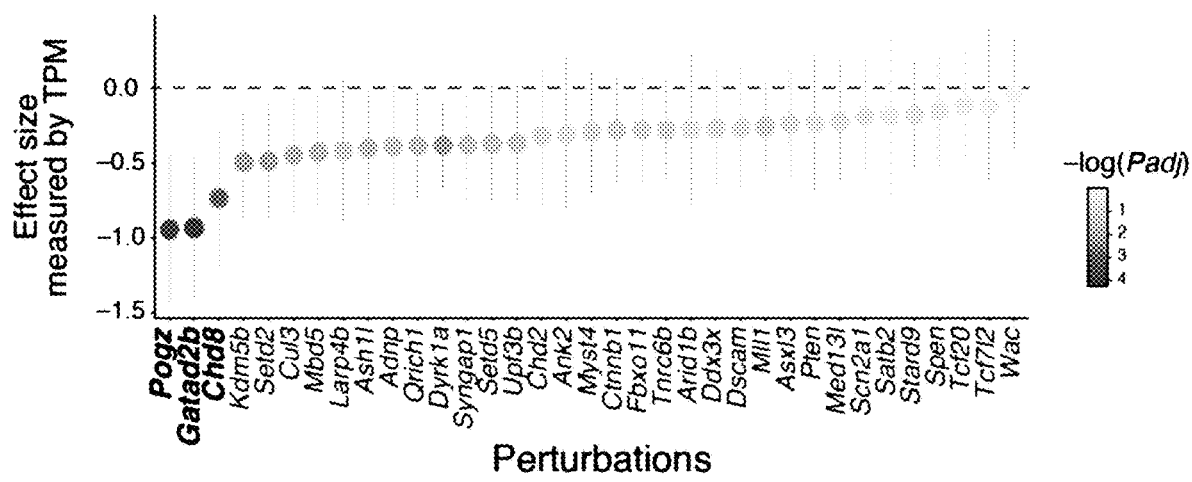
FIGS. 15A-15D—(FIG. 15A) ASD/ND risk gene perturbation effects in gene module ODC1 compared to GFP controls, measured by change in log TPM.
Figure 15B:
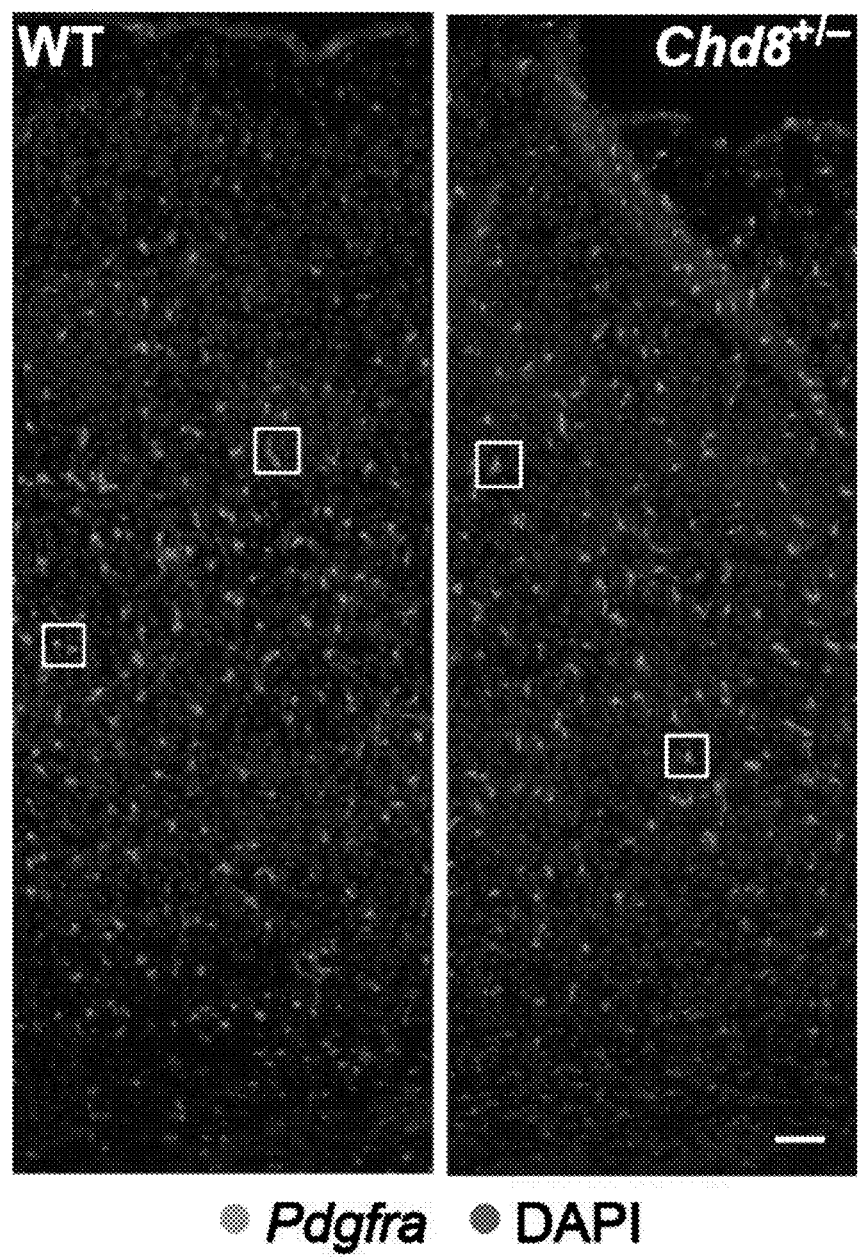
Figure 15C:
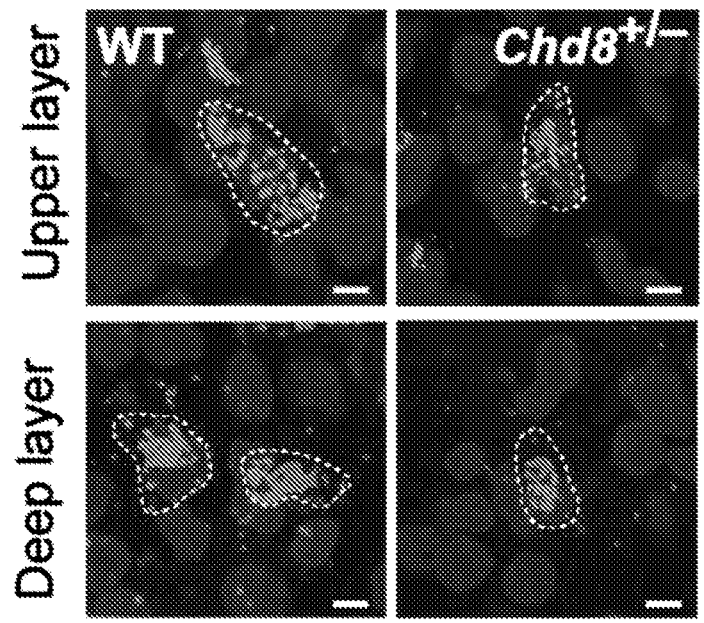
Figure 15D:
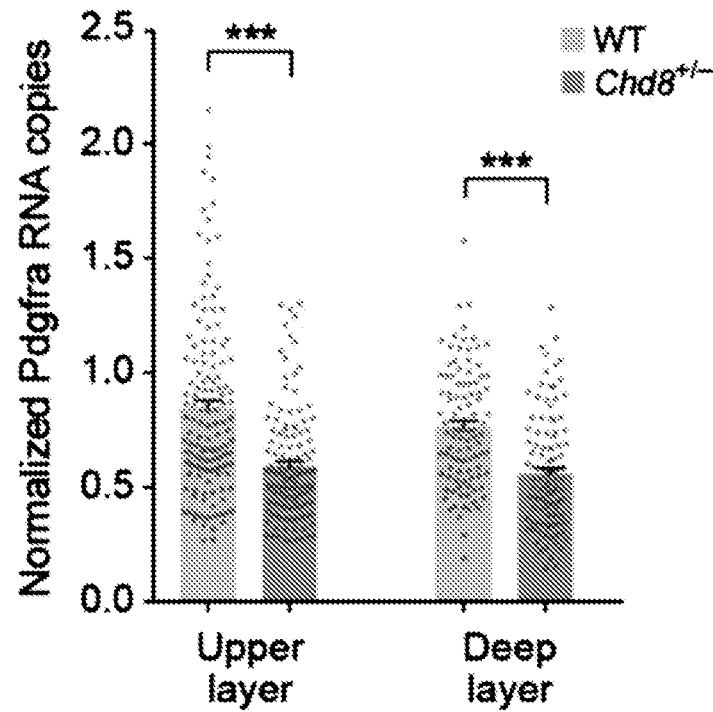

Example 6—the ASD/ND Risk Genes Chd8 and Gatad2b Alter Gene Modules in Oligodendrocyte Progenitors In the Perturb-Seq experiment, Chd8 and Gatad2b perturbations significantly decreased the expression of the ODC1 module in the oligodendrocyte cluster (FIGS. 3A-3D, FDR corrected P<0.05; see alternative measurement of effect size FIG. 15A, estimated by log transcripts per million (TPM) gene expression difference). The ODC1 module is highly expressed in cycling cells and oligodendrocyte precursor cells (OPC), and lowly expressed in committed oligodendrocyte progenitor cells (COP) and newly formed oligodendrocytes (NFOL), suggesting that this module is linked to oligodendrocyte maturation (FIG. 3A), and therefore that perturbation in Chd8 and Gatad2b might accelerate oligodendrocyte maturation. This is consistent with recent reports that Chd8 loss-of-function potentiates an impaired OPC development phenotype caused by deletion of Chd7 (27).

This result was further investigated and validated by examining oligodendrocyte development in a Chd8 germline heterozygous mutant model (as homozygous mutation is embryonic lethal (28)), using several orthogonal methods. First, in situ hybridization was used for two canonical OPC markers known to be involved in fate specification, Cspg4 (a member of the ODC1 module) and Pdgfra. Both were downregulated in P7 Chd8+/− cortex (FIGS. 3E and 15B-15D), consistent with the in vivo Perturb-Seq results demonstrated here and elsewhere herein.

Figure 3A:
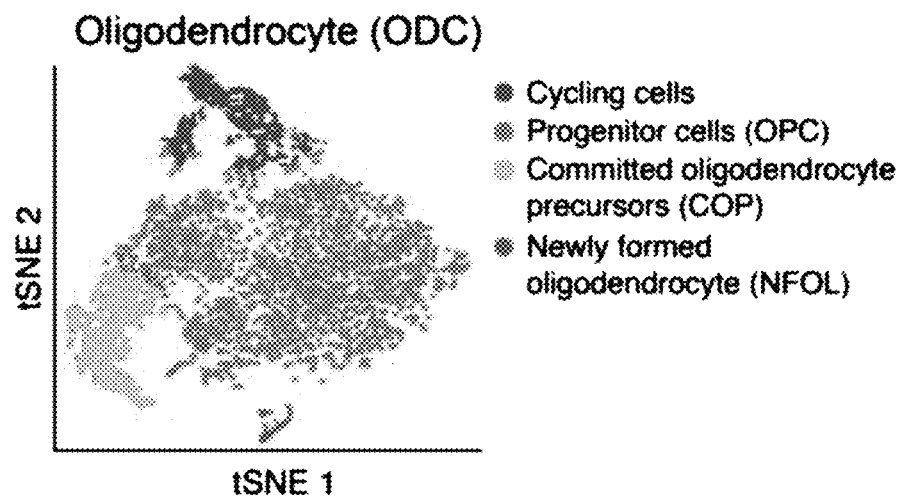
FIGS. 3A-3F—Perturbation effect in oligodendrocytes and validation in the Chd8+/− mouse model.
Figure 3B:
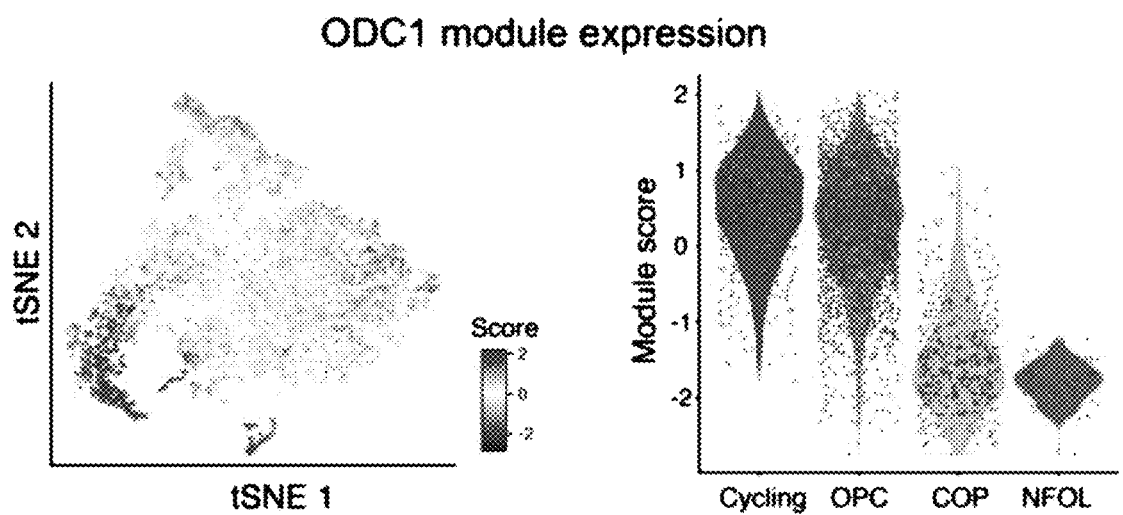
Figure 3C:
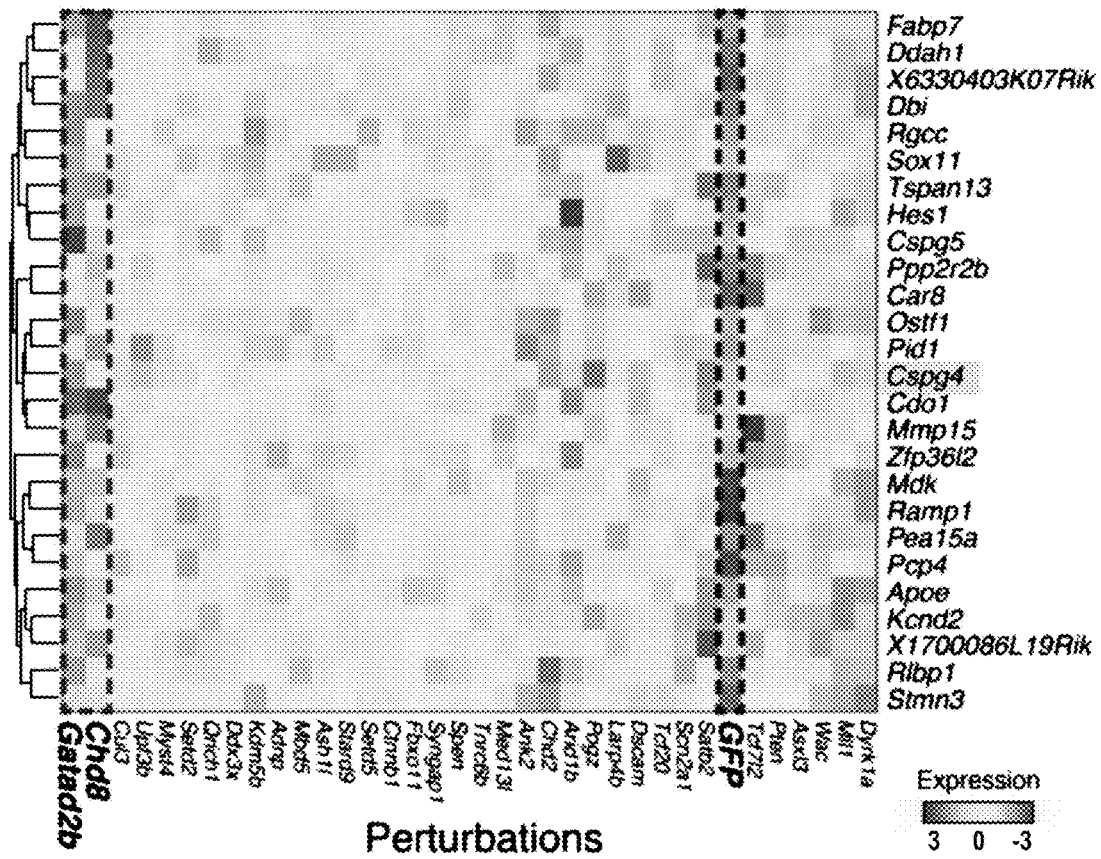
Figure 3D:
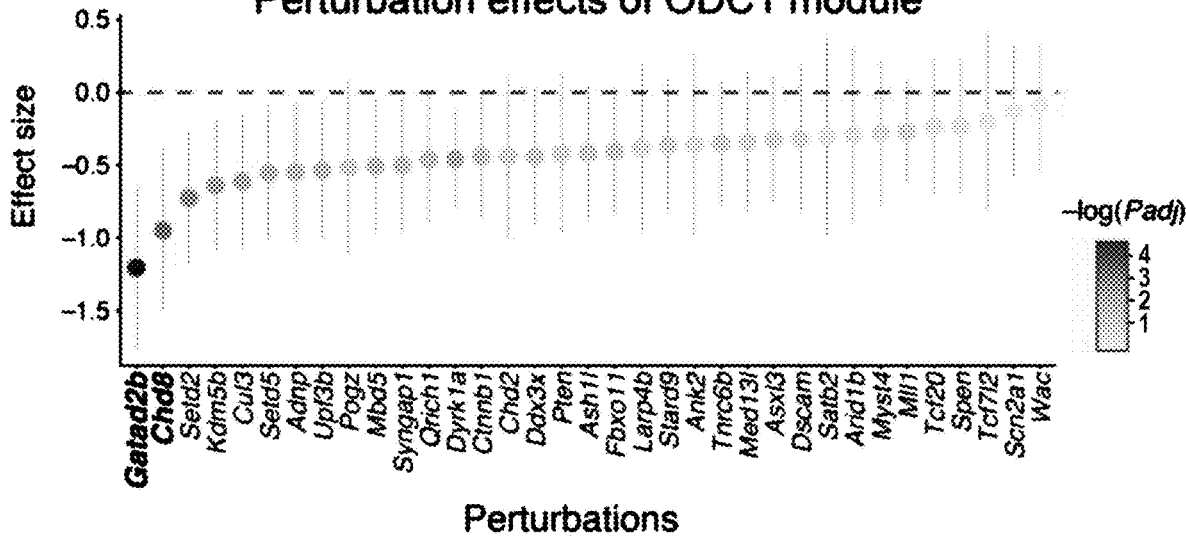
Figure 3E:
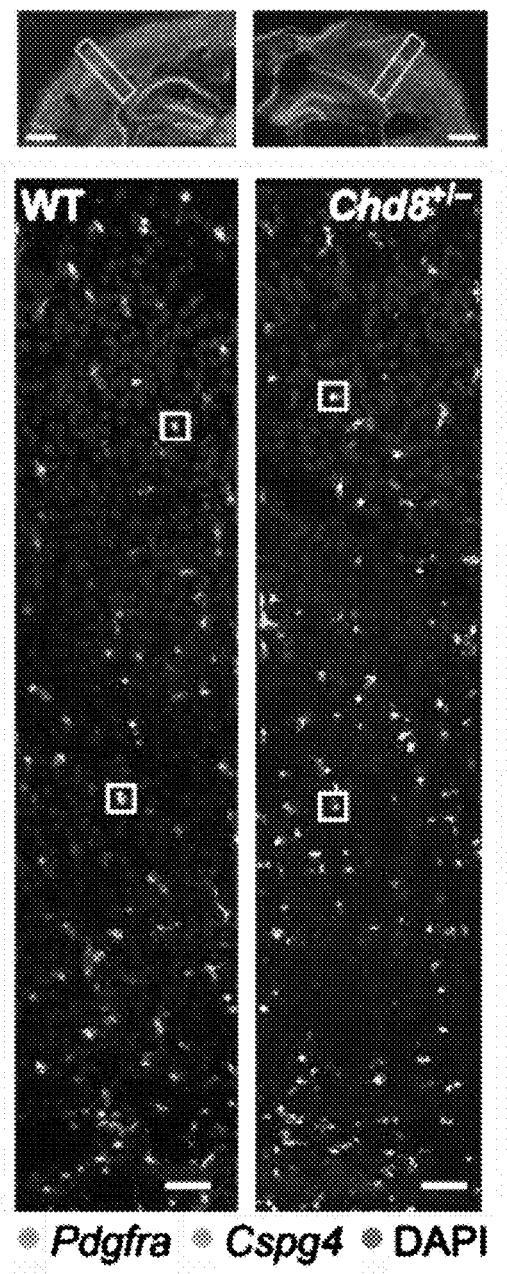
Figure 3E:
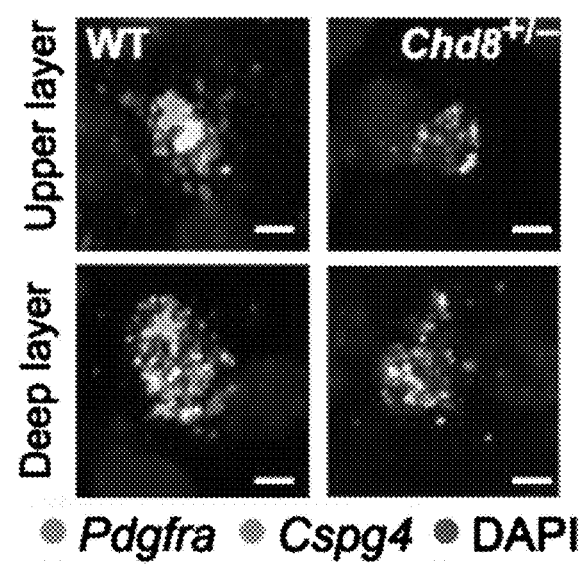
Figure 3E:
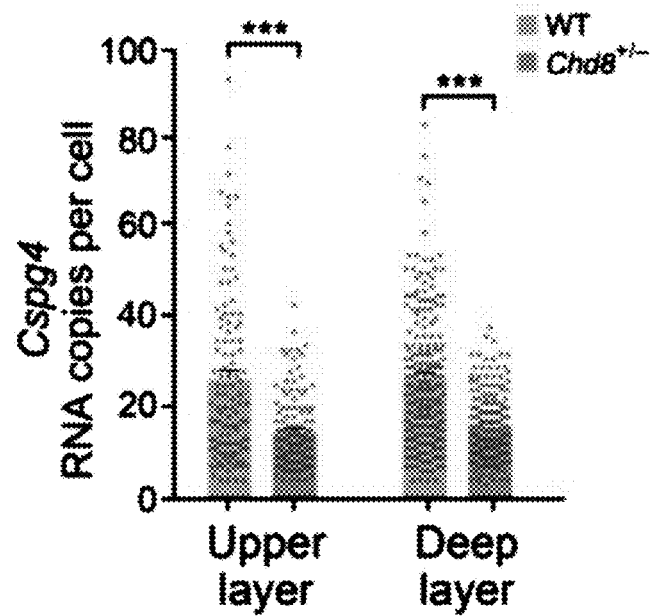
Figure 3F:
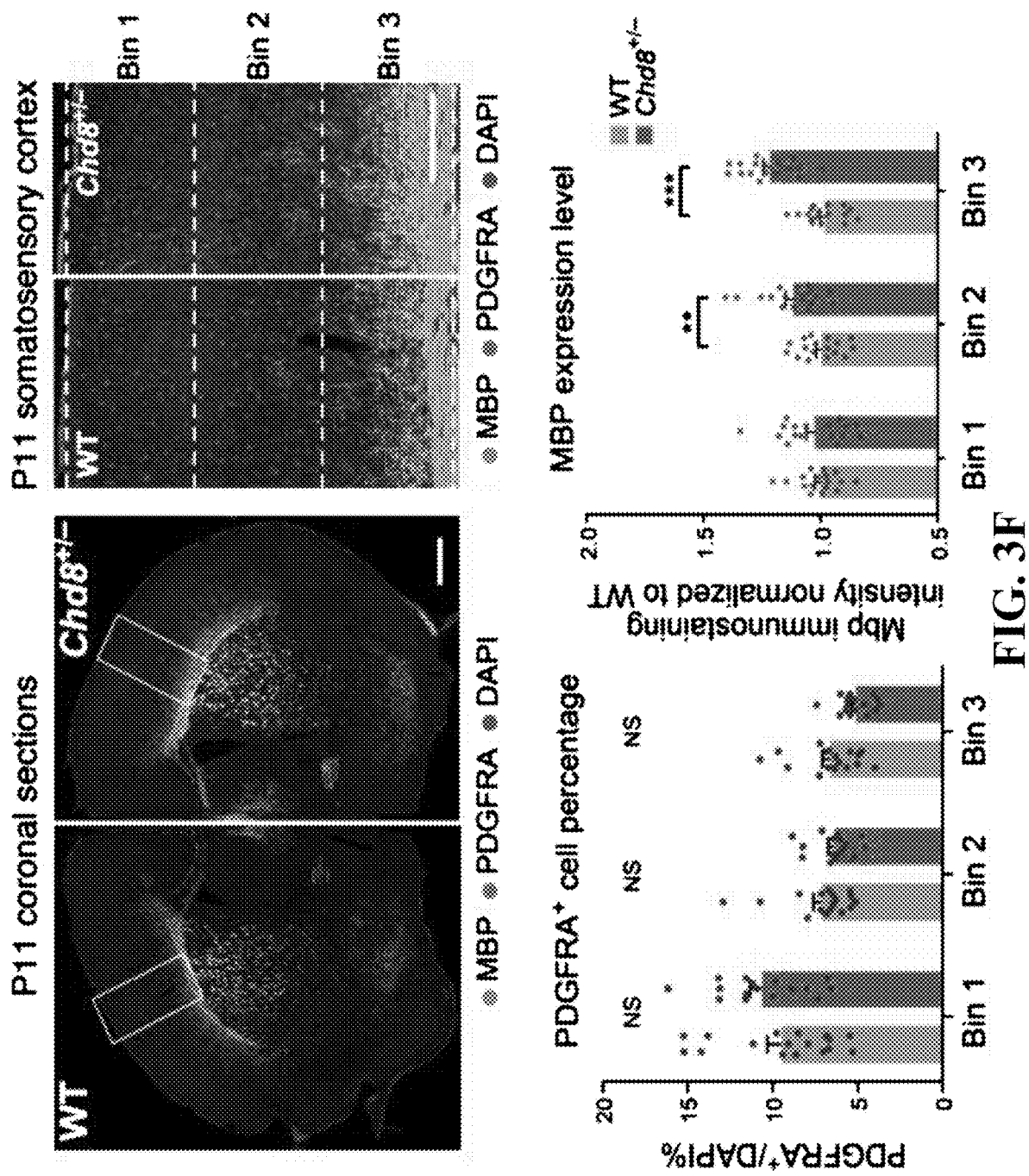

Second, immunohistochemistry was used to examine a later developmental time point, P11. OPC cell number (e.g., PDGFRA+ cells) did not show significant differences between the WT and Chd8+/− littermates, also consistent with in vivo Perturb-Seq; however, cells positive for the MBP protein, a marker of myelinating oligodendrocytes, were increased in number and displayed elevated MBP levels in the Chd8+/− mutant (FDR corrected P<0.05, non-parametric ANOVA test) (FIG. 3F). In combination with the Perturb-Seq result showing reduction in the signature of oligodendrocyte progenitors and of the progenitor-expressed ODC1 module in Chd8-perturbed cells, this suggests that Chd8 perturbation may result in acceleration of the progressive increase in MBP levels that occurs postnatally. These data further demonstrate that in vivo Perturb-Seq has the power to identify cell type-specific molecular changes similar to those observed in a single-gene, germline-modified mouse model.

Example 7—Perturb-Seq Gene Modules are Conserved Between Human and Mouse

Figure 4A:
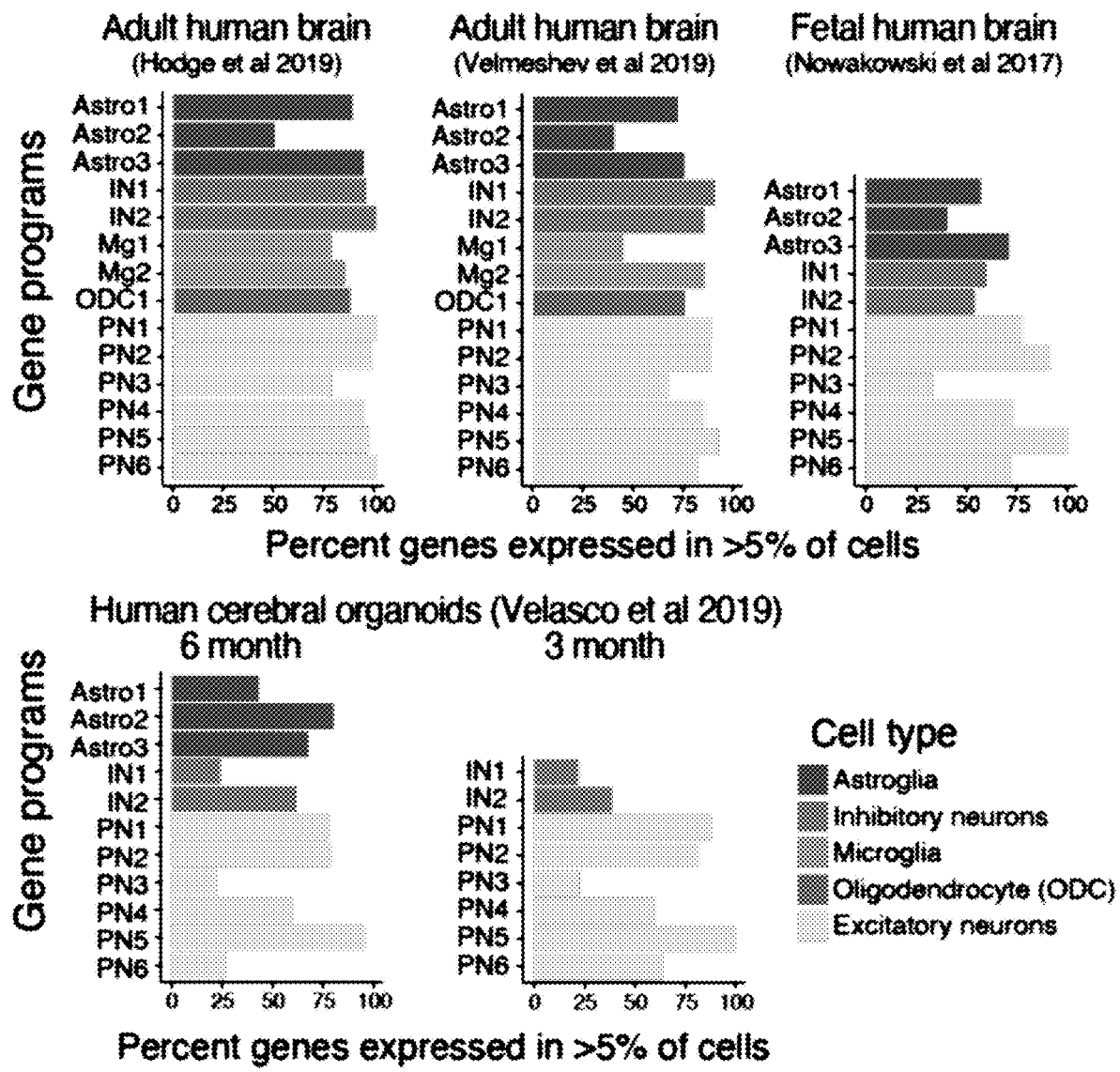
FIGS. 4A-4F—Cell-type specific gene modules from Perturb-Seq are conserved in developing human brains.
Figure 4B:
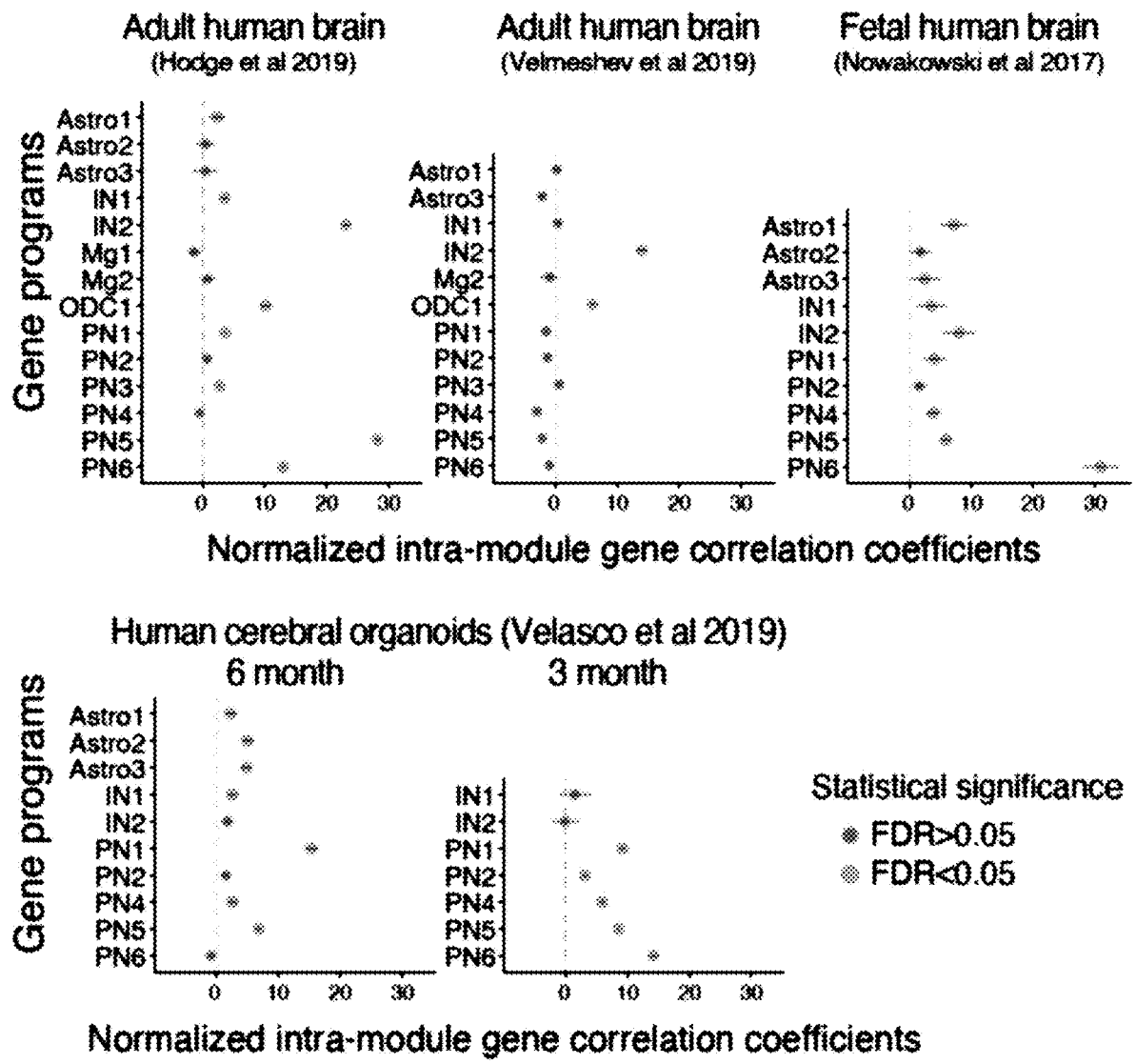
Figure 4C:
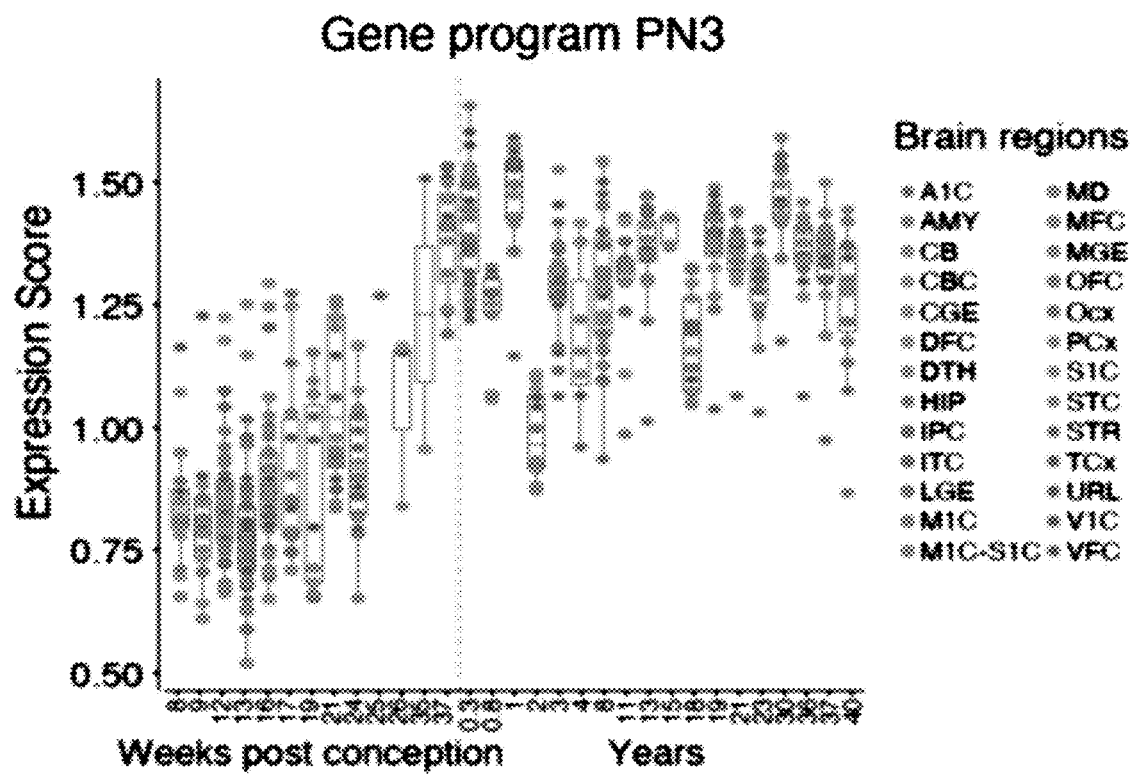
Figure 4D:
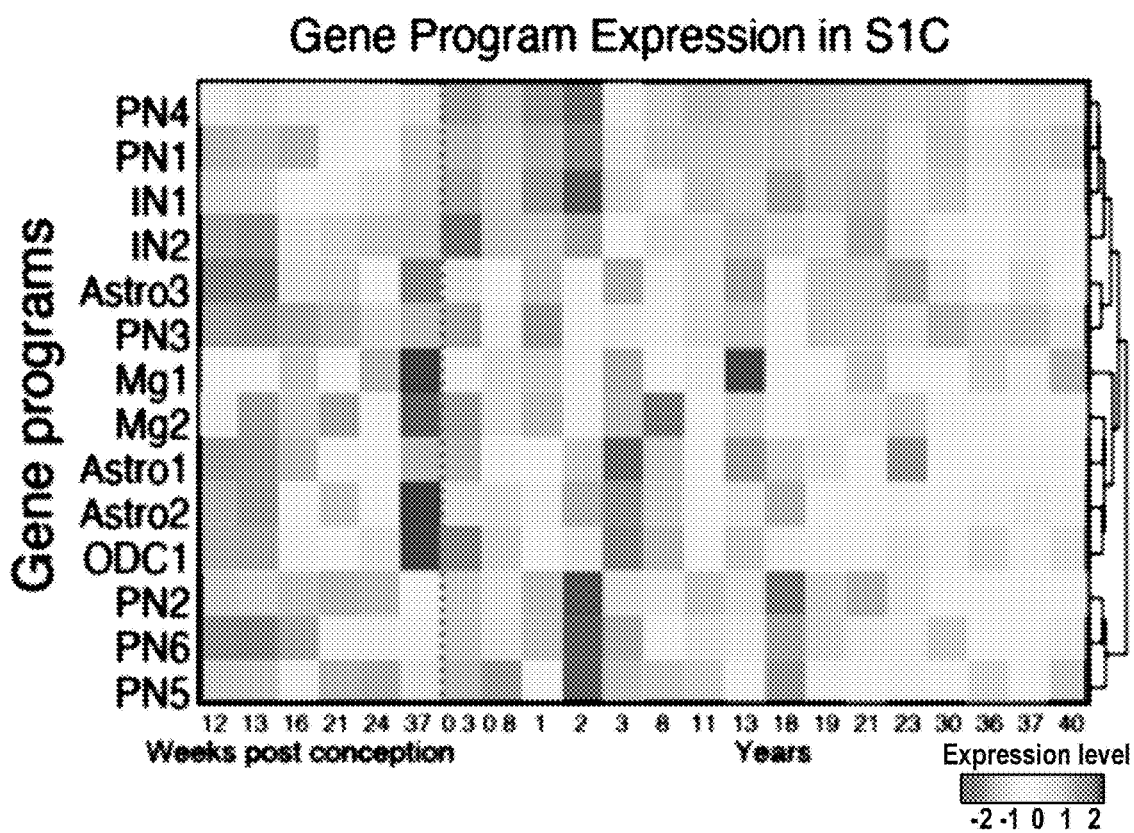
Figure 4E:
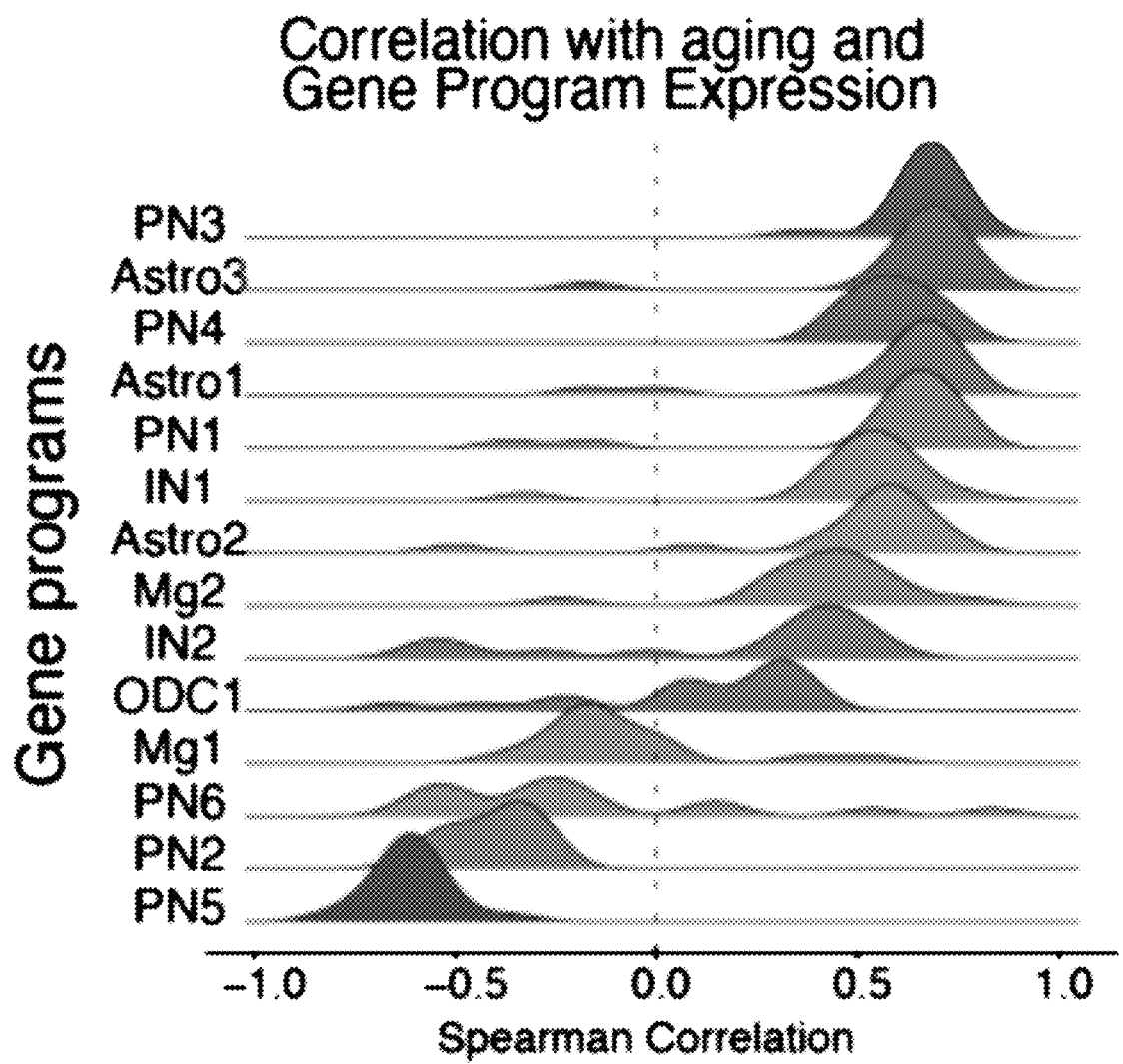
Figure 16A:
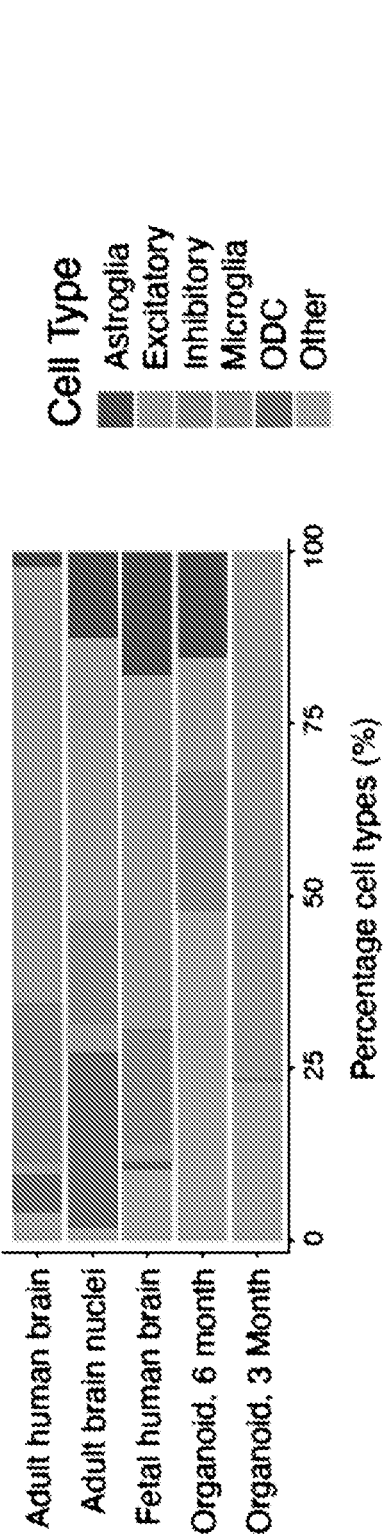
FIGS. 16A-16E—(FIG. 16A) Cell type composition in each human brain and human brain organoid dataset.

To establish whether the perturbed gene modules identified in the mouse cerebral cortex are conserved in human cells, the expression of each module across multiple scRNA-seq datasets from human tissues was examined: adult human cortex (29), ASD donor cortex with matched controls (30), fetal human cortex (31), and 3 month and 6 month-old human brain organoids (32) (FIGS. 4A-4B). In the fetal brain and the 3-month brain organoid samples, glial cell types were sparsely represented due to the early developmental stages of the samples (FIG. 16A). Human genes that had 1:1 orthologs to the mouse genes in each module were identified, and asked whether the modules were conserved, using two metrics: whether the orthologous genes were also expressed in the corresponding cell type in the human datasets, and whether the expression of the genes in each module co-varied across single cells (as estimated by correlation), reflecting the degree of "modularity" of these mouse gene programs in humans.

Figure 16B:
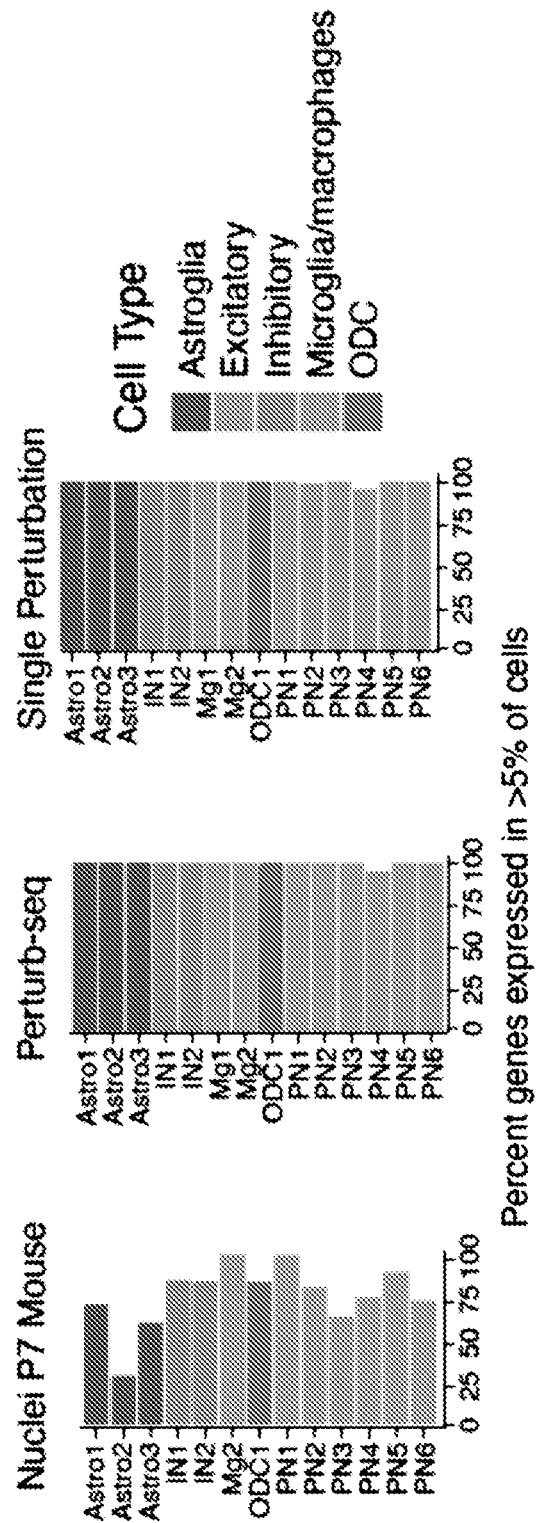
Figure 16C:
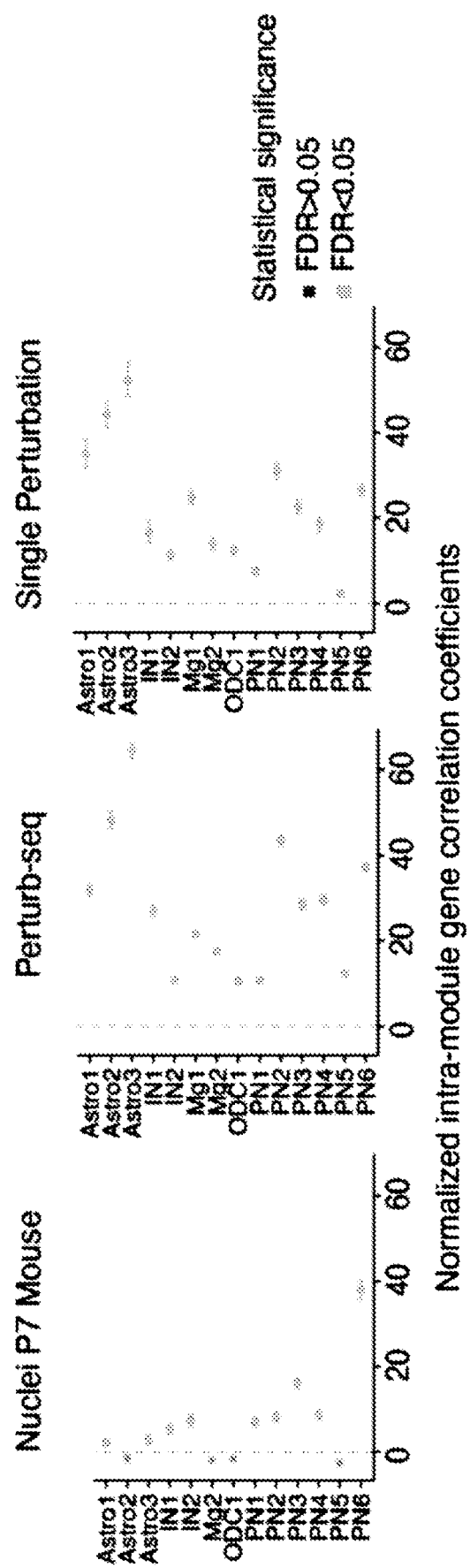

The expression of each module was largely conserved in all human datasets, with different modules showing distinct levels of conservation of expression in each dataset (FIG. 4A). Some modules like PN1, PN2, and PN5 displayed high levels of conservation of expression (with at least 75% of the genes in these modules being expressed by at least 5% of cells in the corresponding associated cell type) across all datasets. The proportions of the genes expressed in the corresponding cell types in human tissues were generally lower than in mouse tissues (FIG. 16B).

Figure 16D:
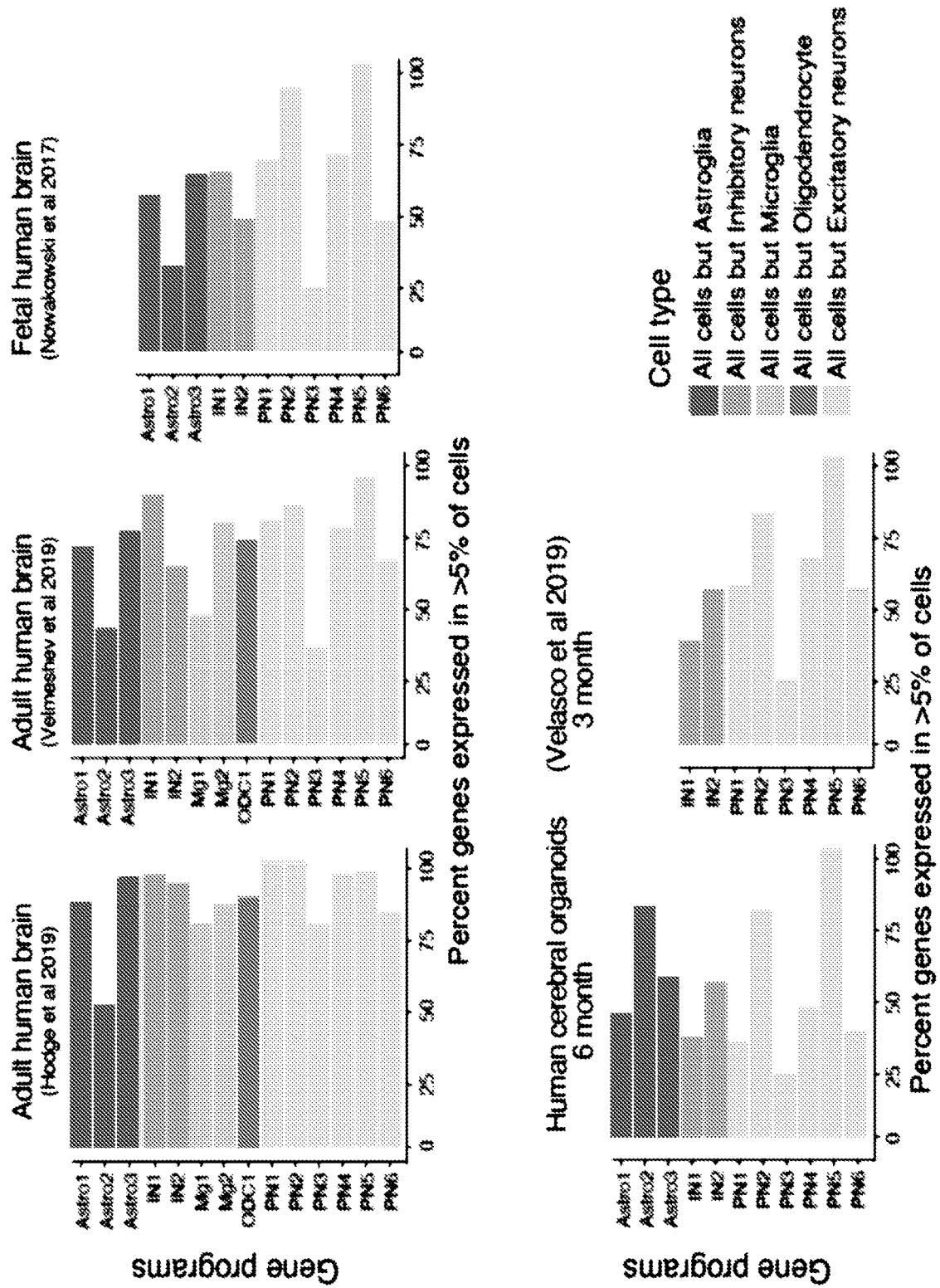
Figure 16E:
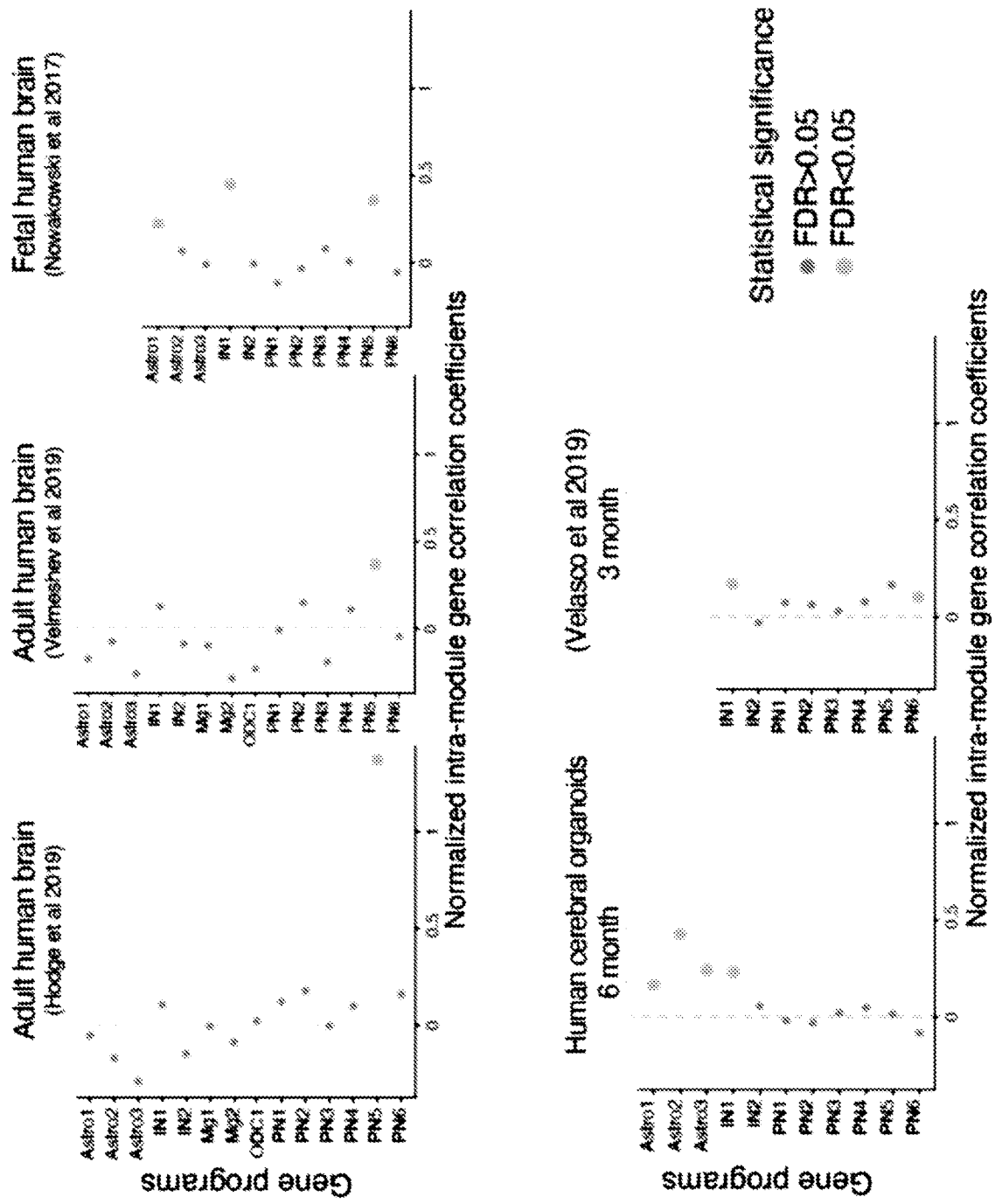
Figure 17A:
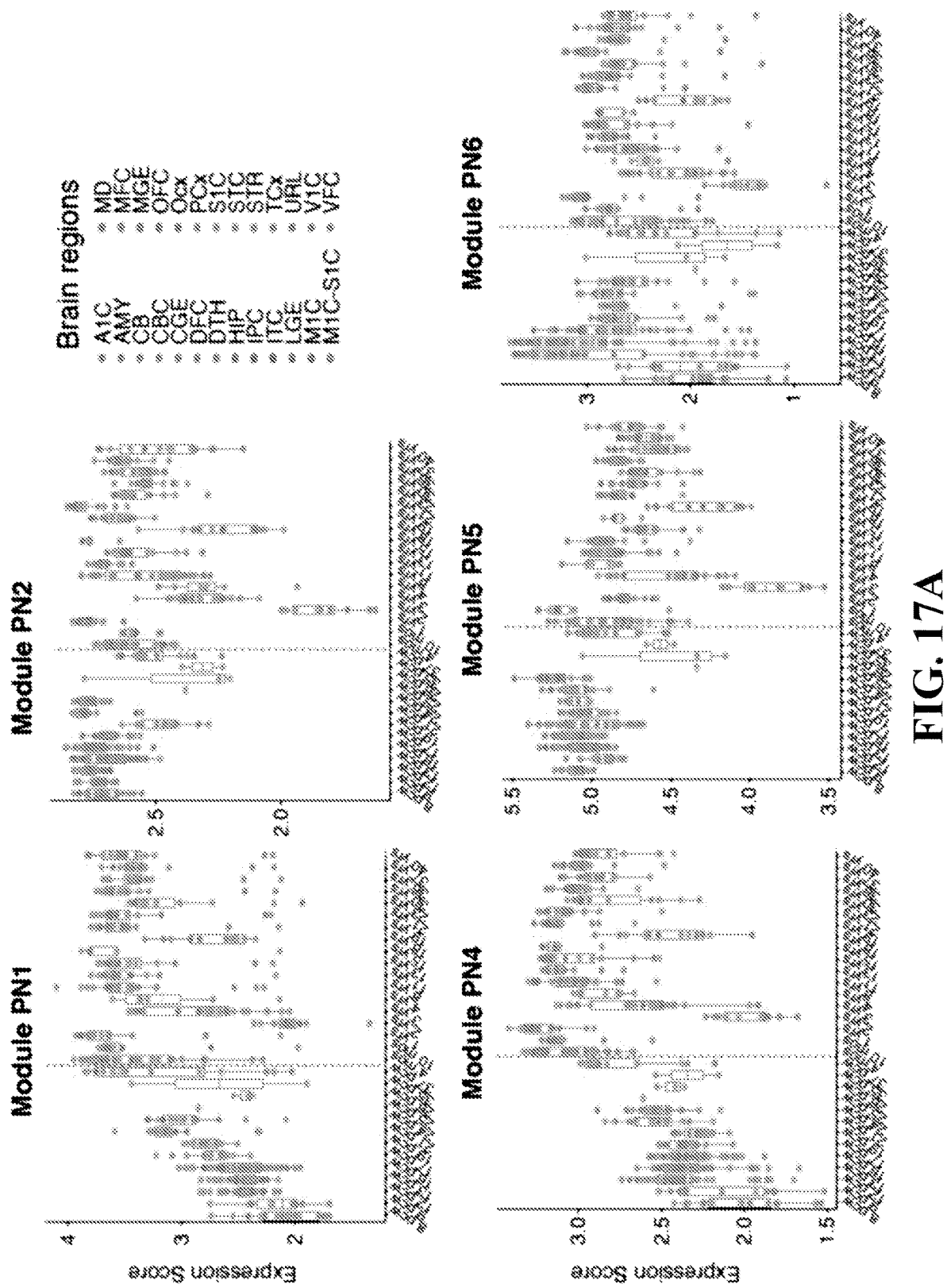
FIGS. 17A-17E—Module expression over developmental time in human brain tissues across regions (BrainSpan data) in 5 major cell types.
Figure 17B:
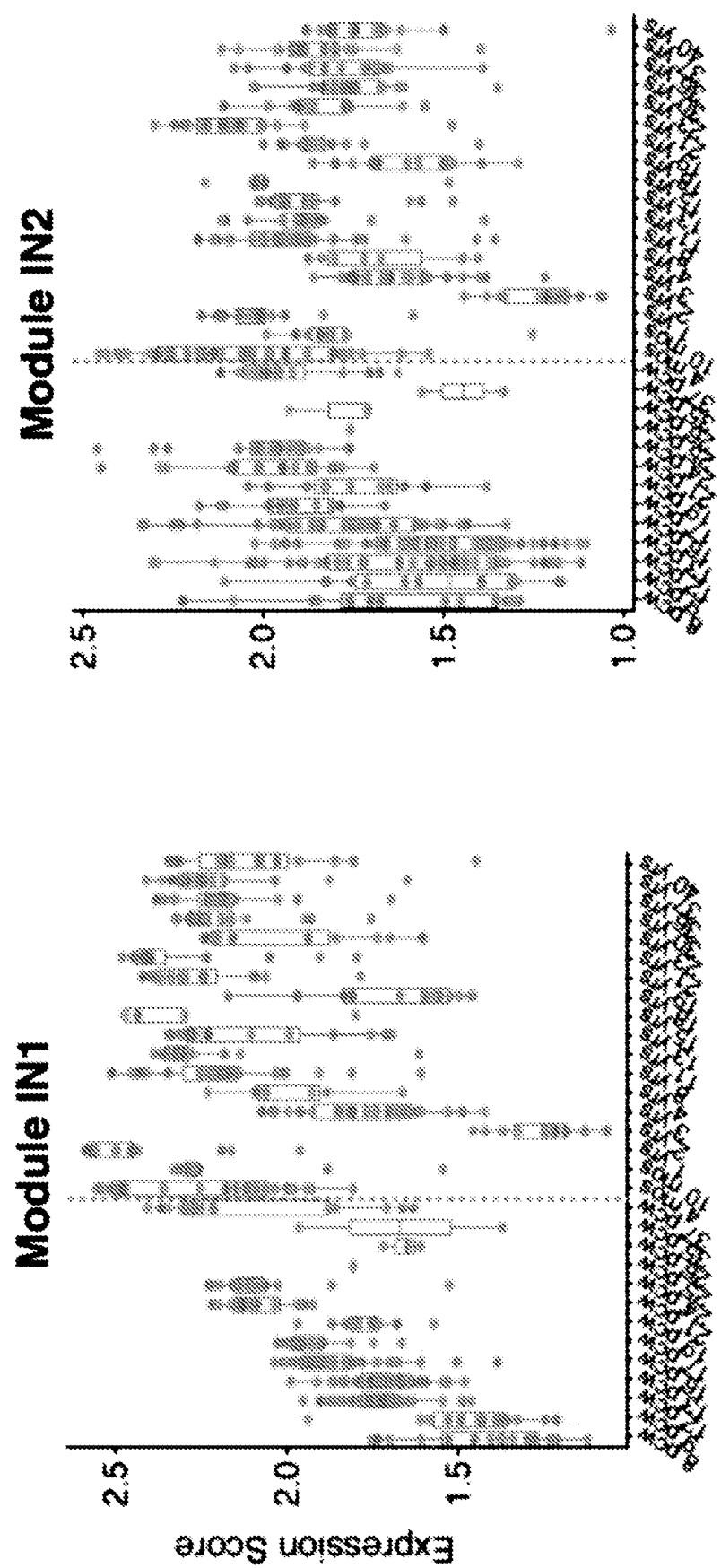
Figure 17C:
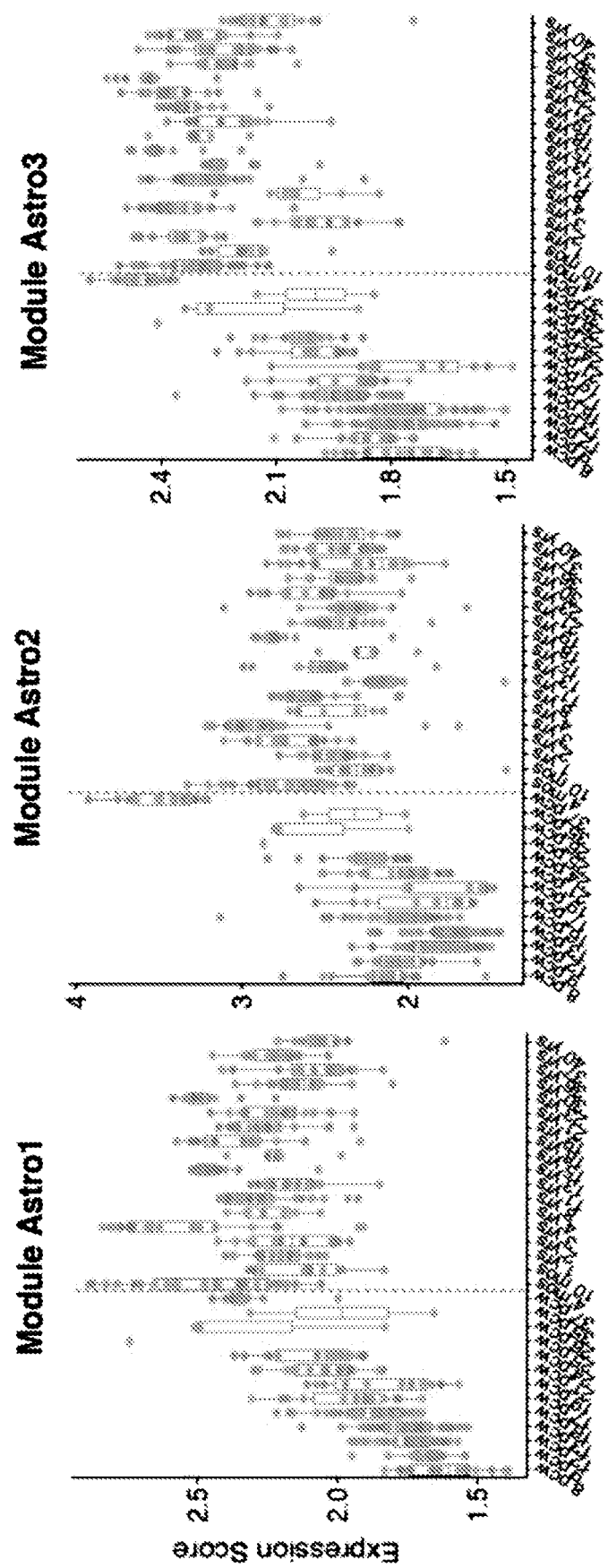
Figure 17D:
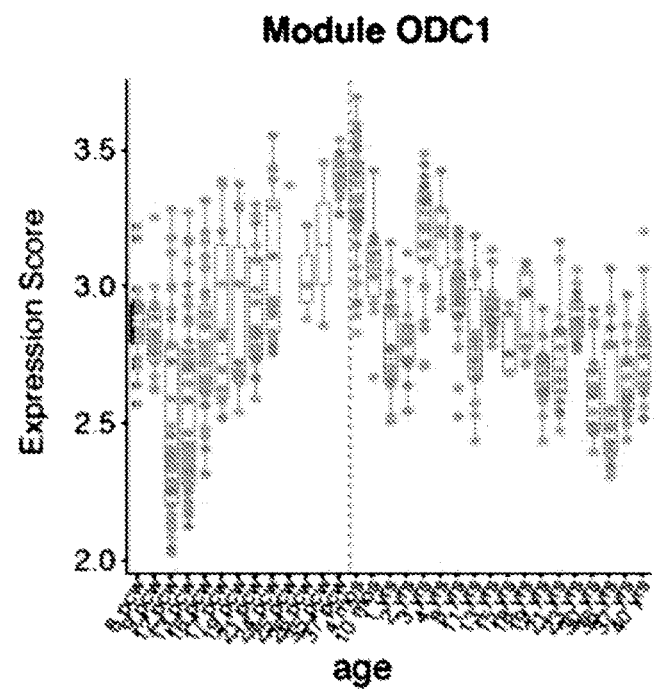
Figure 17E:
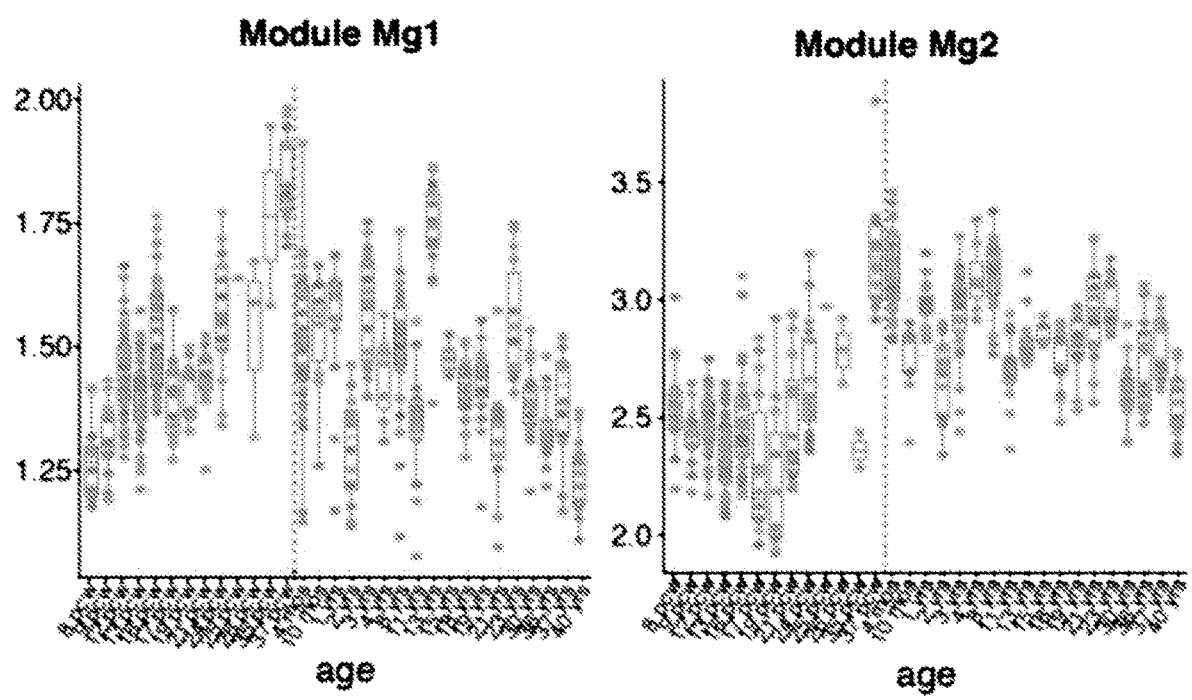

It was further calculated whether the co-variation of expression of the genes in each module (their "modularity") was also comparable in humans. To do so, for each module and each dataset the average pairwise expression correlation coefficient between the genes in a given module was calculated and compared to a module-specific null-distribution based on random gene sets with similar expression levels, to calculate both a P-value for the correlation of these modules and a normalized correlation coefficient. 8 out of 14 modules showed greater intra-module correlation than a comparable random gene set in the adult human brain dataset from Hodge et al (29) (FIG. 4B). Correlation also increased with the age of the human samples across brain regions of the BrainSpan dataset (9) (FIGS. 4C-4E and 17A-17E). As a control, the same approach was used to calculate the expression and modularity of each gene module in non-associated cell types. It was found that the modularity was decreased in non-associated cell types (FIGS. 16D-16E), reflected by both the proportion of comparisons with significant correlation and by the strength of the significant correlations, suggesting that these modules reflect cell type-specific effects.

Altogether, these results suggest that expression and modularity of most gene modules in the mouse are conserved in human brain tissue, pointing at potential shared functions and suggesting that processes identified as affected in the Perturb-Seq experiments demonstrated herein are relevant to biological processes that may be developmentally regulated in the human brain.

Example 8—Mouse Perturb-Seq Results are Correlated with Expression Changes in ASD Patient Brain Tissues Finally, it was explored whether the effects observed in mouse Perturb-Seq may be similar to changes observed in postmortem brains of ASD patients. To this end, the data demonstrated herein was compared to a single-nucleus RNA-seq (snRNA-seq) dataset of postmortem ASD brain samples (30), and bulk RNA-seq of postmortem psychiatric disorder brain samples from the PsychEncode project (33).

Figure 4F:
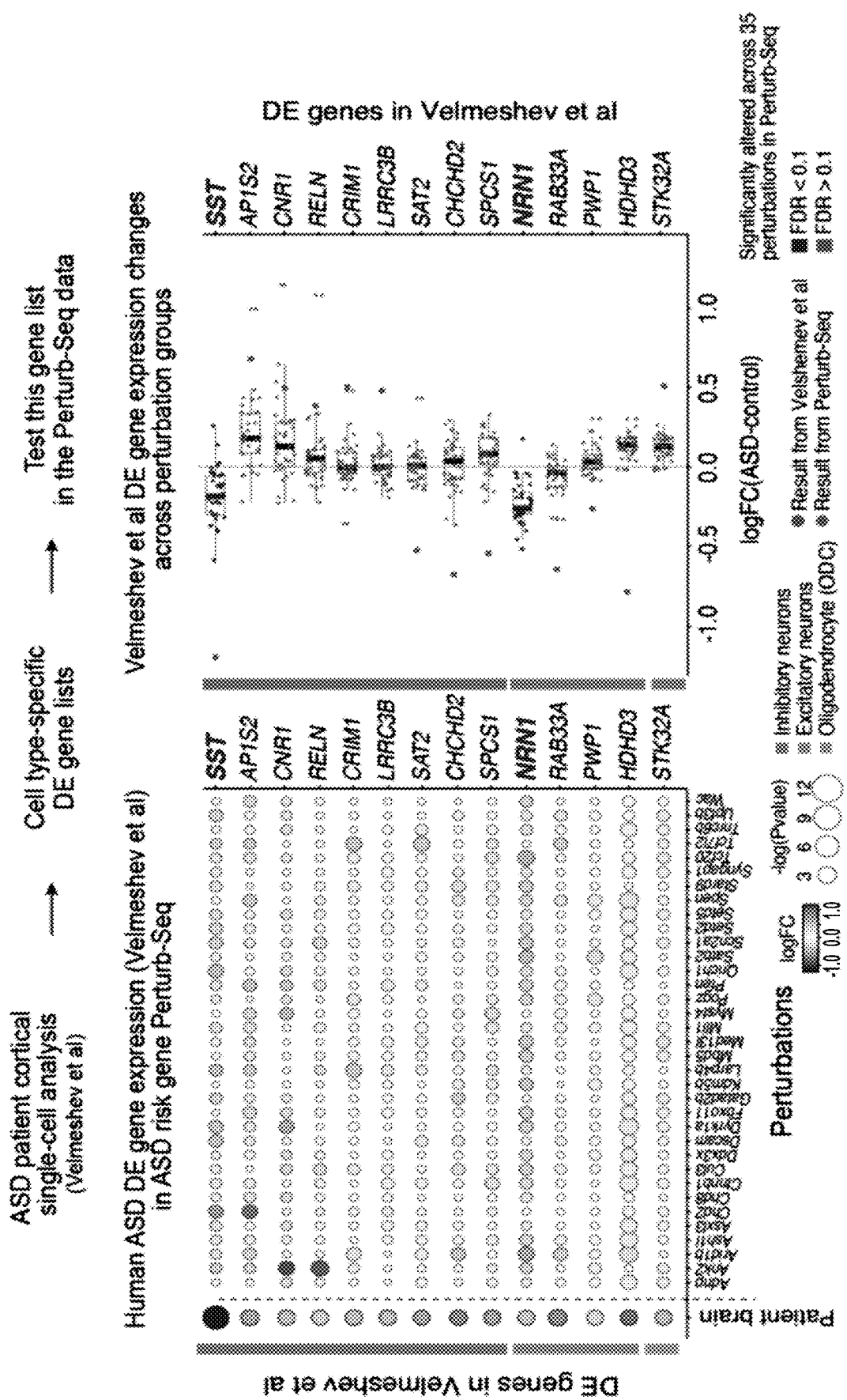

Using a dataset of snRNA-seq profiles from 15 ASD donors and 16 controls (30), defined differentially expressed (DE) genes in each cell type were defined using a statistically conservative pseudobulk-based analysis with DESeq2 (34, 35), correcting for age, sex, and patient-to-patient variability. Genes were identified that were differentially expressed between patients and controls in at least one of three major cell types (inhibitory neurons, excitatory neurons, or oligodendrocytes) with FDR <0.2, and selected those that have 1:1 orthologs in mice, resulting in 14 genes (FIG. 4F).

These 14 genes were then compared to the Perturb-Seq data and asked if these ASD-patient DE genes were also affected by the 35 ASD risk gene perturbations in the dataset. The effects of all 35 perturbations were aggregated, and it was asked whether the aggregated gene expression changes agreed more strongly with the gene expression changes in the ASD patient data than would be expected by chance. For each ASD patient DE gene, its mouse orthologue was taken and the median fold change of expression (log FC) over all perturbations in the Perturb-Seq data was calculated. This log FC was then compared with the corresponding log FC in the ASD patient data and generated an agreement score for each gene, defined as a high median log FC and a similar direction of change as in the human data. Genes were then binned by their expression and each ASD patient DE gene was compared to others in the same bin to extract p-values (with FDR correction). From this analysis, two genes were identified, SST in interneurons and NRN1 in excitatory neurons, both of which showed decreased expression in ASD patients and were likewise significantly decreased in expression across the panel of perturbations (FDR<0.1), albeit with different effect sizes (FIG. 4F). This indicates that despite the different developmental stages, high clinical heterogeneity in ASD, and patient genetic diversity, similar genes and cell types can be identified as affected in both the analyses herein and in studies of human patient tissue.

Figure 18:
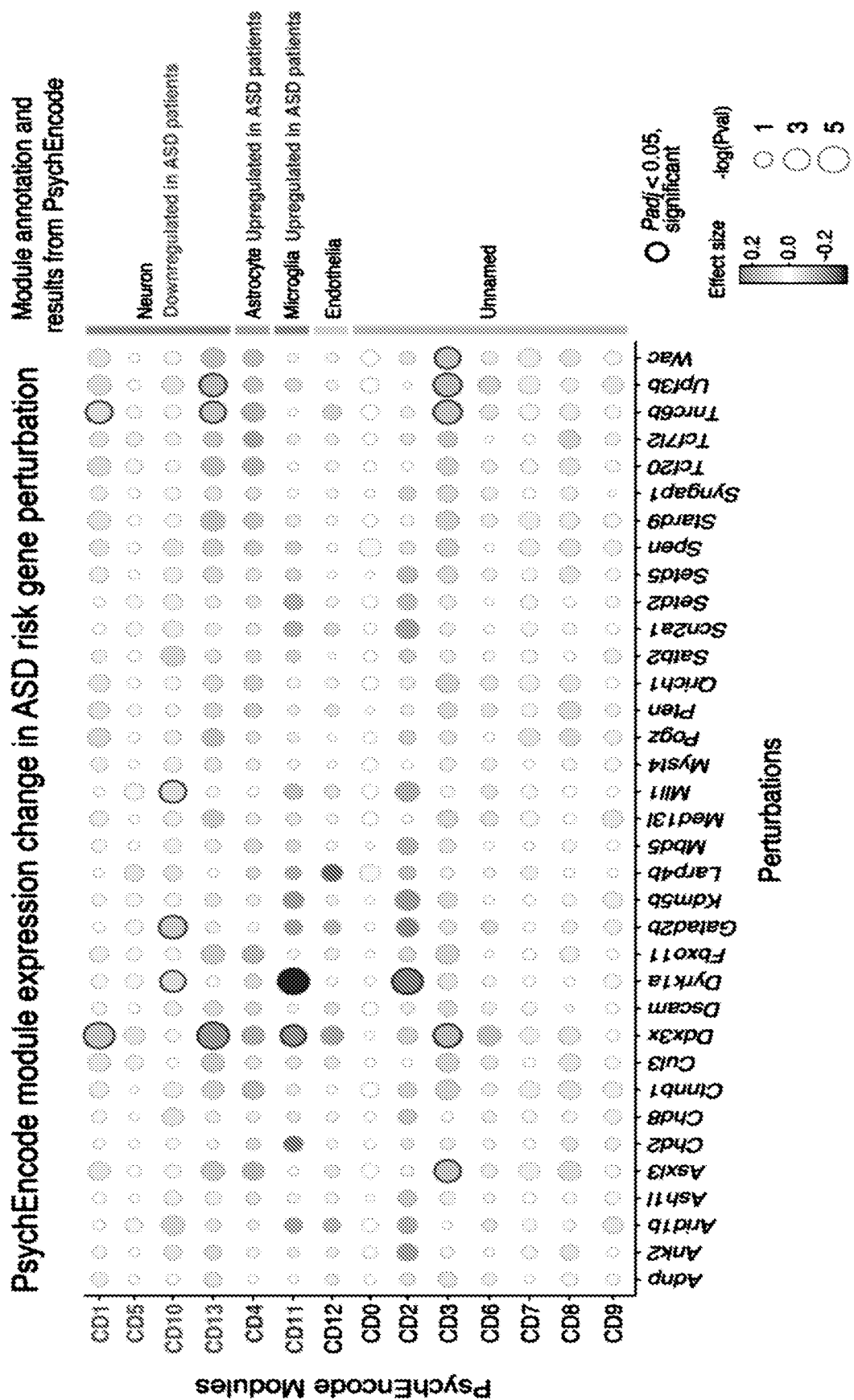
FIG. 18—ASD/ND risk gene perturbation effects in the Perturb-Seq data (compared to GFP control) on 14 gene modules from the PsychEncode study comparing ASD patient and control brain tissue. Dot color corresponds to effect size, dot size corresponds to base 10 log(P-value). Padj was calculated using Benjamini & Hochberg FDR correction.

The 14 gene modules reported in the PsychEncode study of 700 bulk RNA-seq samples of human cortex from a panel of psychiatric disorders was also analyzed (33). 6 of the 14 modules previously reported to be altered in the ASD patients in the PsychEncode analysis were also significantly affected across 8 of the ASD/ND risk gene perturbations (FIG. 18). Although these analyses are limited by the relatively few available datasets of ASD patient brain samples, they suggest that these Perturb-Seq experiments can identify gene program abnormalities seen in human ASD patients.

Example 8—Discussion of Examples 1-7

In vivo Perturb-Seq can serve as a scalable tool for systems genetic studies of large gene panels to reveal their cell-intrinsic functions at single-cell resolution in complex tissues. In this example, at least the application of in vivo Perturb-Seq to ASD/ND risk genes in the developing brain was demonstrated. This method can be applied across diverse diseases and tissues.

ASD/ND affects brain function profoundly, but its cellular and molecular substrates are not yet defined. The large number of highly penetrant de novo risk genes implicated through human genetic studies offers an entry point to identify the cell types, developmental events, and mechanisms underlying ASD/ND. However, this requires scalable methods to define the function of risk-associated genes with cell-type specificity. Using Perturb-Seq to functionally test large gene sets in the developing embryo, gene expression changes were observed to be linked to ASD/ND genes in different cell types and processes. Within the power of the analysis that can be achieved with the number of cells that can be reasonably sequenced, it was found that some recurrent modules are affected across more than one ASD/ND risk gene perturbation. Without being bound by theory, it is likely that this represents an underestimation of the number of convergent modules across perturbations which might be revealed by larger-scale experiments using greater numbers of cells.

Ank2 encodes an ankyrin protein and is expressed broadly in excitatory and inhibitory neurons as well as glial cells in the brain (22). Ankyrin homologs interact with ion channels in many neuronal types, and Ankyrin-G has been shown to stabilize GABAergic synapses (36). The roles of Ank2 in the brain have largely been studied in the context of excitatory neurons. Ank2 loss-of-function results in hypoplasia of the corpus callosum and pyramidal tract, and ultimately optic nerve degeneration (23), suggesting that it is required in the maintenance of premyelinated axons in excitatory neurons in early neurodevelopment. Ank2 mutants showed misregulation of intracellular calcium homeostasis and calcium channel expression in excitatory neurons (24, 25), as well as increased axonal branching and ectopic connectivity (26). The Perturb-Seq data in at least examples 1-7 suggests an additional role of Ank2 in the Ndnf+interneuron subtype, along with its known roles in excitatory neurons.

In addition to neurons, oligodendrocytes and astrocytes were also affected by several perturbations. Oligodendrocytes modulate and consolidate neural circuit refinement, and abnormal maturation of oligodendrocytes may be linked to long-lasting changes in neural wiring and brain function (37). One of the risk genes, Chd8, encodes a protein that binds directly to β-catenin to recruit histone proteins and negatively regulates the Wnt signaling pathway, which plays a crucial role in neuronal progenitor proliferation and differentiation in the forebrain (38-41). The results in these examples at least showed that Chd8 modulates gene modules for oligodendrocyte differentiation and maturation, consistent with previously reported ChIP-Seq results showing that CHD8 interacts directly with OPC maturation genes at perinatal stages of development (27, 42).

Although these examples focused on the perinatal neocortex in this study, in vivo Perturb-Seq can be applied to study gene functions systematically across other tissues and developmental ages to reveal tissue-specific as well as broadly-distributed gene functions. This approach can uncover both the impact of individual disease-associated genes and of combinations of genes and the overall set of processes that they affect. These findings underscore the importance of using single-cell profiles as a rich, comprehensive, and interpretable phenotypic readout. With advances in other single-cell profiling approaches (e.g., single-cell ATAC-seq (43), single-cell multi-omics (44), and spatial genomics (45, 46)), in vivo Perturb-Seq can be coupled in the near future with diverse readouts to better define the function of disease-risk associated variants, from molecular mechanisms to non-cell autonomous effects in tissues. Spatial transcriptomics in combination with in vivo Perturb-Seq can be used to uncover non-cell autonomous effects. In vivo Perturb-Seq can allow for, inter alia, elucidation and understanding of pathways and cell types affected in heterogenous genetic pathologies, directing downstream studies, informing the development of refined models for genetic disorders, and mechanistic studies as interest moves from genetic variants to function.

Example 9—Methods for Examples 1-7

Methods Summary

In Vivo Perturb-Seq Experiment

The backbone plasmid contains antiparallel cassettes of two gRNAs (Table 6) under mouse U6 and human U6 promoters, and the EF1a promoter to express puromycin, BFP, and a polyadenylated barcode unique to each perturbation. Cloning and lentiviral packaging of the 38 vectors were done individually.

All animal experiments were performed according to protocols approved by the Institutional Animal Care and Use Committees (IACUC) of Harvard University and of the Broad Institute of MIT and Harvard. In utero lentiviral injection into the lateral ventricles was performed at E12.5 in Cas9 transgenic mice (14) (4-6 month old, Jax #026179), and each single-cell library was made by combining the BFP+cells from 1-3 litters (4-20 animals) of P7 animals harvested on the same day. Tissue dissociation was performed with the Papain Dissociation kit (Worthington, #LK003152). The FACS-purified cells were sorted into cold Hibernate A/B27 medium and subjected to single-cell RNA sequencing library preparation. The analysis includes 17 independent libraries of Perturb-Seq cells.

Single-cell RNA sequencing libraries were created using the Chromium Single Cell 3' Solution v2 kit (10x Genomics) following the manufacturer's protocol. Each library was sequenced with Illumina NextSeq high-output 75-cycle kit with sequencing saturation above 70%. Dial-out PCR was performed to extract the perturbation barcode in each cell.

Perturbation barcodes were identified by two complementary methods. First, the dial-out sequences were used to create a cell-by-perturbation UMI count matrix by a modification of from the original Perturb-Seq work (12). In addition, barcode sequences were extracted from the 10x Genomics Cell Ranger bam file. Reads were then assigned to the perturbation they mapped best. Cell barcodes and UMIs were extracted, and a cell-by-perturbation UMI count matrix was created. Then, only cells for which either i) the assigned 10x and dialout perturbations agree or ii) the cell was assigned to a perturbation by one method but not assigned to any perturbation in the other were kept.

Perturb-Seq Analysis

UMI count data was loaded into R and processed using the Seurat v 2.2 package (47). Clusters were assigned to cell types based on marker genes from the literature, mousebrain.org (16), and DropViz.com (22). Only on cells of 5 key types (projection neurons, inhibitory neurons, oligodendrocytes, microglia/macrophages, and astroglia) were focused on and rest were removed.

WGCNA and Structural topic modelling (STM) were performed for each cell cluster based on the published pipelines (20, 21). Linear regression was used to test the relationship between perturbations and WGCNA gene scores, correcting for batch and number of genes. To test for correlations between perturbations and topics, the theta matrix (the matrix containing proportions of topics per cell) was extracted from the STM matrix. For each topic, linear regression was used to test how the per-cell proportions for each topic related to perturbations (after setting GFP to be the reference perturbation), correcting for nGene and batch.

RNA In Situ Hybridization and Immunohistochemistry

Multiplexed RNAscope fluorescent in situ hybridization and immunohistochemistry was performed on fixed-frozen tissue. Probes against the following mRNAs were used: Pdgfra, Cspg4, and Fezf2 (ACDBio). The antibodies and dilutions were: Mouse anti-NeuN antibody (mab377, 1:500; Millipore), Mouse anti-GS antibody (mab302, 1:500; Millipore), Goat anti-Pdgfra antibody (AF1062, 1:200; R&D System), Rabbit Iba1 antibody (019-19741, 1:400; Wako), Chicken anti-GFP antibody (ab16901, 1:500; Millipore), Mouse anti-Satb2 (ab51502, 1:50; Abcam), Rat anti-Ctip2 (ab18465, 1:100, Abcam), Rabbit anti-Sox6 (ab30455, 1:500; Abcam), Rat anti-Mbp (mab386, 1:100; Millipore). The staining, imaging, and quantifications were double-blinded.

Analysis of Human Single Nucleus or Single Cell RNA-Seq Data

For each single cell/nucleus human dataset, the UMI count matrix and metadata were downloaded and processed with Seurat to create Seurat objects. Cell types were extracted from the metadata, and combined into more general cell types, namely: Microglia, Astroglia (including Radial Glia), Inhibitory neurons, Excitatory neurons, Oligodendrocytes, and other. For differential expression analysis for data from Velmeshev et al (30), we removed data from all individuals of <12 years of age and separated PFC and ACC regions. For each cell type in each region a pseudobulk profile was constructed and genes expressed in <5% of cells or with <10 reads were removed. DESeq2 v 1.20.0 (35) was then used to perform differential expression analysis between the ASD patients and the controls, correcting for sex and age. All genes with 1:1 mouse orthologs (BioMart) were extracted and the FDR corrected P-values were calculated on these genes for both ACC and PFC. Only analysis on the PFC yielded significant hits, which are presented in FIG. 4F.

To compare these results to the Perturb-Seq data, for each human DE gene, an agreement score was calculated by taking the absolute value of its mouse orthologues' median log FC over all perturbations (calculated with Limma) and giving it a positive sign if its direction agreed with that of the human data, a negative sign otherwise. Finally, genes were binned by expression, and p-values were calculated for each gene by comparing the agreement scores to other genes in the same bin.

Further method details are set forth below.

Lentiviral Vector Construction and Production

Lentiviral vectors were constructed as previously reported (11-13). The backbone plasmid contains antiparallel cassettes of two gRNAs (Table 6) under mouse U6 and human U6 promoters, and the EF1a promoter to express puromycin, BFP, and a polyadenylated barcode unique to each perturbation. Cloning of the 38 vectors were done individually. Association of each gRNA set and perturbation barcode was established by Sanger sequencing. The gRNA designs were defined using the online tool at benchling.com (48). Each lentivirus was packaged individually with the V2 helper plasmids (49), and the functional titer was measured individually through HEK293 cell infection and FACS measurement of the BFP+population before pooling equally for ultracentrifugation. The functional titer of the final lentivirus was $>5 \times 10^9$ U/mL for in utero ventricular injection and transduction.

TABLE 6 gRNA design for the ASD/ND risk gene perturbations.

| gene | Guide1-179 | SEQ ID NO: | Guide2-117 | SEQ ID NO: | Perturbation barcode | SEQ ID NO: |
|---|---|---|---|---|---|---|
| ADNP | CCTGGGCACAAATGCCCGAG | 1 | TTTGAAAAACACTACATGGG | 41 | CTAGTTACTTTAGATAGG | 81 |
| ANK2 | GCATTTCTGCGACTACACTG | 2 | TGTTCCTGAGACAATGACGG | 42 | ACTAAAGCTGCATCGCGG | 82 |
| ANKRD11 | CTGCACGAGGCGTGTAACCG | 3 | GCACCGAGCAGCTATCCGAG | 43 | GTCTTGTTGGAGTCGAGT | 83 |
| ARID1B | GTACCCATCCCATACAACTG | 4 | CCCATGATGAGGAGCTACGG | 44 | GTTGTCCTGTTGGTCTGG | 84 |
| ASH1L | ACTATGAGACTCACTAACTG | 5 | ACTTCTCTTGATGTGATGGG | 45 | CGGGCGAATGGGAACCTG | 85 |
| ASXL3 | TCACACTAACACTCGAGTCG | 6 | AGATTGCAGCCTTACGAACA | 46 | GGTTTTGTTGGGCGACCA | 86 |

TABLE 6-continued gRNA design for the ASD/ND risk gene perturbations.

| gene | Guide1-179 | SEQ ID NO: | Guide2-117 | SEQ ID NO: | Perturbation barcode | SEQ ID NO: |
|---|---|---|---|---|---|---|
| CHD2 | TCAGAAGACGAACAGGAACA | 7 | TAAGGACAAAAGCCAAGAGG | 47 | TCATTCATCCGGCCTATC | 87 |
| CHD8 | TTTCAATCCAGACTACGTAG | 8 | TGCCCTATGAGGACAGTACG | 48 | GTGTTGCGCCCTCTTCAA | 88 |
| CTNNB1 | CCATTCATAAAGGACTTGGG | 9 | GATTAACTATCAGGATGACG | 49 | AGAAGTGATGGTGTCAAG | 89 |
| CUL3 | ATCCAGCGTAAGAATAACAG | 10 | TATGTCTCTAATCATCACCA | 50 | CATCTCCCTGATGGCGTA | 90 |
| DDX3X | ATGACAAAGACAGTTCAGGG | 11 | AAAGAGGTGGAAATAGTCGC | 51 | AAGGTACACCTGGTTTGA | 91 |
| DSCAM | AGTGACGTACGCCTCCACCG | 12 | TAGTGTTTGCAAGCACATCG | 52 | AGAGTAGCTCACTTCCGA | 92 |
| DYRK1A | TGATTATATTGTAAAAAACG | 13 | ATCAAGCCCAGATAGAAGTG | 53 | CTCCGTGAACGTTCGTGA | 93 |
| GFP (control) | ACCAGGATGGGCACCACCCG | 14 | ACCAGGATGGGCACCACCCG | 54 | CGAGCCTCTACTTGGCGC | 94 |
| FBXO11 | ACACGCAAGCAGCTCTACAA | 15 | CCGGCGTTGTTCCGATCCTG | 55 | GGTAGTGGTGCACACACG | 95 |
| FOXP1 | TGTTGAGGAGTGATAACCTG | 16 | CAACCACTTACTAGAGTGCG | 56 | CCCTAGGAATTCTTAATT | 96 |
| GATAD2B | TTGCCTCCCATATCCAACCA | 17 | CGTTGAGACATCAACATGTG | 57 | AATGTTTTCACGGTTGTT | 97 |
| KDM5B | ATTCAGCCTCTGGATCCGCG | 18 | AGACTGGGATCTGTAAGGT | 58 | CACGAGCGCAACCTCAGT | 98 |
| LARP4B | GATATCGGAGTCTACCCCCG | 19 | CAGGCACAGCGAGTCCAGGA | 59 | ATTTCATGACGCAATTTG | 99 |
| MAP1A | GCTGGTCCTATCCTCACCAG | 20 | TGTTGAACATAAGGCTCCGG | 60 | CCGCAGGTAGTGGGCTGT | 100 |
| MBD5 | TCCAGTAGTACCTTCACGGG | 21 | CCATGCTCTGTAATAGACG | 61 | CGGACAATGGAACGAGGA | 101 |
| MED13L | GTTCGCTACCCAGTTCGCCG | 22 | ACGCCATACACACAGCAGGT | 62 | GAGCTTGGTCGCAGAGTA | 102 |
| MLL1 | GGATCATCAAGACTCCCCGG | 23 | AGAAAGGGCGGCGATCAAGG | 63 | AGAAAACTACATACCGCA | 103 |
| MYST4 | ATTGGAATGGGATCGGCACG | 24 | CAAATGTGAAGGCCTTGAGG | 64 | CGGATGCCCGAATCACCA | 104 |
| POGZ | ATTGTGCTGAACGTACAGCA | 25 | CACTACTGTTAGTAACAGTG | 65 | CCAACGCGTCTTCTGGCC | 105 |
| PTEN | TGTGCATATTTATTGCATCG | 26 | TCACCTGGATTACAGACCCG | 66 | CCTATCTTTAGACGGATG | 106 |
| QRICH1 | AGTACATCCGAGTAAAGGCG | 27 | TCCCCAGGAAGCCTACAATG | 67 | CCCGAACTGTTTCACCCA | 107 |
| SATB2 | AGAGCTGTGGGAATACCCCA | 28 | CAGCCGGGCCACCTTCACCG | 68 | CCGCTTCGTGTGTCGAAT | 108 |
| SCN2A | GGGAGTTAAAATGTACAGGG | 29 | GGGATTCCCTGGTAAAGAAG | 69 | TGTGGGCGGTATGGGAGG | 109 |
| SETD2 | TCTAGGTCACCTGAATCCAG | 30 | TAGAAATCCCCCATCTTCGG | 70 | CGGTTGACAGTTCGTCTG | 110 |
| SETD5 | TCGACACCCATGCCTCTGAG | 31 | TCGCCCGTAGAGGAACGCTG | 71 | CAGCTTTTGCAGTTGCGG | 111 |
| SPEN | CCTATGGACACCATGAACGG | 32 | GAATCTTGACACTTTCCACG | 72 | CTTCAGCTTTGACACACA | 112 |
| STARD9 | TATGAACTGGGAGATCCCTG | 33 | GCAGCTGAGGAAGCACATCG | 73 | TTAAAATGCCGCGTTTGG | 113 |
| SUV420H1 | ATTACAGCAGCACTCGGGCA | 34 | CTCCTTGGCGGACATTCCAG | 74 | CAGTGCTACACGGTTGCC | 114 |
| SYNGAP1 | AGGGGGCATAGGACATCGCG | 35 | CCAGCCAGGACGATCGTACG | 75 | CCGGCAGGGGAATACGTG | 115 |
| TCF20 | AGAGCTATGGACCTCCCCAG | 36 | ATCAAACATGAGACTTACCG | 76 | CTAATCGGGTTTCGGCTT | 116 |
| TCF7L2 | GTGTACCCAATCACGACAGG | 37 | CGGAAACTTCGGAGCGAGG | 77 | TTGTATCGTAGGTCATCA | 117 |
| TNRC6B | ATAAAGTGTTACTAAAACGT | 38 | TGTTCCCATGCAAACCAATG | 78 | CTTGCACATGTTGGGAGA | 118 |
| UPF3B | CGATAGGCAGGATCGCAACA | 39 | TGTTCCTTGGTCAAAGTGGG | 79 | AACCTTTATTTGGCGCCG | 119 |
| WAC | TGACAGCACAGGTCACAACA | 40 | TTGAACTATGAAGTGCACTG | 80 | CTGGTACAAGGCGTAGAT | 120 |

In Vivo Perturb-Seq Experiment

The backbone plasmid contains antiparallel cassettes of two gRNAs (Table 6) under mouse U6 and human U6 promoters, and the EF1a promoter to express puromycin, BFP, and a polyadenylated barcode unique to each perturbation. Cloning and lentiviral packaging of the 38 vectors were done individually.

All animal experiments were performed according to protocols approved by the Institutional Animal Care and Use Committees (IACUC) of Harvard University and of the Broad Institute of MIT and Harvard. In utero lentiviral injection into the lateral ventricles was performed at E12.5 in Cas9 transgenic mice (14) (4-6 month old, Jax #026179), and each single-cell library was made by combining the BFP+ cells from 1-3 litters (4-20 animals) of P7 animals harvested on the same day. Tissue dissociation was performed with the Papain Dissociation kit (Worthington, #LK003152). The FACS-purified cells were sorted into cold Hibernate A/B27 medium and subjected to single-cell RNA sequencing library preparation. This analysis included 17 independent libraries of Perturb-Seq cells.

Single-cell RNA sequencing libraries were created using the Chromium Single Cell 3' Solution v2 kit (10x Genomics) following the manufacturer's protocol. Each library was sequenced with Illumina NextSeq high-output 75-cycle kit with sequencing saturation above 70%. Dial-out PCR was performed to extract the perturbation barcode in each cell.

Perturbation barcodes were identified by two complementary methods. The dial-out sequences were first used to create a cell-by-perturbation UMI count matrix by a modification of from the original Perturb-Seq work (12). In addition, barcode sequences were extracted from the 10x Genomics Cell Ranger bam file. Reads were then assigned to the perturbation they mapped best. Cell barcodes and UMIs were extracted, and a cell-by-perturbation UMI count matrix was created. Cells for which either i) the assigned 10x and dialout perturbations agree or ii) the cell was assigned to a perturbation by one method but not assigned to any perturbation in the other were then kept.

This analysis comprises 17 independent libraries of Perturb-Seq cells. In utero lentiviral injection into the lateral ventricles was performed at E12.5 in Cas9 transgenic mice (14) (4-6 month old, Jax #026179), and each 10x single-cell library was made by combining the BFP+cells from 1-3 litters (4-20 animals) of P7 animals harvested on the same day. P7 mice were anesthetized then disinfected with 70% ethanol and decapitated. The brains were quickly extracted into ice-cold PBS and cortices were micro-dissected in ice-cold Hibernate A medium (BrainBits, #HA-Lf) with B27 supplement (ThermoFisher, #17504044) under a dissecting microscope. Tissue dissociation was performed with the Papain Dissociation kit (Worthington, #LK003152) in a modification of a previously described protocol (50). Briefly, cortices were transferred into ice-cold papain solution with DNase in a cell culture dish and cut into small pieces with a blade. The dish was then placed onto a digital rocker in a cell culture incubator for 30 mins with rocking speed at 30 rpm at 37° C. The digested tissues were collected into a 15 mL tube with 5 mL of EBSS buffer (from the Worthington kit). The mixture was triturated with a 10 mL plastic pipette 20 times and the cell suspension was carefully transferred to a new 15 mL tube. 2.7 mL of EBSS, 3 mL of reconstituted Worthington inhibitor solution, and DNAse solution were added to the 15 mL tube and mixed gently. Cells were pelleted by centrifugation at 300 g for 5 mins at RT. Cells were resuspended in 0.5 mL ice-cold Hibernate A with B27 supplement (ThermoFisher, A3582801) and 10% fetal bovine serum (FBS) and subjected to FACS purification. The FACS collected cells were sorted in cold Hibernate A/B27 medium with 10% FBS (VWR, #97068). After collection, the cells were centrifuged and resuspended in ice-cold PBS with 0.04% BSA (NEB, B9000S) for single-cell RNA sequencing library preparation (10x Genomics v2 chemistry). The FACS purification and resuspension was performed within 1.5 h while keeping the cells on ice to prevent necrosis.

Perturb-Seq Analysis

UMI count data was loaded into R and processed using the Seurat v 2.2 package (47). Clusters were assigned to cell types based on marker genes from the literature, mousebrain.org (16), and DropViz.com (22). Only cells of 5 key types (projection neurons, inhibitory neurons, oligodendrocytes, microglia/macrophages, and astroglia) were focused on and the rest were removed. WGCNA and Structural topic modelling (STM) were performed for each cell cluster based on the published pipelines (20, 21). Linear regression was used to test the relationship between perturbations and WGCNA gene scores, correcting for batch and number of genes. To test for correlations between perturbations and topics, the theta matrix (the matrix containing proportions of topics per cell) was extracted from the STM matrix. For each topic, linear regression was used to test how the per-cell proportions for each topic related to perturbations (after setting GFP to be the reference perturbation), correcting for nGene and batch.

RNA In Situ Hybridization and Immunohistochemistry

Multiplexed RNAscope fluorescent in situ hybridization and immunohistochemistry was performed on fixed-frozen tissue. Mice were anesthetized and transcardially perfused with ice-cold PBS followed by ice-cold 4% paraformaldehyde in PBS. Dissected brains were postfixed overnight in 4% paraformaldehyde at 4° C., and cryoprotected in 30% sucrose. Brains were then embedded in optimal cutting temperature (OCT) compound (Tissue-Tek, #4583) and 15-20 m tissue sections were prepared.

Multiplex RNAscope v1 was performed based on manufacturer's instructions. Probes against the following mRNA were used: Pdgfra, Cspg4, and Fezf2 (ACDBio). The staining, imaging, and quantifications were double-blinded. Quantification was performed using the StarSearch program (https://www.seas.upenn.edu/-rajlab/StarSearch/launch.html).

For immunohistochemistry, mice were anesthetized and transcardially perfused with ice-cold PBS followed by ice-cold 4% paraformaldehyde in PBS. Dissected brains were postfixed overnight in 4% paraformaldehyde at 4° C., and cryoprotected in 30% sucrose. The brains were embedded in OCT compound (Tissue-Tek, #4583) and 15 m tissue sections were prepared. The slides with tissue sections were incubated with blocking media (6% donkey serum in 0.3% Triton with PBS) for 1 hr, then incubated with primary antibodies in the incubation media (1:3 dilution of blocking media in PBS with 0.3% Triton) overnight at 4° C. Slides were washed with PBS with 0.3% Triton 4 times to remove the excess primary antibody. Secondary antibodies were applied at 1:800 dilution in blocking media and incubated for 2 hr at room temperature. Slides were then washed 4 times with PBS with 0.3% Triton and incubated with DAPI for 10 mins before mounting with Fluoromount G (Invitrogen, #00-4958-02). The antibodies and dilutions were: Mouse anti-NeuN antibody (mab377, 1:500; Millipore), Mouse anti-GS antibody (mab302, 1:500; Millipore), Goat anti-Pdgfra antibody (AF1062, 1:200; R&D System), Rabbit Iba1 antibody (019-19741, 1:400; Wako), Chicken anti-GFP antibody (ab16901, 1:500; Millipore), Mouse anti-Satb2 (ab51502, 1:50; Abcam), Rat anti-Ctip2 (ab18465, 1:100, Abcam), Rabbit anti-Sox6 (ab30455, 1:500; Abcam), Rat anti-Mbp (mab386, 1:100; Millipore).

All images were acquired using either a custom-built spinning disk confocal microscope equipped with image acquisition NIS-Elements software, or a Carl Zeiss epifluorescent microscope with Zen software. To quantify protein expression levels, the thickness of the cortex was divided into bins and calculated the average pixel value per bin was calculated. The staining, imaging, and quantifications were double-blinded.

Perturb-Seq Profiling

Single-cell RNA sequencing libraries were created using the Chromium Single Cell 3' Solution v2 kit (10x Genomics) following the manufacturer's protocol. Each library was sequenced with Illumina NextSeq high-output 75-cycle kit with sequencing saturation above 70%. Reads were aligned to the mm10 mouse genome reference using the Cell Ranger package (10x Genomics).

To sequence the perturbation barcode, dial-out PCR was performed to extract the perturbation barcode in each cell. This is modified from Dixit et al (12) to be compatible with the 10x Genomic V2 chemistry instead of V1. The PCR product was sequenced along with the 10x libraries, and demultiplexed to extract the perturbation information.

```
Forward primer:
                                      (SEQ ID NO: 121)
CAAGCAGAAGACGGCATACGAGAT-TCGCCTTA-

GTCTCGTGGGCTCGGAGATGTGTATAAGAGACAG-

TAGCAAACTGGGGCACAAGC

Reverse primer (i5):
                                      (SEQ ID NO: 122)
AATGATACGGCGACCACCGAGATCTACAC
```

Data Analysis

Data Pre-Processing

BCL files were transformed into fastq files using the cellranger mkfastq command, using CellRanger V2.1.0. Bam files and expression matrices were generated from these fastq files using the cellranger count command, using force_cells=8000.

Identification of Perturbation Barcode

Perturbation barcodes were identified by two complementary methods. To extract perturbation information from the dial-out reads, code was modified from the original Perturb-Seq work (12) to work with 10x V2 chemistry and was applied to the data (original code at https://github.com/asncd/MIMOSCA). This resulted in a cell-by-perturbation UMI count matrix. To extract perturbation information from the 10x reads, a fasta file was first created with one entry for each perturbation, containing the sequence of the perturbation barcode and the surrounding sequence. This fasta file was turned into a STAR reference (51), referred to as the PBC reference. Unmapped reads containing either AGAATT or CCTAGA as a subsequence were extracted from the Cell Ranger bam file, and then mapped to this new reference. Low quality reads were filtered out using the following filters: (i) used "samtools view -F 2820" to filter out unmapped, multimapped, and low quality reads from the PBC mapped bam file, (ii) removed reads with quality scores <255 (iii) removed reads whose 5' end did not map between 655 and 714 bp into the PBC reference, to help exclude reads that did not overlap enough bases in the perturbation barcode for proper identification of the perturbation, and (iv) removed reads whose edit distance from the PBC reference was >2. Reads were then assigned to the perturbation they mapped best. Cell barcodes and UMIs were extracted, and a cell-by-perturbation UMI count matrix was created. This matrix was used to assign cells to perturbations in the same way as with the dial-out data. As with the dialout data, if a cell had one perturbation with >1.3× the number of UMIs assigned to it than the next best perturbation based on the 10x sequence, that cell was assigned to that perturbation in the 10x data; otherwise, the cell was declared to have multiple perturbations. Only cells for which either i) the assigned 10x and dialout perturbations agree or ii) the cell was assigned to a perturbation by one method but not assigned to any perturbation in the other were kept.

Cell Type Clustering Analysis

UMI count data was loaded into R and processed using the Seurat v 2.2 package (47). Data were scaled to counts per million and log normalized. Cells expressing less than 500 genes were removed. Variable genes were found using FindVariableGenes with x.low.cutoff=1 for each batch separately. Genes that were found to be variable in at least 4 batches were combined into a final combined list of variable genes. The normalized data was scaled with ScaleData on the variable genes, regressing out the effects of nUMI, and PCA was performed. Clustering was performed with the FindClusters function (with default parameters, except for resolution=1.2 and using 28 PCs). tSNE plots were generated with RunTSNE (RunTSNE (with default parameters, except with 17 PCs and pca=F). Clusters were assigned to cell types based on marker genes from the literature, mousebrain.org (16), and DropViz (22). For each cell type, a more refined nGene cutoff was identified (FIGS. 7A-7G), and cells of that cell type with less than that filter were removed from further consideration. Cell clustering does not follow the proportion of mitochondrial reads or nUMIJ in each cell. Only cells of 5 key types (projection neurons, inhibitory neurons, oligodendrocytes, microglia/macrophages, and astroglia) were focused on and the rest were removed.

For subclustering individual cell types, the cells of that cell type were extracted from the larger Seurat object. Variable genes were chosen as above, and data was scaled with ScaleData, regressing out the effects of nUMI and batch, followed by PCA. Clustering was performed with FindClusters (with default parameters except for varying resolutions and number of PCs, Table 7). tSNE was performed with RunTSNE (with default parameters, except with different numbers of PCs and pca=F).

TABLE 7

Parameters used in Seurat for cell type clustering.

| Dataset | #PCs Used | Resolution Used | Variable Genes | Required Batches*** | Note |
|---|---|---|---|---|---|
| Cortex Perturb-seq | 28 | 1.2 | Calculated on each batch and combined** | 4 | |

TABLE 7-continued

Parameters used in Seurat for cell type clustering.

| Dataset | #PCs Used | Resolution Used | Variable Genes | Required Batches*** | Note |
|---|---|---|---|---|---|
| Striatium Perturb-seq | 22 | 1.2 | Calculated on each batch and combined** | 2 | |
| Single Perturb ANK2 and WT joint | 11 | 0.8 | Jointly calculated* | NA | |
| WT P7 Dataset | 15 | 0.8 | Jointly calculated* | NA | |
| 10X E18.5 Dataset | 13 | 0.8 | Jointly calculated* | NA | Publicly available data |
| Cortex CellTypes Subclustering | | | | | |
| Astroglia | 15 | 0.5 | Calculated on each batch and combined** | 4 | |
| Inhibitory Neurons | 11 | 0.8 | Calculated on each batch and combined** | 4 | |
| Excitatory Neurons | 15 | 0.8 | Calculated on each batch and combined** | 4 | |
| Microglia | 11 | 0.3 | Calculated on each batch and combined** | 4 | |
| ODC | 10 | 0.5 | Calculated on each batch and combined** | 4 | |

Testing WGCNA Gene Sets

WGCNA was performed for each cell cluster based on the published pipeline (21). Modules that were driven by outlier cells (these are modules that are highly expressed in a very small number of cells; this is the module level quality control, equivalent of filtering out genes expressed in a small number of cells) were manually removed. For a given cell type, each WGCNA gene set was input into moduleEigengenes to calculate a gene-set score for that set of genes. All cells without an assigned perturbation were removed.

Linear regression was used to test the relationship between perturbations and WGCNA gene scores, correcting for batch and number of genes with the lm function in R, using the formula:

Gene Score~perturbation+batch+$n$Gene

Associated P-values and effect sizes were extracted. In addition, a permutation-based approach was used to calculate an empirical P-value to ensure the model-based P-values reported by lm were accurate. Specifically, the perturbation labels of cells were randomly permuted within each batch, and the absolute effect size for each perturbation was calculated as above on this permuted data. This was repeated 10,000 times. The empirical P-value was the proportion of permutations (including the original data) with absolute effect size larger than that of the original data. FDR correction was performed using the Benjamini & Hochberg procedure.

To implement alternative analytical assumptions that do not rely on individual cells being independent conditional on batch, a linear mixed model-based approach was used. The lmer function from the lmerTest package in R was used. For each module, used this function was used to fit a linear mixed model of the scaled module scores with random interaction effect for each batch/perturbation pair, and fixed effects for batch, perturbation, and scaled nGene. This was performed with the R formula:

WGCNA_Score~batch+perturbation+$n$Gene+ (1|batch:perturbation)

where WGCNA_Score and nGene were mean centered and normalized to have variance 1. The p-values and effect sizes for each perturbation were then extracted from the resulting model.

Structural Topic Modelling

Structural topic modelling (STM) was performed separately on each cell type of interest using the STM package in R (20). Count data from cells of a given type were extracted from the Seurat object, along with corresponding meta data. Genes that occurred in <5% or >90% of cells were removed, as were mitochondrial and ribosomal genes. In addition, only genes that were expressed in at least one cell in all batches were retained in order to help reduce batch effects. The resulting count matrix was provided as input to the STM function, along with the meta data and with parameters LDAbeta=T, interactions=F. The formula used by the STM function was ~perturbation+batch+$n$Gene This specifies a model that assumed topic proportions were dependent on perturbation, number of genes, and batch. This model was run on each dataset with 5 topics. Top 10 genes for each topic were extracted with the labelTopics function.

To test for correlations between perturbations and topics, the theta matrix (the matrix containing proportions of topics per cell) was extracted from the STM matrix. For each topic, linear regression was used to test how the per-cell proportions for each topic related to perturbations (after setting GFP to be the reference perturbation), correcting for nGene and batch. In particular, the lm function in R was used, with the formula:

Proportion Topic~perturbation+batch+$n$Gene

Effect sizes were extracted from the resulting lm object. An empirical P-value was calculated, as for WGCNA. FDR correction was performed using the Benjamini & Hochberg procedure.

Correlation Graph of WGCNA Genes

For each cell type, all genes that appeared in at least one module for that cell type were extracted and the correlation between each pair was calculated. An 11 nearest neighbor graph was constructed, and the results were plotted with the igraph (v1.2.4.1) plot feature.

Analysis of Human Single Nucleus or Single Cell RNA-Seq Data

For each single cell/nucleus human dataset, the UMI count matrix and meta data were downloaded (adult human data: https://portal.brain-map.org/atlases-and-data/rnaseq/human-multiple-cortical-areas-smart-seq/, fetal human data: https://cortex-dev.cells.ucsc.edu/, human cerebral organoids data: https://singlecell.broadinstitute.org/single_cell/study/SCP282/reproducible-brain-organoids/) and processed with Seurat to create Seurat objects, with no nGene cutoff. Cell types were extracted from the metadata, and combined into more general cell types, namely: Microglia, Astroglia (including Radial Glia), Inhibitory neurons, and Excitatory neurons, ODCs, and others. Correlation analysis was then performed on these data as described in the 'Correlation Analysis' section.

Gene Module Conservation and Modularity: Correlation Analysis

For each dataset and each module, the associated cell type was extracted. The number of genes in the module expressed in at least 1% or 5% of cells were calculated. All genes expressed in <5% of cells were then excluded, as were modules with <3 genes surviving this 5% cutoff. The Pearson correlation coefficient between each pair of genes in the module was calculated, and the mean of these coefficients was calculated. For each module, a null distribution of the mean correlation coefficient was calculated as follows: a random set of genes was chosen with the same number of genes as the WGCNA module and roughly the same expression levels (all genes expressed by that cell type were partitioned into 100 mean expression bins, and randomly sampled genes from the matched bin for each gene in the module), and the average correlation coefficient was calculated as above. This was repeated 1,000 times, and an empirical P-value was estimated as the proportion of gene sets with correlation greater than that in the WGCNA module, as was an expected value for this average correlation coefficient. The normalized correlation was calculated by dividing the average correlation of the WGCNA module by the standard deviation of the correlation value from the matching null distribution and subtracting the mean correlation. Confidence intervals were calculated using bootstrapping (boot package v1.3-20 in R). For human single nucleus RNA-seq data, genes in each module were mapped to 1:1 human orthologs (from BioMart), before performing the above analysis.

Analysis of Human Bulk Data

Bulk human RNA-seq data was downloaded from BrainSpan (https://www.brainspan.org/static/download.html) and log transformed. For each module, the average expression of the genes of that module were calculated, and the results were plotted.

Differential Expression Analysis

For each cell type, raw count data was extracted, and genes expressed in <5% of cells were removed. limma v3.36.2 (52) was then used to perform differential expression analysis, fitting a linear model for each gene with batch and perturbation as covariates. For each perturbation, the associated P-value and log FC relative to GFP was calculated, followed by FDR correction. Results are shown in Table 8.

TABLE 8

Analysis of differential gene expression from Perturb-Seq data.

| Estimate | SE | Z | pvalue | Gene | Condition | padj | CellType |
| --- | --- | --- | --- | --- | --- | --- | --- |
| 2.64461235 | 0.06330411 | 41.7763105 | 0 | Plp1 | Ddx3x | 0 | ODC |
| 2.2130509 | 0.06262683 | 35.3371042 | 1.58E−273 | Plp1 | Upf3b | 1.27E−267 | ODC |
| 2.14029504 | 0.06290119 | 34.0263044 | 9.10E−254 | Plp1 | Setd5 | 4.87E−248 | ODC |
| 2.12907122 | 0.06672781 | 31.906806 | 2.15E−223 | Plp1 | Setd2 | 8.63E−218 | ODC |
| 1.96778043 | 0.06277633 | 31.3458988 | 1.11E−215 | Plp1 | Fbxo11 | 3.56E−210 | ODC |
| 2.01760549 | 0.06564918 | 30.7331398 | 2.05E−207 | Plp1 | Myst4 | 5.50E−202 | ODC |
| 1.83789934 | 0.06300006 | 29.1729795 | 4.27E−187 | Plp1 | Qrich1 | 9.80E−182 | ODC |
| 1.80246643 | 0.06306056 | 28.5831012 | 1.09E−179 | Plp1 | Wac | 2.19E−174 | ODC |
| 1.77653611 | 0.06260943 | 28.374895 | 4.13E−177 | Plp1 | Kdm5b | 7.37E−172 | ODC |
| 1.79975815 | 0.06414067 | 28.0595487 | 3.05E−173 | Plp1 | Stard9 | 4.91E−168 | ODC |
| 1.84320151 | 0.06636854 | 27.7722182 | 9.40E−170 | Plp1 | Adnp | 1.37E−164 | ODC |
| 1.19892624 | 0.04843699 | 24.7522878 | 2.93E−135 | Mbp | Upf3b | 3.92E−130 | ODC |
| 1.3717565 | 0.05738902 | 23.9027712 | 2.87E−126 | Mbp | Gatad2b | 3.54E−121 | ODC |
| 1.53098402 | 0.06433277 | 23.7978856 | 3.51E−125 | Plp1 | Cul3 | 4.03E−120 | ODC |
| 1.27727929 | 0.05500932 | 23.2193234 | 2.91E−119 | Plp1 | Dyrk1a | 3.11E−114 | ODC |
| 1.40796073 | 0.06522523 | 21.5861381 | 2.42E−103 | Plp1 | Ctnnb1 | 2.43E−98 | ODC |
| 1.08085901 | 0.0502152 | 21.5245392 | 9.17E−103 | Mbp | Ddx3x | 8.67E−98 | ODC |
| 1.04166875 | 0.04924189 | 21.1541182 | 2.53E−99 | Mbp | Setd5 | 2.26E−94 | ODC |
| 1.1761105 | 0.06569099 | 17.9036811 | 1.10E−71 | Plp1 | Asxl3 | 9.33E−67 | ODC |
| 0.91407848 | 0.05356213 | 17.0657594 | 2.67E−65 | Mbp | Myst4 | 2.14E−60 | ODC |
| 0.84874703 | 0.04994379 | 16.9940443 | 9.09E−65 | Mbp | Stard9 | 6.95E−60 | ODC |
| 1.95714956 | 0.11578085 | 16.9039144 | 4.21E−64 | Hapln1 | Dscam | 3.07E−59 | Inhibitory |
| 1.08598415 | 0.06523423 | 16.6474577 | 3.16E−62 | Plp1 | Tnrc6b | 2.21E−57 | ODC |
| 0.87345148 | 0.05276075 | 16.5549478 | 1.47E−61 | Mbp | Adnp | 9.87E−57 | ODC |
| 2.00154666 | 0.12396699 | 16.1458041 | 1.22E−58 | Hapln1 | Pogz | 7.81E−54 | Inhibitory |
| 1.850412 | 0.11582849 | 15.9754482 | 1.89E−57 | Hapln1 | Setd5 | 1.17E−52 | Inhibitory |
| 0.6100828 | 0.03968568 | 15.3728695 | 2.49E−53 | Mbp | Dyrk1a | 1.48E−48 | ODC |
| 1.76991222 | 0.11589322 | 15.2719218 | 1.18E−52 | Hapln1 | Asxl3 | 6.75E−48 | Inhibitory |
| 1.76803931 | 0.11730127 | 15.0726353 | 2.45E−51 | Cldn11 | Ddx3x | 1.36E−46 | ODC |
| 0.81378625 | 0.05433407 | 14.9774568 | 1.03E−50 | Mbp | Setd2 | 5.52E−46 | ODC |
| 2.12131543 | 0.14226301 | 14.9112224 | 2.79E−50 | Hapln1 | Larp4b | 1.44E−45 | Inhibitory |
| 1.65988811 | 0.11307849 | 14.6790796 | 8.78E−49 | Hapln1 | Stard9 | 4.41E−44 | Inhibitory |
| 1.73764682 | 0.12109719 | 14.3491922 | 1.08E−46 | Hapln1 | Cul3 | 5.25E−42 | Inhibitory |
| 1.79524068 | 0.12644001 | 14.1983588 | 9.38E−46 | Hapln1 | Syngap1 | 4.43E−41 | Inhibitory |
| −2.7570451 | 0.20155739 | −13.67871 | 1.36E−42 | Mbp | Med13l | 6.25E−38 | ODC |
| 1.56334928 | 0.1148096 | 13.6168861 | 3.18E−42 | Cldn11 | Upf3b | 1.42E−37 | ODC |
| 0.68475929 | 0.05036527 | 13.5958615 | 4.24E−42 | Mbp | Cul3 | 1.84E−37 | ODC |

TABLE 8-continued

Analysis of differential gene expression from Perturb-Seq data.

| Estimate | SE | Z | pvalue | Gene | Condition | padj | CellType |
|---|---|---|---|---|---|---|---|
| 1.65812423 | 0.12269634 | 13.5140484 | 1.29E−41 | Hapln1 | Setd2 | 5.46E−37 | Inhibitory |
| 1.122117 | 0.08502534 | 13.1974415 | 9.08E−40 | Plp1 | Gatad2b | 3.74E−35 | ODC |
| 1.13794128 | 0.08704476 | 13.0730593 | 4.69E−39 | Hapln1 | Mll1 | 1.89E−34 | Inhibitory |
| −0.9472644 | 0.07354873 | −12.879412 | 5.88E−38 | Mbp | Spen | 2.30E−33 | ODC |
| 1.52734574 | 0.11876674 | 12.8600464 | 7.55E−38 | Hapln1 | Scn2a1 | 2.89E−33 | Inhibitory |
| 1.51656812 | 0.11840093 | 12.8087523 | 1.46E−37 | Hapln1 | Tcf20 | 5.47E−33 | Inhibitory |
| 1.77633679 | 0.14065845 | 12.6287247 | 1.47E−36 | Hapln1 | Ank2 | 5.35E−32 | Inhibitory |
| 3.58245737 | 0.2854763 | 12.5490536 | 4.02E−36 | Hbb-bs | Setd2 | 1.44E−31 | Excitatory |
| 0.62038203 | 0.04981951 | 12.452591 | 1.35E−35 | Mbp | Wac | 4.73E−31 | ODC |
| 0.90249648 | 0.07254447 | 12.4405965 | 1.57E−35 | Plp1 | Tcf20 | 5.38E−31 | ODC |
| 1.52285969 | 0.1239567 | 12.2854161 | 1.08E−34 | Cldn11 | Setd2 | 3.63E−30 | ODC |
| 1.47879536 | 0.12070608 | 12.2512081 | 1.66E−34 | Hapln1 | Fbxo11 | 5.43E−30 | Inhibitory |
| 0.71217798 | 0.05845683 | 12.1829727 | 3.83E−34 | Plp1 | Mll1 | 1.23E−29 | ODC |
| 1.54224288 | 0.12984273 | 11.8777764 | 1.54E−32 | Hapln1 | Spen | 4.86E−28 | Inhibitory |
| 1.37538193 | 0.11585407 | 11.8716759 | 1.66E−32 | Cldn11 | Setd5 | 5.13E−28 | ODC |
| 0.57932531 | 0.04984933 | 11.621527 | 3.20E−31 | Mbp | Kdm5b | 9.71E−27 | ODC |
| 1.42703337 | 0.12894857 | 11.0666865 | 1.82E−28 | Hapln1 | Med13l | 5.41E−24 | Inhibitory |
| 1.29215236 | 0.11876542 | 10.8798703 | 1.44E−27 | Hapln1 | Qrich1 | 4.20E−23 | Inhibitory |
| 1.51809103 | 0.14395929 | 10.5452801 | 5.34E−26 | Hapln1 | Ddx3x | 1.53E−21 | Inhibitory |
| −1.5248064 | 0.14620497 | −10.429238 | 1.82E−25 | Mbp | Larp4b | 5.14E−21 | ODC |
| −1.2795607 | 0.12425109 | −10.298185 | 7.18E−25 | Mbp | Chd8 | 1.99E−20 | ODC |
| 1.33145689 | 0.12995055 | 10.245873 | 1.24E−24 | Hapln1 | Pten | 3.36E−20 | Inhibitory |
| 4.0057396 | 0.39502809 | 10.1403917 | 3.66E−24 | Ptgds | Satb2 | 9.79E−20 | Astroglia |
| 1.17327934 | 0.11793573 | 9.94846418 | 2.56E−23 | Cldn11 | Stard9 | 6.74E−19 | ODC |
| 1.19524848 | 0.12301362 | 9.71639138 | 2.57E−22 | Cldn11 | Myst4 | 6.65E−18 | ODC |
| 1.17485963 | 0.12253383 | 9.58804264 | 8.98E−22 | Hapln1 | Upf3b | 2.29E−17 | Inhibitory |
| 3.62215404 | 0.37799721 | 9.58248872 | 9.47E−22 | Hba-a1 | Setd2 | 2.38E−17 | Excitatory |
| 0.47847783 | 0.05045429 | 9.48339182 | 2.46E−21 | Mbp | Qrich1 | 6.08E−17 | ODC |
| 0.4792329 | 0.05069892 | 9.45252619 | 3.31E−21 | Mbp | Fbxo11 | 8.05E−17 | ODC |
| −0.6366838 | 0.06803036 | −9.35882 | 8.06E−21 | Mbp | Ash1l | 1.93E−16 | ODC |
| 1.05911863 | 0.11615273 | 9.11832755 | 7.63E−20 | Cldn11 | Wac | 1.80E−15 | ODC |
| 1.15204294 | 0.12913762 | 8.92104812 | 4.62E−19 | Hapln1 | Mbd5 | 1.08E−14 | Inhibitory |
| 0.37270521 | 0.04220241 | 8.83137225 | 1.03E−18 | Mbp | Mll1 | 2.37E−14 | ODC |
| −3.3661644 | 0.38131941 | −8.8276765 | 1.07E−18 | Mbp | Pten | 2.42E−14 | ODC |
| 0.91336914 | 0.10500124 | 8.69865062 | 3.36E−18 | Plp1 | Chd2 | 7.49E−14 | ODC |
| 1.02071367 | 0.11895235 | 8.58086139 | 9.42E−18 | Hapln1 | Tnrc6b | 2.07E−13 | Inhibitory |
| 0.99262981 | 0.11644296 | 8.52460096 | 1.53E−17 | Cldn11 | Fbxo11 | 3.33E−13 | ODC |
| 0.99142087 | 0.11639021 | 8.51807806 | 1.62E−17 | Cldn11 | Qrich1 | 3.47E−13 | ODC |
| −2.8425153 | 0.33891973 | −8.3869869 | 4.99E−17 | Plp1 | Med13l | 1.05E−12 | ODC |
| 0.9872915 | 0.1179803 | 8.36827389 | 5.85E−17 | Cldn11 | Cul3 | 1.21E−12 | ODC |
| 1.37599853 | 0.16444689 | 8.36743397 | 5.89E−17 | Hapln1 | Gatad2b | 1.21E−12 | Inhibitory |
| −3.167479 | 0.38076053 | −8.3188219 | 8.88E−17 | Mbp | Arid1b | 1.81E−12 | ODC |
| −2.1018302 | 0.25505653 | −8.2406446 | 1.71E−16 | Cldn11 | Spen | 3.44E−12 | ODC |
| 1.04359046 | 0.13041485 | 8.0020831 | 1.22E−15 | Hapln1 | Kdm5b | 2.43E−11 | Inhibitory |
| 1.35514731 | 0.17000064 | 7.97142494 | 1.57E−15 | Hapln1 | Tcf7l2 | 3.07E−11 | Inhibitory |
| −2.9980472 | 0.38080679 | −7.8728826 | 3.47E−15 | Mbp | Ank2 | 6.71E−11 | ODC |
| 1.77632847 | 0.22580299 | 7.86671794 | 3.64E−15 | Arpc1b | Upf3b | 6.96E−11 | ODC |
| 1.09290491 | 0.13903834 | 7.86045699 | 3.83E−15 | Hapln1 | Chd8 | 7.23E−11 | Inhibitory |
| 0.39416809 | 0.0508256 | 7.75530564 | 8.81E−15 | Mbp | Tnrc6b | 1.63E−10 | ODC |
| 1.17976347 | 0.15212681 | 7.7551317 | 8.83E−15 | Hapln1 | Satb2 | 1.63E−10 | Inhibitory |
| 0.80871575 | 0.10433448 | 7.75118373 | 9.10E−15 | Cldn11 | Dyrk1a | 1.66E−10 | ODC |
| 1.04939437 | 0.1369567 | 7.66223462 | 1.83E−14 | Hapln1 | Wac | 3.30E−10 | Inhibitory |
| 0.8747889 | 0.11630509 | 7.52150145 | 5.42E−14 | Cldn11 | Kdm5b | 9.67E−10 | ODC |
| 0.80201329 | 0.10727561 | 7.47619396 | 7.65E−14 | Cldn11 | Mll1 | 1.35E−09 | ODC |
| 0.94274224 | 0.12716768 | 7.41337931 | 1.23E−13 | Cldn11 | Adnp | 2.15E−09 | ODC |
| 0.67748142 | 0.09347785 | 7.24750788 | 4.25E−13 | Hapln1 | Dyrk1a | 7.33E−09 | Inhibitory |
| 1.62412777 | 0.23611234 | 6.87862308 | 6.04E−12 | Arpc1b | Adnp | 1.03E−07 | ODC |
| 1.01957062 | 0.14969889 | 6.81080958 | 9.71E−12 | Hapln1 | Adnp | 1.64E−07 | Inhibitory |
| 1.56023689 | 0.23271119 | 6.7046062 | 2.02E−11 | Arpc1b | Ddx3x | 3.38E−07 | ODC |
| −1.5108351 | 0.22672881 | −6.663622 | 2.67E−11 | Plp1 | Larp4b | 4.42E−07 | ODC |
| −1.2393766 | 0.18747519 | −6.6108833 | 3.82E−11 | Cldn11 | Ash1l | 6.26E−07 | ODC |
| 1.56680536 | 0.23826451 | 6.57590736 | 4.84E−11 | Ptgds | Cul3 | 7.85E−07 | Excitatory |
| −0.6373373 | 0.09655679 | −6.5633633 | 5.26E−11 | Plp1 | Spen | 8.45E−07 | ODC |
| 3.33288756 | 0.51125934 | 6.51897632 | 7.08E−11 | Hba-a2 | Setd2 | 1.13E−06 | Excitatory |
| 1.46508737 | 0.2268308 | 6.45894359 | 1.05E−10 | Arpc1b | Wac | 1.66E−06 | ODC |
| 4.20640549 | 0.6563858 | 6.40843466 | 1.47E−10 | Npy | Mbd5 | 2.29E−06 | Inhibitory |
| 2.28899941 | 0.36598588 | 6.25433801 | 3.99E−10 | Ptgds | Tcf20 | 6.17E−06 | Inhibitory |
| −0.883221 | 0.14697577 | −6.0092966 | 1.86E−09 | Plp1 | Chd8 | 2.85E−05 | ODC |
| −0.7019466 | 0.11725546 | −5.986473 | 2.14E−09 | Ntrk2 | Ctnnb1 | 3.25E−05 | Astroglia |
| 4.61448205 | 0.7768471 | 5.94001325 | 2.85E−09 | Ttr | Tcf7l2 | 4.28E−05 | Microglia |
| 0.73546474 | 0.12416788 | 5.92314805 | 3.16E−09 | Hapln1 | Ctnnb1 | 4.70E−05 | Inhibitory |
| 4.00977439 | 0.67920703 | 5.90361146 | 3.56E−09 | Npy | Setd5 | 5.24E−05 | Inhibitory |
| 0.84683051 | 0.14410136 | 5.87663094 | 4.19E−09 | Hapln1 | Myst4 | 6.12E−05 | Inhibitory |
| 4.32983766 | 0.74585461 | 5.8052033 | 6.43E−09 | Hbb-bs | Wac | 9.30E−05 | Microglia |
| −2.9513063 | 0.51244643 | −5.7592484 | 8.45E−09 | Cldn11 | Med13l | 0.00012119 | ODC |
| −2.5460124 | 0.45151862 | −5.638776 | 1.71E−08 | Plp1 | Ank2 | 0.00024349 | ODC |

TABLE 8-continued

Analysis of differential gene expression from Perturb-Seq data.

| Estimate | SE | Z | pvalue | Gene | Condition | padj | CellType |
|---|---|---|---|---|---|---|---|
| −2.3640383 | 0.42321597 | −5.5858911 | 2.33E−08 | Cldn11 | Chd8 | 0.00032483 | ODC |
| −0.3327094 | 0.05956259 | −5.5858786 | 2.33E−08 | Mbp | Scn2a1 | 0.00032483 | ODC |
| 3.37933174 | 0.61620308 | 5.48412013 | 4.16E−08 | Hbb-bt | Setd2 | 0.00057549 | Excitatory |
| −0.6644442 | 0.12248928 | −5.4245093 | 5.81E−08 | Ntrk2 | Fbxo11 | 0.00079797 | Astroglia |
| 5.75439332 | 1.0622646 | 5.41709975 | 6.06E−08 | Hbb-bs | Chd2 | 0.00082469 | Microglia |
| 0.28337487 | 0.0524902 | 5.39862455 | 6.72E−08 | Mbp | Ctnnb1 | 0.0009066 | ODC |
| −0.6336752 | 0.1182088 | −5.360643 | 8.29E−08 | Ntrk2 | Stard9 | 0.0011102 | Astroglia |
| 1.50091129 | 0.28184137 | 5.32537609 | 1.01E−07 | Hbb-bs | Mbd5 | 0.0013376 | Excitatory |
| −0.6875995 | 0.13260917 | −5.1851583 | 2.16E−07 | Ntrk2 | Scn2a1 | 0.00284214 | Astroglia |
| −0.4819589 | 0.0936245 | −5.1477862 | 2.64E−07 | Plp1 | Ash11 | 0.00341268 | ODC |
| 1.20218873 | 0.23354092 | 5.1476578 | 2.64E−07 | Arpc1b | Stard9 | 0.00341268 | ODC |
| 0.61606747 | 0.11970841 | 5.1464011 | 2.66E−07 | Cldn11 | Tnrc6b | 0.00341268 | ODC |
| −0.6989003 | 0.13756709 | −5.0804323 | 3.77E−07 | Ntrk2 | Spen | 0.00480146 | Astroglia |
| −0.7755879 | 0.15313301 | −5.0647991 | 4.09E−07 | Ntrk2 | Adnp | 0.00517167 | Astroglia |
| −0.6123133 | 0.12103527 | −5.0589657 | 4.22E−07 | Ntrk2 | Wac | 0.00529073 | Astroglia |
| 1.38128024 | 0.27525691 | 5.01814926 | 5.22E−07 | Arpc1b | Gatad2b | 0.00649733 | ODC |
| −0.7159794 | 0.14276983 | −5.0149208 | 5.31E−07 | Ntrk2 | Syngap1 | 0.00655656 | Astroglia |
| 0.62367795 | 0.12452019 | 5.0086491 | 5.48E−07 | Ndufs6 | Spen | 0.00672211 | Inhibitory |
| −0.5816956 | 0.11628509 | −5.0023233 | 5.66E−07 | Ntrk2 | Tnrc6b | 0.00689392 | Astroglia |
| 3.36831358 | 0.67386477 | 4.99850081 | 5.78E−07 | Npy | Wac | 0.0069791 | Inhibitory |
| −0.6435378 | 0.12916958 | −4.9821154 | 6.29E−07 | Ntrk2 | Ddx3x | 0.00754027 | Astroglia |
| 3.38642605 | 0.68725869 | 4.92744014 | 8.33E−07 | Npy | Ash11 | 0.00991457 | Inhibitory |
| −1.0102543 | 0.2075061 | −4.8685523 | 1.12E−06 | Clu | Adnp | 0.01327976 | Astroglia |
| −0.6560352 | 0.13537765 | −4.8459641 | 1.26E−06 | Prnp | Ddx3x | 0.01477523 | Astroglia |
| −0.5893215 | 0.12244623 | −4.8129005 | 1.49E−06 | Ntrk2 | Upf3b | 0.01731745 | Astroglia |
| −0.8949596 | 0.18834467 | −4.7517119 | 2.02E−06 | Clu | Setd2 | 0.02331228 | Astroglia |
| 3.56988215 | 0.7515853 | 4.74980305 | 2.04E−06 | Ttr | Fbxo11 | 0.02336531 | Inhibitory |
| −0.5087962 | 0.10742482 | −4.7363005 | 2.18E−06 | Mbp | Tcf7l2 | 0.0247635 | ODC |
| 2.96267387 | 0.62567552 | 4.73516031 | 2.19E−06 | Npy | Tnrc6b | 0.0247635 | Inhibitory |
| 1.08505114 | 0.23096742 | 4.69785359 | 2.63E−06 | Arpc1b | Tnrc6b | 0.02953663 | ODC |
| 2.16848391 | 0.46218431 | 4.69181638 | 2.71E−06 | Hbb-bs | Upf3b | 0.03021068 | Inhibitory |
| −2.403628 | 0.51248771 | −4.6901183 | 2.73E−06 | Cldn11 | Larp4b | 0.03025239 | ODC |
| −0.8675184 | 0.18534916 | −4.6804548 | 2.86E−06 | Plp1 | Pten | 0.0314968 | ODC |
| −0.7529819 | 0.16208886 | −4.6454887 | 3.39E−06 | Mbp | Satb2 | 0.03707843 | ODC |
| 0.98248998 | 0.21234995 | 4.62674924 | 3.71E−06 | Tsc22d1 | Spen | 0.04032075 | Inhibitory |
| −0.4464993 | 0.09766198 | −4.571884 | 4.83E−06 | Ntrk2 | Mll1 | 0.05211626 | Astroglia |
| 0.68408923 | 0.14977381 | 4.56748238 | 4.94E−06 | Arpp19 | Setd5 | 0.05286413 | Astroglia |
| 2.54395958 | 0.5572094 | 4.56553603 | 4.98E−06 | Sox9 | Chd8 | 0.05286413 | Inhibitory |
| 0.38752117 | 0.08489488 | 4.56471795 | 5.00E−06 | Rpl13 | Adnp | 0.05286413 | Astroglia |
| 1.17339961 | 0.25715884 | 4.56293703 | 5.04E−06 | Taldo1 | Setd5 | 0.05296625 | Inhibitory |
| 0.93008445 | 0.2045507 | 4.54696286 | 5.44E−06 | Hnrnpr | Arid1b | 0.05677703 | Inhibitory |
| 2.23421275 | 0.4915416 | 4.54531769 | 5.49E−06 | Gpr12 | Spen | 0.05685316 | Inhibitory |
| 2.16012919 | 0.48047013 | 4.4958657 | 6.93E−06 | Zbtb20 | Ank2 | 0.07080412 | Excitatory |
| 1.35202256 | 0.30074561 | 4.49556872 | 6.94E−06 | Smc5 | Larp4b | 0.07080412 | Excitatory |
| −0.5905943 | 0.13139495 | −4.4948022 | 6.96E−06 | Ntrk2 | Setd5 | 0.07080412 | Astroglia |
| 0.99702063 | 0.22241062 | 4.48279229 | 7.37E−06 | Mrps18c | Arid1b | 0.07443878 | Inhibitory |
| 1.8859329 | 0.42113384 | 4.47822693 | 7.53E−06 | C2cd4c | Larp4b | 0.07557298 | Excitatory |
| 1.11874681 | 0.2498978 | 4.47681735 | 7.58E−06 | Arpc1b | Myst4 | 0.07560096 | ODC |
| −0.6055725 | 0.1353468 | −4.4742282 | 7.67E−06 | Ntrk2 | Setd2 | 0.07605041 | Astroglia |
| 1.14072146 | 0.25568367 | 4.46145611 | 8.14E−06 | Arpc1b | Setd2 | 0.08023274 | ODC |
| 0.64779745 | 0.14527577 | 4.45908805 | 8.23E−06 | Hapln1 | Ash11 | 0.08062955 | Inhibitory |
| 0.88618226 | 0.19892483 | 4.45485989 | 8.39E−06 | Arpc1b | Dyrk1a | 0.08119682 | ODC |
| 1.08547175 | 0.24370886 | 4.45396924 | 8.43E−06 | Tada1 | Arid1b | 0.08119682 | Excitatory |
| 0.86721561 | 0.19471817 | 4.45369638 | 8.44E−06 | Dgcr6 | Arid1b | 0.08119682 | Excitatory |
| −0.6822827 | 0.15333088 | −4.4497408 | 8.60E−06 | Lsm5 | Dscam | 0.08221442 | Excitatory |
| 0.36259888 | 0.08158909 | 4.4442078 | 8.82E−06 | Rps10 | Tnrc6b | 0.08385952 | Astroglia |
| 3.46651448 | 0.78048929 | 4.44146323 | 8.93E−06 | Hbb-bs | Scn2a1 | 0.08443685 | Microglia |
| −0.4935346 | 0.11130412 | −4.4341092 | 9.25E−06 | Cpe | Adnp | 0.08685975 | Astroglia |
| 1.1449619 | 0.25933007 | 4.41507578 | 1.01E−05 | Sfpq | Dscam | 0.09431352 | ODC |
| 1.06384831 | 0.24135437 | 4.40782707 | 1.04E−05 | Taldo1 | Stard9 | 0.09696122 | Inhibitory |
| −0.6849412 | 0.15552345 | −4.4041028 | 1.06E−05 | Camk2g | Mll1 | 0.09807489 | Inhibitory |
| 1.11130918 | 0.25354834 | 4.3830268 | 1.17E−05 | Txn2 | Gatad2b | 0.10697917 | Microglia |
| 1.70644766 | 0.38935676 | 4.38273543 | 1.17E−05 | Zfp422 | Larp4b | 0.10697917 | Astroglia |
| −0.518819 | 0.11860238 | −4.3744401 | 1.22E−05 | Ntrk2 | Asxl3 | 0.11050104 | Astroglia |
| 2.33295455 | 0.53349027 | 4.37300303 | 1.23E−05 | Cpsf3l | Chd2 | 0.11060634 | Astroglia |
| −1.3170531 | 0.30214946 | −4.3589458 | 1.31E−05 | Lengl | Dyrk1a | 0.11666096 | Astroglia |
| 3.14734913 | 0.72204898 | 4.35891359 | 1.31E−05 | Tamm41 | Upf3b | 0.11666096 | Excitatory |
| 0.2506886 | 0.05757107 | 4.35441951 | 1.33E−05 | mt-Co1 | Dscam | 0.11842204 | Excitatory |
| 0.30013747 | 0.06901224 | 4.34904685 | 1.37E−05 | Rps10 | Mll1 | 0.12069359 | Astroglia |
| 0.64521472 | 0.148931 | 4.33230649 | 1.48E−05 | Agfg1 | Pogz | 0.12953706 | Excitatory |
| −1.1307645 | 0.26302777 | −4.299031 | 1.72E−05 | Nnat | Larp4b | 0.14925226 | Inhibitory |
| −0.8278531 | 0.19261385 | −4.2979936 | 1.72E−05 | Cldn11 | Dscam | 0.14925226 | ODC |
| 1.77608614 | 0.41329156 | 4.29741695 | 1.73E−05 | Polr3k | Larp4b | 0.14925226 | Astroglia |
| 0.98747829 | 0.23049792 | 4.2841093 | 1.83E−05 | Arpc1b | Kdm5b | 0.15762317 | ODC |

GO Term Gene Signatures

The mm10 GO ontology was downloaded, and terms with >500 or <5 genes were removed. For each GO Term and each cell type, the genes in that term that appeared in <5% of cells of that cell types were removed. For each term the average log TPM expression score was calculated and a linear regression model was fit to this score incorporating nGene, batch, and perturbation as covariates. P-values and effect sizes for each perturbation (relative to GFP) were calculated, and FDR correction was performed.

Analysis of Human Single Nucleus or Single Cell RNA-Seq Data

For each single cell/nucleus human dataset, the UMI count matrix and metadata were downloaded from their website (https://autism.cells.ucsc.edu/) and processed with Seurat to create Seurat objects. Cell types were extracted from the metadata and were combined into more general cell types, namely: Microglia, Astroglia (including Radial Glia), Inhibitory neurons, Excitatory neurons, Oligodendrocytes, and other. For differential expression analysis for data from Velmeshev et al (30), data from all individuals of <12 years of age was removed and separated PFC and ACC regions. For each cell type in each region, a pseudobulk profile was constructed and genes expressed in <5% of cells or with <10 reads were removed. DESeq2 v 1.20.0 (34) was then used to perform differential expression analysis between the ASD patients and the controls, correcting for sex and age (note: age was encoded as a discrete value, not continuous). All genes were then extracted with 1:1 mouse orthologs (BioMart) and calculated FDR corrected P-values on these genes for both ACC and PFC. Only analysis on the PFC yielded significant hits, which are presented in FIG. 4F.

To compare these results to the Perturb-Seq data, for each gene and cell type in the final DE table produced (data not shown), the median log fold change (log FC) for that gene's mouse orthologue over all perturbations was calculated from the Perturb-Seq data (see Differential expression analysis) and took the absolute value to get an absolute log FC score for each gene. Those genes for whom the sign (+1 or −1) of the median log FC agreed with the sign in the human data had their absolute log FC score multiplied by 1; those that disagreed had their absolute log FC score multiplied by −1, such that genes whose direction of change in the Perturb-Seq data agreed with the human data had positive scores, and those whose direction of change disagreed had negative scores.

Finally, genes were binned into 5% wide bins based on the % of cells expressing the gene in the Perturb-Seq data and assigned p-values to each gene based on the percent of genes in the same bin that had an equal or higher score. Finally, the list was filtered to contain only genes also differentially expressed in the human ASD data, and FDR correction was performed.

Scoring of PsychEncode Modules in Perturb-Seq Single Cell Data

PsychEncode modules were downloaded from the Science website, and 1:1 mouse orthologs were extracted for the genes in each module. The same linear regression analysis that was used on the WGCNA modules herein to determine effect size was applied to the PsychEncode modules (using all cells instead of just one cell type), as was correlation analysis.

Cell Type Gene Expression

Expression data for the E18.5 mouse brain (9 k dataset) was downloaded from the 10X website (10). The WT P7 data were generated from this paper. The P7 fastq files were run through the standard Cellranger pipeline. The data from both datasets were loaded into Seurat separately and transformed to log counts per million. Cells with <500 genes were removed in both datasets. Variable genes were found using FindVariableGenes with x.low.cutoff=1, and the data was scaled with ScaleData, correcting for nUMI. PCA was performed, followed by TSNE and clustering with Find-Clusters. Cell types were identified with marker genes and contaminating/vascular cell types were removed.

In each dataset MAST (53) was used to find the differentially expressed genes in each cluster, relative to all cells outside that cluster. This was done correcting for the scaled nUMI and removing genes that occurred in less than 10 cells. Average expression was calculated for each gene in each cluster.

REFERENCES FOR EXAMPLES

1. L. de la Torre-Ubieta, H. Won, J. L. Stein, D. H. Geschwind, Advancing the understanding of autism disease mechanisms through 345-361 (2016).
2. C. Schizophrenia Working Group of the Psychiatric Genomics, Biological insights from 108 schizophrenia-associated genetic loci. Nature 511, 421-427 (2014).
3. L. Jostins et al., Host-microbe interactions have shaped the genetic architecture of inflammatory bowel disease. Nature 491, 119-124 (2012).
4. F. K. Satterstrom et al., Novel genes for autism implicate both excitatory and inhibitory cell lineages in risk. bioRxiv, 484113 (2018).
5. S. J. Sanders et al., De novo mutations revealed by whole-exome sequencing are strongly associated with autism. Nature 485, 237-241 (2012).
6. J. A. Chen, O. Penagarikano, T. G. Belgard, V. Swarup, D. H. Geschwind, The emerging picture of autism spectrum disorder: genetics and pathology. Annu Rev Pathol 10, 111-144 (2015).
7. C. Mullins, G. Fishell, R. W. Tsien, Unifying Views of Autism Spectrum Disorders: A Consideration of Autoregulatory Feedback Loops. Neuron 89, 1131-1156 (2016).
8. F. K. Satterstrom et al., Large-Scale Exome Sequencing Study Implicates Both Developmental and Functional Changes in the Neurobiology of Autism. Cell 180, 568-584 e523 (2020).
9. J. A. Miller et al., Transcriptional landscape of the prenatal human brain. Nature 508, 199-206 (2014).
10. Data of 9 k brain cells from an E18 mouse, 10x Genomics: https:1/support.10xgenomics.com/single-cell-gene-expression/datasets/2.1.0/neuron_9k.
11. B. Adamson et al., A Multiplexed Single-Cell CRISPR Screening Platform Enables Systematic Dissection of the Unfolded Protein Response. Cell 167, 1867-1882 e1821 (2016).
12. A. Dixit et al., Perturb-Seq: Dissecting Molecular Circuits with Scalable Single-Cell RNA Profiling of Pooled Genetic Screens. Cell 167, 1853-1866 e1817 (2016).
13. D. A. Jaitin et al., Dissecting Immune Circuits by Linking CRISPR-Pooled Screens with Single-Cell RNA-Seq. Cell 167, 1883-1896 e1815 (2016).
14. R. J. Platt et al., CRISPR-Cas9 knockin mice for genome editing and cancer modeling. Cell 159, 440-455 (2014).
15. V. D. Blondel, J.-L. Guillaume, R. Lambiotte, E. Lefebvre, Fast unfolding of communities in large networks. Journal of Statistical Mechanics: Theory and Experiment 2008, P10008 (2008).
16. A. Zeisel et al., Molecular Architecture of the Mouse Nervous System. Cell 174, 999-1014 e1022 (2018).

17. A. L. Haber et al., A single-cell survey of the small intestinal epithelium. Nature 551, 333-339 (2017).
18. B. Duan et al., Model-based understanding of single-cell CRISPR screening. Nat Commun 10, 2233 (2019).
19. C. The Gene Ontology, The Gene Ontology Resource: 20 years and still Going strong. Nucleic Acids Res 47, D330-D338 (2019).
20. M. Roberts, B. Stewart, D. Tingley, stm: R Package for Structural Topic Models. Journal of Statistical Software.
21. P. Langfelder, S. Horvath, WGCNA: an R package for weighted correlation network analysis. BMC Bioinformatics 9, 559 (2008).
22. A. Saunders et al., Molecular Diversity and Specializations among the Cells of the Adult Mouse Brain. Cell 174, 1015-1030 e1016 (2018).
23. P. Scotland, D. Zhou, H. Benveniste, V. Bennett, Nervous system defects of AnkyrinB (−/−) mice suggest functional overlap between the cell adhesion molecule L1 and 440-kD AnkyrinB in premyelinated axons. J Cell Biol 143, 1305-1315 (1998).
24. S. Tuvia, M. Buhusi, L. Davis, M. Reedy, V. Bennett, Ankyrin-B is required for intracellular sorting of structurally diverse Ca2+ homeostasis proteins. J Cell Biol 147, 995-1008 (1999).
25. C. F. Kline, J. Scott, J. Curran, T. J. Hund, P. J. Mohler, Ankyrin-B regulates Cav2.1 and Cav2.2 channel expression and targeting. J Biol Chem 289, 5285-5295 (2014).
26. R. Yang et al., ANK2 autism mutation targeting giant ankyrin-B promotes axon branching and ectopic connectivity. Proc Natl Acad Sci USA 116, 15262-15271 (2019).
27. C. Marie et al., Oligodendrocyte precursor survival and differentiation requires chromatin remodeling by Chd7 and Chd8. Proc Natl Acad Sci USA, (2018).
28. M. Nishiyama et al., Early embryonic death in mice lacking the beta-catenin-binding protein Duplin. Mol Cell Biol 24, 8386-8394 (2004).
29. R. D. Hodge et al., Conserved cell types with divergent features in human versus mouse cortex. Nature 573, 61-68 (2019).
30. D. Velmeshev et al., Single-cell genomics identifies cell type-specific molecular changes in autism. Science 364, 685-689 (2019).
31. T. J. Nowakowski et al., Spatiotemporal gene expression trajectories reveal developmental hierarchies of the human cortex. Science 358, 1318-1323 (2017).
32. S. Velasco et al., Individual brain organoids reproducibly form cell diversity of the human cerebral cortex. Nature 570, 523-527 (2019).
33. M. J. Gandal et al., Shared molecular neuropathology across major psychiatric disorders parallels polygenic overlap. Science 359, 693-697 (2018).
34. M. I. Love, W. Huber, S. Anders, Moderated estimation of fold change and dispersion for RNA-seq data with DESeq2. Genome Biol 15, 550 (2014).
35. A. T. L. Lun, J. C. Marioni, Overcoming confounding plate effects in differential expression analyses of single-cell RNA-seq data. Biostatistics 18, 451-464 (2017).
36. W. C. Tseng, P. M. Jenkins, M. Tanaka, R. Mooney, V. Bennett, Giant ankyrin-G stabilizes somatodendritic GABAergic synapses through opposing endocytosis of GABAA receptors. Proc Natl Acad Sci USA 112, 1214-1219 (2015).
37. K. K. Bercury, W. B. Macklin, Dynamics and mechanisms of CNS myelination. Dev Cell 32, 447-458 (2015).
38. R. J. Platt et al., Chd8 Mutation Leads to Autistic-like Behaviors and Impaired Striatal Circuits. Cell Rep 19, 335-350 (2017).
39. Y. Katayama et al., CHD8 haploinsufficiency results in autistic-like phenotypes in mice. Nature 537, 675-679 (2016).
40. O. Durak et al., Chd8 mediates cortical neurogenesis via transcriptional regulation of cell cycle and Wnt signaling. Nat Neurosci 19, 1477-1488 (2016).
41. I. Sakamoto et al., A novel beta-catenin-binding protein inhibits beta-catenin-dependent Tcf activation and axis formation. J Biol Chem 275, 32871-32878 (2000).
42. C. Zhao et al., Dual Requirement of CHD8 for Chromatin Landscape Establishment and Histone Methyltransferase Recruitment to Promote CNS Myelination and Repair. Dev Cell 45, 753-768 e758 (2018).
43. A. J. Rubin et al., Coupled Single-Cell CRISPR Screening and Epigenomic Profiling Reveals Causal Gene Regulatory Networks. Cell 176, 361-376 e317 (2019).
44. S. Bian et al., Single-cell multiomics sequencing and analyses of human colorectal cancer. Science 362, 1060-1063 (2018).
45. S. G. Rodriques et al., Slide-seq: A scalable technology for measuring genome-wide expression at high spatial resolution. Science 363, 1463-1467 (2019).
46. X. Wang et al., Three-dimensional intact-tissue sequencing of single-cell transcriptional states. Science 361, (2018).
47. A. Butler, P. Hoffman, P. Smibert, E. Papalexi, R. Satija, Integrating single-cell transcriptomic data across different conditions, technologies, and species. Nat Biotechnol 36, 411-420 (2018).
48. J. G. Doench et al., Optimized sgRNA design to maximize activity and minimize off-target effects of CRISPR-Cas9. Nat Biotechnol 34, 184-191 (2016).
49. J. Joung et al., Genome-scale CRISPR-Cas9 knockout and transcriptional activation screening. Nat Protoc 12, 828-863 (2017).
50. P. Arlotta et al., Neuronal subtype-specific genes that control corticospinal motor neuron development in vivo. Neuron 45, 207-221 (2005).
51. A. Dobin et al., STAR: ultrafast universal RNA-seq aligner. Bioinformatics 29, 15-21 (2013).
52. M. E. Ritchie et al., limma powers differential expression analyses for RNA-sequencing and microarray studies. Nucleic Acids Res 43, e47 (2015).
53. G. Finak et al., MAST: a flexible statistical framework for assessing transcriptional changes and characterizing heterogeneity in single-cell RNA sequencing data. Genome Biology 16, (2015).
54. S. Mancinelli et al. Decoding neuronal diversity in the developing cerebral cortex: from single cells to functional networks. Curr Opin Neurobiol. 53:146-155 (2018).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of identifying functions of a plurality of target genes in parallel in vivo, comprising:
   a. introducing, in vivo, a plurality of genetic perturbations in each of a plurality of progenitor cells in a Cas animal model, wherein the plurality of genetic perturbations are introduced by delivering a pool of guide RNAs (gRNAs) to the plurality of progenitor cells,
   wherein the pool of gRNAs comprises two or more different gRNAs that bind each target gene of the plurality of target genes,
   wherein the two or more different gRNAs for each target gene are operatively coupled to a reporter gene and a unique barcode corresponding the perturbation identity,
   b. generating an enriched perturbed cell population by enriching for cells expressing the reporter gene;
   c. identifying cell types and corresponding perturbations via scRNA-seq in the enriched perturbed cell population; and
   d. detecting one or more target gene modules that co-vary within a cell type in the enriched perturbed cell population.

2. The method of claim 1, wherein the enriched perturbed cell population comprises progenitor cell progeny.

3. The method of claim 1, wherein the two or more gRNAs each bind to a sequence of an exon, an intron, or both at a 5' end of a target gene.

4. The method of claim 3, wherein two or more gRNAs each bind to a sequence of a coding exon at the 5' end of a target gene.

5. The method of claim 3, wherein each of the two or more gRNAs are controlled by a different pol III promoter.

6. The method of claim 5, wherein expression of a first gRNA of the two or more gRNAs is driven by a human pol III promoter and wherein expression of a second gRNA of the two or more gRNAs is driven by a non-human pol III promoter.

7. The method of claim 6, wherein the human pol III promoter and the non-human pol III promoter are each independently selected from a U6, a 7SK, or an H1 promoter.

8. The method of claim 5, wherein at least one pol III promoter is constitutive.

9. The method of claim 5, wherein at least one pol III promoter is inducible.

10. The method of claim 1, wherein the barcode is polyadenylated.

11. The method of claim 6, wherein the reporter gene is controlled by a constitutive pol II promoter.

12. The method of claim 1, wherein introducing further comprises delivering to the plurality of progenitor cells a pool of engineered virus particles comprising equal genetic perturbation representation.

13. The method of claim 12, wherein the pool of engineered virus particles comprise engineered lentiviral particles.

14. The method of claim 12, wherein introducing further comprises delivering the pool of engineered virus particles to a target tissue of a developing embryo of the Cas animal model in utero.

15. The method of claim 14, wherein the developing embryo is at stage between E5-E15 or an equivalent stage thereof.

16. The method of claim 10, wherein the reporter gene encodes an optically active protein.

17. The method of claim 10, wherein the reporter gene encodes a cell surface molecule selected from the group consisting of: CD3, CD4, CD19, CD20, CD22, CD34, CD45, CD80, a cell surface receptor, a cluster differentiation (CD) molecule, and any combination thereof.

18. The method of claim 1, wherein the Cas animal model constitutively or inducibly expresses a Cas protein in one of, a plurality of, or all of its cells.

19. The method of claim 18, wherein the Cas protein is a Cas Type I, II, III, IV, or V protein.

20. The method of claim 1, wherein identifying further comprises a genomic analysis, an epigenomic analysis, a transcriptomic analysis, a proteomic analysis, or a combination thereof.

21. The method of claim 1, further comprising identifying cell states in the enriched perturbed cell population.

22. The method of claim 1, wherein the plurality of genes are autism spectrum disorder associated genes.

23. The method of claim 1, further comprising isolating single progeny cells for subsequent analyses after the introduction of genetic perturbations.

24. The method of claim 23, wherein the progeny cells are analyzed for their genomic, genetic, epigenetic, proteomic, or phenotypic profiles to determine the function of each gene in a cell type-specific manner.

* * * * *

SEQUENCE LISTING

<160> NUMBER OF SEQ ID NOS: 122

<210> SEQ ID NO 1
<211> LENGTH: 20
<212> TYPE: DNA
<213> ORGANISM: Artificial
<220> FEATURE:
<223> OTHER INFORMATION: gRNA

<400> SEQUENCE: 1
cctgggcaca aatgcccgag                                           20

<210> SEQ ID NO 2
<211> LENGTH: 20
<212> TYPE: DNA
<213> ORGANISM: Artificial
<220> FEATURE:
<223> OTHER INFORMATION: gRNA

<400> SEQUENCE: 2
gcatttctgc gactacactg                                           20

<210> SEQ ID NO 3
<211> LENGTH: 20
<212> TYPE: DNA
<213> ORGANISM: Artificial
<220> FEATURE:
<223> OTHER INFORMATION: gRNA

<400> SEQUENCE: 3
ctgcacgagg cgtgtaaccg                                           20

<210> SEQ ID NO 4
<211> LENGTH: 20
<212> TYPE: DNA
<213> ORGANISM: Artificial
<220> FEATURE:
<223> OTHER INFORMATION: gRNA

<400> SEQUENCE: 4
gtacccatcc catacaactg                                           20

<210> SEQ ID NO 5
<211> LENGTH: 20
<212> TYPE: DNA
<213> ORGANISM: Artificial
<220> FEATURE:
<223> OTHER INFORMATION: gRNA

<400> SEQUENCE: 5
actatgagac tcactaactg                                           20

<210> SEQ ID NO 6
<211> LENGTH: 20
<212> TYPE: DNA
<213> ORGANISM: Artificial
<220> FEATURE:
<223> OTHER INFORMATION: gRNA

<400> SEQUENCE: 6
tcacactaac actcgagtcg                                           20

<210> SEQ ID NO 7

```
<211> LENGTH: 20
<212> TYPE: DNA
<213> ORGANISM: Artificial
<220> FEATURE:
<223> OTHER INFORMATION: gRNA

<400> SEQUENCE: 7
tcagaagacg aacaggaaca                                            20

<210> SEQ ID NO 8
<211> LENGTH: 20
<212> TYPE: DNA
<213> ORGANISM: Artificial
<220> FEATURE:
<223> OTHER INFORMATION: gRNA

<400> SEQUENCE: 8
tttcaatcca gactacgtag                                            20

<210> SEQ ID NO 9
<211> LENGTH: 20
<212> TYPE: DNA
<213> ORGANISM: Artificial
<220> FEATURE:
<223> OTHER INFORMATION: gRNA

<400> SEQUENCE: 9
ccattcataa aggacttggg                                            20

<210> SEQ ID NO 10
<211> LENGTH: 20
<212> TYPE: DNA
<213> ORGANISM: Artificial
<220> FEATURE:
<223> OTHER INFORMATION: gRNA

<400> SEQUENCE: 10
atccagcgta agaataacag                                            20

<210> SEQ ID NO 11
<211> LENGTH: 20
<212> TYPE: DNA
<213> ORGANISM: Artificial
<220> FEATURE:
<223> OTHER INFORMATION: gRNA

<400> SEQUENCE: 11
atgacaaaga cagttcaggg                                            20

<210> SEQ ID NO 12
<211> LENGTH: 20
<212> TYPE: DNA
<213> ORGANISM: Artificial
<220> FEATURE:
<223> OTHER INFORMATION: gRNA

<400> SEQUENCE: 12
agtgacgtac gcctccaccg                                            20

<210> SEQ ID NO 13
<211> LENGTH: 20
<212> TYPE: DNA
<213> ORGANISM: Artificial
<220> FEATURE:
<223> OTHER INFORMATION: gRNA

<400> SEQUENCE: 13
```
tgattatatt gtaaaaaacg                                          20

<210> SEQ ID NO 14
<211> LENGTH: 20
<212> TYPE: DNA
<213> ORGANISM: Artificial
<220> FEATURE:
<223> OTHER INFORMATION: gRNA

<400> SEQUENCE: 14
accaggatgg gcaccacccg                                          20

<210> SEQ ID NO 15
<211> LENGTH: 20
<212> TYPE: DNA
<213> ORGANISM: Artificial
<220> FEATURE:
<223> OTHER INFORMATION: gRNA

<400> SEQUENCE: 15
acacgcaagc agctctacaa                                          20

<210> SEQ ID NO 16
<211> LENGTH: 20
<212> TYPE: DNA
<213> ORGANISM: Artificial
<220> FEATURE:
<223> OTHER INFORMATION: gRNA

<400> SEQUENCE: 16
tgttgaggag tgataacctg                                          20

<210> SEQ ID NO 17
<211> LENGTH: 20
<212> TYPE: DNA
<213> ORGANISM: Artificial
<220> FEATURE:
<223> OTHER INFORMATION: gRNA

<400> SEQUENCE: 17
ttgcctccca tatccaacca                                          20

<210> SEQ ID NO 18
<211> LENGTH: 20
<212> TYPE: DNA
<213> ORGANISM: Artificial
<220> FEATURE:
<223> OTHER INFORMATION: gRNA

<400> SEQUENCE: 18
attcagcctc tggatccgcg                                          20

<210> SEQ ID NO 19
<211> LENGTH: 20
<212> TYPE: DNA
<213> ORGANISM: Artificial
<220> FEATURE:
<223> OTHER INFORMATION: gRNA

<400> SEQUENCE: 19
gatatcggag tctaccccccg                                         20

<210> SEQ ID NO 20
<211> LENGTH: 20
<212> TYPE: DNA

```
<213> ORGANISM: Artificial
<220> FEATURE:
<223> OTHER INFORMATION: gRNA

<400> SEQUENCE: 20
gctggtccta tcctcaccag                                                  20

<210> SEQ ID NO 21
<211> LENGTH: 20
<212> TYPE: DNA
<213> ORGANISM: Artificial
<220> FEATURE:
<223> OTHER INFORMATION: gRNA

<400> SEQUENCE: 21
tccagtagta ccttcacggg                                                  20

<210> SEQ ID NO 22
<211> LENGTH: 20
<212> TYPE: DNA
<213> ORGANISM: Artificial
<220> FEATURE:
<223> OTHER INFORMATION: gRNA

<400> SEQUENCE: 22
gttcgctacc cagttcgccg                                                  20

<210> SEQ ID NO 23
<211> LENGTH: 20
<212> TYPE: DNA
<213> ORGANISM: Artificial
<220> FEATURE:
<223> OTHER INFORMATION: gRNA

<400> SEQUENCE: 23
ggatcatcaa gactccccgg                                                  20

<210> SEQ ID NO 24
<211> LENGTH: 20
<212> TYPE: DNA
<213> ORGANISM: Artificial
<220> FEATURE:
<223> OTHER INFORMATION: gRNA

<400> SEQUENCE: 24
attggaatgg gatcggcacg                                                  20

<210> SEQ ID NO 25
<211> LENGTH: 20
<212> TYPE: DNA
<213> ORGANISM: Artificial
<220> FEATURE:
<223> OTHER INFORMATION: gRNA

<400> SEQUENCE: 25
attgtgctga acgtacagca                                                  20

<210> SEQ ID NO 26
<211> LENGTH: 20
<212> TYPE: DNA
<213> ORGANISM: Artificial
<220> FEATURE:
<223> OTHER INFORMATION: gRNA

<400> SEQUENCE: 26
tgtgcatatt tattgcatcg                                                  20
```

<210> SEQ ID NO 27
<211> LENGTH: 20
<212> TYPE: DNA
<213> ORGANISM: Artificial
<220> FEATURE:
<223> OTHER INFORMATION: gRNA

<400> SEQUENCE: 27
agtacatccg agtaaaggcg                                          20

<210> SEQ ID NO 28
<211> LENGTH: 20
<212> TYPE: DNA
<213> ORGANISM: Artificial
<220> FEATURE:
<223> OTHER INFORMATION: gRNA

<400> SEQUENCE: 28
agagctgtgg gaataccca                                           20

<210> SEQ ID NO 29
<211> LENGTH: 20
<212> TYPE: DNA
<213> ORGANISM: Artificial
<220> FEATURE:
<223> OTHER INFORMATION: gRNA

<400> SEQUENCE: 29
gggagttaaa atgtacaggg                                          20

<210> SEQ ID NO 30
<211> LENGTH: 20
<212> TYPE: DNA
<213> ORGANISM: Artificial
<220> FEATURE:
<223> OTHER INFORMATION: gRNA

<400> SEQUENCE: 30
tctaggtcac ctgaatccag                                          20

<210> SEQ ID NO 31
<211> LENGTH: 20
<212> TYPE: DNA
<213> ORGANISM: Artificial
<220> FEATURE:
<223> OTHER INFORMATION: gRNA

<400> SEQUENCE: 31
tcgacaccca tgcctctgag                                          20

<210> SEQ ID NO 32
<211> LENGTH: 20
<212> TYPE: DNA
<213> ORGANISM: Artificial
<220> FEATURE:
<223> OTHER INFORMATION: gRNA

<400> SEQUENCE: 32
cctatggaca ccatgaacgg                                          20

<210> SEQ ID NO 33
<211> LENGTH: 20
<212> TYPE: DNA
<213> ORGANISM: Artificial
<220> FEATURE:

```
<223> OTHER INFORMATION: gRNA

<400> SEQUENCE: 33
tatgaactgg gagatccctg                                              20

<210> SEQ ID NO 34
<211> LENGTH: 20
<212> TYPE: DNA
<213> ORGANISM: Artificial
<220> FEATURE:
<223> OTHER INFORMATION: gRNA

<400> SEQUENCE: 34
attacagcag cactcgggca                                              20

<210> SEQ ID NO 35
<211> LENGTH: 20
<212> TYPE: DNA
<213> ORGANISM: Artificial
<220> FEATURE:
<223> OTHER INFORMATION: gRNA

<400> SEQUENCE: 35
agggggcata ggacatcgcg                                              20

<210> SEQ ID NO 36
<211> LENGTH: 20
<212> TYPE: DNA
<213> ORGANISM: Artificial
<220> FEATURE:
<223> OTHER INFORMATION: gRNA

<400> SEQUENCE: 36
agagctatgg acctccccag                                              20

<210> SEQ ID NO 37
<211> LENGTH: 20
<212> TYPE: DNA
<213> ORGANISM: Artificial
<220> FEATURE:
<223> OTHER INFORMATION: gRNA

<400> SEQUENCE: 37
gtgtacccaa tcacgacagg                                              20

<210> SEQ ID NO 38
<211> LENGTH: 20
<212> TYPE: DNA
<213> ORGANISM: Artificial
<220> FEATURE:
<223> OTHER INFORMATION: gRNA

<400> SEQUENCE: 38
ataaagtgtt actaaaacgt                                              20

<210> SEQ ID NO 39
<211> LENGTH: 20
<212> TYPE: DNA
<213> ORGANISM: Artificial
<220> FEATURE:
<223> OTHER INFORMATION: gRNA

<400> SEQUENCE: 39
cgataggcag gatcgcaaca                                              20
```

```
<210> SEQ ID NO 40
<211> LENGTH: 20
<212> TYPE: DNA
<213> ORGANISM: Artificial
<220> FEATURE:
<223> OTHER INFORMATION: gRNA

<400> SEQUENCE: 40
tgacagcaca ggtcacaaca                                              20

<210> SEQ ID NO 41
<211> LENGTH: 20
<212> TYPE: DNA
<213> ORGANISM: Artificial
<220> FEATURE:
<223> OTHER INFORMATION: gRNA

<400> SEQUENCE: 41
tttgaaaaac actacatggg                                              20

<210> SEQ ID NO 42
<211> LENGTH: 20
<212> TYPE: DNA
<213> ORGANISM: Artificial
<220> FEATURE:
<223> OTHER INFORMATION: gRNA

<400> SEQUENCE: 42
tgttcctgag acaatgacgg                                              20

<210> SEQ ID NO 43
<211> LENGTH: 20
<212> TYPE: DNA
<213> ORGANISM: Artificial
<220> FEATURE:
<223> OTHER INFORMATION: gRNA

<400> SEQUENCE: 43
gcaccgagca gctatccgag                                              20

<210> SEQ ID NO 44
<211> LENGTH: 20
<212> TYPE: DNA
<213> ORGANISM: Artificial
<220> FEATURE:
<223> OTHER INFORMATION: gRNA

<400> SEQUENCE: 44
cccatgatga ggagctacgg                                              20

<210> SEQ ID NO 45
<211> LENGTH: 20
<212> TYPE: DNA
<213> ORGANISM: Artificial
<220> FEATURE:
<223> OTHER INFORMATION: gRNA

<400> SEQUENCE: 45
acttctcttg atgtgatggg                                              20

<210> SEQ ID NO 46
<211> LENGTH: 20
<212> TYPE: DNA
<213> ORGANISM: Artificial
<220> FEATURE:
<223> OTHER INFORMATION: gRNA
```

```
<400> SEQUENCE: 46
agattgcagc cttacgaaca                                              20

<210> SEQ ID NO 47
<211> LENGTH: 20
<212> TYPE: DNA
<213> ORGANISM: Artificial
<220> FEATURE:
<223> OTHER INFORMATION: gRNA

<400> SEQUENCE: 47
taaggacaaa agccaagagg                                              20

<210> SEQ ID NO 48
<211> LENGTH: 20
<212> TYPE: DNA
<213> ORGANISM: Artificial
<220> FEATURE:
<223> OTHER INFORMATION: gRNA

<400> SEQUENCE: 48
tgccctatga ggacagtacg                                              20

<210> SEQ ID NO 49
<211> LENGTH: 20
<212> TYPE: DNA
<213> ORGANISM: Artificial
<220> FEATURE:
<223> OTHER INFORMATION: gRNA

<400> SEQUENCE: 49
gattaactat caggatgacg                                              20

<210> SEQ ID NO 50
<211> LENGTH: 20
<212> TYPE: DNA
<213> ORGANISM: Artificial
<220> FEATURE:
<223> OTHER INFORMATION: gRNA

<400> SEQUENCE: 50
tatgtctcta atcatcacca                                              20

<210> SEQ ID NO 51
<211> LENGTH: 20
<212> TYPE: DNA
<213> ORGANISM: Artificial
<220> FEATURE:
<223> OTHER INFORMATION: gRNA

<400> SEQUENCE: 51
aaagaggtgg aaatagtcgc                                              20

<210> SEQ ID NO 52
<211> LENGTH: 20
<212> TYPE: DNA
<213> ORGANISM: Artificial
<220> FEATURE:
<223> OTHER INFORMATION: gRNA

<400> SEQUENCE: 52
tagtgtttgc aagcacatcg                                              20

<210> SEQ ID NO 53
<211> LENGTH: 20
```

```
<212> TYPE: DNA
<213> ORGANISM: Artificial
<220> FEATURE:
<223> OTHER INFORMATION: gRNA

<400> SEQUENCE: 53
atcaagccca gatagaagtg                                              20

<210> SEQ ID NO 54
<211> LENGTH: 20
<212> TYPE: DNA
<213> ORGANISM: Artificial
<220> FEATURE:
<223> OTHER INFORMATION: gRNA

<400> SEQUENCE: 54
accaggatgg gcaccacccg                                              20

<210> SEQ ID NO 55
<211> LENGTH: 20
<212> TYPE: DNA
<213> ORGANISM: Artificial
<220> FEATURE:
<223> OTHER INFORMATION: gRNA

<400> SEQUENCE: 55
ccggcgttgt tccgatcctg                                              20

<210> SEQ ID NO 56
<211> LENGTH: 20
<212> TYPE: DNA
<213> ORGANISM: Artificial
<220> FEATURE:
<223> OTHER INFORMATION: gRNA

<400> SEQUENCE: 56
caaccactta ctagagtgcg                                              20

<210> SEQ ID NO 57
<211> LENGTH: 20
<212> TYPE: DNA
<213> ORGANISM: Artificial
<220> FEATURE:
<223> OTHER INFORMATION: gRNA

<400> SEQUENCE: 57
cgttgagaca tcaacatgtg                                              20

<210> SEQ ID NO 58
<211> LENGTH: 19
<212> TYPE: DNA
<213> ORGANISM: Artificial
<220> FEATURE:
<223> OTHER INFORMATION: gRNA

<400> SEQUENCE: 58
agactgggat ctgtaaggt                                               19

<210> SEQ ID NO 59
<211> LENGTH: 20
<212> TYPE: DNA
<213> ORGANISM: Artificial
<220> FEATURE:
<223> OTHER INFORMATION: gRNA

<400> SEQUENCE: 59
```
caggcacagc gagtccagga                                                    20

<210> SEQ ID NO 60
<211> LENGTH: 20
<212> TYPE: DNA
<213> ORGANISM: Artificial
<220> FEATURE:
<223> OTHER INFORMATION: gRNA

<400> SEQUENCE: 60
tgttgaacat aaggctccgg                                                    20

<210> SEQ ID NO 61
<211> LENGTH: 20
<212> TYPE: DNA
<213> ORGANISM: Artificial
<220> FEATURE:
<223> OTHER INFORMATION: gRNA

<400> SEQUENCE: 61
ccatgctctg taatagacgg                                                    20

<210> SEQ ID NO 62
<211> LENGTH: 20
<212> TYPE: DNA
<213> ORGANISM: Artificial
<220> FEATURE:
<223> OTHER INFORMATION: gRNA

<400> SEQUENCE: 62
acgccataca cacagcaggt                                                    20

<210> SEQ ID NO 63
<211> LENGTH: 20
<212> TYPE: DNA
<213> ORGANISM: Artificial
<220> FEATURE:
<223> OTHER INFORMATION: gRNA

<400> SEQUENCE: 63
agaaagggcg gcgatcaagg                                                    20

<210> SEQ ID NO 64
<211> LENGTH: 20
<212> TYPE: DNA
<213> ORGANISM: Artificial
<220> FEATURE:
<223> OTHER INFORMATION: gRNA

<400> SEQUENCE: 64
caaatgtgaa ggccttgagg                                                    20

<210> SEQ ID NO 65
<211> LENGTH: 20
<212> TYPE: DNA
<213> ORGANISM: Artificial
<220> FEATURE:
<223> OTHER INFORMATION: gRNA

<400> SEQUENCE: 65
cactactgtt agtaacagtg                                                    20

<210> SEQ ID NO 66
<211> LENGTH: 20
<212> TYPE: DNA
<213> ORGANISM: Artificial

```
<220> FEATURE:
<223> OTHER INFORMATION: gRNA

<400> SEQUENCE: 66
tcacctggat tacagacccg                                              20

<210> SEQ ID NO 67
<211> LENGTH: 20
<212> TYPE: DNA
<213> ORGANISM: Artificial
<220> FEATURE:
<223> OTHER INFORMATION: gRNA

<400> SEQUENCE: 67
tccccaggaa gcctacaatg                                              20

<210> SEQ ID NO 68
<211> LENGTH: 20
<212> TYPE: DNA
<213> ORGANISM: Artificial
<220> FEATURE:
<223> OTHER INFORMATION: gRNA

<400> SEQUENCE: 68
cagccgggcc accttcaccg                                              20

<210> SEQ ID NO 69
<211> LENGTH: 20
<212> TYPE: DNA
<213> ORGANISM: Artificial
<220> FEATURE:
<223> OTHER INFORMATION: gRNA

<400> SEQUENCE: 69
gggattccct ggtaaagaag                                              20

<210> SEQ ID NO 70
<211> LENGTH: 20
<212> TYPE: DNA
<213> ORGANISM: Artificial
<220> FEATURE:
<223> OTHER INFORMATION: gRNA

<400> SEQUENCE: 70
tagaaatccc ccatcttcgg                                              20

<210> SEQ ID NO 71
<211> LENGTH: 20
<212> TYPE: DNA
<213> ORGANISM: Artificial
<220> FEATURE:
<223> OTHER INFORMATION: gRNA

<400> SEQUENCE: 71
tcgcccgtag aggaacgctg                                              20

<210> SEQ ID NO 72
<211> LENGTH: 20
<212> TYPE: DNA
<213> ORGANISM: Artificial
<220> FEATURE:
<223> OTHER INFORMATION: gRNA

<400> SEQUENCE: 72
gaatcttgac actttccacg                                              20
```

```
<210> SEQ ID NO 73
<211> LENGTH: 20
<212> TYPE: DNA
<213> ORGANISM: Artificial
<220> FEATURE:
<223> OTHER INFORMATION: gRNA

<400> SEQUENCE: 73
gcagctgagg aagcacatcg                                              20

<210> SEQ ID NO 74
<211> LENGTH: 20
<212> TYPE: DNA
<213> ORGANISM: Artificial
<220> FEATURE:
<223> OTHER INFORMATION: gRNA

<400> SEQUENCE: 74
ctccttggcg gacattccag                                              20

<210> SEQ ID NO 75
<211> LENGTH: 20
<212> TYPE: DNA
<213> ORGANISM: Artificial
<220> FEATURE:
<223> OTHER INFORMATION: gRNA

<400> SEQUENCE: 75
ccagccagga cgatcgtacg                                              20

<210> SEQ ID NO 76
<211> LENGTH: 20
<212> TYPE: DNA
<213> ORGANISM: Artificial
<220> FEATURE:
<223> OTHER INFORMATION: gRNA

<400> SEQUENCE: 76
atcaaacatg agacttaccg                                              20

<210> SEQ ID NO 77
<211> LENGTH: 20
<212> TYPE: DNA
<213> ORGANISM: Artificial
<220> FEATURE:
<223> OTHER INFORMATION: gRNA

<400> SEQUENCE: 77
cggaaacttt cggagcgagg                                              20

<210> SEQ ID NO 78
<211> LENGTH: 20
<212> TYPE: DNA
<213> ORGANISM: Artificial
<220> FEATURE:
<223> OTHER INFORMATION: gRNA

<400> SEQUENCE: 78
tgttcccatg caaaccaatg                                              20

<210> SEQ ID NO 79
<211> LENGTH: 20
<212> TYPE: DNA
<213> ORGANISM: Artificial
<220> FEATURE:
<223> OTHER INFORMATION: gRNA
```

```
<400> SEQUENCE: 79
tgttccttgg tcaaagtggg                                          20

<210> SEQ ID NO 80
<211> LENGTH: 20
<212> TYPE: DNA
<213> ORGANISM: Artificial
<220> FEATURE:
<223> OTHER INFORMATION: gRNA

<400> SEQUENCE: 80
ttgaactatg aagtgcactg                                          20

<210> SEQ ID NO 81
<211> LENGTH: 18
<212> TYPE: DNA
<213> ORGANISM: Artificial
<220> FEATURE:
<223> OTHER INFORMATION: gRNA

<400> SEQUENCE: 81
ctagttactt tagatagg                                            18

<210> SEQ ID NO 82
<211> LENGTH: 18
<212> TYPE: DNA
<213> ORGANISM: Artificial
<220> FEATURE:
<223> OTHER INFORMATION: gRNA

<400> SEQUENCE: 82
actaaagctg catcgcgg                                            18

<210> SEQ ID NO 83
<211> LENGTH: 18
<212> TYPE: DNA
<213> ORGANISM: Artificial
<220> FEATURE:
<223> OTHER INFORMATION: gRNA

<400> SEQUENCE: 83
gtcttgttgg agtcgagt                                            18

<210> SEQ ID NO 84
<211> LENGTH: 18
<212> TYPE: DNA
<213> ORGANISM: Artificial
<220> FEATURE:
<223> OTHER INFORMATION: gRNA

<400> SEQUENCE: 84
gttgtcctgt tggtctgg                                            18

<210> SEQ ID NO 85
<211> LENGTH: 18
<212> TYPE: DNA
<213> ORGANISM: Artificial
<220> FEATURE:
<223> OTHER INFORMATION: gRNA

<400> SEQUENCE: 85
cgggcgaatg ggaacctg                                            18

<210> SEQ ID NO 86
```

```
<211> LENGTH: 18
<212> TYPE: DNA
<213> ORGANISM: Artificial
<220> FEATURE:
<223> OTHER INFORMATION: gRNA

<400> SEQUENCE: 86
ggttttgttg ggcgacca                                                 18

<210> SEQ ID NO 87
<211> LENGTH: 18
<212> TYPE: DNA
<213> ORGANISM: Artificial
<220> FEATURE:
<223> OTHER INFORMATION: gRNA

<400> SEQUENCE: 87
tcattcatcc ggcctatc                                                 18

<210> SEQ ID NO 88
<211> LENGTH: 18
<212> TYPE: DNA
<213> ORGANISM: Artificial
<220> FEATURE:
<223> OTHER INFORMATION: gRNA

<400> SEQUENCE: 88
gtgttgcgcc ctcttcaa                                                 18

<210> SEQ ID NO 89
<211> LENGTH: 18
<212> TYPE: DNA
<213> ORGANISM: Artificial
<220> FEATURE:
<223> OTHER INFORMATION: gRNA

<400> SEQUENCE: 89
agaagtgatg gtgtcaag                                                 18

<210> SEQ ID NO 90
<211> LENGTH: 18
<212> TYPE: DNA
<213> ORGANISM: Artificial
<220> FEATURE:
<223> OTHER INFORMATION: gRNA

<400> SEQUENCE: 90
catctccctg atggcgta                                                 18

<210> SEQ ID NO 91
<211> LENGTH: 18
<212> TYPE: DNA
<213> ORGANISM: Artificial
<220> FEATURE:
<223> OTHER INFORMATION: gRNA

<400> SEQUENCE: 91
aaggtacacc tggtttga                                                 18

<210> SEQ ID NO 92
<211> LENGTH: 18
<212> TYPE: DNA
<213> ORGANISM: Artificial
<220> FEATURE:
<223> OTHER INFORMATION: gRNA

<400> SEQUENCE: 92
```
agagtagctc acttccga                                              18

<210> SEQ ID NO 93
<211> LENGTH: 18
<212> TYPE: DNA
<213> ORGANISM: Artificial
<220> FEATURE:
<223> OTHER INFORMATION: gRNA

<400> SEQUENCE: 93
ctccgtgaac gttcgtga                                              18

<210> SEQ ID NO 94
<211> LENGTH: 18
<212> TYPE: DNA
<213> ORGANISM: Artificial
<220> FEATURE:
<223> OTHER INFORMATION: gRNA

<400> SEQUENCE: 94
cgagcctcta cttggcgc                                              18

<210> SEQ ID NO 95
<211> LENGTH: 18
<212> TYPE: DNA
<213> ORGANISM: Artificial
<220> FEATURE:
<223> OTHER INFORMATION: gRNA

<400> SEQUENCE: 95
ggtagtggtg cacacacg                                              18

<210> SEQ ID NO 96
<211> LENGTH: 18
<212> TYPE: DNA
<213> ORGANISM: Artificial
<220> FEATURE:
<223> OTHER INFORMATION: gRNA

<400> SEQUENCE: 96
ccctaggaat tcttaatt                                              18

<210> SEQ ID NO 97
<211> LENGTH: 18
<212> TYPE: DNA
<213> ORGANISM: Artificial
<220> FEATURE:
<223> OTHER INFORMATION: gRNA

<400> SEQUENCE: 97
aatgttttca cggttgtt                                              18

<210> SEQ ID NO 98
<211> LENGTH: 18
<212> TYPE: DNA
<213> ORGANISM: Artificial
<220> FEATURE:
<223> OTHER INFORMATION: gRNA

<400> SEQUENCE: 98
cacgagcgca acctcagt                                              18

<210> SEQ ID NO 99
<211> LENGTH: 18
<212> TYPE: DNA

```
<213> ORGANISM: Artificial
<220> FEATURE:
<223> OTHER INFORMATION: gRNA

<400> SEQUENCE: 99
atttcatgac gcaatttg                                                 18

<210> SEQ ID NO 100
<211> LENGTH: 18
<212> TYPE: DNA
<213> ORGANISM: Artificial
<220> FEATURE:
<223> OTHER INFORMATION: gRNA

<400> SEQUENCE: 100
ccgcaggtag tgggctgt                                                 18

<210> SEQ ID NO 101
<211> LENGTH: 18
<212> TYPE: DNA
<213> ORGANISM: Artificial
<220> FEATURE:
<223> OTHER INFORMATION: gRNA

<400> SEQUENCE: 101
cggacaatgg aacgagga                                                 18

<210> SEQ ID NO 102
<211> LENGTH: 18
<212> TYPE: DNA
<213> ORGANISM: Artificial
<220> FEATURE:
<223> OTHER INFORMATION: gRNA

<400> SEQUENCE: 102
gagcttggtc gcagagta                                                 18

<210> SEQ ID NO 103
<211> LENGTH: 18
<212> TYPE: DNA
<213> ORGANISM: Artificial
<220> FEATURE:
<223> OTHER INFORMATION: gRNA

<400> SEQUENCE: 103
agaaaactac ataccgca                                                 18

<210> SEQ ID NO 104
<211> LENGTH: 18
<212> TYPE: DNA
<213> ORGANISM: Artificial
<220> FEATURE:
<223> OTHER INFORMATION: gRNA

<400> SEQUENCE: 104
cggatgcccg aatcacca                                                 18

<210> SEQ ID NO 105
<211> LENGTH: 18
<212> TYPE: DNA
<213> ORGANISM: Artificial
<220> FEATURE:
<223> OTHER INFORMATION: gRNA

<400> SEQUENCE: 105
ccaacgcgtc ttctggcc                                                 18
```

<210> SEQ ID NO 106
<211> LENGTH: 18
<212> TYPE: DNA
<213> ORGANISM: Artificial
<220> FEATURE:
<223> OTHER INFORMATION: gRNA

<400> SEQUENCE: 106
cctatcttta gacggatg                                                18

<210> SEQ ID NO 107
<211> LENGTH: 18
<212> TYPE: DNA
<213> ORGANISM: Artificial
<220> FEATURE:
<223> OTHER INFORMATION: gRNA

<400> SEQUENCE: 107
cccgaactgt ttcaccca                                                18

<210> SEQ ID NO 108
<211> LENGTH: 18
<212> TYPE: DNA
<213> ORGANISM: Artificial
<220> FEATURE:
<223> OTHER INFORMATION: gRNA

<400> SEQUENCE: 108
ccgcttcgtg tgtcgaat                                                18

<210> SEQ ID NO 109
<211> LENGTH: 18
<212> TYPE: DNA
<213> ORGANISM: Artificial
<220> FEATURE:
<223> OTHER INFORMATION: gRNA

<400> SEQUENCE: 109
tgtgggcggt atgggagg                                                18

<210> SEQ ID NO 110
<211> LENGTH: 18
<212> TYPE: DNA
<213> ORGANISM: Artificial
<220> FEATURE:
<223> OTHER INFORMATION: gRNA

<400> SEQUENCE: 110
cggttgacag ttcgtctg                                                18

<210> SEQ ID NO 111
<211> LENGTH: 18
<212> TYPE: DNA
<213> ORGANISM: Artificial
<220> FEATURE:
<223> OTHER INFORMATION: gRNA

<400> SEQUENCE: 111
cagcttttgc agttgcgg                                                18

<210> SEQ ID NO 112
<211> LENGTH: 18
<212> TYPE: DNA
<213> ORGANISM: Artificial
<220> FEATURE:

<223> OTHER INFORMATION: gRNA

<400> SEQUENCE: 112
cttcagcttt gacacaca                                           18

<210> SEQ ID NO 113
<211> LENGTH: 18
<212> TYPE: DNA
<213> ORGANISM: Artificial
<220> FEATURE:
<223> OTHER INFORMATION: gRNA

<400> SEQUENCE: 113
ttaaaatgcc gcgtttgg                                           18

<210> SEQ ID NO 114
<211> LENGTH: 18
<212> TYPE: DNA
<213> ORGANISM: Artificial
<220> FEATURE:
<223> OTHER INFORMATION: gRNA

<400> SEQUENCE: 114
cagtgctaca cggttgcc                                           18

<210> SEQ ID NO 115
<211> LENGTH: 18
<212> TYPE: DNA
<213> ORGANISM: Artificial
<220> FEATURE:
<223> OTHER INFORMATION: gRNA

<400> SEQUENCE: 115
ccggcagggg aatacgtg                                           18

<210> SEQ ID NO 116
<211> LENGTH: 18
<212> TYPE: DNA
<213> ORGANISM: Artificial
<220> FEATURE:
<223> OTHER INFORMATION: gRNA

<400> SEQUENCE: 116
ctaatcgggt ttcggctt                                           18

<210> SEQ ID NO 117
<211> LENGTH: 18
<212> TYPE: DNA
<213> ORGANISM: Artificial
<220> FEATURE:
<223> OTHER INFORMATION: gRNA

<400> SEQUENCE: 117
ttgtatcgta ggtcatca                                           18

<210> SEQ ID NO 118
<211> LENGTH: 18
<212> TYPE: DNA
<213> ORGANISM: Artificial
<220> FEATURE:
<223> OTHER INFORMATION: gRNA

<400> SEQUENCE: 118
cttgcacatg ttgggaga                                           18

```
<210> SEQ ID NO 119
<211> LENGTH: 18
<212> TYPE: DNA
<213> ORGANISM: Artificial
<220> FEATURE:
<223> OTHER INFORMATION: gRNA

<400> SEQUENCE: 119
aacctttatt tggcgccg                                                           18

<210> SEQ ID NO 120
<211> LENGTH: 18
<212> TYPE: DNA
<213> ORGANISM: Artificial
<220> FEATURE:
<223> OTHER INFORMATION: gRNA

<400> SEQUENCE: 120
ctggtacaag gcgtagat                                                           18

<210> SEQ ID NO 121
<211> LENGTH: 86
<212> TYPE: DNA
<213> ORGANISM: Artificial
<220> FEATURE:
<223> OTHER INFORMATION: Forward primer

<400> SEQUENCE: 121
caagcagaag acggcatacg agattcgcct tagtctcgtg ggctcggaga tgtgtataag             60
agacagtagc aaactggggc acaagc                                                  86

<210> SEQ ID NO 122
<211> LENGTH: 29
<212> TYPE: DNA
<213> ORGANISM: Artificial
<220> FEATURE:
<223> OTHER INFORMATION: Reverse primer

<400> SEQUENCE: 122
aatgatacgg cgaccaccga gatctacac                                               29
```